(12) United States Patent
Britton et al.

(10) Patent No.: US 6,245,761 B1
(45) Date of Patent: *Jun. 12, 2001

(54) INDOLYL NEUROPEPTIDE Y RECEPTOR ANTAGONISTS

(75) Inventors: Thomas C. Britton; Robert F. Bruns, Jr., both of Carmel; Donald R. Gehlert, Indianapolis; Philip A. Hipskind, New Palestine; Karen L. Lobb; James A. Nixon, both of Indianapolis; Paul L. Ornstein, Carmel; Edward C. R. Smith, Indianapolis; Hamideh Zarrinmayeh, Carmel; Dennis M. Zimmerman, Zionsville, all of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/705,379

(22) Filed: Aug. 29, 1996

Related U.S. Application Data

(60) Provisional application No. 60/003,150, filed on Sep. 1, 1995, and provisional application No. 60/021,638, filed on Jul. 12, 1996.

(30) Foreign Application Priority Data

Nov. 23, 1995 (GB) .................................................. 9523999

(51) Int. Cl.[7] ...................... A61K 31/454; A61K 31/404; C07D 209/12; C07D 401/06
(52) U.S. Cl. .................. 514/235.2; 514/254.09; 514/292; 514/316; 514/323; 514/414; 514/415; 514/418; 514/419; 514/143; 514/373; 546/87; 546/187; 546/201; 548/468; 548/483; 548/486; 548/492; 548/493; 548/507; 548/509; 548/510
(58) Field of Search ...................................... 544/111, 366, 544/143, 373; 546/133, 187, 87, 201; 548/312.1, 465, 468, 483, 486, 492, 493, 494, 507, 509, 510

(56) References Cited

U.S. PATENT DOCUMENTS

| | | | |
|---|---|---|---|
| 2,825,734 | 3/1958 | Speeter et al. | 260/319 |
| 4,374,846 | 2/1983 | Heinemann et al. | 424/274 |
| 4,536,499 | 8/1985 | Brand et al. | 514/212 |
| 4,582,848 | 4/1986 | Nadelson | 514/419 |
| 4,960,786 | * 10/1990 | Salituro et al. | 514/419 |
| 5,206,382 | 4/1993 | Costa et al. | 548/494 |
| 5,264,420 | 11/1993 | Duggan et al. | 514/19 |
| 5,401,855 | * 3/1995 | Gubin et al. | 548/486 |
| 5,464,861 | * 11/1995 | Dobrusin et al. | 514/414 |
| 5,482,949 | 1/1996 | Black et al. | 514/324 |
| 5,494,928 | 2/1996 | Bös | 514/415 |
| 5,496,844 | 3/1996 | Inai et al. | 514/415 |
| 5,565,484 | * 10/1996 | Herbert et al. | 514/418 |
| 5,616,620 | * 4/1997 | Rudolf et al. | 514/620 |

FOREIGN PATENT DOCUMENTS

| | | |
|---|---|---|
| 3312107 | 10/1993 | (DE) . |
| 530907 | * 3/1993 | (EP) . |
| WO 90/05721 | 5/1990 | (WO) . |
| 9417035 | * 8/1994 | (WO) . |
| WO 95/10513 | 4/1995 | (WO) . |
| 95/24200 | 9/1995 | (WO) . |
| WO 96 12489 | 5/1996 | (WO) . |

OTHER PUBLICATIONS

Mitsui et. al., "Mondamine Oxidase Inhibitors . . . ", Chem. Pharm. Bull., vol. 37(2), 1989, pp. 363–366.*
Kinoshita et. al., "Inhibitory Effects of Plant . . . ", Planta Med., vol. 58, 1992, pp. 137–145.*
Unangst et. al., "Novel Indolecarboxamidotetrazoles . . . ", J. Med. Chem., vol. 32, 1989, pp. 1360–1366.*

* cited by examiner

*Primary Examiner*—Richard L. Raymond
(74) *Attorney, Agent, or Firm*—Manisha A. Desai; Paul J. Gaylo

(57) ABSTRACT

This invention provides a series of substituted indoles which are useful in treating or preventing a condition associated with an excess of neuropeptide Y. This invention also provides the novel substituted indoles as well as pharmaceutical formulations with comprise as an active ingredient one or more of these substituted indoles.

33 Claims, No Drawings

INDOLYL NEUROPEPTIDE Y RECEPTOR ANTAGONISTS

PRIORITY CLAIM

This application claims the benefit of U.S. Provisional Applications Ser. No. 60/003,150, filed Sep. 1, 1995, and Ser. No. 60/021,638, filed Jul. 12, 1996 and United Kingdom Patent Application 9523999.2, filed Nov. 23, 1995.

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced in 1982 from porcine brain as part of a general screening protocol to discover carboxy-terminal amidated peptides and was named neuropeptide Y due to its isolation from neural tissue and the presence of tyrosine as both the amino and carboxy terminal amino acid. Neuropeptide Y is a member of the pancreatic family of peptides and shares significant sequence homology with pancreatic polypeptide and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main criteria for a role as a neurotransmitter, as it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanylnucleotide binding proteins, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and other members of the PP family of peptides. The Y1 receptor subtype appears to be the major vascular neuropeptide Y receptor. The Y2 receptor subtypes can also occur postjunctionally on vascular smooth muscle. The as-yet-unisolated Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see. e.g., C. Wahlestedt and D. Reis, *Annual Review of Pharmacology and Toxicology*, 33:309–352 (1993); D. Gehlert and P. Hipskind, *Current Pharmaceutical Design*, 1:295–304 (1995)].

In view of the wide number of clinical maladies associated with an excess of neuropeptide Y, the development of neuropeptide Y receptor antagonists will serve to control these clinical conditions. The earliest such receptor antagonists, such as Patent Cooperation Treaty Patent Publication WO 91/08223, published Jun. 13, 1991, and Patent Cooperation Treaty Patent Publication WO 94/00486, published Jan. 6, 1994, were peptide derivatives. These antagonists are of limited pharmaceutical utility because of their metabolic instability.

This invention provides a class of potent non-peptide neuropeptide Y receptor antagonists. By virtue of their non-peptide nature, the compounds of the present invention do not suffer from the shortcomings, in terms of metabolic instability, of known peptide-based neuropeptide Y receptor antagonists.

SUMMARY OF THE INVENTION

This invention encompasses methods for the treatment or prevention of a disorder associated with an excess of neuropeptide Y, which method comprises administering to a mammal in need of said treatment an effective amount of a compound of Formula I

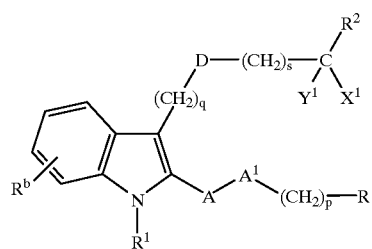

wherein:
$R^b$ is hydrogen, $C_1$–$C_6$ alkyl, $C_1$–$C_6$ alkoxy, $C_2$–$C_6$ alkanoyl, trifluoromethyl, hydroxy, or halo;
$R^1$ is hydrogen, $C_1$–$C_6$ alkyl, or —$(CH_2)_v$—$R^{1a}$;
  where v is 1 to 12, and $R^{1a}$ is phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl, any one of which phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl groups may be substituted with one or more moieties selected from the groups consisting of $C_1$–$C_6$ alkyl, halo, trifluoromethyl, benzyl, phenyl, di($C_1$–$C_6$ alkyl)amino, $C_1$–$C_6$ alkylamino, $C_2$–$C_6$ alkanoyl, $C_2$–$C_6$ alkanoyloxy, and $C_3$–$C_8$ cycloalkyl,
said said phenyl, benzyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy,
or $R^{1a}$ may be substituted with —$(CH_2)_w$—$R^{1b}$, where w is 1 to 12 and $R^{1b}$ is piperidinyl, pyrimidyl, pyrrolidinyl, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, phenyl, $C_3$–$C_8$ cycloalkyl, pyrrolidinyl, and acetamido,
said phenyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy;

A is a bond, —$(CH_2)_m$— or —C(O)—;

$A^1$ is a bond, —$NR^a$—, —O—, —$(CH_2)_m$—, or —$S(O)_n$—;

q is 0 to 6;

p is 0 to 6;

n is 0, 1, or 2;

m is 0 to 6;

s is 0 to 6;

$R^a$ is hydrogen, $C_1$–$C_6$ alkyl, or $C_2$–$C_6$ alkanoyl;

D is a bond, $C_2$–$C_4$ alkenylenyl, or —C(X)(Y)—,
where one of X and Y is hydroxy and the other is hydrogen, or both X and Y are hydrogen, or X and Y combine to form =O, or =$NOR^c$;
$R^c$ is hydrogen, benzyl, acetyl, benzoyl, or $C_1$–$C_6$ alkyl;

one of $X^1$ and $Y^1$ is hydroxy and the other is hydrogen, or both $X^1$ and $Y^1$ are hydrogen, or $X^1$ and $Y^1$ combine to form =O, or =$NOR^d$;
$R^d$ is hydrogen or $C_1$–$C_6$ alkyl;

$R^2$ is hydroxy, $C_1$–$C_6$ alkyl, $C_1$–$C_6$ alkoxy, phenoxy, or a group of the formula

wherein $R^4$ and $R^5$ are independently hydrogen, $C_1$–$C_6$ alkyl, phenyl, or phenyl($C_1$–$C_6$ alkylenyl)-, or $R^2$ is a heterocyclic ring selected from the group consisting of hexamethyleneiminyl, piperazinyl, heptamethyleneiminyl, imidazolinyl, piperidinyl, 2-tryptolinyl, pyrrolidinyl, quinuclidinyl, or morpholinyl;

any one of which hexamethyleneiminyl, piperazinyl, heptamethyleneiminyl, imidazolinyl, piperidinyl, 2-tryptolinyl, pyrrolidinyl, quinuclidinyl, or morpholinyl groups may be substituted with one or more moieties selected from the group consisting of $C_1$–$C_6$ alkyl, halo, trifluoromethyl, benzyl, phenyl, di($C_1$–$C_6$ alkyl)amino, di($C_1$–$C_6$ alkyl)amino($C_1$–$C_6$ alkylenyl)-, $C_1$–$C_6$ alkylamino($C_1$–$C_6$ alkylenyl)-, $C_2$–$C_6$ alkanoyl, carboxamido, 2-aminoacetyl, $C_2$–$C_6$ alkanoyloxy, $C_1$–$C_6$ alkoxycarbonyl-, $C_1$–$C_6$ alkylamino, $C_3$–$C_8$ cycloalkyl, piperidinyl, pyrrolidinyl, pyrimidyl, phenyl($C_1$–$C_6$ alkylenyl)-, phenoxy($C_1$–$C_6$ alkylenyl)-, piperidinyl($C_1$–$C_6$ alkylenyl)-, pyrrolidinyl($C_1$–$C_6$ alkylenyl)-, pyrimidyl($C_1$–$C_6$ alkylenyl)-, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, and acetamido, any one of which benzyl, phenyl, piperidinyl, $C_3$–$C_8$ cycloalkyl, phenyl($C_1$–$C_6$ alkylenyl)-, phenoxy($C_1$–$C_6$ alkylenyl)-, pyrrolidinyl, piperidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl group may be substituted with one or more moieties selected from the group consisting of $C_1$–$C_6$ alkyl, halo, trifluoromethyl, acetamido, $C_2$–$C_6$ alkanoyl, $C_2$–$C_7$ alkanoyloxy, and $C_1$–$C_6$ alkoxy, or the nitrogen on said piperidinyl, pyrrolidinyl, piperidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl may be substituted with an amino-protecting group, or $R^2$ is a group of the formula

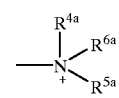

where $R^{4a}$, $R^{5a}$, and $R^{6a}$ are independently hydrogen, $C_1$–$C_6$ alkyl, trifluoromethyl, or $C_1$–$C_6$ alkoxy, or $R^{4a}$ is hydrogen, $C_1$–$C_6$ alkyl, trifluoromethyl, or $C_1$–$C_6$ alkoxy and $R^{5a}$ and $R^{6a}$ combine to form, together with the nitrogen to which they are attached, pyrrolidinyl, piperidinyl, hexamethyleneiminyl, or heptamethyleneiminyl, or $R^{4a}$ is oxygen, and $R^{5a}$ and $R^{6a}$ combine to form, together with the nitrogen to which they are attached, pyrrolidinyl, piperidinyl, hexamethyleneiminyl, or heptamethyleneiminyl;

R is phenyl, naphthyl, dihydronaphthyl, tetrahydronaphthyl, $C_3$–$C_8$ cycloalkyl, pyrazinyl, allyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl, any one of which phenyl, naphthyl, dihydronaphthyl, tetrahydronaphthyl, $C_3$–$C_8$ cycloalkyl, pyrazinyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl groups may be substituted with one or more moieties selected from the group consisting of $C_1$–$C_{12}$ alkyl, $C_2$–$C_{10}$ alkenyl, $C_2$–$C_{10}$ alkynyl, halo, trifluoromethyl, carboxamido, cyano, benzyl, phenyl, di($C_1$–$C_6$ alkyl)amino, $C_2$–$C_6$ alkanoyl, $C_2$–$C_6$ alkanoyloxy, $C_1$–$C_6$ alkylamino, oxazolyl, dihydrooxazolyl, piperidinyl($C_1$–$C_{12}$ alkoxy)-, piperidinyl($C_1$–$C_{12}$ alkoxy)($C_1$–$C_6$ alkylenyl)-, piperidinyl($C_1$–$C_{12}$ alkylenyl)-, phenyl($C_1$–$C_{12}$ alkoxy)-, phenyl($C_2$–$C_{12}$ alkylenyl)-, $C_3$–$C_8$ cycloalkyl, piperidinyl, pyrimidyl, $C_1$–$C_6$ alkoxy, $C_1$–$C_6$ alkylthio, a group of the formula $R^xR^yN$—G—L—($C_0$–$C_6$ alkylenyl)-, and acetamido, where $R^x$ and $R^y$ are independently hydrogen, $C_1$–$C_6$ alkyl, phenyl, benzyl, piperidinyl, pyrrolidinyl, hexamethyleneiminyl, heptamethyleneiminyl, morpholinyl, piperazinyl, or $C_3$–$C_8$ cycloalkyl, or where R$^x$R$^y$N is a ring selected from the group consisting of piperidinyl, pyrrolidinyl, hexamethyleneiminyl, heptamethyleneiminyl, azetidinyl, which may be attached to G at any appropriate place on the ring, G is $C_1$–$C_{12}$ alkylenyl, $C_2$–$C_{12}$ alkenylenyl, or $C_2$–$C_{12}$ alkynylenyl, and L is a bond, —O—, —S—, —S(O)—, —S(O)$_2$—, or —NH—;

with the proviso that when, A$^1$ is —NR$^a$—, —O—, or —S(O)$_n$—, and A is —CH$_2$—, R$^1$ is not hydrogen;

or a pharmaceutically acceptable salt or solvate thereof

This invention also encompasses the novel compounds of Formula I as well as pharmaceutical formulations comprising a compound of Formula I in combination with one or more pharmaceutically acceptable carriers, diluents, or excipients therefor.

DETAILED DESCRIPTION AND PREFERRED EMBODIMENTS

The current invention concerns the discovery that a select group of substituted indoles, those of Formula I, are useful as neuropeptide Y receptor antagonists.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the terms "$C_1$–$C_4$ alkoxy" and "$C_1$–$C_3$ alkoxy,".

As used herein, the term "$C_1$–$C_{12}$ alkyl" refers to straight or branched, monovalent, saturated aliphatic chains of 1 to 12 carbon atoms and includes, but is not limited to, methyl, ethyl, propyl, isopropyl, butyl, isobutyl, t-butyl, pentyl, isopentyl, and hexyl. The term "$C_1$–$C_{12}$ alkyl" includes within its definition the terms "$C_1$–$C_6$ alkyl" and "$C_1$–$C_4$ alkyl".

"$C_2$–$C_7$ alkanoyloxy" represents a straight or branched alkyl chain having from one to six carbon atoms attached to a carbonyl moiety joined through an oxygen atom. Typical $C_2$–$C_7$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

"Halo" represents chloro, fluoro, bromo or iodo.

"$C_1$–$C_{10}$ alkylthio" represents a straight or branched alkyl chain having from one to ten carbon atoms attached to a sulfur atom. Typical $C_1$–$C_{10}$ alkylthio groups include methylthio, ethylthio, propylthio, isopropylthio, butylthio and the like. The term "$C_1$–$C_{10}$ alkylthio" includes within its definition the term "$C_1$–$C_6$ alkylthio" and "$C_1$–$C_3$ alkylthio".

"$C_1$–$C_{12}$ alkylenyl" refers to a straight or branched, divalent, saturated aliphatic chains of 1 to 12 carbon atoms and includes, but is not limited to, methylenyl, ethylenyl, propylenyl, isopropylenyl, butylenyl, isobutylenyl, t-butylenyl, pentylenyl, isopentylenyl, hexylenyl, octylenyl, 3-methyloctylenyl, decylenyl. The term "$C_1$–$C_6$ alkylenyl" is encompassed within the term "$C_1$–$C_{12}$ alkylenyl". The term "$C_0$ alkylenyl" or any term incorporating this designation, refers to a bond, for example "$C_0$–$C_6$ alkylenyl" refers to a bond or $C_1$–$C_6$ alkylenyl, as such is defined herein.

"$C_1$–$C_{10}$ alkylamino" represents a group of the formula

—NH($C_1$–$C_{10}$ alkyl)

wherein a chain having from one to ten carbon atoms is attached to an amino group. Typical $C_1$–$C_4$ alkylamino groups include methylamino, ethylamino, propylamino, isopropylamino, butylamino, sec-butylamino and the like.

The term "$C_2$–$C_{12}$ alkenyl" as used herein represents a straight or branched, monovalent, unsaturated aliphatic chain having from two to twelve carbon atoms. Typical $C_2$–$C_{12}$ alkenyl groups include ethenyl (also known as vinyl), 1-methylethenyl, 1-methyl-1-propenyl, 1-butenyl, 1-hexenyl, 2-methyl-2-propenyl, 2,4-hexadienyl, 1-propenyl, 2-propenyl, 2-butenyl, 2-pentenyl, and the like.

The term "$C_2$–$C_{12}$ alkynyl" as used herein represents a straight or branched, monovalent, unsaturated aliphatic chain having from two to ten carbon atoms with at least one triple bond. Typical $C_2$–$C_{12}$ alkynyl groups include ethynyl, 1-propynyl, 1-butynyl, 1-hexynyl, 2-propynyl, 2-butynyl, 2-pentynyl, and the like.

The term "$C_2$–$C_{12}$ alkenylenyl" as used herein represents a straight or branched, divalent, unsaturated aliphatic chain having from two to twelve carbon atoms. Typical $C_2$–$C_{12}$ alkenylenyl groups include —CH=CH—, —CH$_2$—CH=CH—, —CH$_2$—C(CH$_3$)=CH—CH$_2$CH$_2$—, and the like.

The term "$C_2$–$C_{12}$ alkynylenyl" as used herein represents a straight or branched, divalent, unsaturated aliphatic chain having from two to ten carbon atoms with at least one triple bond. Typical $C_2$–$C_{12}$ alkynylenyl groups include —C≡C—, —CH$_2$—C≡C—, —CH$_2$—C≡C—CH$_2$CH$_2$—, and the like.

"$C_3$–$C_8$ cycloalkenyl" represents a hydrocarbon ring structure containing from three to eight carbon atoms and having at least one double bond within that ring.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_3$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_6$ alkoxycarbonyl" represents a straight or branched alkoxy chain having from one to six carbon atoms attached to a carbonyl moiety. Typical $C_1$–$C_6$ alkoxycarbonyl groups include methoxycarbonyl, ethoxycarbonyl, propoxycarbonyl, isopropoxycarbonyl, butoxycarbonyl, t-butoxycarbonyl and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1- diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BoC, Boc, or t-Boc), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, PROTECTIVE GROUPS IN ORGANIC SYNTHESIS, (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra. at Chapter 5, and T. W. Greene, et al., supra, at Chapter 5.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups may be found in T. W. Greene and P. G. M. Wuts, PROTECTIVE GROUPS IN ORGANIC SYNTHESIS, (1991) at Chapter 3.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The compounds of the present invention are derivatives of indole which are named and numbered according to the RING INDEX, The American Chemical Society, as follows.

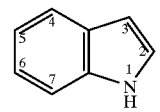

The compounds of the present invention may have one or more asymmetric centers. As a consequence of these chiral centers, those compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system may also be used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., ENANTIOMERS, RACEMATES, AND RESOLUTIONS, (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthtalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quarternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form;

or any combination of 1 to 3, supra. Conventional procedures for the selection and preparation of suitable prodrug derivatives are described, for example, in H, Bundgaard, *Design of Prodrugs*, (1985).

The preferred compounds of the present invention are those compounds of Formula I in which:

a) $R^b$ is hydrogen, chloro, fluoro, methyl, ethyl, hydroxy, or acetyl;
b) $R^1$ is methyl, ethyl; or $R^{1a}$ is phenyl, piperidinyl, pyrrolidinyl, hexamethyleneiminyl, piperazinyl, and v is 1 to 6;
c) $A^1$ is a bond, —NH—, —N(CH$_3$)—, —S—, or —O—;
d) A is —CH$_2$— or —CH$_2$CH$_2$—;
e) q is 0, 1, or 2;
f) p is 0, 1, or 2;
g) s is 0, 1, 2, or 3;
h) D is a bond, —C(O)—, —CH(OH)—, or —CH$_2$—;
i) $R^2$ is a group of the formula -NR$^4$R$^5$ or -N$^+$R$^{4a}$R$^{5a}$R$^{6a}$;
j) $R^4$ and $R^5$ are independently hydrogen, methyl, ethyl, benzyl, or combine to form, together with the nitrogen to which they are attached, a piperidinyl, pyrrolidinyl, or hexamethyleneiminyl group;
k) $R^{4a}$, $R^{5a}$, $R^{6a}$ are independently hydrogen, methyl, ethyl, or $R^{5a}$ and $R^{6a}$ combine to form, together with the nitrogen to which they are attached, a piperidinyl, pyrrolidinyl, or hexamethyleneiminyl group; and
l) R is phenyl, piperidinyl, pyrrolidinyl, hexamethyleneiminyl, heptamethyleneiminyl, naphthyl, thiazolyl, furyl, quinolinyl, isoquinolinyl, morpholinyl, cyclohexyl, cyclopentyl, pyrazinyl, triazolyl, or quinuclidinyl;

or a pharmaceutically acceptable salt or solvate thereof.

The preferred methods of the present invention are those methods employing compounds of Formula I in which a) $R^b$ is hydrogen, chloro, fluoro, methyl, ethyl, hydroxy, or acetyl;
b) $R^1$ is methyl, ethyl, or $R^{1a}$ is phenyl, piperidinyl, pyrrolidinyl, hexamethyleneiminyl, piperazinyl, and v is 1 to 6;
c) $A^1$ is a bond, —NH—, —N(CH$_3$)—, —S—, or —O—;
d) A is —CH$_2$— or —CH$_2$CH$_2$—;
e) q is 0, 1, or 2;
f) p is 0, 1, or 2;
g) s is 0, 1, 2, or 3;
h) D is a bond, —C(O)—, —CH(OH)—, or —CH$_2$—;
i) $R^2$ is a group of the formula -NR$^4$R$^5$ or N$^+$R$^{4a}$R$^{5a}$R$^{6a}$;
j) $R^4$ and $R^5$ are independently hydrogen, methyl, ethyl, benzyl, or combine to form, together with the nitrogen to which they are attached, a piperidinyl, pyrrolidinyl, or hexamethyleneiminyl group;
k) $R^{4a}$, $R^{5a}$, $R^{6a}$ are independently hydrogen, methyl, ethyl, or $R^{5a}$ and $R^{6a}$ combine to form, together with the nitrogen to which they are attached, a piperidinyl, pyrrolidinyl, or hexamethyleneiminyl group; and
l) R is phenyl, piperidinyl, pyrrohdinyl, hexamethyleneiminyl, heptamethyleneiminyl, naphthyl, thiazolyl, furyl, quinolinyl, isoquinolinyl, morpholinyl, cyclohexyl, cyclopentyl, pyrazinyl, triazolyl, or quinuclidinyl;

or a pharmaceutically acceptable salt or solvate thereof.

Especially preferred compounds of the present invention are those compounds of Formula I in which:

a) $R^b$ is hydrogen, fluoro, or methyl;
b) $R^1$ is methyl, or $R^{1a}$ is piperidinyl, pyrrolidinyl, or hexamethyleneiminyl, and v is 1, 2, or 3;
c) $A^1$ is a bond, —NH—, —S—, or —O—;
d) A is —CH$_2$— or —CH$_2$CH$_2$—;
e) q is 0 or 1;
f) p is 0 or 1;
g) s is 0 or 1;
h) D is a bond, or —C(O)—;
i) $R^2$ is a group of the formula -NR$^4$R$^5$;
j) $R^4$ and $R^5$ are independently methyl, or combine to form, together with the nitrogen to which they are attached, a piperidinyl, piperazinyl, or pyrrolidinyl group;
k) R is optionally substituted phenyl, naphthyl, or cyclohexyl;

or a pharmaceutically acceptable salt or solvate thereof.

Especially preferred methods and formulations of the present invention are those methods and formulations employing especially preferred compounds.

Particularly preferred compounds are those of Formula I in which:

a) $R^b$ is hydrogen;
b) $R^1$ is methyl, piperidinyl(C$_1$–C$_4$ alkylenyl)-, or pyrroldinyl(C$_1$–C$_4$ alkylenyl)-;
c) $A^1$ is a bond or —O—;
d) A is —CH$_2$—;
d) q is 0;
e) p is 0 or 1;
f) s is 0 or 1;
g) D is a bond, or —C(O)—;
h) $R^2$ is a piperidinyl, or pyrrolidinyl group, substituted with amino, di(C$_1$–C$_6$ alkyl)amino, (C$_1$–C$_6$ alkyl)amino, piperdinyl, or pyrrolidinyl, or $R^2$ is a piperazinyl group substituted with phenyl, cyclohexyl, or benzyl; and
j) R is phenyl, substituted with one to three groups selected from C$_1$–C$_6$ alkyl, trifluoromethyl, and halo;

or a pharmaceutically acceptable salt or solvate thereof.

Especially preferred methods and formulations of the present invention are those methods and formulations employing especially preferred compounds.

A most preferred class of compounds of the present invention are those compounds of Formula I of the Formula

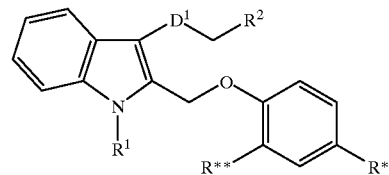

where:
$D^1$ is —C(O)—, or —CH$_2$—;
$R^1$ is methyl, piperidin-3-yl—CH$_2$—CH$_2$—, piperidin-3-yl—CH$_2$—CH$_2$—CH$_2$—, piperidin-2-yl—CH$_2$—CH$_2$—, piperidin-2-yl—CH$_2$—CH$_2$—CH$_2$—, pyrrolidin-3-yl—CH$_2$—CH$_2$—, pyrrolidin-3-yl—CH$_2$—CH$_2$—CH$_2$—, piperidin-4-yl—CH$_2$—CH$_2$—, or piperidin-4-yl—CH$_2$—CH$_2$—CH$_2$—;
$R^2$ is piperidinyl, or pyrrolidinyl group, substituted with amino, di(C$_1$–C$_6$ alkyl)amino, (C$_1$–C$_6$ alkyl)amino, piperidinyl, or pyrrolidinyl, or $R^2$ is a piperazinyl group substituted with phenyl or cyclohexyl;
R* is chloro or bromo; and
R** hydrogen or chloro;

or a pharmaceutically acceptable salt or solvate thereof

Methods and formulations employing any of this class of most preferred compounds are also most preferred.

The compounds of Formula I may be prepared by a number of methods known to those skilled in the art. One protocol for preparing those compounds of Formula I in whch $R^1$ is methyl, is depicted in Scheme I, infra.

Scheme I

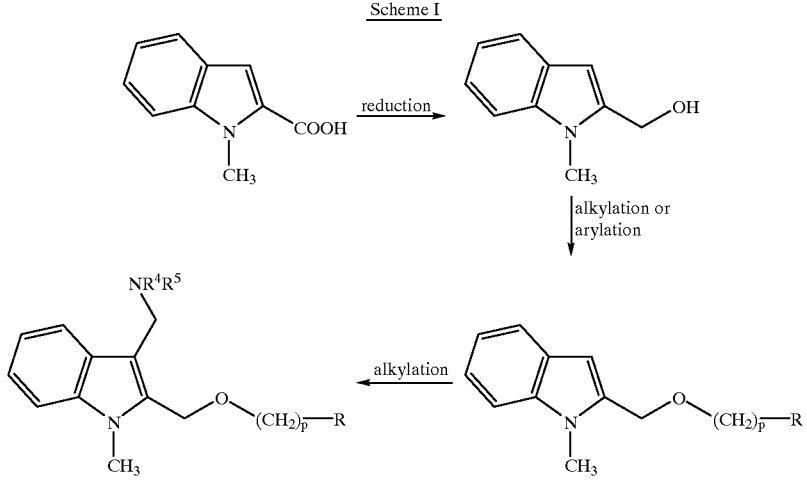

As would be appreciated by those skilled in the art, there are numerous ways of performing each of the steps depicted supra. Typical such methods are described infra in the general teachings and the examples.

Reduction

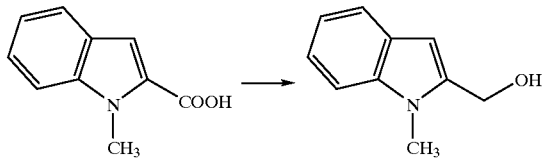

Many of the compounds of Formula I are prepared through the reduction of 1-methyl-2-indolecarboxylic acid to the corresponding 2-hydroxymethyl-1-methylindole. This reduction may be prepared by several methods known in the art including catalytic hydrogenation. A most preferred method for this reduction is by using a reducing agent such as sodium borohydride, lithium borohydride, diisobutylaluminumhydride hydride, lithium triethylborohydride, boranemethyl sulfide complex in refluxing tetrahydrofuran, and triethoxysilane. Another means of reducing the carboxylic acid is by means of sodium in ethanol, a method known as the Bouveault-Blanc procedure. A most preferred reducing agent employed in this procedure is lithium aluminum hydride.

Alkylation or Arylation

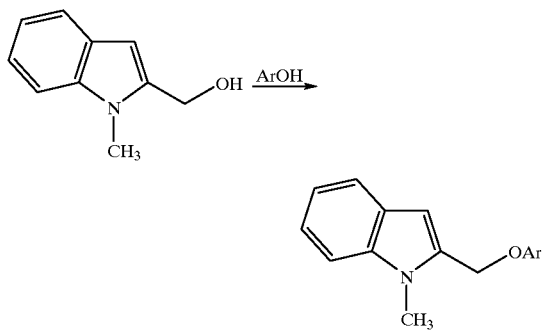

The coupling of the aryl group to the above alcohol may be performed using standard techniques. For those compounds of Formula I in which A is —O—, p is 0, and R is substituted phenyl, for example, a most preferred method involves a phenolic coupling using a Mitsunobu reagent. O. Mitsunobu, et al., *Bulletin of the Chemical Society of Japan,* 44:3427 (1971); O. Mitsunobu, etal., *Journal of the American Chemical Society,* 94:679 (1972). In this reaction triphenylphosphine, in combination with diethyl azodicarboxylate (DEAD), converts alcohols in situ to the corresponding alkoxyphosphonium salts, which are useful alkylating agents.

Although this coupling can be accomplished using various concentrations of the reactants and reagents, it is best to use 1 to 2 equivalents of the indole methyl alcohol, triphenylphosphine, and DEAD per each equivalent of the substituted phenol (ArOH) used.

This reaction also is best carried out in the presence of an inert solvent such as, for example, toluene, benzene, or, preferably tetrahydrofuran. The reaction is performed at temperatures from about 0° C. to about 40° C., preferably at ambient temperature, until the desired compound is prepared. Typically, the reaction takes about 18 hours when run at ambient temperature, but the progress of the reaction can be monitored via standard chromatographic techniques.

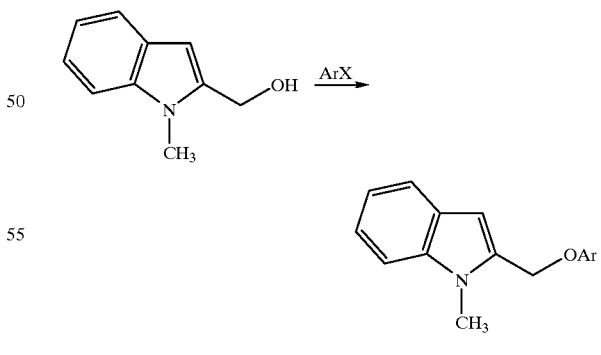

An alternative method of arylating the alcohol involves nucleophilic aromatic substitution of an aryl fluoride with a preformed alkoxide. This reaction is performed by first adding a base to the alcohol, followed by the addition of the aryl halide. An especially preferred base is sodium hydride. Another preferred base is sodium hexamethyldisilazide. The reaction is generally performed in a polar aprotic solvent, for example, acetonitrile, N,N-dimethylformamide, N,N-dimethylphenylacetamide, dimethylsulfoxide, or hexamethylphosphoric triamide.

Alkylation

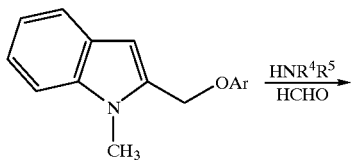

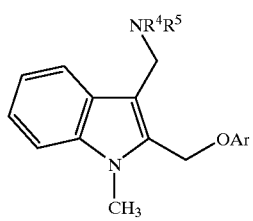

Alkylation of the 1,2-disubstituted indole may be done by a variety of methods known to those skilled in the art. A preferred method of alkylating this substituted indole is by way of a Mannich reaction. [For reviews of this reaction, see, Tramontini, *Synthesis*, 703–775 (1973); House, MODERN SYNTHETIC REACTIONS, (2d ed., 1972) at pages 654–660.]

In this reaction formaldehyde (or sometimes another aldehyde) is condensed with $HNR^4R^5$, in the form of its salt, and a compound containing an active hydrogen. Instead of ammonia, the reaction can be carried out with salts of primary ($RNH_2$) or secondary amines ($R_2NH$), or with amides ($RCONH_2$), in which cases the product is substituted on the nitrogen with R, $R_2$, and RCO, respectively. This reaction is generally carried out in a lower alkyl alcohol, such as methanol or ethanol, or in an acid, such as acetic acid.

One process for preparing those compounds of Formula I in which A is an alkylenyl group is by first oxidizing the alcohol to form the corresponding aldehyde.

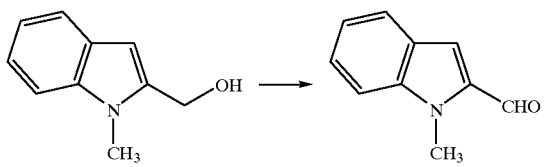

This reaction is generally performed using an oxidizing agent such as pyridinium dichromate (PDC) or pyridinium chlorochromate (PCC) in a solvent such as methylene chloride. The resulting aldehyde is then reacted with a substituted phosphonate in the presence of a base.

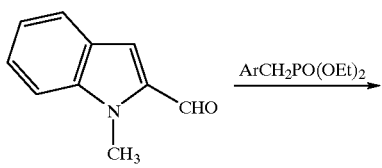

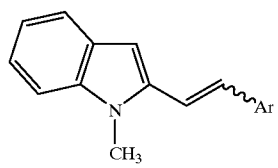

This Wittig-type reaction results in the formation of an aralkenyl group. A preferred base employed in this reaction is sodium hydride. This reaction generally results in a mixture of the (E) and (Z) stereoisomers. The double bond is then reduced using either a reducing agent as described supra or by means of catalytic hydrogenation using standard means. Preferred solvents for this reaction include dichloroethane.

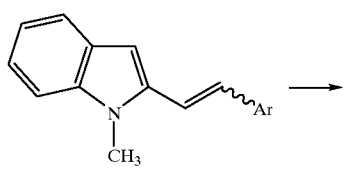

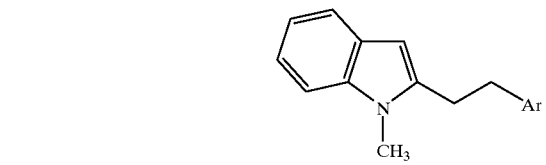

The resulting 1,2-disubstituted indole may then be substituted at the 3 position essentially as described above for the Mannich chemistry.

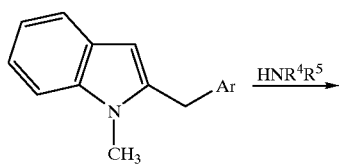

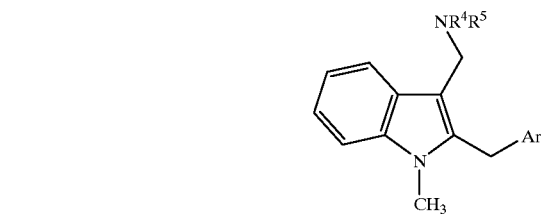

Those compounds in which $R^1$ is a substituted alkylenyl group $[(CH_2)_v—R^{1a}]$ may be prepared as illustrated in Scheme II, infra.

Scheme II
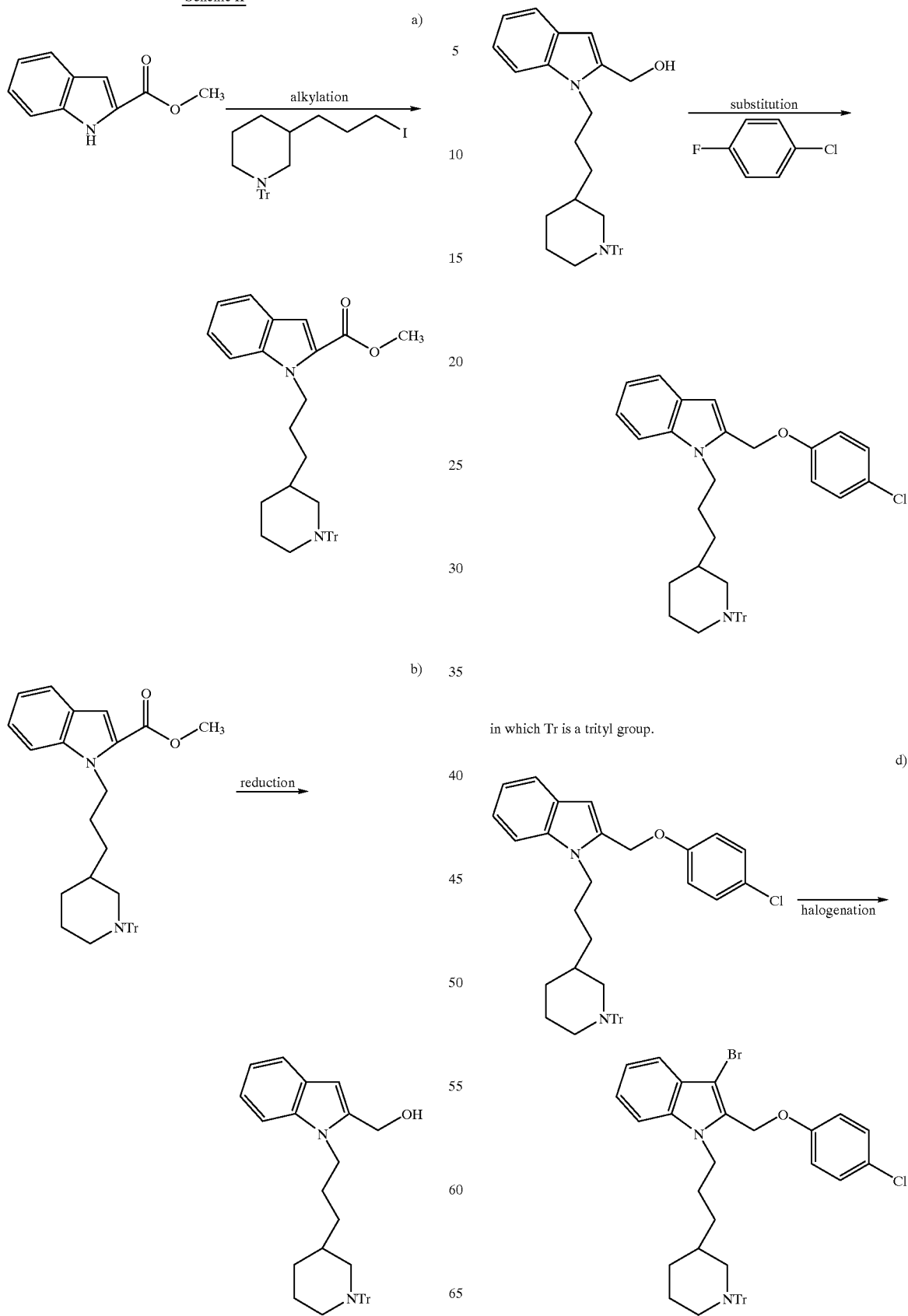
in which Tr is a trityl group.

e)

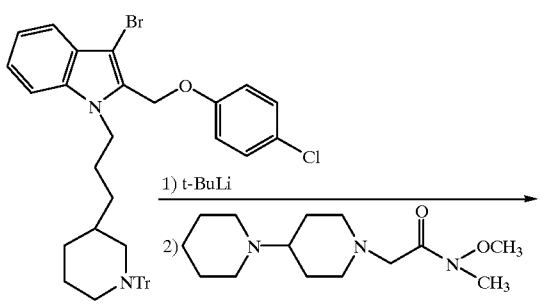

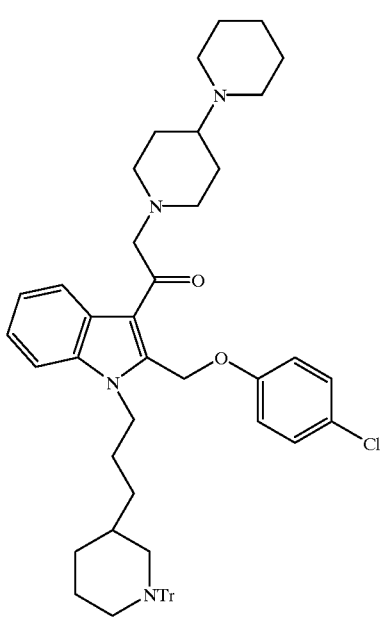

f)

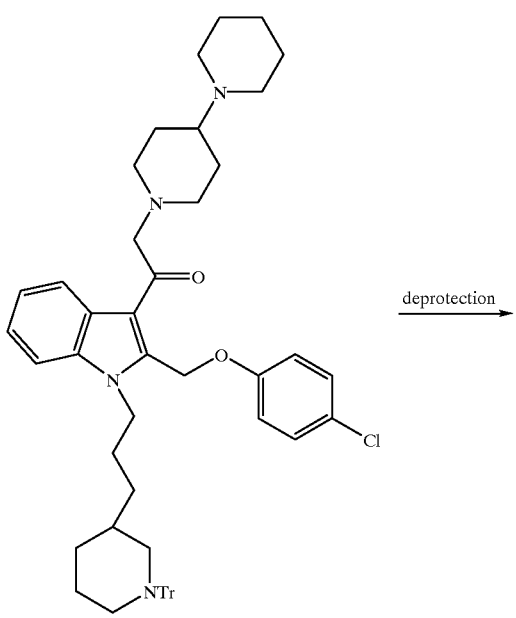

deprotection →

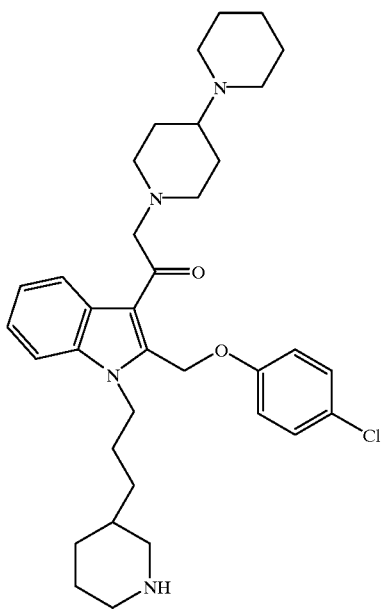

For those compounds of Formula I in which L is —S—, the thio derivatives and intermediates of this invention may be transformed into the corresponding sulfoxide (—SO—) compounds upon treatment with a mild oxidizing agent, such as hydrogen peroxide in methanol, metachloroperbenzoic acid (MCPBA) in methylene chloride at 0° C., or an alkali metal periodate in aqueous alcohol. The corresponding sulfones (—$SO_2$—) are prepared from the thio or sulfoxide compounds on treatment with a strong oxidizing agent, such as hydrogen peroxide in acetic acid or m-chloroperbenzoic acid in methylene chloride at 20° C.–30° C.

Those compounds of Formula I in which the benzo ring of the indole has been substituted may be prepared by a number of ways known to those skilled in the art. For example, those compounds of Formula I in which the 4-position of the indole ring has been substituted with methyl may be prepared as described in Scheme III, infra.

In step a), below, a Knoevenagel condensation reaction is performed, resulting (after the dehydration step of the reaction) in an olefin. This reaction is generally performed with an excess of the azide, although an equimolar mixture of the two reagents may be employed.

The olefin product of step a) is then cyclized to form an indole ring. The usual means of this cyclization is by heating the olefin. The progress of the cyclization may be followed by thin layer chromatography.

Scheme III a)

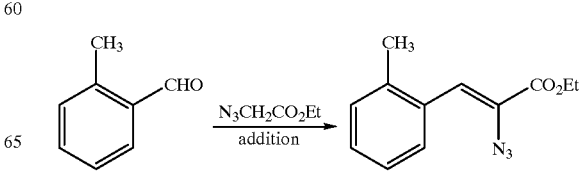

b)
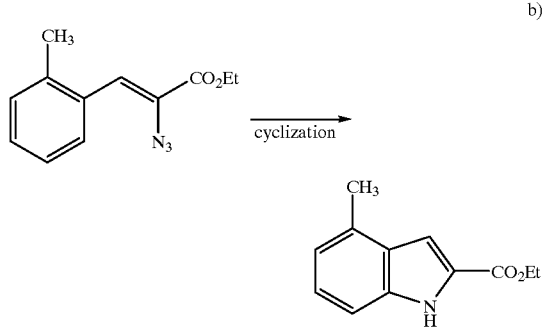
c)
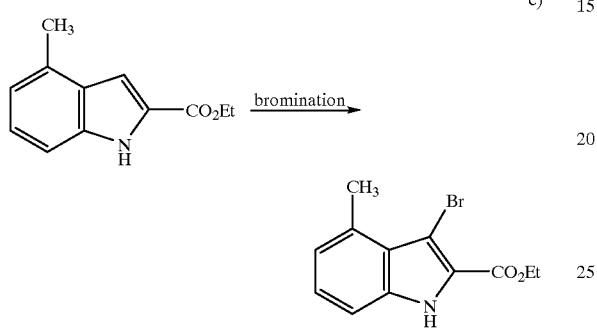
d)
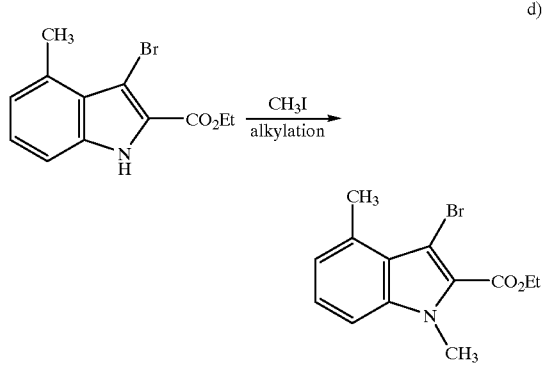
e)
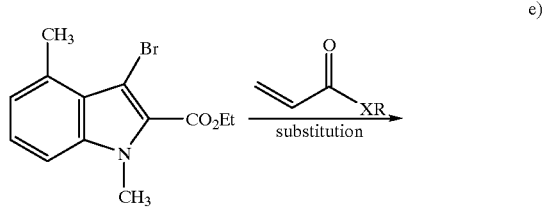
f)
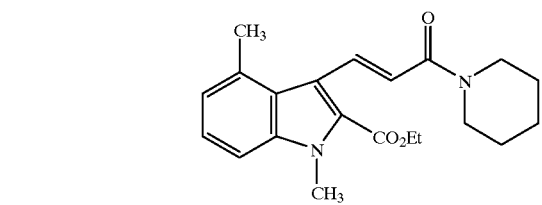
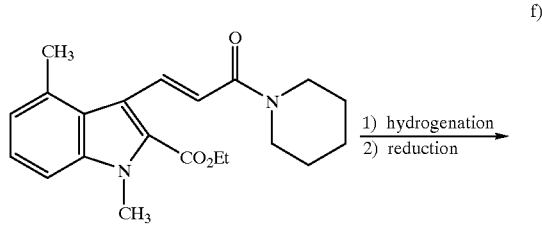
g)
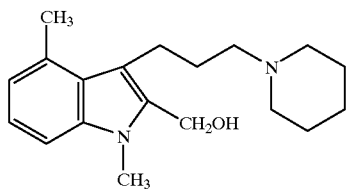
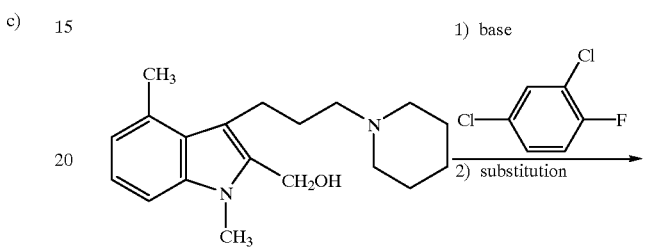
Scheme IV
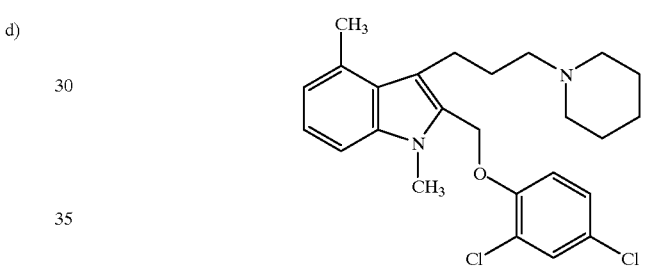
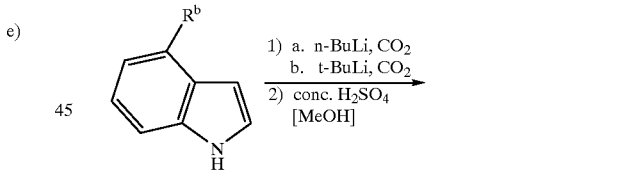

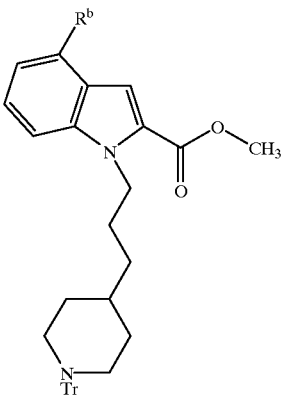

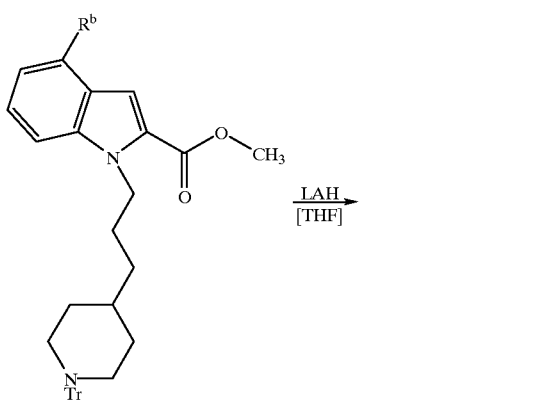

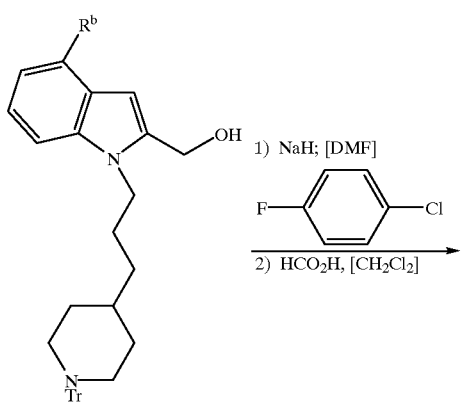

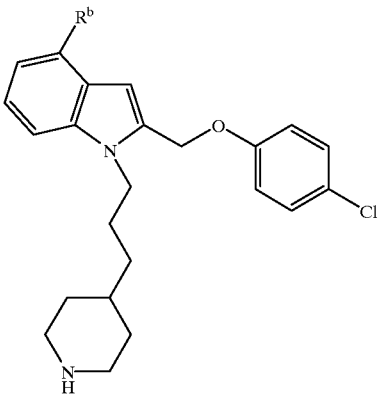

An alternative method of preparing those compounds of Formula I in which $R^b$ is not hydrogen may be prepared as described in Scheme V, infra.

The intermediates and other reagents necessary for the preparations fo the compounds of the present invention, are commercially available, are known in the literature, or can be prepared by known methods. In addition, those of ordinary skill in the art will recognize that variations on the methods for preparing the claimed compounds as described above may be performed without detracting from the synthesis of these compounds. For example, other esters may be employed, as may protecting groups, precursors, the direct introduction of the carboxylic acid group onto the benzo ring of the indole (Kolbe-Schmitt reaction ), etc. Moreover, certain $R^b$ groups may be introduced directly onto the benzo ring. For example, a chloro group can be introduced by treating with iodobenzene, chlorine, and pyridine [Murakami, et al., Chem. Pharm. Bull., 19:1696 (1971)] or N-chlorosuccinimide in dimethylformamide [U.S. Pat. No. 4,623,657, the entire contents of which are herein incorporated by reference]. In addition to those described supra, other transformations, intraconversions, and derivatizations are either described in the Examples, infra, or are well known to those of ordinary skill in the art.

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use.

Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz, or a like model. (Unless designated otherwise, the term "NMR" as employed herein refers to proton nuclear magnetic resonance.) Free atom bombardment mass spectroscopy (FAB) was performed on a VG ZAB-2SE instrument. Field desorption mass spectroscopy (FDMS) was performed using either a VG 70SE or a Varian MAT 731 instrument.

Optical rotations were measured with a Perkin-Elmer 241 polarimeter. Chromatographic separation on a Waters Prep

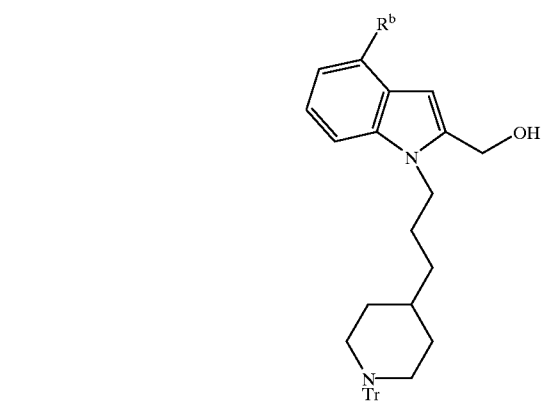

500 LC was generally carried out using a linear gradient of the solvents indicated in the text unless otherwise specified.

The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 ml of 10% aqueous sulfuric acid] and then heated on a hot plate). Preparative centrifugal thin layer chromatography was performed on a Harrison Model 7924A Chromatotron using Analtech silica gel GF rotors.

Cation exchange chromatography was performed with Dowex® 50X8–100 ion exchange resin. Anion exchange chromatography was performed with Bio-Rad AG®) 1-X8 anion-exchange resin (acetate form converted to hydroxide form). Flash chromatography was performed as described by Still, etal., *Journal of Organic Chemistry*, 43:2923 (1978).

Optical rotations are reported at the sodium-D-line (354 nm). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Thomas Hoover capillary melting point apparatus or a Büchi melting point apparatus, and are uncorrected.

The following methods provide illustrative protocols for preparing the compounds of Formula I as depicted in the Schemes supra. Throughout the Methods and Examples, infra, the terms "NMR", "IR", and "UV" indicate that the proton nuclear magnetic resonance, infrared, and ultraviolet spectroscopy, respectively, were consistent with the desired title product.

Preparation 1

Preparation of (3'R) ethyl 2-(piperidin-3-yl)acetate

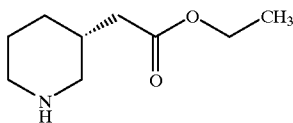

Ethyl-3-pyridylacetate (100 g, 0.606 mol) was dissolved in ethanol (1.8 liters), treated with 5% rhodium on alumina (100 g) and hydrogenated at 60° C. and 60 psi hydrogen gas overnight. The catalyst was removed by filtration and the solvent evaporated to give a brown liquid (101.4 g, 98%). The brown liquid was dissolved in ethyl acetate (600 15 ml) and treated with L-(+)-mandelic acid in warm ethyl acetate (600 ml). After cooling in the refrigerator for four hours, the solid was collected and the crystallization fluid reserved for processing to the other enantiomer, infra. The solid was again recrystallized from ethyl acetate (1.55–1.6 liters, overnight at ambient temperature) to give the desired title product as white needles. Yield: 81.6 grams, 41%. O.R. (EtOH) @589 nm=+44.9°, @365 nm=+173.730. mp 118–119° C.

Preparation 2

Preparation of (3'S) ethyl 2-(piperidin-3-yl)acetate

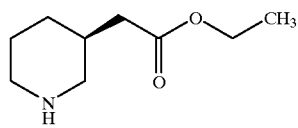

The crystallization fluid from Preparation 1, supra, was evaporated to give a dark oil (100.3 g). This was dissolved in a cold solution of potassium carbonate (52 g, 0.377 mol) in water (250 ml) and extracted with ethyl acetate (5×150 ml). The extracts were combined and dried over magnesium sulfate. The solvents were removed in vacuo to give a dark liquid (40.25 g). The dark liquid was treated with a warm solution of D-(−)-mandelic acid (36 g) in ethyl acetate (650 ml) and stirred at ambient temperatures overnight. The crystals were recrystallized twice more from ethyl acetate (1.2 liters and 1.1 liters, respectively) to give the desired title product as white needles. Yield: 48.7 g, 24.9%. O.R. (EtOH) @589 nm=−43.14°, @365 nm=−164.31°. mp 115.5–117° C.

Chiral Analytical Method

Cold aqueous potassium carbonate (0.15 g in 10 ml of water) was treated with 0.3 g of the mandelic acid salt and the mixture was extracted with ethyl acetate (3×5 ml). The combined extracts were dried over magnesium sulfate and the solvents were removed in vacuo. The residue was dissolved in diethyl ether (10 ml) and treated with S-(−)-α-methylbenzylisocyanate (0.12 ml). After 2.5 hours, the reaction was treated wtih 1 N hydrochloric acid (2 ml). The ether was separated and then washed sequentially with brine, a saturated aqueous sodium bicarbonate solution, and brine. The organic fraction was dried over magnesium sulfate and the solvents were removed by evaporation. The residue was analyzed on a CHIRACEL OJ™ high performance liquid chromatography column (4.6×250 mm), eluting with 5% ethanol in hexanes at a flow rate of 2.5 ml/minute. The slower component comes from the 1-(+)-mandelic acid salt and the faster from the d-(−)-mandelic acid salt. HPLC analysis of the final crystallization products of both enantiomers show less than three percent of the opposite enantiomer.

Preparation 3

Preparation of (3'R) ethyl 2-[N-(t-butoxycarbonyl)piperidin-3-yl]acetate

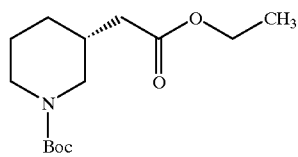

(3'R)-Ethyl 2-(piperidin-3-yl)acetate (10.9 g, 34 mmol) as prepared in Preparation 1 was dissolved in 50 ml of a 12% sodium carbonate in water solution and the resulting solution was extracted with chloroform. The extracts were dried and the solvents removed by evaporation. The residue was suspended in diethyl ether, filtered, and evaporated to give the free base (5.36 g). The liquid was dissolved in ether (50 ml) and treated dropwise with di-t-butyldicarbonate (7.9 g) in ether (10 ml). After stirring overnight, the solution was cooled in an ice water bath and treated dropwise with saturated aqueous citric acid (25 ml). The aqueous fraction was extracted with diethyl ether. The organic fractions were combined, washed with water, a saturated sodium bicarbonate solution, and then brine, and then dried over magnesium sulfate. The solvents were removed in vacuo to give the desired title product was a clear liquid. NMR was consistent with proposed title structure.

Preparation 4

Preparation of (3'S) ethyl 2-[N-(t-butoxycarbonyl)piperidin-3-yl]acetate

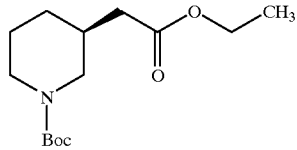

(3'S)-Ethyl 2-(piperidin-3-yl)acetate (48.6 g, 150 mmol), as prepared in Preparation 2, was treated with a solution of potassium carbonate (30 g, 0.217 mol) in water (220 ml) and the resulting solution was extracted with chloroform (3×100 ml). The extracts were dried over sodium sulfate and the solvents were removed in vacuo. The residue was mixed with diethyl ether (200 ml) and filtered to remove some suspended solids. Evaporation of the ether gave a brownish liquid (25 g, Theory=25.7 g). The residue was dissolved in diethyl ether (200 ml), cooled in an ice water bath, and a solution of di-t-butyldicarbonate (31.8 g, 0.146 mol) in ether (25 ml) was added dropwise with stirring. Cooling was removed and reaction was stirred overnight. The solution was again cooled in ice water and a solution of saturated aqueous citric acid (100 ml) was added dropwise. The organics were washed with brine, a saturated aqueous sodium bicarbonate solution, then brine, and then dried over sodium sulfate. The solvents were removed in vacuo to give the desired title product as a clear liquid (38.6 g, >99%). NMR was consistent with desired title structure.

Preparation 5

Preparation of ethyl 3-[pyrid-3-yl]prop-2-enoate

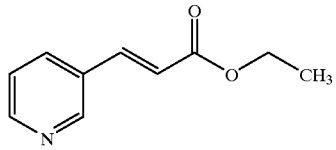

A solution of ethylphosphinoacetate (98.6 g, 0.44 mol) in dry tetrahydrofuran (1200 ml) was treated with 60% sodium hydride (17.5 g, 0.44 mol). The mixture was stirred at room temperature for two hours and was then cooled down to 0° C. To this mixture 3-pyridine carboxaldehyde (38.9 g, 0.36 mol) was added and the resulting reaction mixture was stirred for 1–2 hours while warming to room temperature. The progress of the reaction was monitored by thin layer chromatography.

Water (1000 ml) was added to the reaction mixture. The organic fraction was extracted with ethyl acetate (3×1000 ml). The organic fractions were combined, washed with water (2×1000 ml), brine (1×1000 ml), and the dried over sodium sulfate. The solvents were removed in vacuo to yield 62.5 grams (97%) of the desired title product.

Preparation 6

Preparation of (RS) ethyl 3-[piperidin-3-yl]propionate

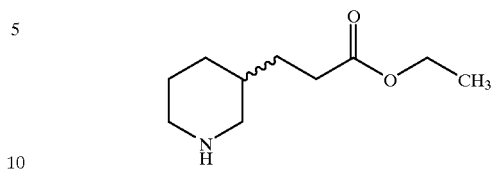

A solution of ethyl 3-[pyrid-3-yl]prop-2-enoate (60 g, 0.34 mol) in ethanol (600 ml) was treated with 5% rhodium on alumina powder (17.2 g). The mixture was placed under a hydrogen atmosphere (55 psi) for five hours at 60° C. The reaction was stopped by removing the hydrogen and the reaciton mixture was filtered through a layer of CELITE™. The residue was washed with hot ethanol. The filtrate was concentrated and purified by flash chromatography to provide 39.6 grams (63%) of the desired title product. IR, NMR, and IR were consistent with the proposed title structure.

Preparation 7

Preparation of (3'S) ethyl 3-[piperidin-3-yl]propionate mandelic acid salt

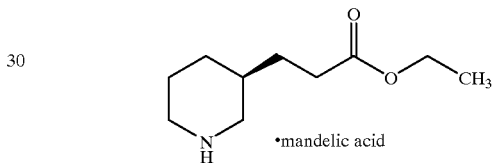

A solution of (RS) ethyl 3-[piperidin-3-yl]propionate (52.0 g, 281 mmol) in hot ethyl acetate (300 ml) was added to the hot solution of R-(−)mandelic acid (42.7 g, 281 mmol). The resulting mixture was then filtered and the clear solution was left at room temperature overnight. The newly formed white crystals of the salt were filtered from the solution. These crystals were recrystallized twice by dissolution in hot ethyl acetate (300 ml) and letting it cool down to room temperature each time. The final pure crystals were dried to yield 33.1 grams (70%). NMR and IR were consistent with the desired title product. The conformation about the chiral center was confirmed by X-ray crystallography.

Preparation 8

Preparation of (3'R) ethyl 3-[piperidin-3-yl]propionate mandelic acid salt

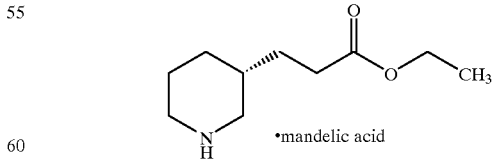

The title compound was prepared essentially as described in Preparation 7, supra, except that S-(+) mandelic acid was employed instead of the R-(−) mandelic acid employed therein. NMR and IR were consistent with the desired title product.

Preparation 9
Preparation of (3'S) ethyl 3-[piperidin-3-yl]propionate

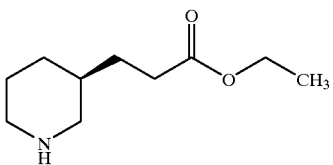

A suspension of (3'S) ethyl 3-[piperidin-3-yl]propionate mandelic acid salt (33.1 g, 98 mmol) in ethyl acetate (500 ml) was treated with a 30% aqueous solution of potassium carbonate until all the organic layer was clear. The mixture was poured into a separatory funnel and the organic fraction was extracted with ethyl acetate (3×300 ml). The combined organic fraction was washed with water (2×300 ml), then brine (1×300 ml), and then dried over sodium sulfate. The solvents were removed in vacuo to yield an oily product in nearly 100% yield. NMR and IR were consistent with the desired title product.

Preparation 10
Preparation of (3'R) ethyl 3-[piperidin-3-yl]propionate

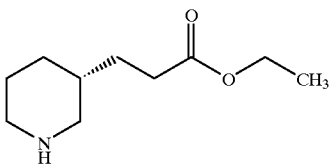

The title compound was prepared essentially as described in Preparation 9, supra, except that (3'R) ethyl 3-[piperidin-3-yl]propionate mandelic acid salt was employed instead of the (3'S) ethyl 3-[piperidin-3-yl]propionate mandelic acid salt therein. NMR and IR were consistent with the desired title product.

Preparation 11
Preparation of (3'S) ethyl 3-[1-(t-butoxycarbonyl)piperidin-3-yl]propionate

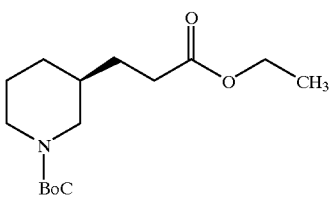

A solution of (3'S) ethyl 3-[piperidin-3-yl]propionate (12.5 g, 67.5 mmol) in tetrahydrofuran:water (2:1, 335:168 ml) was treated with potassium carbonate (14 g, 101 mmol) and di-tert-butyl dicarbonate (17.7 g, 81 mmol). The reaction mixture was stirred at room temperature for five hours. The mixture was then poured into water (200 ml). The organic fraction was extracted with ethyl acetate (3×200 ml). The organic fractions were combined, washed with water (2×200 ml) and then brine (1×200 ml), and then dried over sodium sulfate. The solvents were removed in vacuo and the title product was further purified by flash chromatography. Yield: 19.1 grams (99.2%). NMR and IR were consistent with the desired title product.

Preparation 12
Preparation of (3'R) ethyl 3-[1-(t-butoxycarbonyl)piperidin-3-yl]propionate

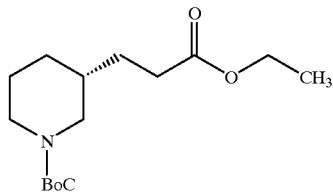

The title product was prepared essentially as described in Preparation 11, supra, except that an equimolar amount of (3'R) ethyl 3-[piperidin-3-yl]propionate was employed instead of the (3'S) ethyl 3-[piperidin-3-yl]propionate employed therein.

Preparation 13
Preparation of (3'S) 3-[1-(t-butoxycarbonyl)piperidin-3-yl]propanol

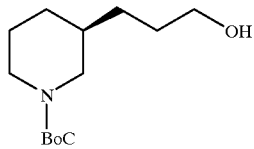

A solution of (3'S) ethyl 3-[1-(t-butoxycarbonyl)piperidin-3-yl]propionate (17.1 g, 60 mmol) in dry diethyl acetate (600 ml) was cooled to 0° C. Lithium aluminum hydride powder (2.5 g, 65 mmol) was gradually added to the mixture. The resulting mixture was stirred at 0° C. and slowly warmed to room temperature within two hours. The reaction was stopped by the slow addition of water (200 ml) and 15% aqueous sodium hydroxide (50 ml). The organic fraction was extracted with diethyl ether (3×300 ml). The combined layer was washed with water (2×200 ml) and then brine (1×200 ml) and then dried over sodium sulfate. The solvents were removed in vacuo to provide 13.2 grams (90% yield) of the title product.

NMR and IR were consistent with the desired title product.

Preparation 14
Preparation of (3'S) 3-[1-(t-butoxycarbonyl)piperidin-3-yl]propanol

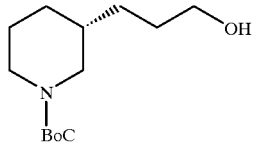

The title product was prepared essentially as described in Preparation 13, supra, except that an equimolar amount of (3'S) ethyl 3-[1-(t-butoxycarbonyl)piperidin-3-yl]propionate was employed instead of the (3'R) ethyl 3-[1-(t-butoxycarbonyl)piperidin-3-yl]propionate employed therein.

Preparation 15
Preparation of (3'S) 3-[1-(t-butoxycarbonyl)piperidin-3-yl]propyl bromide

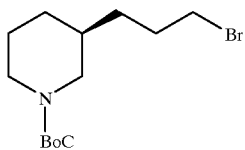

To a cold (0° C.) solution of triphenylphosphine (19.95 g, 76 mmol) in anhydrous methylene chloride (110 ml) was added bromine dropwise until the solution turned pale yellow. A few crystals of triphenylphosphine were added to the mixture to bring the color back to white. To this mixture was added a suspension of (3'S) 3-[1-(t-butoxycarbonyl)piperidin-3-yl]propanol (13.2 g, 54.4 mmol) and pyridine (8.0 g, 76 mmol) in dry methylene chloride (110 ml). The resulting mixture was stirred for five hours while warming to room temperature.

The reaction was stopped by adding water (200 ml). The organic fraction was extracted with methylene chloride (3×200 ml). The combined organic layer was washed with water (2×200 ml), then brine (1×100 ml), and then dried over sodium sulfate. The solvents were removed in vacuo to provide a light brownish crude product, which was further purified by flash chromatography to yield 11.6 grams (70%) of the desired title product.

NMR and IR were consistent with the title product.

Preparation 16
Preparation of (3'R) 3-[1-(t-butoxycarbonyl)piperidin-3-yl]propyl bromide

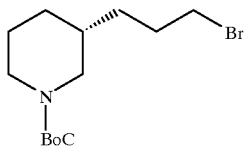

The title product was prepared essentially as described in Preparation 15, supra, except that an equimolar amount of (3'R) 3-[1-(t-butoxycarbonyl)piperidin-3-yl]propanol was employed instead of the (3'S) 3-[1-(t-butoxycarbonyl)piperidin-3-yl]propanol employed therein.

Method A
Preparation of 1-methyl-2-hydroxymethyl-1H-indole.

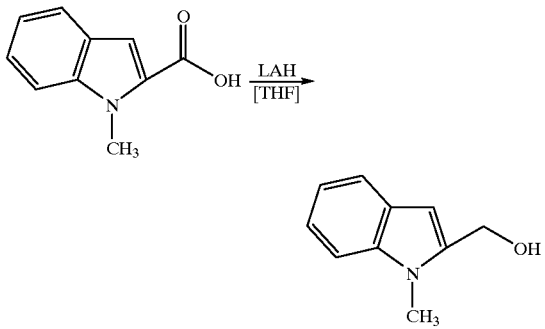

In 950 ml of dry tetrahydrofuran under an argon atmosphere was added lithium aluminum hydride (18.40 g, 0.49 mol). The resulting mixture was placed over an ice bath. An aliquot of 1-methylindole-2-carboxylic acid (84.92 g, 0.49 mol) was dissolved in an additional 475 ml of dry tetrahydrofuran and then added slowly (over about 45–50 minutes) to the lithium aluminum hydride mixture.

The ice was removed from around the round bottom flask and warm water was added to the bath to raise the reaction temperature. The reaction mixture was then stirred at room temperature for 60–90 minutes. The progress of the reaction was monitored by thin layer chromatography.

Once the reaction had progressed sufficiently, the reaction vessel was placed in an ice bath and 20 ml of water were slowly added to the reaction mixture. This was followed by the sequential addition of 20 ml of 5 N sodium hydroxide and then 60 ml of water. The organic fraction was dried using CELITE™ followed by sodium sulfate. The organic solvents were then removed by vacuum to yield a white solid.

The white solid was then dissolved in toluene heated to reflux. The mixture was then cooled to room temperature and then permitted to remain overnight in a refrigerator. The off-white crystals were then collected, washed with cool toluene, and then dried in a vacuum oven. Yield 63.65 grams (81.4%). FDMS 161.

Analysis for $C_{10}H_{11}NO$: Theory: C, 74.51; H, 6.88; N, 8.69. Found: C, 74.73; H, 6.90; N, 8.76.

Preparation of 1-methyl-2-(4-chlorophenoxymethyl)-1H-indole

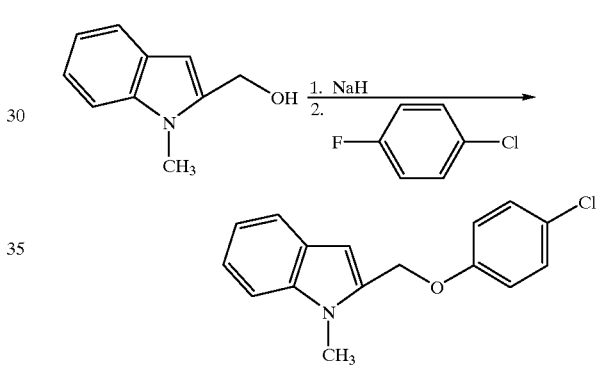

A one liter round bottom flask with a nitrogen atmosphere was charged with sodium hydride (9.28 grams of a 60% NaH solution in mineral oil, 0.232 mol) and N,N-dimethylformamide (211 ml). To the resulting mixture was slowly added 1-methyl-2-hydroxymethyl-1H-indole (34.0 g, 0.211 mol) dissolved in 100 ml of N,N-dimethylformamide. This addition resulted in the formation of a slight exotherm. The resulting reaction mixture was stirred at room temperature for about three hours.

1-Chloro-4-fluorobenzene (30.29 g, 0.232 mmol) was then added to the above reaction mixture, after which the resulting mixture was heated to 80° C. and maintained at this temperature overnight. The progress of the reaction was monitored by thin layer chromatography. The reaction mixture was then allowed to cool. The reaction mixture was then poured into about one liter of water and stirred for about one hour. The solids were removed by filtration and washed with water.

The desired product was then recrystallized from benzene and the solvents were removed in vacuo. IR, NMR, and UV were consistent with the desired title compound. FDMS 271 (M+).

Analysis for $C_{16}H_{14}ClNO$: Theory: C, 70.72; H, 5.19; N, 5.15. Found: C, 70.98; H, 5.18; N, 5.37.

Preparation of 1-methyl-2-(4-chlorophenoxymethyl)-3-(4-methylpiperidin-1-yl)methyl-1H-indole (Example 14)

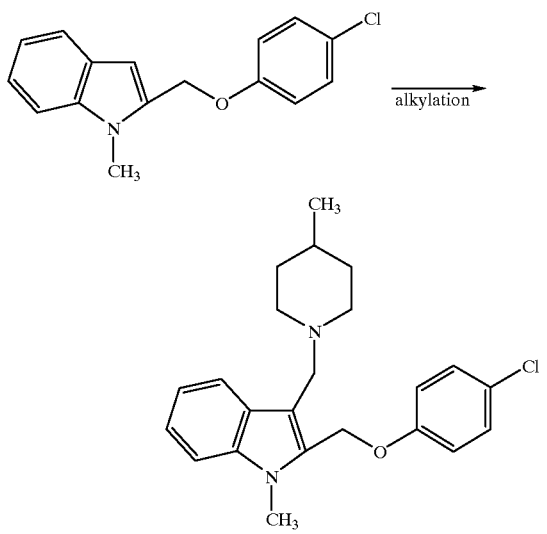

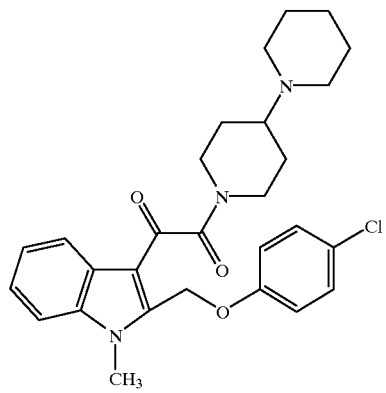

1-Methyl-2-(4-chlorophenoxymethyl)-1H-indole (0.30 g, 1.10 mmol), dissolved in 2.0 ml of tetrahydrofuran, was placed in a round bottom flask under an argon atmosphere. To this solution was added oxalyl chloride (0.294 g, 2.32 mmol). The resulting mixture was stirred at room temperature for about 45 minutes. The solvents were removed in vacuo, leaving a dark brown oil.

The brown oil was taken up in 2.0 ml of dry tetrahydrofuran and 4-(piperidin-1-yl)piperidine (1.07 g, 6.38 mmol), dissolved in about 10 ml of dry tetrahydrofuran, was added. The resulting reaction mixture was stirred at room temperature for about 30 minutes. The progress of the reaction was monitored by thin layer chromatography.

The solids were removed by filtration and the solvents in filtrate were removed by evaporation. The residue from the filtrate was then taken up in methylene chloride and washed with a saturated sodium bicarbonate solution, followed by three extractions with 1.0 N hydrochloric acid.

The aqueous fractions from the above extractions were combined, basified with 1 N sodium hydroxide and then extracted thrice with methylene chloride. This organic fraction was dried over sodium sulfate and the solvents were removed in vacuo. The desired title product was further purified by radial chromatography. NMR and IR were consistent with the proposed title structure. FDMS (M+) 493.

Analysis for $C_{28}H_{32}ClN_3O_3$: Theory: C, 68.07; H, 6.53; N, 8.51. Found: C, 67.97; H, 6.66; N, 8.27.

Preparation of 1-methyl-2-(4-chlorophenoxymethyl)-3-[4-(phenyl)piperazin-1-yl]methyl-1H-indole (Example 20)

Under a nitrogen atmosphere 4-methylpiperidine (0.109 ml, 0.09 g, 0.92 mmol), dissolved in 2.0 ml of ethyl acetate, was added to a round bottom flask which was then placed in an ice bath. Concentrated hydrochloric acid (0.084 ml) was then added and the reaction mixture was removed from the ice bath. To the reaction mixture were added formaldehyde (0.304 g, 1.01 mmol), sodium acetate (0.113 g, 1.38 mmol), and 1-methyl-2-(4-chlorophenoxymethyl)-1H-indole (0.250 g, 0.92 mmol). The resulting mixture was then heated to reflux and maintained at this temperature overnight. The progress of the reaction was monitored by thin layer chromatography.

The solvents were removed in vacuo. The solids were then taken up in methylene chloride. The solvents were then removed in vacuo. The desired product was then recrystallized from ethyl acetate. The desired title product was further purified by chromatography. NMR was consistent with the proposed title structure.

FDMS 382.

Analysis for $C_{23}H_{27}ClN_2O$: Theory: C, 72.14; H, 7.11; N, 7.31. Found: C, 72.33; H, 7.22; N, 7.47.

Method B

Preparation of 1-methyl-2-(4-chlorophenoxymethyl)-3-[2-[4-(piperidin-1-yl)piperidin-1-yl]-1,2-ethanedionyl]-1H-indole (Example 106)

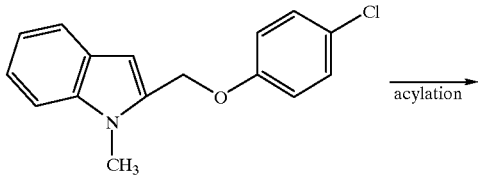

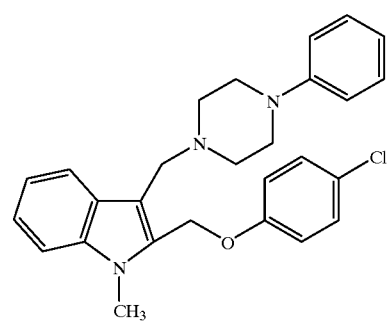

Under a nitrogen atmosphere in a round bottom flask, phenylpiperazine (0.149 g, 0.920 mmol) was dissolved in 2.0 ml of dichloroethane. The reaction vessel was placed in an ice bath. Concentrated hydrochloric acid (0.084 ml, 1.01 mmol) was added and the reaction vessel was removed from the ice bath. Paraformaldehyde (0.304 g, 1.01 mmol) and sodium acetate (0.113 g, 0.920 mmol) were then added, followed by the addition of 1-methyl-2-(4-chlorophenoxymethyl)-1H-indole (0.250 g, 0.920 mmol). The reaction mixture was then heated to reflux and maintained at this temperature for about six hours. The progress of the reaction was monitored by thin layer chromatography. The reaction mixture was then stirred at room temperature for about three days.

The solvents were removed by vacuum and the residue was partitioned between ethyl acetate and a 10% potassium carbonate solution. The organic fraction was washed with water, followed by 1.0 N hydrochloric acid. The acidic aqueous fraction was basified with a 10% potassium carbonate solution. The organic component was dried by dripping through sodium sulfate. The solvents were removed in vacuo.

The desired product was recrystallized from ethyl acetate. NMR was consistent with the desired title structure.

FDMS 445 (M+).

Analysis for $C_{27}H_{28}ClN_3O$: Theory: C, 72.71; H, 6.33; N, 9.42. Found: C, 73.00; H, 6.41; N, 9.51.

Method C1

Preparation of 1-methyl-2-(4-chlorophenoxymethyl)-3-[2-chloro-1,2-ethanedionyl]-1H-indole

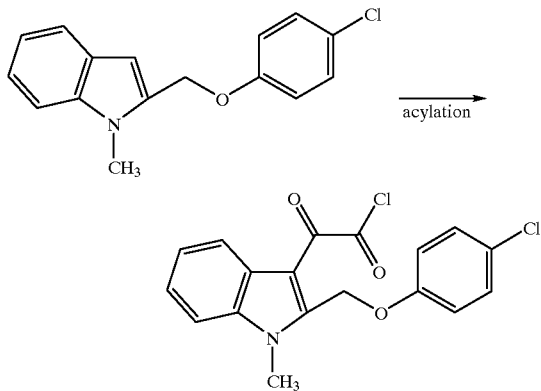

1-Methyl-2-(4-chlorophenoxymethyl)-1H-indole (1.00 g, 3.68 mmol), dissolved in 7.0 ml of diethyl ether in a round bottom flask under a nitrogen atmosphere. To the above solution was added oxalyl chloride (0.981 g, 7.73 mmol). The reaction mixture was stirred at room temperature for about 60 minutes. The progress of the reaction was monitored by thin layer chromatography.

The solvents were removed by decanting and the crystals were rinsed five times with cold diethyl ether. The solvents and rinses were collected, and placed in a freezer for about three days. The crystals were collected and dried in a vacuum oven to yield 1.15 grams (86.3%) of the desired title product.

Preparation of 1-methyl-2-(4-chlorophenoxymethyl)-3-[2-(4-methylpiperidin-1-yl)-1,2-ethanedionyl]-1H-indole (Example 102)

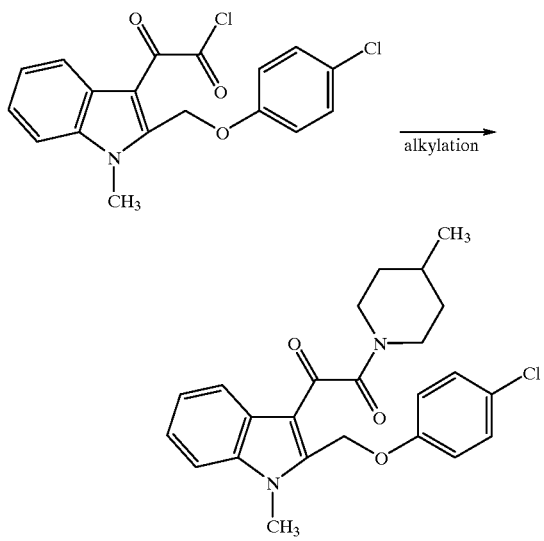

Under a nitrogen atmosphere, 4-methylpiperidine (0.490 ml, 0.411 g, 4.14 mmol) was dissolved in 3.0 ml of dry tetrahydrofuran in a round bottom flask over an ice bath. To this reaction mixture was added 1-methyl-2-(4-chlorophenoxymethyl)-3-[2-chloro-1,2-ethanedionyl]-1H-indole (0.500 g, 1.39 mmol) and the resulting mixture was stirred at room temperature overnight. The progress of the reaction was monitored by thin layer chromatography.

The solvents were removed in vacuo and the residue was partitioned between methylene chloride and 1.0 N sodium hydroxide. The organic fraction was washed with 1.0 N sulfuric acid, followed by a wash with brine. The organic fraction was then dried over sodium sulfate and the solvents were removed in vacuo. The desired title product was recrystallized from ethyl acetate. NMR and IR were consistent with the desired title structure.

FDMS 425 (M+).

Analysis for $C_{24}H_{25}ClN_2O_3$: Theory: C, 67.84; H, 5.93; N, 6.59. Found: C, 68.04; H, 5.85; N, 6.74.

Method C2

Preparation of 2-[(4-chlorophenoxy)methyl]-1-methyl-3-[1-hydroxy-1-[[4-(piperidin-1-yl)piperidin-1-yl]carbonyl]methyl]-1H-indole (Example 77)

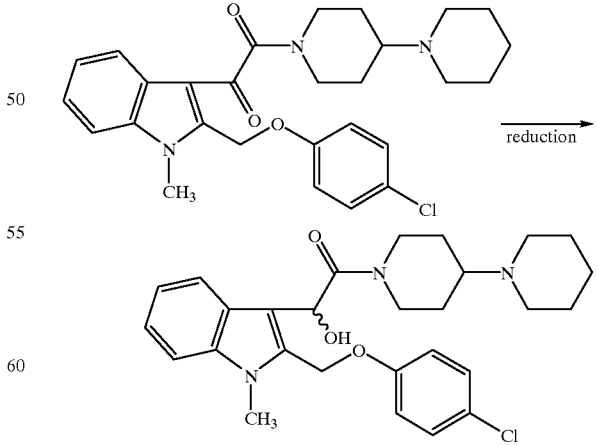

A round bottom flask under a nitrogen atmosphere was charged with 1-methyl-2-(4-chlorophenoxymethyl)-3-[2-[4-(piperidin-1-yl)piperidin-1-yl]-1,2-ethanedionyl]-1H-indole (0.1414 g, 0.282 mmol) and 2.8 ml of denatured ethanol. To this mixture was added sodium borohydride (0.064 g, 1.69 mmol). The reaction mixture was then stirred at room temperature overnight. The progress of the reaction was monitored by thin layer chromatography.

The solvents were removed by evaporation and the residue was partitioned between methylene chloride and water. The aqueous fraction was washed twice with methylene chloride. The organic fractions were combined, washed with brine, and dried over sodium sulfate. The solvents were removed in vacuo. The desired title product was further purified by chromatography. NMR was consistent with the proposed title product.

FDMS 495 (M+).

Analysis for $C_{28}H_{34}ClN_3O_3$: Theory: C, 67.80; H, 6.91; N, 8.47. Found: C, 67.86; H, 6.90; N, 8.45.

Method D

Preparation of methyl indole-2-carboxylate.

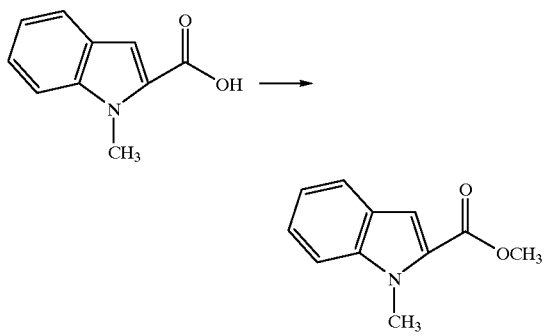

Indole-2-carboxylic acid (47.0 g, 292 mmol) was dissolved in 200 ml of methanol. To this solution was added 6 ml of concentrated sulfuric acid. The resulting mixture was heated to reflux and maintained at this temperature for about 16 hours. The reaction mixture was then cooled to room temperature and the solids were removed by filtration and then washed with 200 ml of methanol. The crystals were dried in a vacuum oven, yielding 39.5 grams (77%) of the desired title product as white needles. Analytical data obtained was consistent with the proposed title structure.

Preparation of methyl 1-[2-(1-tritylpiperidin-4-yl)ethyl] indole-2-carboxylate.

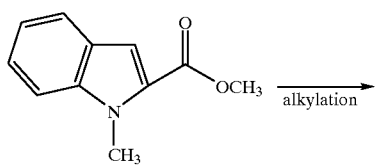

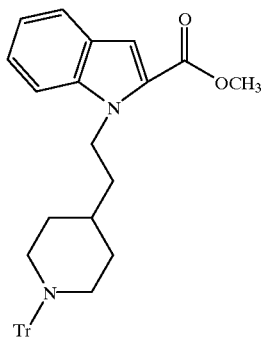

Under an argon atmosphere methyl indole-2-carboxylate (1.50 g, 8.56 mmol) was dissolved in 8.6 ml of N,N-dimethylformamide. The solution was placed in an ice bath and sodium hydride (0.377 g, 9.42 mmol) was added. The resulting mixture was stirred for 20 minutes over ice and then permitted to warm to room temperature. The reaction mixture was then stirred for about 90 minutes at room temperature, after which time it was placed again in an ice bath.

2-(1-Tritylpiperidin-4-yl)ethyl iodide (4.53 g, 9.42 mmol), prepared essentially as described in Preparation 15, dissolved in 15 ml of N,N-dimethylformamide was then added and the resulting mixture was stirred in an ice bath for about three days. The reaction mixture was then poured over water and the solids were collected by filtration. The solids were taken up in methylene chloride and dried over magnesium sulfate. The solvents were removed in vacuo to yield 4.98 grams (>99%) of the desired title product as a yellowish white foam. Analytical data obtained was consistent with the proposed title structure.

Preparation of methyl 1-[3-(1-tritylpiperidin-3-yl)propyl] indole-2-carboxylate.

Under an argon atmosphere methyl indole-2-carboxylate (1.00 g, 5.71 mmol) was dissolved in 5.7 ml of N,N-dimethylformamide. The solution was placed in an ice bath and sodium hydride (0.251 g of a 60% solution, 6.28 mmol) was added. The resulting mixture was stirred for 20 minutes over ice and then permitted to warm to room temperature. The reaction mixture was then stirred for about 60 minutes at room temperature, after which time it was placed again in an ice bath.

3-(1-Tritylpiperidin-3-yl)propyl iodide (3.11 g, 6.28 mmol), dissolved in 8 ml of N,N-dimethylformamide was then added and the resulting mixture was stirred in an ice bath overnight. The reaction mixture was then poured over water and the solids were collected by filtration. The solids were taken up in methylene chloride, washed with water, then brine, and then dried over sodium sulfate. The solvents were removed in vacuo to yield 3.38 grams (>99%) of the desired title product. Analytical data obtained was consistent with the proposed title structure.

Preparation of 2-hydroxymethyl-1-[2-(1-tritylpiperidin-4-yl)ethyl]-1H-indole.

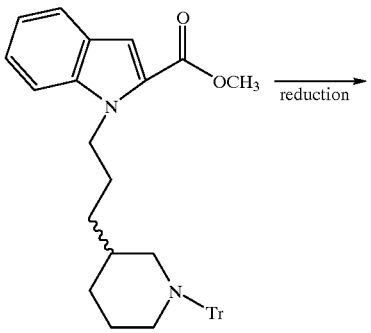

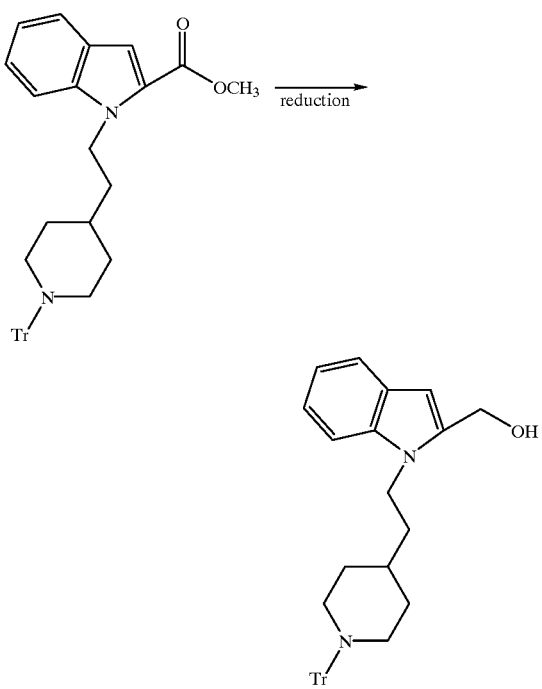

Under an argon atmosphere lithium aluminum hydride (0.325 g, 8.56 mmol) was dissolved in 8.6 ml of dry tetrahydrofuran. The resulting solution was placed in an ice bath and methyl 1-[2-(1-tritylpiperidin-4-yl)ethyl]indole-2-carboxylate (4.68 g, 8.52 mmol), dissolved in about 10 ml of dry tetrahydrofuran, was added. The resulting mixture was stirred overnight at room temperature.

To the reaction mixture 0.35 ml of water were crefully added, followed by the addition of 0.35 ml of 5.0 N sodium hydroxide, and then 1.0 ml of water. The solids were removed by filtration and the solvents in the filtrate were removed in vacuo. The residue from the filtrate was redissolved in methylene chloride. The desired product was then dried over magnesium sulfate and the solvents were removed in vacuo to yield 3.96 grams (92.4%) of the title product as a foam. Analytical data obtained was consistent with the proposed title structure.

Preparation of 2-hydroxymethyl-1-[3-(1-tritylpiperidin-3-yl)propyl]-1H-indole.

Under an argon atmosphere methyl indole-2-carboxylate (1.00 g, 5.71 mmol) was dissolved in 5.7 ml of N,N-dimethylformamide. The solution was placed in an ice bath

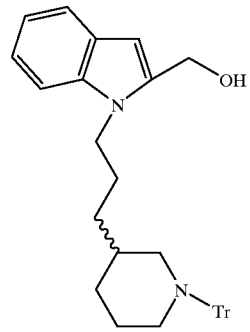

Under an argon atmosphere methyl 1-[3-(1-tritylpiperidin-3-yl)propyl]indole-2-carboxylate (3.38 g, 6.23 mmol) was dissolved in 3.1 ml of dry tetrahydrofuran. The reaction vessel was then placed in an ice bath and lithium aluminum hydride (0.236 g, 6.23 mmol) was added. The resulting mixture was stirred in an ice bath for about ten minutes and then at room temperature overnight. The progress of the reaction was monitored by thin layer chromatography.

To the reaction mixture were added 0.24 ml water, followed by 0.24 ml of 5.0 N sodium hydroxide, followed by 0.72 ml of water. The residue was redissolved in methylene chloride. The desired product was then dried over sodium sulfate and the solvents were removed in vacuo to yield 2.89 grams (90.1%) of the title product as a foam. Analytical data obtained was consistent with the proposed title structure.

Preparation of 2-[(4-chlorophenoxy)methyl]-1-[2-(1-tritylpiperidin-4-yl)ethyl]-1H-indole.

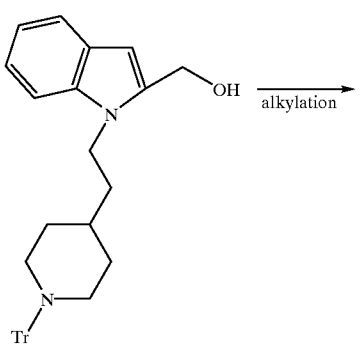

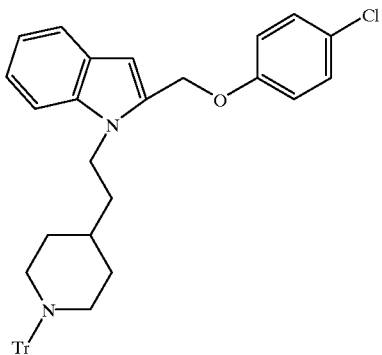

Under an argon atmosphere 2-hydroxymethyl-1-[2-(1-tritylpiperidin-4-yl)ethyl]-1H-indole (3.91 g, 7.81 mmol) was dissolved in about 10 ml of N,N-dimethylformamide. The resulting solution was then placed in an ice bath and sodium hydride (0.468 g, 11.71 mmol) was added and the resulting mixture was stirred at room temperature for about 30 minutes. To the reaction mixture 1-chloro-4-fluorobenzene (0.915 ml, 1.12 g, 8.59 mmol) was added and the resulting mixture was stirred at room temperature for about four days, protected from light.

The reaction mixture was poured into ice water and the solids were collected by filtration. After a washing with water, the solids were dried in a vacuum oven. The desired product was recrystallized from ethyl acetate and washed with cool ethyl acetate to yield 2.62 grams (54.9%). Analytical data obtained was consistent with the proposed title structure.

Preparation of 2-[(4-chlorophenoxy)methyl]-1-[3-(1-tritylpiperidin-3-yl)propyl]-1H-indole.

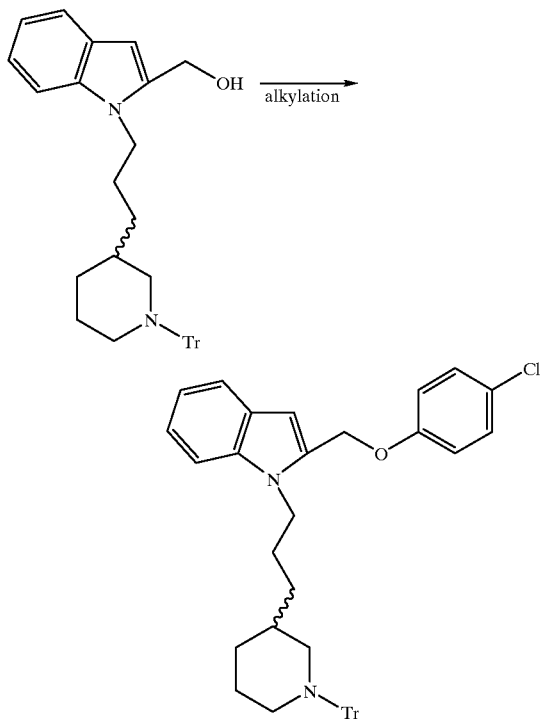

Under an argon atmosphere 2-hydroxymethyl-1-[3-(1-tritylpiperidin-3-yl)propyl]-1H-indole (2.89 g, 5,61 mmol) was dissolved in about 11.2 ml of N,N-dimethylformamide. The resulting solution was then placed in an ice bath and sodium hydride (0.247 g of a 60% suspension in mineral oil, 6.18 mmol) was added and the resulting mixture was stirred at room temperature for about 60 minutes. To the reaction mixture 1-chloro-4-fluorobenzene (0.658 ml, 0.807 g, 6.18 mmol) was added and the resulting mixture was stirred at room temperature overnight. The reaction mixture was then heated to 80° C. and maintained at this temperature for about eight hours. The reaction mixture was then cooled to room temperature and stirred at this temperature overnight. Another half equivalence of sodium hydride was added and the reaction mixture was stirred at room temperature overnight again. Another half equivalence of 1-chloro-4-fluorobenzene was added and the reaction mixture was heated to 80° C.

The reaction mixture was poured into ice water and then partitioned between methylene chloride and brine. The aqueous fraction was extracted twice with methylene chloride. The organic fractions were combined, washed with brine, and dried over sodium sulfate. The desired product was further purified by chromatography to yield 1.0 grams (29%). Analytical data obtained was consistent with the proposed title structure.

Preparation of 2-[(4-chlorophenoxy)methyl]-1-[2-(piperidin-4-yl)ethyl]-1H-indole (Example 137)

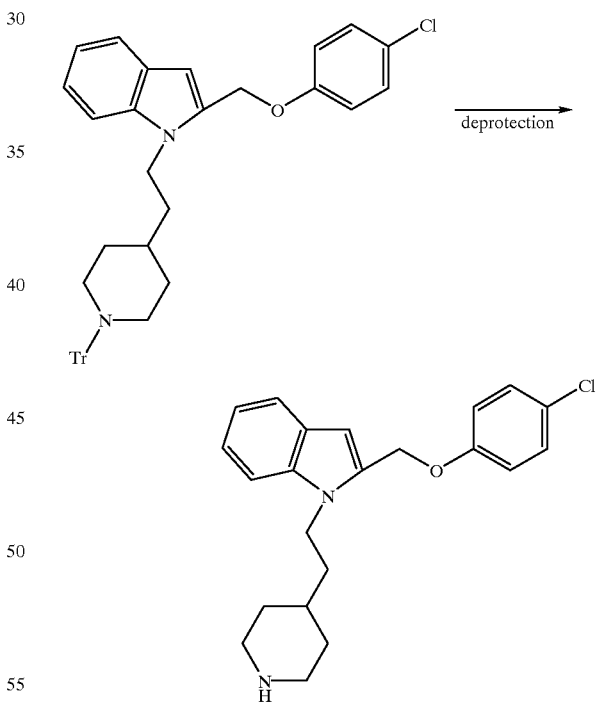

Under an argon atmosphere 2-[(4-chlorophenoxy)methyl]-1-[2-(1-tritylpiperidin-4-yl)ethyl]-1H-indole was dissolved in 7.0 ml of methylene chloride. The reaction solution was then placed on an ice bath and formic acid (0.3383 g) was added. The resulting mixture was stirred in the ice bath for about five hours. The progress of the reaction was monitored by thin layer chromatography.

The reaction mixture was partitioned between methylene chloride and 1.0 N sodium hydroxide. The aqueous fraction was extracted twice with methylene chloride. The organic fractions were combined and dried over sodium sulfate. The solvents were removed in vacuo to yield a foam. The desired product was further purified by chromatography to yield 0.1864 grams (68.7%). NMR was consistent with the proposed title structure.

FDMS 368 (M+).

Analysis for $C_{22}H_{25}ClN_2O$: Theory: C, 71.63; H, 6.83; N, 7.59. Found: C, 71.66; H, 6.86; N, 7.87.

Preparation of 2-[(4-chlorophenoxy)methyl]-1-[3-(piperidin-3-yl)propyl]-1H-indole. (Example 139)

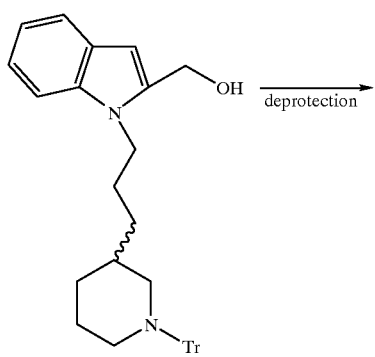

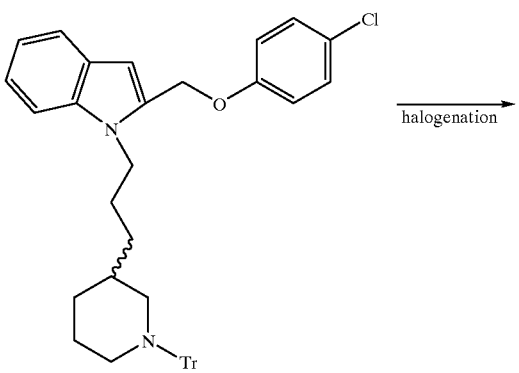

The title compound was prepared essentially as described above for 2-[(4-chlorophenoxy)methyl]-1-[2-(piperidin-4-yl)ethyl]-1H-indole except that an equimolar amount of 2-[(4-chlorophenoxy)methyl]-1-[3-(1-tritylpiperidin-3-yl)propyl]-1H-indole was employed instead of the 2-[(4-chlorophenoxy)methyl]-1-[2-(1-tritylpiperidin-4-yl)ethyl]-1H-indole employed therein.

NMR was consistent with the proposed title strucuture. Single compound of high purity as evidenced by chromatographic methods.

Method E

Preparation of 3-bromo-2-[(4-chlorophenoxy)methyl]-1-[3-(1-tritylpiperidin-3-yl)propyl]-1H-indole.

Under an argon atmosphere in a round bottom flask 2-[(4-chlorophenoxy)methyl]-1-[3-(1-tritylpiperidin-3-yl)propyl]-1H-indole (0.992 g, 1.59 mmol) was dissolved in 4.0 ml of dry tetrahydrofuran. The reaction vessel was then placed in an ice bath and N-bromosuccinimide (0.282 g, 1.587 mmol of a recently recrystallized lot), dissolved in 4.0 ml of tetrahydrofuran, was slowly added. The reaction mixture was stirred for about three hours over an ice bath.

The reaction mixture was poured over water in which 2.5 grams of sodium sulfate was dissolved, and the aqueous phase was extracted thrice with methylene chloride. The organic fractions were combined and dried over sodium sulfate. The solvents were removed in vacuo, yielding 0.26 grams (23%) of the desired compound. The solvents were removed in vacuo from the mother liquor and the resulting residue was recrystallized in ethyl acetate and hexanes to obtain an additional 0.65 grams (58%) of the desired material. Analytical data obtained was consistent with the proposed title structure.

Preparation of (RS) 2-[(4-chlorophenoxy)methyl]-1-[3-(1-tritylpiperidin-3-yl)propyl]-3-[[4-(piperidin-1-yl)piperidin-1-yl]acetyl]-1H-indole.

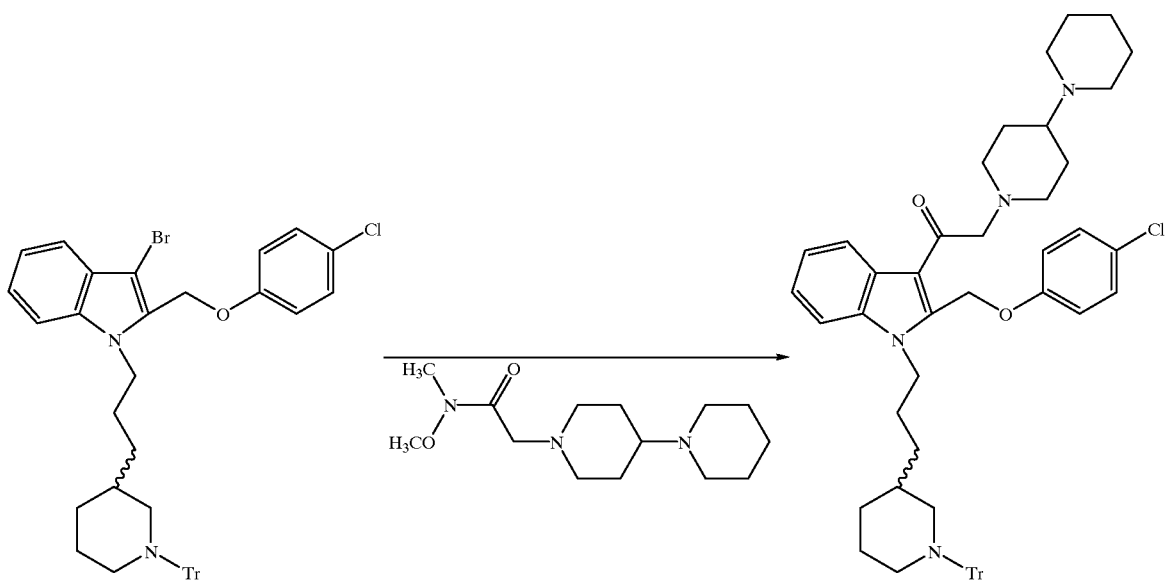

Under an argon atmosphere in a round bottom flask, 3-bromo-2-[(4-chlorophenoxy)methyl]-1-[3-(1-tritylpiperidin-3-yl)propyl]-1H-indole (0.225 g, 0.319 mmol) was dissolved in dry tetrahydrofuran. The reaction vessel was placed in a dry ice/acetone bath. To this solution was added a solution of t-butyllithium (0.64 mmol) dropwise. The resulting mixture was stirred for 35 minutes in the dry ice/acetone bath.

To this reaction mixture was added the Weinreb amide N-methyl-N-methoxy-[4-(piperidin-1-yl)piperidin-1-yl] acetamide (0.0903 g, 0.335 mmol), which had been dissolved in 2.0 ml of tetrahydrofuran and cooled in the dry ice/acetone bath. The resulting mixture was stirred for about two hours and then poured into a saturated ammonium chloride solution. The aqueous fraction was extracted thrice with methylene chloride. the organic fractions were combined and dried over sodium sulfate. The solvents were removed in vacuo. The desired title product was further purified by chromatography. Analytical data obtained was consistent with the proposed title structure.

Preparation of (RS) 2-[(4-chlorophenoxy)methyl]-1-[3-(piperidin-3-yl)propyl]-3-[[4-(piperidin-1-yl)piperidin-1-yl]acetyl]-1H-indole. (Example 70)

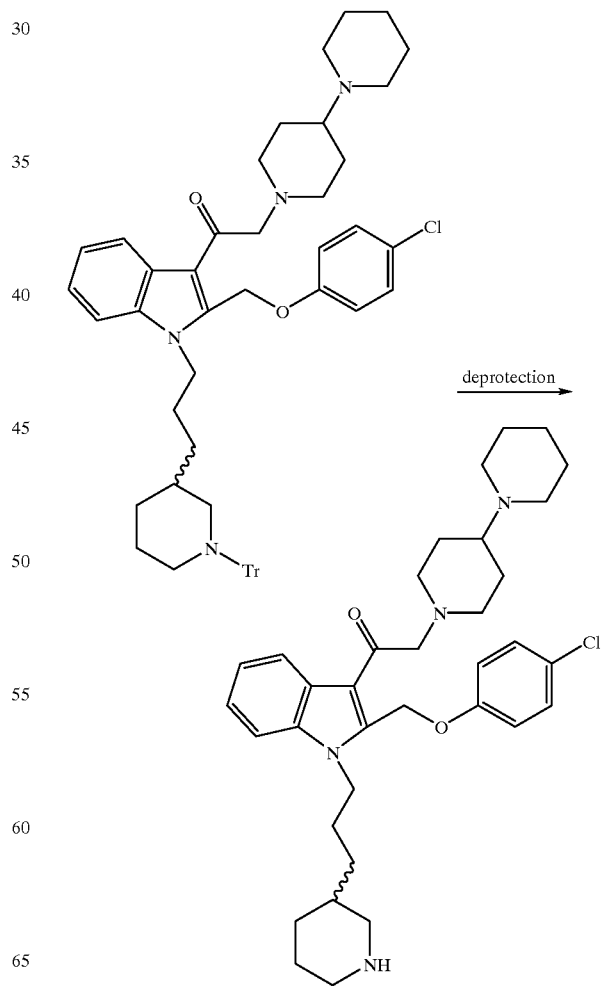

Under an argon atmosphere (RS) 2-[(4-chlorophenoxy)methyl]-1-[3-(1-tritylpiperidin-3-yl)propyl]-3-[[4-(piperidin-1-yl)piperidin-1-yl]acetyl]-1H-indole (0.0162 g, 0.0194 mmol) was dissolved in 0.2 ml methylene chloride. The reaction vessel was then placed in an ice bath and formic acid (0.073 ml, 0.194 mmol) was slowly added. The resulting mixture was stirred for about one hour over ice. The progress of the reaction was monitored by thin layer chromatography. The reaction mixture was then stirred at room temperature for two additional hours and then an additional 5.0 equivalents of formic acid were added, followed by stirring at room temperature.

The reaction mixture was partitioned between 1.0 N sodium hydroxide and methylene chloride. The aqueous fraction was extracted twice with methylene chloride. The organic fractions were combined and dried over sodium sulfate. The solvents were removed by evaporation.

NMR was consistent with the proposed title structure.

Exact Mass (M$^{+1}$) for $C_{35}H_{48}ClN_4O_2$: Theory: 591.3476. Found: 591.3476.

Method F
Preparation of 2-[(4-chlorophenoxy)methyl]-1-methyl-3-[1-hydroxy-2-(piperidin-1-yl)ethyl]-1H-indole (Example 47)

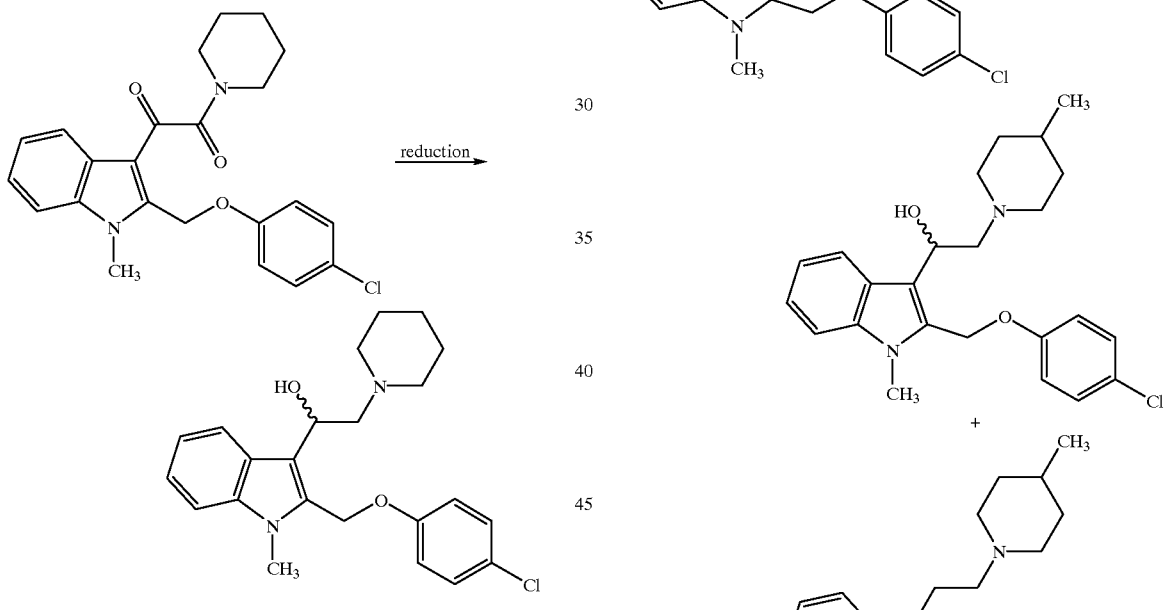

Under an argon atmosphere a round bottom flask was charged with 2-[(4-chlorophenoxy)methyl]-1-methyl-3-[1-(piperidin-1-yl)-1,2-ethanedionyl]-1H-indole (Example 100) (0.203 g, 0.493 mmol), dissolved in 2.0 ml of dry tetrahydrofuran. Lithium aluminum hydride (3.0 ml of a 1.0 M solution in tetrahydrofuran) was then added. The resulting mixture was then heated to reflux and maintained at this temperature for about four hours. The progress of the reaction was monitored by thin layer chromatography.

The reaction mixture was then cooled to room temperature and 10 ml of a 1:1 tetrahydrofuran:methanol solution was added. To this mixture was then added 5 ml of a saturated Rochelle's salt solution. The solvents were then removed in vacuo.

The residue was then partitioned between methylene chloride and a saturated Rochelle's salt solution. The organic fraction was washed with water and brine. The organic fraction was then dried with sodium sulfate and the solvents were removed in vacuo.

The desired title product was further purified by chromatography to yield 0.1112 grams (56.9%). NMR was consistent with the proposed title structure.

FDMS 398 (M+).

Analysis for $C_{23}H_{27}ClN_2O_2$: Theory: C, 69.25; H, 6.82; N, 7.02. Found: C, 69.51; H, 6.86; N, 6.81.

Method G
Preparation of 2-[(4-chlorophenoxy)methyl]-1-methyl-3-[1-hydroxy-2-(4-methylpiperidin-1-yl)ethyl]-1H-indole (Example 48) and 2-[(4-chlorophenoxy)methyl]-1-methyl-3-[2-(4-methylpiperidin-1-yl)ethyl]-1H-indole (Example 33)

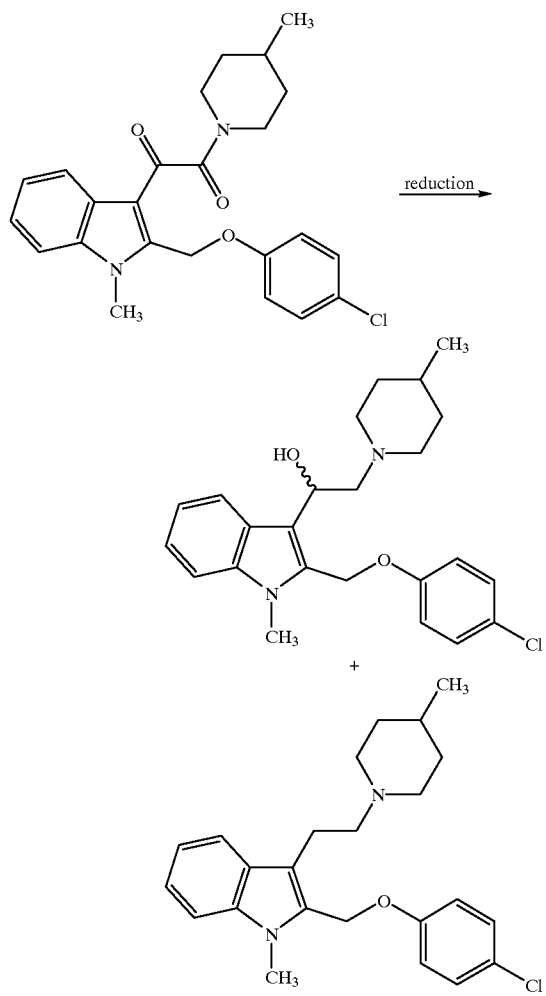

Under a nitrogen atmosphere a round bottom flask was charged with 2-[(4-chlorophenoxy)methyl]-1-methyl-3-[1-(piperidin-1-yl)-1,2-ethanedionyl]-1H-indole (Example 100) (0.305 g, 0.824 mmol). Borane-tetrahydrofuran complex (4.12 ml of a 1.0 M borane solution in THF, 4.12 mmol) was added slowly and the resulting mixture was stirred for about 30 minutes. The progress of the reaction was monitored by thin layer chromatography. The reaction mixture was stirred a total of one hour and then quenched with methanol.

To the reaction mixture was added ethanol, sodium carbonate, and cesium fluoride, and the resulting mixture was heated to reflux and maintained at this temperature overnight. The reaction mixture was partitioned between 10% sodium carbonate and methylene chloride. The aqueous fraction was extracted twice more with methylene chloride. The organic fractions were combined and dried over sodium sulfate. The solvents were removed in vacuo. The desired products were further purified by radial chromatography. 2-[(4-chlorophenoxy)methyl]-1-methyl-3-[2-(4-methylpiperidin-1-yl)ethyl]-1H-indole (Example 33)

NMR was consistent with the proposed title structure.

FDMS 396 (M+).

Analysis for $C_{24}H_{29}ClN_2O$: Theory: C, 72.62; H, 7.36; N, 7.06. Found: C, 72.40; H, 7.35; N, 7.25.

2-[(4-chlorophenoxy)methyl]-1-methyl-3-[1-hydroxy-2-(4-methylpiperidin-1-yl)ethyl]-1H-indole (Example 48)

NMR was consistent with the proposed title structure.

FDMS 412 (M+).

Analysis for $C_{24}H_{29}ClN_2O_2$: Theory: C, 69.80; H, 7.08; N, 6.78. Found: C, 70.02; H, 7.13; N, 7.00.

Preparation of 2-[(2,4-dichlorophenoxy)methyl]-1-methyl-3-[1-hydroxy-2-[N-methyl-N-(1-methylpiperidin-4-yl)amino]ethyl]-1H-indole (Example 54) and 2-[(2,4-dichlorophenoxy)methyl]-1-methyl-3-[2-[N-methyl-N-(1-methylpiperidin-4-yl)amino]ethyl]-1H-indole (Example 38)

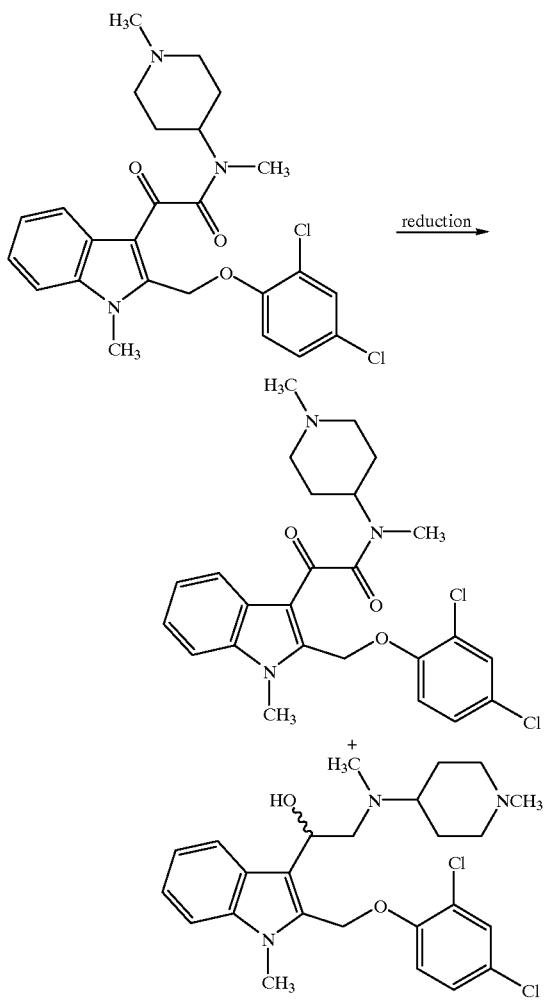

Under a nitrogen atmosphere a round bottom flask was charged with 2-[(2,4-dichlorophenoxy)methyl]-1-methyl-3-[2-[N-methyl-N-(1-methylpiperidin-4-yl)amino]-1,2-ethanedionyl]-1H-indole (0.3349 g, 0.686 mmol) and placed in an ice bath Borane-tetrahydrofuran complex (4.11 ml of a 1.0 M borane solution in THF, 4.11 mmol) was added slowly and the ice bath was removed. The progress of the reaction was monitored by thin layer chromatography. The reaction mixture was stirred for about one hour and then 0.33 ml of a 1:1 tetrahydrofuran:methanol solution was added. Sodium hydroxide (1.74 ml of a 5.0 N solution) was then added and the resulting mixture was heated to reflux and maintained at this temperature overnight.

The aqueous fraction was extracted twice more with tetrahydrofuran. The organic fractions were combined, washed twice with brine, and dried over sodium sulfate. The solvents were removed in vacuo. The desired products were further purified by radial chromatography.

2-[(2,4-dichlorophenoxy)methyl]-1-methyl-3-[2-[N-methyl-N-(1-methylpiperidin-4-yl)amino]ethyl]-1H-indole (Example 38)

NMR (CDCl$_3$) was consistent with the proposed title structure.

FDMS 459 (M+).

Analysis for $C_{25}H_{31}Cl_2N_3O$: Theory: C, 65.21; H, 6.79; N, 9.13. Found: C, 65.07; H, 6.85; N, 9.06.

2-[(2,4-dichlorophenoxy)methyl]-1-methyl-3-[1-hydroxy-2-[N-methyl-N-(1-methylpiperidin-4-yl)amino]ethyl]-1H-indole (Example 54)

NMR (CDCl$_3$) was consistent with the proposed title structure.

FDMS 475 (M+).

Analysis for $C_{25}H_{31}Cl_2N_3O_2$: Theory: C, 63.02; H, 6.55; N, 8.82. Found: C, 63.43; H, 6.88; N, 8.92.

Preparation of 2-[(4-chlorophenoxy)methyl]-1-methyl-3-[2-[(3-dimethylaminopropyl)amino]ethyl]-1H-indole (Example 30) and 2-[(4-chlorophenoxy)methyl]-1-methyl-3-[[[3-(dimethylamino)propylamino]carbonyl]methyl]-1H-indole (Example 76)

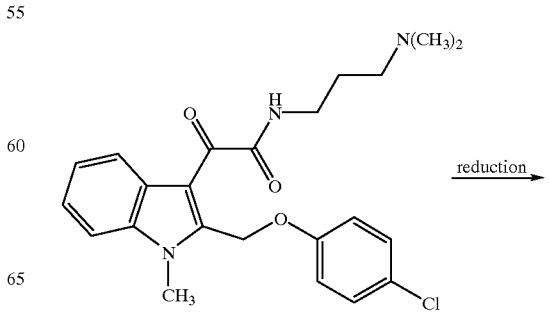

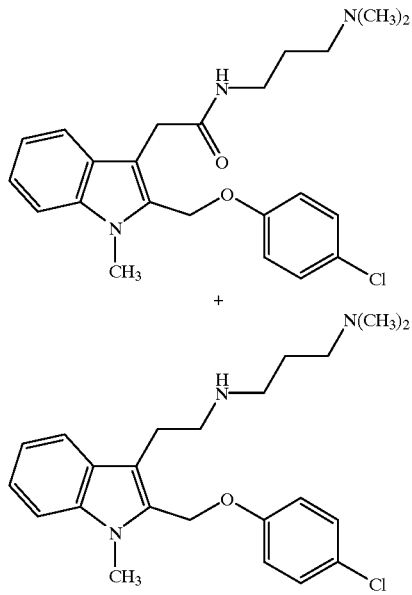

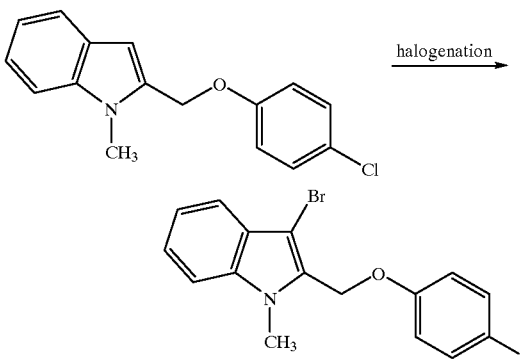

Under a nitrogen atmosphere borane-tetrahydrofuran complex (7.42 ml of a 1.0 M solution in THF, 7.42 mmol) was added to a round bottom flask containing 2-[(4-chlorophenoxy)methyl]-1-methyl-3-[2-[3-(dimethylamino)propylamino]-1,2-ethanedionyl]-1H-indole (0.529 g, 1.24 mmol). The reaction mixture was stirred at room temperature for about one hour. The progress of the reaction was monitored by thin layer chromatography. The reaction was then quenched by the addition of a 1:1 tetrafuran:methanol solution.

The solvents were removed by evaporation. The residue was taken up in a mixture of ethanol (8 ml), sodium carbonate (2.62 g, 24.72 mmol), and cesium fluoride (2.88 g, 18.94 mmol). The resulting mixture was heated to reflux and maintained at this temperature overnight.

The reaction mixture was partitioned between methylene chloride and a 10% sodium bisulfate solution. The aqueous fraction was extracted twice with methylene chloride. The organic fractions were combined, and dried over sodium sulfate. The solvents were removed in vacuo. The desired products were further purified by chromatography.

2-[(4-chlorophenoxy)methyl]-1-methyl-3-[2-[(3-dimethylaminopropyl)aminolethyl]-1H-indole (Example 30)

NMR (CDCl$_3$) was consistent with the proposed title structure.

FDMS 399 (M+).

Analysis for C$_{23}$H$_{30}$ClN$_3$O: Theory: C, 69.07; H, 7.56; N, 10.51. Found: C, 69.23; H, 7.79; N, 10.52.

2-[(4-chlorophenoxy)methyl]-1-methyl-3-[[[3-(dimethylamino)propylaminolcarbonyl]methyl)-1H-indole (Example 76)

NMR (CDCl$_3$) was consistent with the proposed title structure.

FDMS 413 (M+).

Analysis for C$_{23}$H$_{28}$ClN$_3$O$_2$: Theory: C, 66.74; H, 6.82; N, 10.15. Found: C, 66.89; H, 6.96; N, 10.11.

Method H

Preparation of 3-bromo-2-[(4-chlorophenoxy)methyl]-1-methyl-1H-indole

Under an argon atmosphere in a round bottom flask 2-[(4-chlorophenoxy)methyl]-1-methyl-1H-indole (5.0 g, 18.40 mmol) was dissolved in 46 ml of tetrahydrofuran. To this solution was added N-bromosuccinimide (3.28 g, 18.4 mmol of a freshly recrystallized lot), dissolved in 46 ml of tetrahydrofuran. The resulting mixture was stirred over an ice bath for about 3.5 hours, after which time the reaction mixture was poured into about 500 ml of water in which 5.0 grams of sodium sulfate had been dissolved.

The aqueous fraction was extracted thrice with methylene chloride. The organic fractions were combined, washed with a saturated sodium bicarbonate solution and, then washed with brine. The organic fraction was dried over sodium sulfate and the solvents were removed in vacuo.

The desired title product was recrystallized from ethyl acetate. Yield: 5.36 g (83.1%). Analytical data obtained was consistent with the proposed title structure.

Preparation of 2-[(4-chlorophenoxy)methyl]-1-methyl-3-[[2-(1-tritylpiperidin-4-yl)ethyl]carbonyl]-1H-indole

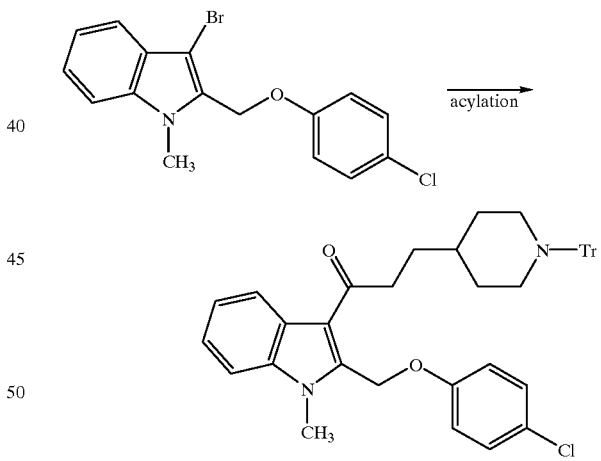

Under an argon atmosphere in a round bottom flask, 3-bromo-2-[(4-chlorophenoxy)methyl]-1-methyl-1H-indole (0.500 g, 1.426 mmol) was dissolved in 3.0 ml of tetrahydrofuran. The reaction vessel was then placed over a dry ice/acetone bath. To this solution was added a solution of t-butyllithium (1.68 ml, 2.85 mmol) and the Weinreb amide, N-methyl-N-methoxy-[2-(1-tritylpiperidin-4-yl)ethyl]acetamide (0.631 g, 1.426 mmol). The resulting mixture was stirred over dry ice/acetone for about 30 minutes, followed by thirty minutes of stirring on a methanol/dry ice bath. The progress of the reaction was monitored by thin layer chromatography.

The reaction mixture was poured into a saturated ammonium chloride solution. The aqueous fraction was extracted thrice with methylene chloride, and dried over sodium sulfate. The solvents were removed in vacuo. The desired title product was further purified by chromatography and then recrystallized from ethyl acetate. Analytical data obtained was consistent with the proposed title structure.

Preparation of 2-[(4-chlorophenoxy)methyl]-1-methyl-3-[[2-(piperidin-4-yl)ethyl]carbonyl]-1H-indole (Example 67)

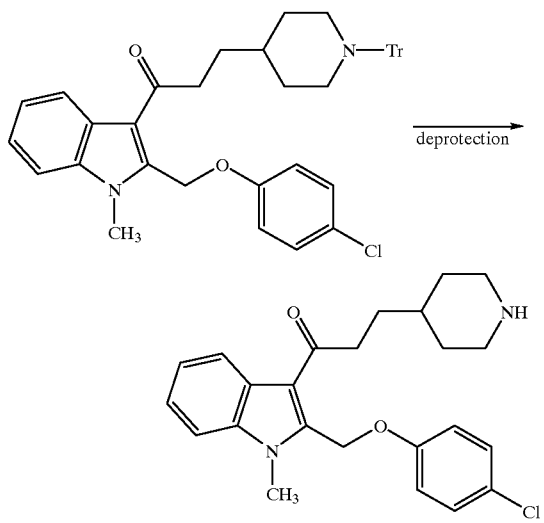

Under an argon atmosphere 2-[(4-chlorophenoxy)methyl]-1-methyl-3-[[2-(1-tritylpiperidin-4-yl)ethyl]carbonyl]-1H-indole (0.2723 g, 0.417 mmol) was dissolved in 2.1 ml of methylene chloride. To this solution formic acid (0.079 ml, 0.096 g, 2.084 mmol) was added and the resulting mixture was stirred at room temperature for about 2.5 hours. The progress of the reaction was monitored by thin layer chromatography.

The reaction mixture was partitioned between methylene chloride and 1.0 N sodium hydroxide. The aqueous fraction was extracted twice with methylene chloride. The organic fractions were combined and dried over sodium sulfate. The solvents were removed in vacuo to yield the desired title product.

NMR (CDCl$_3$) was consistent with the proposed title structure.

FDMS 411 (M$^{+1}$)

Analysis for C$_{24}$H$_{27}$ClN$_2$O$_2$: Theory: C, 70.15; H, 6.62; N, 6.82. Found: C, 69.87; H, 6.54; N, 6.79.

Method I

Preparation of 2-[(4-chlorophenoxy)methyl]-1-methyl-3-carboxy-1H-indole

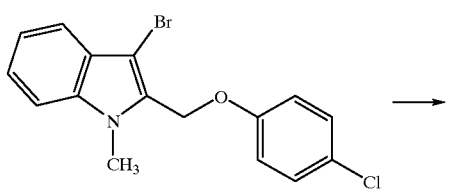

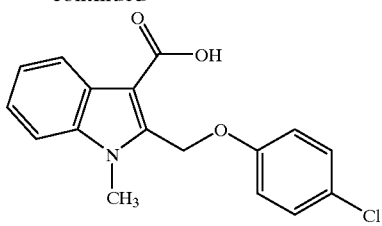

Under an argon atmosphere 2-[(4-chlorophenoxy)methyl]-1-methyl-3-carboxy-1H-indole (0.500 g, 1.426 mmol) was dissolved in 14.3 ml of dry tetrahydrofuran. The reaction vessel was then placed over a dry ice/acetone bath. To this solution t-butyllithium (1.72 ml of a 1.7 M solution in pentane, 2.92 mmol) was added dropwise. The resulting mixture was stirred for about 15 minutes over the dry ice/acetone bath. Carbon dioxide was then bubbled through the reaction mixture for about ten minutes and then the mixture was stirred for an additional ten minutes. The reaction vessel was then placed on a methanol/ice/dry ice bath and carbon dioxide was bubbled through the reaction mixture for an additional ten minutes.

The reaction mixture was allowed to warm to room temperature and was then poured into 100 ml of 1.0 N hydrochloric acid to which about 50 grams of dry ice had been added. The resulting mixture was stirred for about thirty minutes. The solids were collected by filtration. The desired product was triturated in methylene chloride.

Yield: 0.37 g (82%)

Analysis for C$_{17}$H$_{14}$ClNO$_3$: Theory: C, 64.67; H, 4.47; N, 4.44. Found: C, 64.84; H, 4.60; N, 4.54.

Preparation of 2-[(4-chlorophenoxy)methyl]-1-methyl-3-[[N,N-bis(3-dimethylaminopropyl)amino]carbonyl]-1H-indole (Example 58)

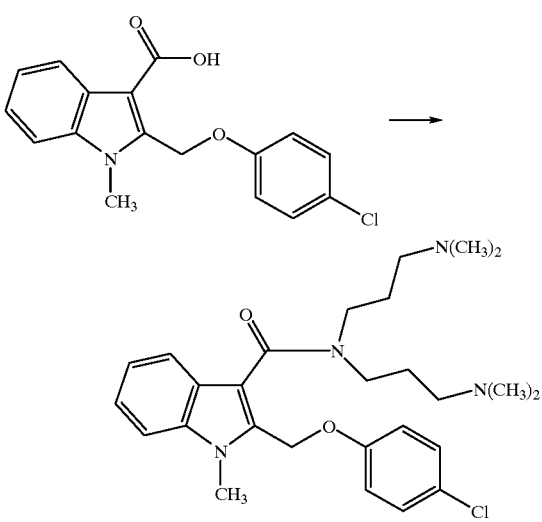

Under an argon atmosphere 2-[(4-chlorophenoxy)methyl]-1-methyl-3-carboxy-1H-indole (0.100 g, 0.317 mmol) was dissolved in 3.2 ml of N,N-dimethylformamide. To this solution were added N,N-bis(3-dimethylaminopropyl)amine (0.074 ml, 0.0623 g, 0.332 mmol), 1-(3-dimethylaminopropyl)-3-ethylcarbodiimide hydrochloride (0.091 g, 0.475 mmol), and hydroxybenztriazole (0.0642 g, 0.475 mmol). The resulting mixture was then heated for 6 hours and then stirred at room temperature overnight. The progress of the reaction was monitored by thin layer chromatography.

The reaction mixture was then partitioned between methylene chloride and water. The aqueous fraction was extracted thrice with methylene chloride. The organic fractions were combined and dried over sodium sulfate. The solvents were removed in vacuo. The desired title product was further purified by radial chromatography.

NMR (CDCl₃) was consistent with the proposed title structure.

FDMS 483 (M−1).
FABMS 485 (M+1)
Analysis for $C_{27}H_{37}ClN_4O_2$: Theory: C, 66.86; H, 7.69; N, 11.55. Found: C, 66.91; H, 7.54; N, 11.69.

Method J
Preparation of 2-[(4-chlorophenoxy)methyl]-1-methyl-3-[[2-[1-[3-(1-tritylpiperidin-3-yl)propyl]piperidin-4-yl]]ethyl]carbonyl]-1H-indole (Example 69 B)

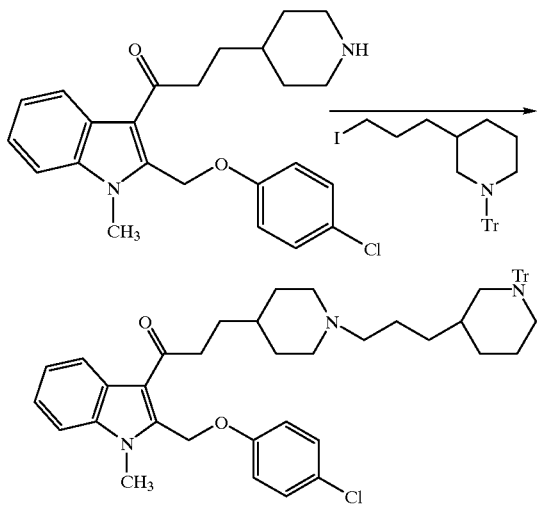

Under a nitrogen a 10 ml round bottom flask was charged with 2-[(4-chlorophenoxy)methyl]-1-methyl-3-[[(piperidin-4-yl)ethyl]carbonyl]-1H-indole (0.091 g, 0.222 mmol), 3-(1-tritylpiperidin-3-yl)propyl iodide (0.110 g, 0.2224 mmol), potassium carbonate (0.0450 g, 0.3255 mmol), and 1.5 ml of anhydrous N,N-dimethylformamide. The resulting mixture was stirred overnight and then poured into ice water. The solids were collected by filtration and rinsed with cold water. The solids were dissolved in methylene chloride and then dried over sodium sulfate. The solvents were removed in vacuo. The desired product was further purified by chromatography. Yield: 0.1166 grams (67.3%).

FDMS 779 (M+2).

Analysis for $C_{51}H_{56}ClN_3O_2$: Theory: C, 78.69; H, 7.25; N, 5.40. Found: C, 78.92; H, 7.41; N, 5.27.

Preparation of 2-[(4-chlorophenoxy)methyl]-1-methyl-3-[[2-[1-[3-(piperidin-3-yl)propyl]piperidin-4-yl]]ethyl] carbonyl-1H-indole (Example 69C)

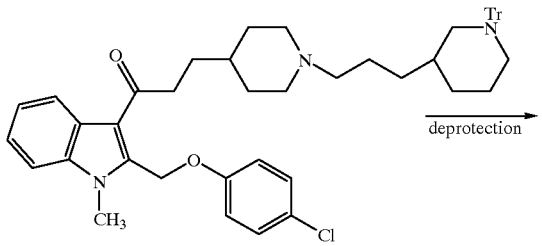

deprotection

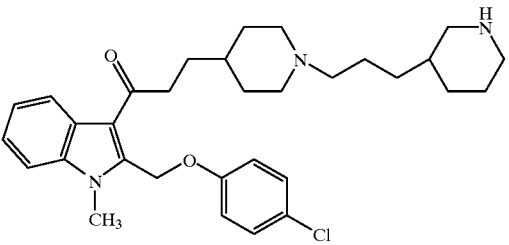

Under a nitrogen atmosphere in a round bottom flask 2-[(4-chlorophenoxy)methyl]-1-methyl-3-[[2-[1-[3-(1-tritylpiperidin-3 -yl)propyl]piperidin-4-yl]]ethyl]carbonyl]-1H-indole (0.1006 g, 0.1292 mmol) was dissolved in 0.6 ml of of methylene chloride. To this solution was added formic acid (0.0244 ml, 0.0297 g, 0.646 mmol). The resulting mixture was stirred for several hours at room temperature, protected from light. The progress of the reaction was monitored by thin layer chromatography.

The reaction mixture was partitioned between methylene chloride and 1.0 N sodium hydroxide. The aqueous fraction was extracted twice with methylene chloride. The organic fractions were combined and dried over sodium sulfate. The solvents were removed in vacuo. The desired title product was further purified by radial chromatography.

NMR (CDCl₃) was consistent with the proposed title structure.

FDMS 536 (M+1).
Analysis for $C_{32}H_{42}ClN_3O_2$: Theory: C, 71.69; H, 7.90; N, 7.84. Found: C, 71.45; H, 7.85; N, 7.61.

Method K
Preparation of 2-[(4-chlorophenoxy)methyl]-1-methyl-3-formyl-1H-indole (Example 236)

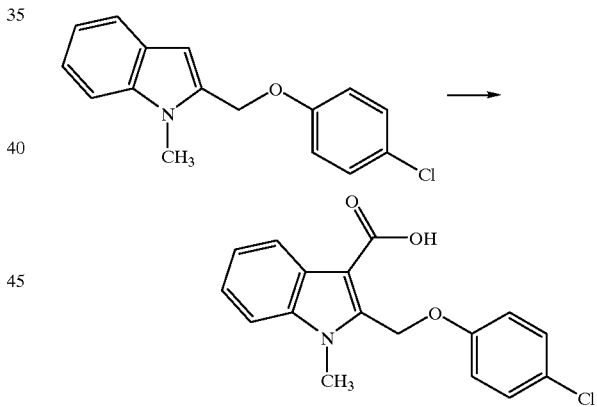

Under a nitrogen atmosphere a round bottom flask was charged with 0.63 ml of anhydrous N,N-dimethylformamide. The reaction vessel was placed in a −20° C. bath and then phosphorous oxychloride (0.187 ml, 0.310 g, 2.02 mmol) was carefully added. The resulting mixture was stirred in an ice bath for about twenty minutes and 2-[(⁴-chlorophenoxy)methyl]-1-methyl-1H-indole (0.50 g, 1.84 mmol) in 3.4 ml of N,N-dimethylformamide, was added. The resulting mixture was stirred at room temperature for about ninety minutes. The reaction mixture was then placed over an oil bath and heated to 55° C. and maintained at this temperature for about one hour. The reaction mixture was then permitted to cool to room temperature and was then poured into water. Sodium hydroxide (10 ml of a 5.0 N solution) was added and heated to reflux. The resulting mixture was cooled and the solids were then collected by filtration.

NMR (CDCl$_3$) was consistent with the proposed title structure.

FDMS 299 (M+).

Analysis for C$_{17}$H$_{14}$ClNO$_2$: Theory: C, 68.12; H, 4.71; N, 4.67. Found: C, 67.90; H, 4.66; N, 4.76.

Preparation of 2-[(2,4-dichlorophenoxy)methyl]-1-methyl-3-[1-hydroxy-2-(methoxycarbonyl)ethyl]-1H-indole (Example 55)

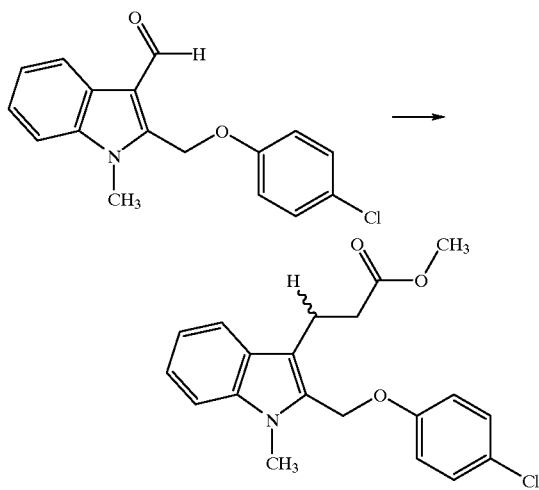

Under a nitrogen atmosphere a round bottom flask was charged with 6.7 ml of dry tetrahydrofuran. To this was added diisopropylamine (0.196 ml, 0.1417 g, 1.401 mmol) and the reaction vessel was placed in an ice bath. To this mixture was slowly added n-butyllithium (0.88 ml of a 1.6 M solution in hexanes, 1.401 mmol) and the resulting mixture was stirred in an ice bath for about 15 minutes. The reaction mixture was placed in a dry ice/acetone bath, methyl acetate was added and the reaction mixture was stirred for fifteen minutes over a dry ice/acetone bath. Starting aldehyde was added in a total of 7.0 ml of tetrahydrofuran and stirred over a dry ice/acetone bath of one hour and then placed in an ice bath for about 30 minutes. The reaction mixture was poured into an ammonium chloride solution (32 g in 100 ml of water). The aqueous fraction was extracted with methylene chloride. The organic fractions were combined and dried over sodium sulfate. The solvents were removed in vacuo. The desired title product was further by radial chromatography.

NMR (CDCl$_3$) was consistent with the proposed title structure.

IR was consistent with the desired title structure. FDMS 373 (M+).

Analysis for C$_{20}$H$_{20}$ClNO$_4$: Theory: C, 64.26; H, 5.39; N, 3.75. Found: C, 64.55; H, 5.23; N, 3.79.

Preparation of 3-{2-[(4-chlorophenoxy)methyl]-1-methyl-1H-indol-3-yl}prop-2-enoic acid

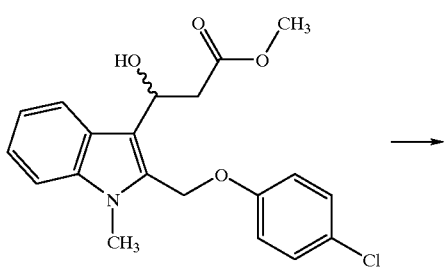

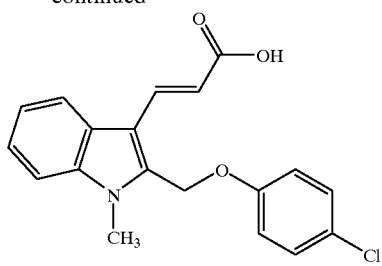

Under a nitrogen atmosphere a round bottom flask is charged with 2-[(2,4-dichlorophenoxy)methyl]-1-methyl-3-[1-hydroxy-2-(methoxycarbonyl)ethyl]-1H-indole (Example 55) (0.149 g, 0.398 mmol) and 6.11 ml of dry tetrahydrofuran. To this solution is added 1.22 ml of a 2.0 N lithium hydroxide aqueous solution and the resulting mixture was stirred at room temperature for about two hours. The solvents were removed in vacuo and the residue is partitioned between methylene chloride and water. The aqueous fraction was extracted twice with methylene chloride. The organic fractions were combined and dried over sodium sulfate. The solvents were removed in vacuo. The desired title product was triturated with diethyl ether.

Analytical data was consistent with the proposed title structure.

Preparation of 2-[(4-chlorophenoxy)methyl]-1-methyl-3-[2-[[4-(dimethylamino)piperidin-1-yl]carbonyl]ethenyl]-1H-indole (Example 44)

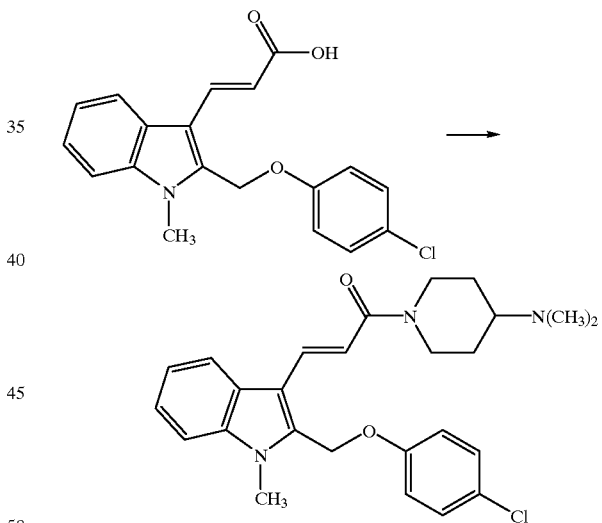

Under a nitrogen atmosphere dimethylaminopiperidine was dissolved in 3.0 ml of methylene chloride. To this solution were added 3-(2-[(4-chlorophenoxy)methyl]-1-methyl-1H-indol-3-yl]prop-2-enoic acid (0.050 g, 0.1462 mmol) and 1-(3-dimethylaminopropyl)-3-ethylcarbodiimide hydrochloride (0.0356 g, 0.278 mmol). The resulting mixture was stirred at room temperature overnight.

The reaction mixture was partitioned between a saturated sodium bicarbonate solution and methylene chloride. The aqueous fraction was basified with 1.0 N sodium hydroxide and extracted twice with methylene chloride. The organic fractions were combined, washed with 1.0 N hydrochloric acid, then with brine, and then dried over sodium sulfate. The solvents were removed in vacuo. The desired title product was further purified by radial chromatography.

NMR (CDCl$_3$) was consistent with the proposed title structure.

Exact Mass for $C_{26}H_{30}ClN_3O_2$: Theory: 452.2105. Found: 452.2099.

Method L
Preparation of 2-[(4-chlorophenoxy)methyl]-1-methyl-3-[2-(methoxycarbonyl)ethyl]-1H-indole

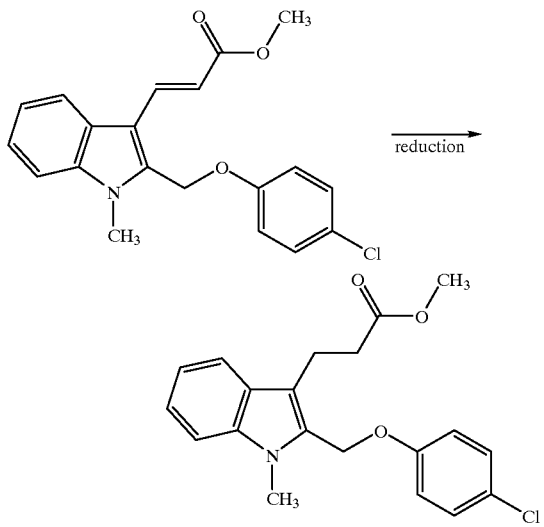

A round bottom flask was charged with 10% palladium on activated carbon (0.150 g), 20 ml of N,N-dimethylformamide and 2-[(4-chlorophenoxy)methyl]-1-methyl-3-[2-(methoxycarbonyl)ethenyl]-1H-indole (1.44 g, 4.22 mmol). The reaction vessel was then placed under a hydrogen atomsphere for two hours. The reaction mixture was then passed through a CELITE™ pad and then partitioned between water and methylene chloride. The aqueous fraction was extracted twice with methylene chloride. The organic fractions were combined, washed with water and then brine, and dried over sodium sulfate. The solvents were removed in vacuo. The desired title product was further purified by chromatography.

Preparation of 3-{2-[(4-chlorophenoxy)methyl]-1-methyl-1H-indol-3-yl}propanoic acid

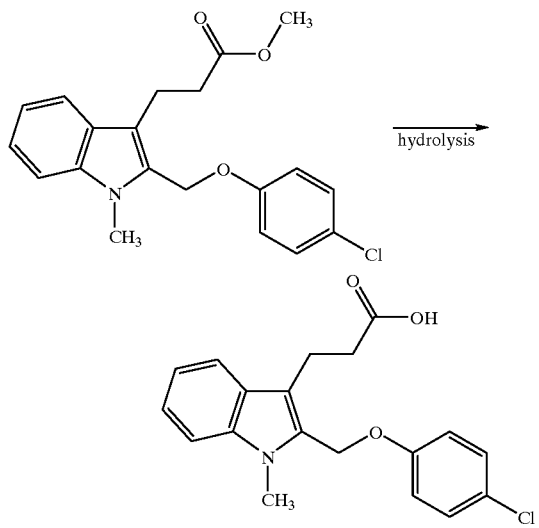

Under a nitrogen atmosphere in a round bottom flask 2-[(4-chlorophenoxy)methyl]-1-methyl-3-[2-(methoxycarbonyl)ethyl]-1H-indole (0.275 g, 0.771 mmol) was dissolved in 8 ml of dry tetrahydrofuran. To this solution was added 4.0 ml of a 2.0 N lithium hydroxide solution. The reaction mixture was stirred at room temperature overnight. The progress of the reaction was monitored by thin layer chromatography.

The solvents were removed in vacuo and the residue was partitioned between methylene chloride and 5% citric acid. The aqueous fraction was extracted twice with methylene chloride. The organic fractions were combined, washed with brine, and dried over sodium sulfate. The solvents were removed in vacuo to yield the desired title product. Yield 0.2984 grams (>99%).

Preparation of 2-[(4-chlorophenoxy)methyl]-1-methyl-3-[2-[[4-(dimethylamino)piperidin-1-yl]carbonyl]ethyl]-1H-indole (Example 43).

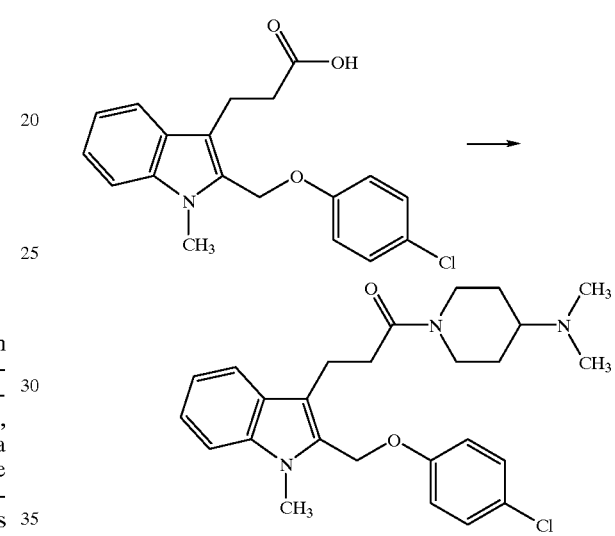

Under a nitrogen atmosphere 3-{2-[(4-chlorophenoxy)methyl]-1-methyl-1H-indol-3-yl}propanoic acid (0.286 g, 0.832 mmol) was dissolved in 6 ml of dry tetrahydrofuran. To this solution 1,1'-carbonyldiimidazole (0.141 g, 0.874 mmol) was added and the resulting mixture was stirred at room temperature for about two hours. The progress of the reaction was monitored by thin layer chromatography. The reaction mixture was then heated to 65° C. and maintained at this temperature for about 35 minutes. To this reaction mixture dimethylaminopiperidine (0.112 g, 0.874 mmol), dissolved in about 3.6 ml of tetrahydrofuran. This mixture was stirred at room temperature overnight.

The reaction mixture was then heated to 60° C. and maintained at this temperature for about 30 minutes. The solvents were removed in vacuo and the residue was partitioned between methylene chloride and water. The aqueous fraction was extracted with methylene chloride again. The organic fractions were combine, washed twice with water, then with brine, and then dried over sodium sulfate. The solvents were removed in vacuo. The desired title product was further purified by chromatography.

NMR (CDCl$_3$) was consistent with the proposed title structure.

IR was consistent with the desired title structure.

FDMS 453 (M+)

Analysis for $C_{26}H_{32}ClN_3O_2$: Theory: C, 68.78; H, 7.10; N, 9.26. Found: C, 68.74; H, 7.04; N, 9.38.

Method M
Preparation of 2-[(4-chlorophenoxy)methyl]-1-methyl-3-[3-[4-(N,N-dimethylamino)piperidin-1-yl]propyl]-1H-indole (Example 41).

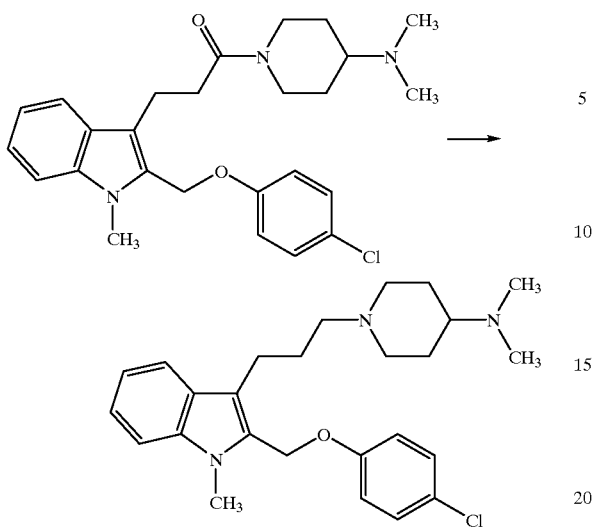

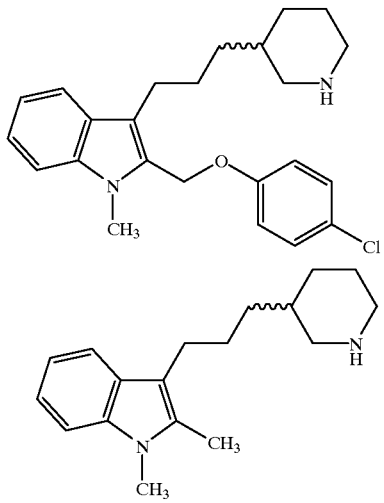

Under a nitrogen atmosphere around bottom flask is charged with 2-[(4-chlorophenoxy)methyl]-1-methyl-3-[2-[[4-(dimethylamino)piperidin-1-yl]carbonyl]ethyl]-1H-indole (0.194 g, 0.428 mmol). The flask was then placed in an ice bath and boranetetrahydrofuran complex (1.71 ml of a 1.0 M solution in THF, 1.71 mmol) was added. The reaction mixture was then removed from the ice bath and stirred at room temperature for about 90 minutes. The progress of the reaction was monitored by thin layer chromatography. A 1:1 tetrahydrofuran:methanol solution (0.20 ml total) was added, followed by the addition of 2.0 ml of 5.0 N sodium hydroxide.

The resulting mixture was refluxed overnight. The solvents were removed by evaporation and the residue was partitioned between water and methylene chloride. The organic fraction was washed with brine and dried over sodium sulfate. The solvents were removed in vacuo.

NMR (CDCl$_3$) was consistent with the proposed title structure.

FABMS 440 (M+1)

IR was consistent with the desired title structure.

Analysis for $C_{26}H_{34}ClN_3O$: Theory: C, 70.97; H, 7.79; N, 9.55. Found: C, 70.73; H, 7.65; N, 9.44.

Method N

Preparation of 2-[(4-chlorophenoxy)methyl]-1-methyl-3-[3-(piperidin-3-yl)propyl]-1H-indole (Example 42) and 1,2-dimethyl-3-[3-(piperidin-3-yl)propyl]-1H-indole (Example 237)

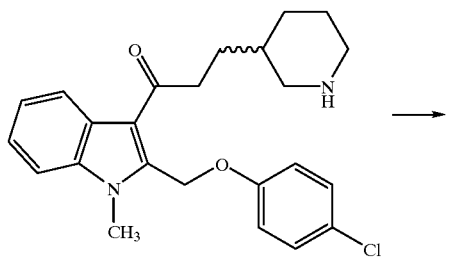

Under a nitrogen atmosphere 2-[(4-chlorophenoxy)methyl]-1-methyl-3-[3-(piperidin-3-yl)propanoyl]-1H-indole (0.0737 g, 0.1793 mmol) was dissolved in 1.8 ml of dioxane and borane-dimethylsulfide complex (0.108 ml, 1.07 mmol) was added. The resulting mixture was stirred overnight at room temperature. The progress of the reaction was monitored by thin layer chromatography. A 1:1 tetrahydrofuran:water mixture (0.3 ml) was then added as well as 1.5 ml of 5.0 N sodium hydroxide. The reaction mixture was heated to 85° C. and maintained at this temperature overnight, and then briefly raised to 225° C.

The solvents were removed in vacuo and the residue was partitioned between methylene chloride and 1.0 N sodium hydroxide. The organic fraction was washed with brine and dried over sodium sulfate. The solvents were removed in vacuo. The desired title products were further purified by chromatography. Analytical data obtained was consistent with the proposed title structure (See Examples 42 and 237, infra).

Preparation of 2,4-dichloro-1-ethynylbenzene

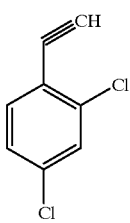

In a 500 ml round bottom flask 2,4-dichloroiodobenzene (3 ml, 22.1 mmol), triethylamine (6.16 ml, 44.2 mmol), and (trimethylsilyl)acetylene (3.12 ml, 22.1 mmol) were admixed in acetonitrile (6.16 ml, 44.2 mmol) under a nitrogen atmosphere. The mixture was bubbled with nitrogen gas for 10 minutes. To this mixture bis(triphenylphosphine)palladium(II) chloride (775 mg, 1.10 mmol) and cuprous iodide (105 mg, 0.552 mmol) were added and the resulting mixture was refluxed for four hours. The progress of the reaction was monitored by thin layer chromatography. The reaction mixture was cooled to ambient temperature and evaporated to leave an oily product.

The residue was dissolved in methanol (50 ml) and tetrahydrofuran (150 ml), and solid potassium carbonate (30.54 g, 0.221 mol) was added. The resulting mixture was stirred at ambient temperature for 19 hours. The progress of this reaction was monitored by thin layer chromatography.

The reaction mixture was partitioned between 1M potassium carbonate and ethyl acetate. The aqueous fraction was back-extracted thrice with ethyl acetate. The organic fractions were combined and dried over sodium sulfate. The solvents were removed in vacuo to yield 2.6 grams of the desired title product.

NMR was consistent with the proposed title structure.

Preparation of 2,4-dichloro-1-(2-bromoethen-1-yl)benzene

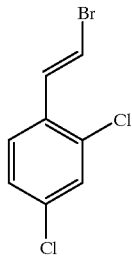

In a 100 ml round bottom flask borane tetrahydrofuran complex (1M in tetrahydrofuran, 4.8 ml, 4.82 mmol) was cooled to 0° C. under a nitrogen atmosphere. To this complex 2-methylprop-2-ene (1.02 ml, 9.65 mmol) was added dropwise and the mixture was slowly warmed to ambient temperature and stirred at ambient temperature for one hour. The reaction mixture was diluted with hexamethylphosphoramide (5 ml), tetrahydrofuran (5 ml), cupric bromide (2.15 g, 9.65 mmol), and cupric acetate (3.85 g, 19.3 mmol), followed by the addition of water (86 μl, 4.82 mol). The resulting mixture was stirred at ambient temperature for six hours. The progress of the reaction was monitored by thin layer chromatography. The reaction mixture was diluted with brine and extracted thrice with diethyl ether. The organic fractions were combined and dried over sodium sulfate. The solvents were removed in vacuo. The residue was further purified by liquid chromatography. Yield: 426 mg. NMR was consistent with the proposed title structure.

Preparation of 4-hydroxy-N-isopropylbutylamine

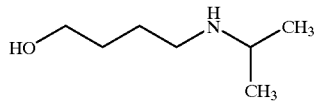

To a solution of 4-aminobutanol (2.0 mg, 22.4 mmol) in 110 ml of dichloroethane were added acetone (3.3 ml, 44.8 mmol), acetic acid (5 eq.), and sodium acetoxyborohydride (11.9 g, 56.09 mmol). The cloudy mixture was stirred at ambient temperature for about 18 hours. The reaction was quenched with saturated sodium bicarbonate. Sodium hydroxide (1 M) was added to adjust the pH to about 10. The aqueous layer was extracted with a mixture of isopropyl alcohol and methylene chloride (1:3). The organic fractions were combined and dried over sodium sulfate, filtered, and concentrated. The desired intermediate was further purified by bulb to bulb distillation to yield 1.4 grams as a dear oil. If desired, additional yield may be recovered by extracting the aqueous fraction with 3:1 toluene:butanol.

Preparation of N-(t-butoxycarbonyl)-4-hydroxy-N-isopropylbutylamine

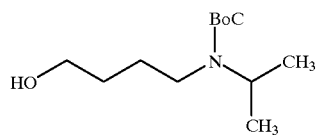

A solution of 4-hydroxy-N-isopropylbutylamine (3.0 g, 22.8 mmol) in dioxane:water:1N sodium hydroxide (91 ml:28 ml:28 ml) was treated with di(t-butoxycarbonyl)ether (4.98 g, 22.8 mmol). The cloudy reaction mixture was stirred for five hours. The reaction mixture was extracted with methylene chloride. The organic phase was dried, filtered, and concentrated. The desired title product was further purified by high performance liquid chromatography affording 2.6 grams (49%) of a colorless oil.

Preparation of 2-fluoro-5-chlorobenzaldehyde

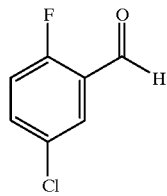

Lithium diisopropylamide was prepared by admixing diisopropylamine (5.79 ml, 41.3 mmol) in 5 ml of tetrahydrofuran. The resulting mixture was cooled to −78° C. and treated with n-butyllithium in such a manner that the temperature did not raise above 64° C. After stirring the suspension for 45 minutes, the remainder of the tetrahydrofuran was added (70 ml), followed by the dropwise addition of 4-chlorophenyl fluoride (4.0 ml, 37.6 mmol). After 45 minutes N,N-dimethylformamide was added, also in a dropwise fashion. The resulting reaction mixture was stirred an additional ten minutes prior to quenching with acetic acid (6 ml), followed by water (100 ml). The cold mixture was transferred to a separatory funnel and extracted twice with methylene chloride. The organic fractions were combined, dried over sodium sulfate, and filtered. The solvents were removed by vacuum. The residue was further purified by high performance liquid chromatography, affording 4.00 grams of a white solid. mp 41–43° C.

Preparation of 2-fluoro-5-methylbenzyl alcohol

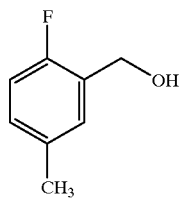

A solution of 2-fluoro-5-methylbenzaldeyde (1.80 g, 12.3 mmol) in 3:1 tetrahydrofuran:methanol (82 ml total) at 0° C. was treated with sodium borohydride (0.93 g, 24.6 mmol). The reaction was slowly warmed to ambient temperature and stirred for about three hours. The reaction was quenched with water, transferred to a separatory funnel, and extracted with methylene chloride. The organic fraction was dried over sodium sulfate, filtered, and concentrated in vacuo. The residue was further purified by high performance liquid chromatography to yield 1.3 grams (76%) of a clear oil.

Preparation of 2-fluoro-5-chlorobenzyl alcohol

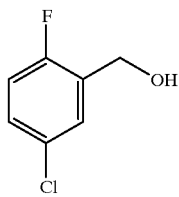

The title intermediate was prepared essentially as was 2-fluoro-5-methylbenzyl alcohol, supra, except that an equimolar amount of 2-fluoro-5-chlorobenzaldehyde was employed instead of the 2-fluoro-5-methylbenzaldehyde employed therein.

Yield: 2.16 grams (86%) as a clear oil.

Preparation of 2-fluoro-5-chlorobenzyl bromide

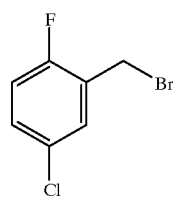

A solution of 2-fluoro-5-chlorobenzyl alcohol (1.28 g, 7.97 mmol) in diethyl ether (26 ml) was treated with triphenylphosphine (2.72 g, 10.36 mmol), followed by carbon tetrabromide (3.44 g, 10.36 mmol). The resultant suspension was stirred for 3.5 hours, then filtered, washing with diethyl ether. The filtrate was concentrated, then passed through a plug of silica to remove triphenylphosphate. The residue was then purified by liquid chromatography affording 2.0 grams of a clear oil.

Preparation of 4-(2-fluorobenzyloxy)-N-(t-butoxycarbonyl)-N-(isopropyl)butylamine

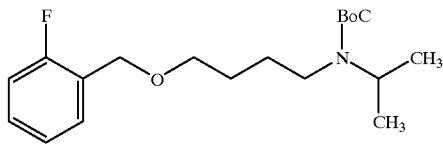

A solution of N-(t-butoxycarbonyl)-4-hydroxy-N-isopropylbutylamine (539 mg, 2.33 mmol) in tetrahydrofuran (11 ml) at −40° C. was treated with potassium t-butoxide (1 M in tetrahydrofuran, 2.54 ml, 2.54 mmol). After 40 minutes, the suspension was cooled to −78° C. and treated with a solution of 2-fluorobenzyl bromide (400 mg, 2.12 mmol) in tetrahydrofuran (4 ml). The reaciton was slowly warmed to room temperature and stirred for about five hours. The reaction was diluted with methylene chloride and washed with 1 M potassium carbonate and brine. The organic fraction was dried over sodium sulfate, filtered, and concentrated. The crude oil was purified by liquid chromatography to yield 555 mg (77%) of the title intermediate as a clear oil.

Preparation of 4-(2-fluoro-5-chlorobenzyloxy)-N-(t-butoxycarbonyl)-N-(isopropyl)butylamine

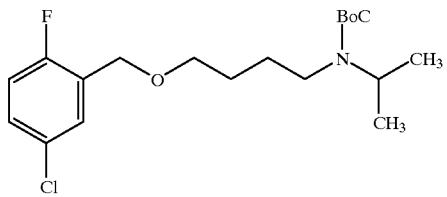

The title intermediate was prepared essentially as described supra for 4-(2-fluorobenzyloxy)-N-(t-butoxycarbonyl)-N-(isopropyl)butylamine, except that an equimolar amount of 2-fluoro-5-chlorobenzyl bromide was employed instead of the 2-fluorobenzyl bromide employed therein.

Yield 237 mg (35%).

Preparation of 4-(2-fluorobenzyloxy)-N-(isopropyl)butylamine

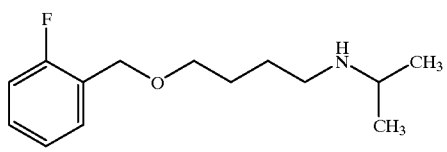

The desired intermediate was prepared from the deprotection of 4-(2-fluorobenzyloxy)-N-(t-butoxycarbonyl)-N-(isopropyl)butylamine using standard techniques. The 4-(2-fluorobenzyloxy)-N-(t-butoxycarbonyl)-N-(isopropyl)butylamine was admixed with a 4:1 mixture of methylene chloride and trifluoroacetic acid. The progress of the reaction was monitored by thin layer chromatography.

Preparation of 4-(5-chloro-2-fluorobenzyloxy)-N-(isopropyl)butylamine

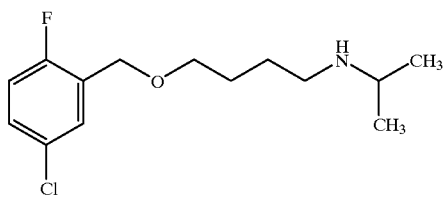

The desired intermediate was prepared essentially as described for the 4-(2-fluorobenzyloxy)-N-(isopropyl)butylamine above, except that an equimolar amount of 4-(5-chloro-2-fluorobenzyloxy)-N-(t-butoxycarbonyl)-N-(isopropyl)butylamine was employed in place of the 4-(2-fluorobenzyloxy)-N-(t-butoxycarbonyl)-N-(isopropyl)butylamine employed therein.

Yield: 138 mg (98%).

Preparation of 3-(5-bromo-2-fluorobenzyloxy)-1-[1-(t-butoxycarbonyl)piperidin-2-yl]propane

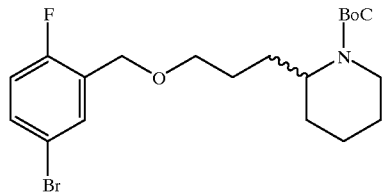

3-[1-(t-Butoxycarbonyl)piperidin-2-yl]propanol (800 mg, 3.29 mmol) was taken up in tetrahydrofuran (17 ml), cooled to −40° C., and treated with potassium t-butoxide (1 M in tetrahydrofuran, 3.62 ml, 3.62 mmol). The resulting mixture was stirred at −40° C. for about 35 minutes, then cooled to −78° C. To this mixture was then added 5-bromo-2-fluorobenzyl bromide (881 mg, 3.29 mmol) as a solution in tetrahydrofuran (5 ml). The resultant yellow reaction mixture was slowly warmed to 0° C. and stirred for about four hours. The reaction mixture was diluted with methylene chloride and washed with 1 M potassium carbonate and brine. The organic fraction was dried over sodium sulfate, filtered, and concentrated in vacuo. The crude oil was purified by high performance liquid chromatography, yielding 707 mg (50%) of the title intermediate as a clear oil.

Analysis for $C_{20}H_{29}BrFNO_3$: Theory: C, 55.82; H, 6.79; N, 3.25. Found: C, 55.54; H, 6.88; N, 3.34.

Preparation of 3-(5-bromo-2-fluorobenzyloxy)-1-(piperidin-2-yl)propane

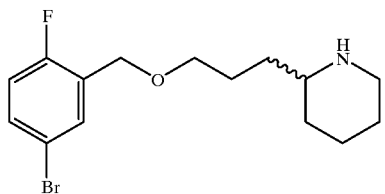

3-(5-Bromo-2-fluorobenzyloxy)-1-[1-(t-butoxycarbonyl)piperidin-2-yl]propane (590 mg, 1.37 mmol) was dissolved in methylene chloride (11 ml), cooled to 0° C., and treated with 3 ml of trifluoroacetic acid. The reaction mixture was stirred at 0° C. for 20 minutes, then warmed to ambient temperature, and stirred an additional ten minutes. The reaction mixture was diluted with methylene chloride and quenched with saturated sodium bicarbonate. The pH was adjusted to about 10 with 1 N sodium hydroxide. The aqueous fraction was back-extracted with methylene chloride. The organic fractions were combined, dried over sodium sulfate, filtered, and concentrated.

Yield: 420 mg (93%).

The resulting intermediate was used without further purification.

Preparation of 2-fluoro-5-bromobenzyl bromide

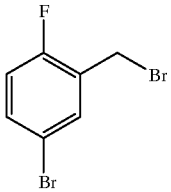

A solution of 2-fluoro-5-bromobenzyl alcohol (20.0 g, 97.5 mmol) in diethyl ether (325 ml) was treated with triphenylphosphine (33.3 g, 127 mmol), followed by carbon tetrabromide (42.1 g, 127 mmol). The mixture was stirred at ambient temperature for about four hours. The precipitate was removed and washed with diethyl ether. The desired title product was further purified by bulb to bulb distillation [150° C., 5 mm Hg (house vacuum)].

Yield: 24.36 grams (93%) of a white, low melting solid.

Preparation of 4-(2-fluoro-5-bromobenzyloxy)-but-2-ynyl alcohol)

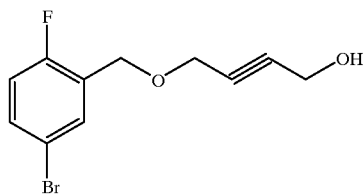

A solution of 2-fluoro-5-bromobenzyl bromide (15.6 g, 58.1 mmol) in N,N-dimethylformamide (290 ml) was added over 35 minutes to a mixture of 1,4-dihydroxy-2-butyne (20.0 g, 232 mmol) and sodium hydride (15.6 g of a 60% solution, 58.1 mmol). The resulting mixture was stirred for 4.5 hours at ambient temperature. The reaction was quenched with 100 ml of a 1:1:1 brine:water:1 M potassium carbonate solution. The aqueous fraction was extracted with methylene chloride (3×300 ml). The desired title product was further purified by chromatography to yield 8.90 grams (56%).

Preparation of 4-(2-fluoro-5-bromobenzyloxy)butanol

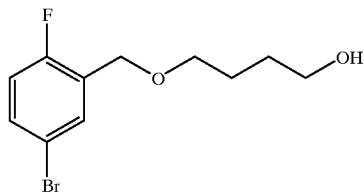

A solution of 1,4-dihydroxybutane (4.0 ml, 45.13 mmol) in N,N-dimethylformamide (62 ml) was treated with sodium hydride (1.98 g of a 60% solution, 49.63 mmol), and stirred for about 50 minutes at ambient temperature. The resulting mixture was cooled to 0° C. and treated with 2-fluoro-5-bromobenzyl bromide (3.0 g, 11.28 mmol). The reaction mixture was then stirred for four hours at ambient temperature. The reaction was quenched with water. The aqueous fraction was extracted with methylene chloride. The organic fractions were combined, and dried over sodium sulfate. The solvents were removed in vacuo. The desired title intermediate was further purified by high performance liquid chromatography.

Yield: 1.8 grams (58%) as a clear oil. $\lambda_{max}$=271 nm.

Analysis for $C_{11}H_{14}BrFO_2$: Theory: C, 47.67; H, 5.09; Br, 28.83. Found: C, 47.37; H, 5.15; Br, 28.55.

Preparation of N-(t-butoxycarbonyl)-4-(2-fluoro-5-bromobenzyloxy)-3,3-dimethylbutylamine

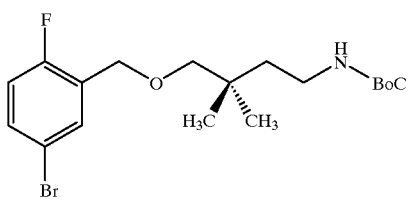

A stirred solution of 4-(t-butoxycarbonylamino)-2,2-dimethylbutan-1-ol (1.5 g, 6.90 mmol) in tetrahydrofuran (49 ml) at −45° C. was treated with potassium t-butoxide (1 M in tetrahydrofuran, 7.59 ml, 7.59 mmol). The anion was stirred for 30 minutes at −45° C., then cooled to −78° C. and treated with a tetrahydrofuran solution of 2-fluoro-5-bromobenzyl bromide (1.85 g, 6.90 mmol). The resulting yellow mixture was slowly warmed to ambient temperature and stirred for about 18 hours. The cloudy reaction mixture was diluted wtih methylene chloride and washed with 1 M potassium carbonate. The organic fraction was dried over sodium sulfate, filtered, and the solvents were removed in vacuo. The residue was further purified by preparative high performance liquid chromatography to yield 1.45 grams (52%) of the title intermediate as a colorless oil.

Preparation of N-(t-butoxycarbonyl)-4-(2-fluoro-5-bromobenzyloxy)-2,2-dimethylbutylamine

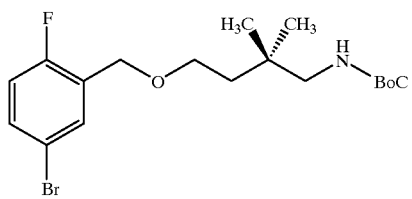

A stirred solution of 4-(t-butoxycarbonylamino)-3,3-dimethylbutan-1-ol (1.0 g, 4.60 mmol) in tetrahydrofuran (33 ml) at −45° C. was treated with potassium t-butoxide (1 M in tetrahydrofuran, 5.06 ml, 5.06 mmol). The anion was stirred for 30 minutes at −45° C., then cooled to −78° C. and treated with a tetrahydrofuran solution of 2-fluoro-5-bromobenzyl bromide (1.23 g, 4.60 mmol). The resulting yellow mixture was slowly warmed to 0° C. and stirred for about four hours. The cloudy reaction mixture was diluted wtih methylene chloride (100 ml) and washed with 1 M potassium carbonate. The organic fraction was dried over sodium sulfate, filtered, and the solvents were removed in vacuo. The residue was further purified by preparative high performance liquid chromatography to yield 1.38 grams (74%) of the title intermediate as a colorless oil.

Preparation of 2-[(t-butoxycarbonyl)amino]-5-(2-fluoro-5-bromobenzyloxy)-2-methylpentane

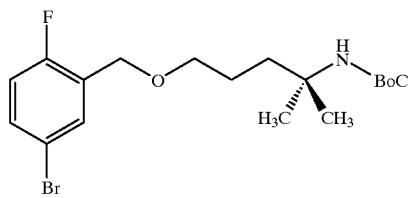

A stirred solution of 4-(t-butoxycarbonylamino)-4,4-dimethylbutan-1-ol (1.11 g, 5.11 mmol) in tetrahydrofuran (49 ml) at −45° C. was treated with potassium t-butoxide (1 M in tetrahydrofuran, 5.62 ml, 5.62 mmol). The anion was stirred for 30 minutes at −45° C., then cooled to −78° C. and treated with a tetrahydrofuran solution of 2-fluoro-5-bromobenzyl bromide (1.23 g, 4.60 mmol). The resulting yellow mixture was slowly warmed to 0° C. and stirred for about four hours. The reaction mixture was diluted wtih methylene chloride (100 ml) and washed with 1 M potassium carbonate (20 ml). The organic fraction was dried over sodium sulfate, filtered, and the solvents were removed in vacuo. The residue was further purified by preparative high performance liquid chromatography to yield 1.53 grams (74%) of the title intermediate as a colorless oil.

Preparation of trans-4-(t-butoxycarbonylamino)cyclohexanol

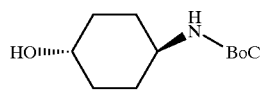

To a solution of trans-4-aminocyclohexanol (5.00 g, 33.0 mmol) in dioxane (132 ml), water (41 ml) and 1 N sodium hydroxide (41 ml) was added t-butoxycarbonyl anhydride (14.4 g, 66 mmol). The cloudy solution was stirred overnight. The reaction mixture was acidified to pH 3.0 with solid sodium bisulfate. The resulting mixture was thrice extracted with methylene chloride. The organic fractions were combined, dried over sodium sulfate, and concentrated in vacuo. The desired title intermediate was recrystallized from hexanes/ethyl acetate to yield 6.5 grams (92%).

MS 216.24

Analysis for $C_{11}H_{21}NO_3$: Theory: C, 61.37; H, 9.83; N, 6.50. Found: C, 61.16; H, 9.54; N, 6.39.

Preparation of trans-{4-(butoxycarbonylamino)-1-[2-fluoro-5-bromobenzyloxy]}cyclohexane

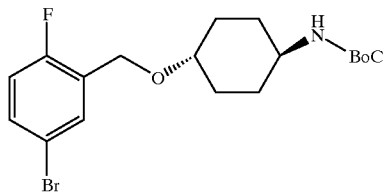

A solution of trans-{4-(butoxycarbonylamino)}cyclohexanol (550 mg, 2.32 mmol) in dry tetrahydrofuran (16.6 ml) was cooled to −40° C. and treated with potassium t-butoxide (1 M in tetrahydrofuran, 2.55 ml, 2.55 mmol). The cloudy yellow reaction mixture was stirred for about thirty minutes, cooled to −78° C., and treated with 2-fluoro-5-bromobenzyl bromide (622 mg, 2.32 mmol). The resulting yellow mixture was gradually warmed to 0° C. and stirred for about two hours. The reaction mixture was diluted with methylene chloride, and washed with saturated sodium bicarbonate. The organic fraction was dried over sodium sulfate, and the solvents were removed in vacuo. The residue was purified further by high performance liquid chromatography to yield 558 mg (62%) of the desired title intermediate as a white solid.

Analysis for $C_{18}H_{25}BrFNO_3$: Theory: C, 53.74; H, 6.26; N, 3.48. Found: C, 53.87; H, 6.16; N, 3.11.

Preparation of 3,3-dimethyl-1-(t-butoxycarbonyl)pyrrolidin-2-one

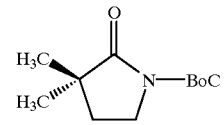

The desired intermediate was prepared essentially as described in F. Scheinmann and A. V. Stachulski, *Journal of Chemical Research*, 1993:414 (1993). A solution of 3-methyl-1-(t-butoxycarbonyl)pyrrolidin-2-one (8.63 g, 43.3 mmol) in tetrahydrofuran (48 ml) was cooled to −78° C. The solution was treated with $NaN[Si(CH_3)_2]_2$ (56.3 ml, 56.3 mmol) and stirred for about 50 minutes prior to quenching with methyl iodide (8.1 ml, 130 mmol). The reaction mixture was slowly warmed to ambient temperature, and stirring was continued for about one hour. The reaction mixture was diluted with ethyl acetate (100 ml) and washed with phosphate buffer, pH 7.0 (40 ml), water (40 ml) and brine (40 ml). The organic fraction was dried over sodium sulfate, filtered, and concentrated in vacuo. The precipitate was collected, and further purified by flash chromatography to yield 8.49 grams (92%) of the title intermediate as a semi-solid.

NMR was consistent with the title structure.

Preparation of 4-(t-butoxycarbonylamino)-2,2-dimethylbutanol

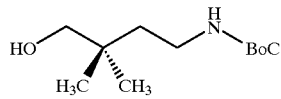

A solution of 3,3-dimethyl-1-(t-butoxycarbonyl) pyrrolidin-2-one (3.35 g, 15.7 mmol) in absolute ethanol under a nitrogen atmosphere was treated with sodium borohydride (1.79 g, 47.1 mmol). The resulting mixture was stirred at ambient tempeature for about 24 hours. The progress of the reaction was monitored by thin layer chromatography. The reaction mixture was concentrated in vacuo. The residue was dissolved in ethyl acetate and washed with sodium bicarbonate. The aqueous fraction was back extracted twice with ethyl acetate. The organic phase was dried over sodium sulfate and concentrated in vacuo. The residue was further purified by chromatography to yield 3.17 grams (93%) of the title intermediate as a clear oil. mp 75.5–76.5° C.

Preparation of 4-(2-fluoro-5-bromobenzyloxy)-1-methoxybut-2-yne

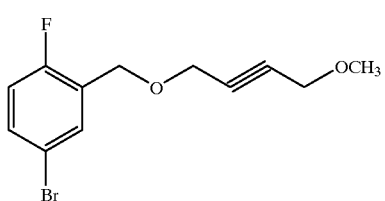

A solution of 4-(2-fluoro-5-bromobenzyloxy)-but-2-ynyl alcohol (1.07 g, 3.92 mmol) in tetrahydrofuran (26 ml) was cooled to −40° C. and then treated with potassium t-butoxide (4.31 ml of a 1 M solution in tetrahydrofuran, 4.31 mmol). The resulting dark orange solution was stirred for thirty minutes, cooled to −78° C. and treated with methyl iodide (0.49 ml, 7.84 mmol). The reaction was warmed to 0° C. and stirred for 1.5 hours. The reaction mixture was then partitioned between methylene chloride and saturated sodium bicarbonate. The organic fraction was dried over sodium sulfate, and the solvents were removed in vacuo. The desired title intermediate was further purified by high performance liquid chromatography to yield 790 mg (70%) as a clear oil.

Preparation of 4-(2-fluoro-5-bromobenzyloxy)-but-2-ynyl bromide

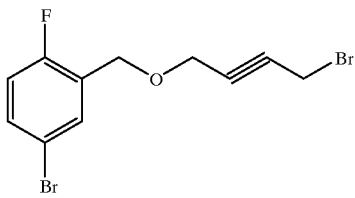

A solution of 4-(2-fluoro-5-bromobenzyloxy)-but-2-ynyl alcohol (8.9 g, 32.6 mmol) in diethyl ether (109 ml) was treated with triphenylphosphine (11.1 g, 42.4 mmol) and carbon tetrabromide (14.1 g, 42.4 mmol). The cloudy solution was stirred at ambient temperature for about 14 hours. The precipitate was removed by filtration and the filtrate was concentrated. The desired title intermediate was purified from the filtrate by flash chromatography. Yield 9.83 grams (90%) as a clear oil.

Elemental analysis and NMR were consistent with the proposed title structure.

Preparation of N-methyl-4-(2-fluoro-5-bromobenzyloxy) but-2-ynyl amine

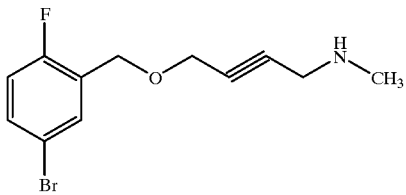

A solution of aminomethane (89 ml of a 2 M solution in tetrahydrofuran, 178 mmol) was added to a solution of 4-(2-fluoro-5-bromobenzyloxy)but-2-ynyl bromide (6.0 g, 17.8 mmol) in tetrahydrofuran (89 ml). The cloudy reaction mixture was stirred for about fifteen minutes, at which time no starting material remained, as determined by thin layer chromatography. The solvents were removed in vacuo. The residue was taken up in methylene chloride and washed with 1 M potassium carbonate. The aqueous phase was back-extracted thrice with methylene chloride. The organic fractions were combined, and dried over sodium sulfate. The solvents were removed in vacuo. The resulting oil was further purified by flash chromatography, affording 4.24 grams (83%) of the title intermediate as a yellow oil.

NMR was consistent with the title structure.

Preparation of N-benzyl-4-(2-fluoro-5-bromobenzyloxy) but-2-ynyl amine

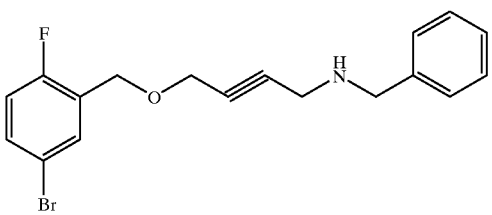

A solution of benzylamine (0.98 ml, 8.93 mmol) was added to a solution of 4-(2-fluoro-5-bromobenzyloxy)but-2-ynyl bromide (300 mg, 0.893 mmol) in tetrahydrofuran (4.5 ml). The cloudy reaction mixture was stirred for about twenty hours, at which time no starting material remained, as determined by thin layer chromatography. The solvents were removed in vacuo. The residue was taken up in methylene chloride and washed with 1 M potassium carbonate. The aqueous phase was back extracted with methylene chloride (2×15 ml). The organic fractions were combined, and dried over sodium sulfate. The solvents were removed in vacuo. The resulting oil was further purified by flash chromatography, affording 200 mg (62%) of the title intermediate.

Preparation of N-isopropyl-4-(2-fluoro-5-bromobenzyloxy) but-2-ynyl amine

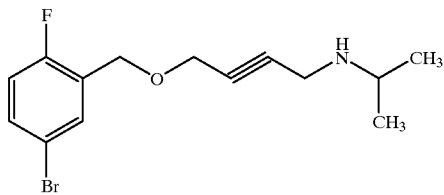

A solution of isopropylamine (0.25 ml, 2.9 mmol) was added to a solution of 4-(2-fluoro-5-bromobenzyloxy)but-2-ynyl bromide (97 mg, 0.29 mmol) in tetrahydrofuran (1.4 ml). The cloudy reaction mixture was stirred for about twenty hours, at which time no starting material remained, as determined by thin layer chromatography. The solvents were removed in vacuo. The residue was taken up in methylene chloride and washed with 1 M potassium carbonate. The aqueous phase was back extracted with methylene chloride (2×5 ml). The organic fractions were combined, and dried over sodium sulfate. The solvents were removed in vacuo. The resulting oil was further purified by flash chromatography, affording 78 milligrams (86%) of the title intermediate.

NMR was consistent with the title structure.

Preparation of N-cyclopropyl-4-(2-fluoro-5-bromobenzyloxy)but-2-ynyl amine

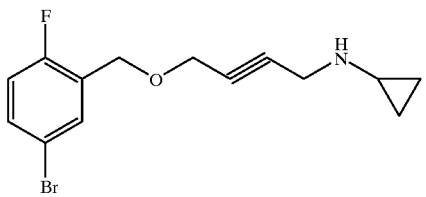

A solution of cyclopropylamine (1.10 ml, 15.8 mmol) was added to a solution of 4-(2-fluoro-5-bromobenzyloxy)but-2-ynyl bromide (530 mg, 1.58 mmol) in tetrahydrofuran (8 ml). The cloudy reaction mixture was stirred for about thrity minutes. The reaction mixture was then cooled to 0° C., and held at this temperature for about four hours, at which time no starting material remained, as determined by thin layer chromatography. The reaction mixture was diluted with methylene chloride (50 ml) and washed with 1 M potassium carbonate (10 ml). The organic fraction was dried over sodium sulfate. The solvents were removed in vacuo. The resulting oil was further purified by preparative high performance liquid chromatography, affording 362 mg (73%) of the title intermediate as a clear oil.

Preparation of 4,5-dihydro-2-(2-fluoro-5-bromophenyl)oxazole

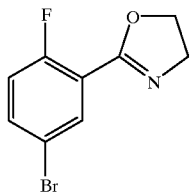

A solution of N-(2-hydroxyethyl)-5-bromo-2-fluorobenzamide (956 mg, 3.65 mmol) in methylene chloride was treated with thionyl chloride (0.35 ml, 4.75 mmol). The resulting mixture was stirred at ambient temperature as the progress of the reaction was monitored by thin layer chromatography. After one hour of stirring, no starting material was visible. The reaction mixture was diluted with methylene chloride, and the reaction was quenched by the addition of water and 1 N sodium hydroxide. The organic fraction was dried over sodium sulfate, and concentrated to a white solid. The solid was dissolved in 80% aqueous acetonitrile (25 ml) and an excess of potassium carbonate was added. The resulting mixture was stirred for about 72 hours at ambient temperature, heated to reflux for thirty hours, and worked up as before. The desired title product was then further purified by liquid chromatography, yielding 260 mg as a yellow oil.

Preparation of N,N-dimethyl-2-fluoro-5-bromobenzamide

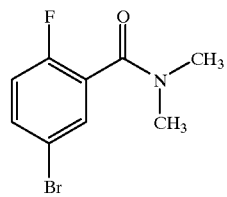

A suspension of 2-fluoro-5-bromobenzoic acid (680 mg, 3.10 mmol) in methylene chloride (20 ml) was treated with oxalyl chloride (0.35 ml, 4.04 mmol), followed by four drops of N,N-dimethylformamide. The resulting clear solution was stirred for about three hours. The solvents were removed in vacuo and the residue was redissolved in methylene chloride and treated with dimethylamine (4.6 ml, 9.3 mmol). Stirring was continued for 18 hours. The reaction mixture was diluted with methylene chloride, and washed with saturated sodium bicarbonate and brine. The organic fraciton was dried over sodium sulfate, and the solvents were removed in vacuo. The desired title product was further purified by liquid chromatography.

Yield: 632 mg (83%) as a clear oil.

Preparation of 1-methoxy-4-(2-fluoro-5-bromobenzyloxy)butane

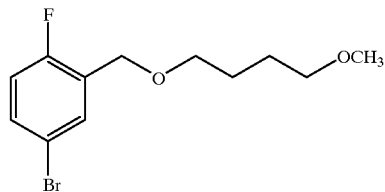

A solution of 4-(2-fluoro-5-bromobenzyloxy)butanol (897 mg, 3.24 mmol) in tetrahydrofuran (22 ml) was cooled to −40° C. and then treated with potassium t-butoxide (3.56 ml of a 1 M solution in tetrahydrofuran, 3.56 mmol). The resulting orange solution was stirred for thirty minutes, cooled to −78° C. and treated with methyl iodide (0.40 ml, 6.48 mmol). The reaction was warmed to 0° C. and stirred for 1.5 hours. The reaction mixture was then partitioned between methylene chloride and saturated sodium bicarbonate. The organic fraction was dried over sodium sulfate, and the solvents were removed in vacuo. The desired title intermediate was further purified by high performance liquid chromatography to yield 687 mg (73%) as a clear oil.

FDMS 291.99

Preparation of 4-(2-fluoro-5-bromobenzyloxy)butyl bromide

A solution of 4-(2-fluoro-5-bromobenzyloxy)butanol (7.03 g, 26.3 mmol) in diethyl ether (88 ml) was treated with triphenylphosphine (8.97 g, 34.2 mmol) and carbon tetrabromide (11.3 g, 34.2 mmol). The cloudy solution was stirred at ambient temperature for about 30 hours. The precipitate was removed by filtration and the filtrate was concentrated. The desired title intermediate was purified from the filtrate by bulb to bulb distillation.

Yield 8.68 grams (86%) as a clear oil.

Elemental analysis and NMR were consistent with the proposed title structure.

Preparation of N,N-dimethyl-4-(2-fluoro-5-bromobenzyloxy)butylamine

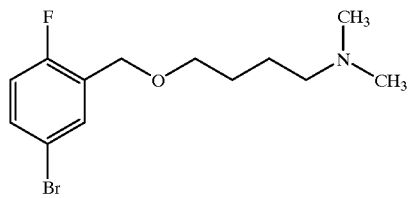

Diethylamine (17.6 ml, 35.3 mmol) was added to a solution of 4-(2-fluoro-5-bromobenzyloxy)butyl bromide (1.2 g, 3.53 mmol) in tetrahydrofuran (18 ml). The resulting mixture was stirred at ambient temperature for about 18 hours. The reaction mixture was diluted with methylene chloride and washed with saturated sodium bicarbonate. The aqueous fraction was back extracted with methylene chloride. The organic fractions were combined and dried over sodium sulfate. The solvents were removed in vacuo. The desired title intermediate was further purified by high performance liquid chromatography.

Yield: 842 mg (79%) as a pale yellow oil.

Preparation of N-ethyl-4-(2-fluoro-5-bromobenzyloxy)butylamine

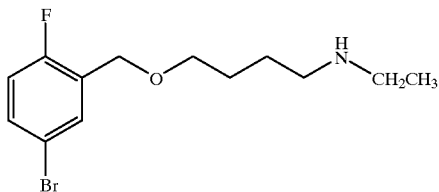

A solution of 4-(2-fluoro-5-bromobenzyloxy)butyl bromide (500 mg, 1.47 mmol) in acetone (7.3 ml) was treated with sodium iodide (242 mg, 1.6 mmol). The resulting mixture was stirred at ambient temperature. After 1.5 hours, the sodium bromide was removed by filtration, and the filtrate concentrated. The residue was treated with a tetrahydrofuran solution of ethylamine (11 ml, 22.0 mmol). The resulting mixture was stirred for about 17 hours at ambient temperature. The progress of the reaction was monitored by thin layer chromatography. The reaction mixture was diluted with methylene chloride, and washed with 25 mM phosphate buffer and brine. The organic fraction was dried over sodium sulfate and the solvents were removed in vacuo. The desired title intermediate was further purified by radial chromatography.

Yield: 337 mg (75%) as a yellow oil.

NMR was consistent with the proposed title structure.

Preparation of N-isopropyl-4-(2-fluoro-5-bromobenzyloxy)butylamine

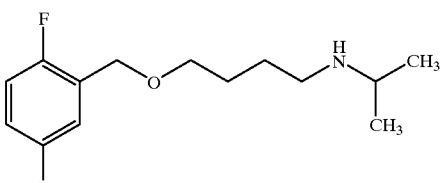

A solution of 4-(2-fluoro-5-bromobenzyloxy)butyl bromide (1.2 g, 3.53 mmol) in tetrahydrofuran (18 ml) was treated with sodium iodide (484 mg, 3.2 mmol). The resulting mixture was stirred at ambient temperature. After 1.5 hours, the sodium bromide was removed by filtration, and the filtrate concentrated. The residue was treated with a tetrahydrofuran solution of isopropylamine (3.01 ml, 35.3 mmol). The progress of the reaction was monitored by thin layer chromatography. The resulting mixture was stirred for about 18 hours at ambient temperature, after which time an additional 10 equivalents of isopropylamine was added to drive the reaction. The reaction mixture was diluted with methylene chloride, and washed with 25 mM phosphate buffer and brine. The organic fraction was dried over sodium sulfate and the solvents were removed in vacuo. The desired title intermediate was further purified by liquid chromatography.

Yield: 517 mg (46%) as a yellow oil.

Analysis for $C_{14}H_{21}BrFNO$: Theory: C, 52.84; H, 6.65; N, 4.40. Found: C, 52.87; H, 6.77; N, 4.64.

Preparation of N-(t-butyl)-4-(2-fluoro-5-bromobenzyloxy)butylamine

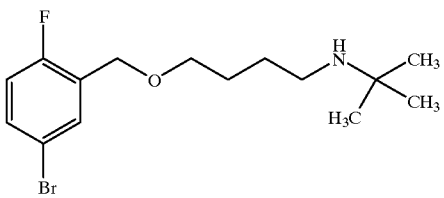

A solution of 4-(2-fluoro-5-bromobenzyloxy)butyl bromide (400 mg, 1.18 mmol) in tetrahydrofuran (6 ml) was treated with sodium iodide (242 mg, 1.6 mmol). The resulting mixture was stirred at ambient temperature. After 1.5 hours, the sodium bromide was removed by filtration, and the filtrate concentrated. The residue was treated with a tetrahydrofuran solution of tert-butylamine (1.24 ml, 11.8 mmol). The progress of the reaction was monitored by thin layer chromatography. The resulting mixture was stirred for about 19 hours at ambient temperature. The reaction mixture was diluted with methylene chloride, and washed with saturated sodium bicarbonate. The organic fraction was dried over sodium sulfate and the solvents were removed in vacuo. The desired title intermediate was further purified by radial chromatography.

Yield: 261 mg (66%) as a yellow oil.

NMR was consistent with the proposed title structure.

Preparation of 1-(piperidin-1-yl)-4-(2-fluoro-5-bromobenzyloxy)butane

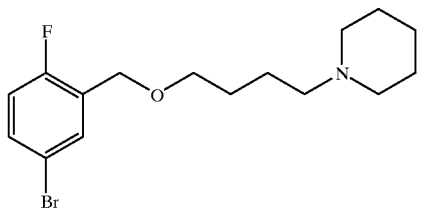

A solution of 4-(2-fluoro-5-bromobenzyloxy)butyl bromide (520 mg, 1.53 mmol) in tetrahydrofuran (8 ml) was treated with piperidine (1.5 ml, 15.3 mmol). The resulting reaction mixture was stirred for about 24 hours. The reaction mixture was then diluted with methylene chloride and washed with saturated sodium bicarbonate. The organic fraction was dried over sodium sulfate and the solvents were removed in vacuo. The desired title intermediate was further purified by radial chromatography.

Yield: 399 mg (76%).

Preparation of 1-(morpholin-4-yl)-4-(2-fluoro-5-bromobenzyloxy)butane

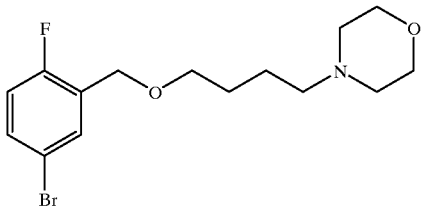

A solution of 4-(2-fluoro-5-bromobenzyloxy)butyl bromide (550 mg, 1.62 mmol) in tetrahydrofuran (8 ml) was treated with morpholine (1.4 ml, 16.2 mmol). The resulting reaction mixture was stirred for about 72 hours. The reaction mixture was then diluted with methylene chloride and washed with saturated sodium bicarbonate. The organic fraction was dried over sodium sulfate and the solvents were removed in vacuo. The desired title intermediate was further purified by radial chromatography.

Yield: 446 mg (79%) as a clear oil.

Preparation of 1-[2-fluoro-5-bromobenzyloxy]-3-[1-(t-butoxycarbonyl)piperidin-3-yl]propane

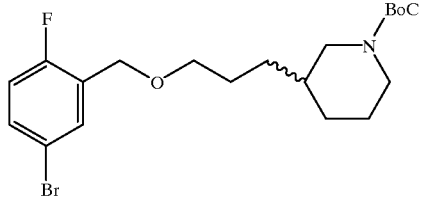

An amount of 3-[1-(t-butoxycarbonyl)piperidin-3-yl] propyl bromide (180 mg, 0.588 mmol) was dissolved in N,N-dimethylformamide (1.5 ml) in a 10 ml flask under a nitrogen atmosphere. Sodium iodide (176 mg, 1.18 mmol) was added at ambient temperature, and the resulting mixture was stirred for ten minutes. The reaction mixture was treated with 2-fluoro-5-bromobenzyl alcohol (121 mg, 0.588 mmol), delivered as a solution in 0.5 ml of N,N-dimethylformamide. To this mixture was then added sodium hydride (60%, 35 mg, 0.882 mmol) and the resulting mixture was stirred at ambient temperature for three hours. The progress of the reaction was monitored by thin layer chromatography. The reaction mixture was partitioned between 1 M potassium carbonate and methylene chloride. The aqueous fraction was back extracted with methylene chloride. The organic fractions were combined, and dried over sodium sulfate. The solvents were removed in vacuo. The desired title product was further purified by liquid chromatography.

Yield: 0.115 g.

MS (M+) 430.

Analysis for $C_{20}H_{29}BrFNO_3$: Theory: C, 55.82; H, 6.79; N, 3.26. Found: C, 55.70; H, 6.59; N, 3.04.

Preparation of 1-[2-fluoro-5-bromobenzyloxy]-3-(piperidin-3-yl)propane

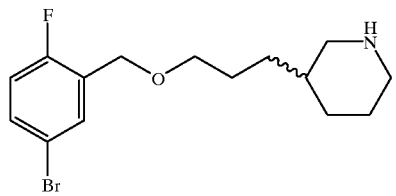

In a 100 ml round bottom flask, 1-[2-fluoro-5-bromobenzyloxy]-3-[1-(t-butoxycarbonyl)piperidin-3-yl] propane (0.395 g) was dissolved in methylene chloride (4.2 ml). The solution was cooled to 0° C. and trifluoroacetic acid (0.8 ml) was slowly added dropwise. The resulting mixture was stirred at 0° C. for thirty minutes, followed by stirring at ambient temperature for thirty minutes. The progress of the reaction was monitored by thin layer chromatography. The reaction mixture was partitioned between 1 M potassium carbonate and methylene chloride. The aqueous fraction was back extracted with methylene chloride. The organic fractions were combined, and dried over sodium sulfate. The solvents were removed in vacuo. The desired title intermediate was further purified by liquid chromatography.

Yield: 210 mg as a clear yellow oil.

Analysis for $C_{16}H_{21}BrFNO$: Theory: C, 54.54; H, 6.41; N, 4.24. Found: C, 54.32; H, 6.41 N, 4.34.

Preparation of 2-fluoro-5-bromobenzyl bromide

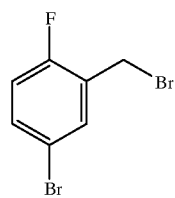

In a 250 ml round bottom flask, under a nitrogen atmosphere, 2-fluoro-5-bromobenzyl alcohol (5.85 g, 28.5 mmol) was dissolved in diethy ether (125 ml). To this solution triphenylphosphine (9.73 g, 37.1 mmol) and carbon tetrabromide (12.30 g, 37.1 mmol) were added. The resulting mixture was stirred at ambient temperature for about three hours. The progress of the reaction was monitored by thin layer chromatography. The mixture was then stirred at ambient temperature for about 19 additional hours. The reaction mixture was filtered and washed with cold diethyl ether. The filtrate was evaporated, yielding a light yellow oil. The oil was further purified by chromatography on a silica gel with hexanes. The desired fractions were purified by evaporation to yield 5.8 grams of the desired title intermediate. The material crystallized upon standing.

Analysis for $C_7H_6Br_2F$: Theory: C, 31.39; H, 1.88. Found: C, 31.18; H, 1.91.

Preparation of N,N-dimethyl-3-(2-fluoro-5-bromobenzyloxy)propylamine

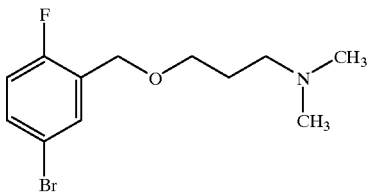

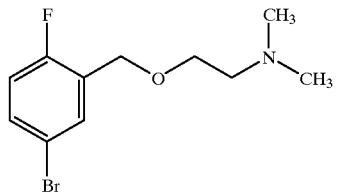

In a 10 ml round bottom flask, under a nitrogen atmosphere, 2-fluoro-5-bromobenzyl bromide (245 mg, 0.914 mmol) was dissolved in N,N-dimethylformamide (2.0 ml). To this solution sodium iodide (137 mg, 0.914 mmol) was added and the resulting mixture was stirred at ambient temperature for thirty minutes. In another 10 ml flask, under a nitrogen atmosphere, 3-(N,N-dimethylamino)propanol (0.162 ml, 1.37 mmol) was dissolved in N,N-dimethylformamide (2.0 ml).

Sodium hydride (60%, 62 mg, 1.55 mmol) was then added to the propanol solution. After thirty minutes of stirring, the benzyl bromide, sodium iodide solution was added to the propanol mixture. Some frothing occurred, but quickly dissipated. The resulting mixture was stirred for two hours at ambient temperature. The progress of the reaction was monitored by thin layer chromatography.

The reaction mixture was partitioned between 1 M potassium carbonate and methylene chloride. The aqueous fraction was back extracted with methylene chloride. The organic fractions were combined and dried over sodium sulfate. The solvents were removed in vacuo. The desired intermediate was further purified by liquid chromatography to yield 182 mg (69%) of the title intermediate.

NMR, IR, and MS were consistent with the proposed title structure.

Analysis for $C_{12}H_{17}BrFNO$: Theory: C, 49.67; H, 5.91; N, 4.83. Found: C, 49.46; H, 5.92; N, 4.99.

Preparation of 2-(2-fluoro-5-bromobenzyloxy)-1-methoxyethane

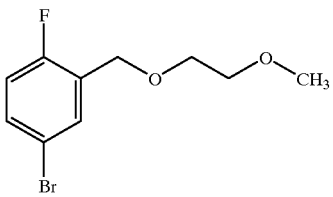

In a 10 ml flask, under a nitrogen atmosphere, 2-methoxyethanol (0.125 ml, 1.60 mmol) was dissolved in N,N-dimethylformamide (2 ml). Sodium hydride (60%, 72 mg, 1.81 mmol) was added and the mixture was stirred at ambient temperature for about thirty minutes. To this reaction mixture was added 2-fluoro-5-bromobenzyl bromide (285 mg, 1.06 mmol) as a solution in N,N-dimethylformamide (2 ml). The resulting mixture was stirred at ambient temperature for two hours. The progress of the reaction was monitored by thin layer chromatography. The reaction mixture was partitioned between 1 M potassium carbonate and diethyl ether. The aqueous fraction was back extracted with diethyl ether. The organic fractions were combined, washed with brine (7x) and dried over sodium sulfate. The solvents were removed in vacuo. The title intermediate was used without further purification.

Yield: 165 mg

Preparation of 2-(2-fluoro-5-bromobenzyloxy)-(N,N-dimethyl)ethylamine

In a 50 ml flask, under a nitrogen atmosphere, 2-(N,N-dimethylamino)ethanol (1.319 g, 4.92 mmol) was dissolved in N,N-dimethylformamide (16 ml). Sodium hydride (60%, 335 mg, 8.37 mmol) was added and the mixture was stirred at ambient temperature for about twenty minutes. To this reaction mixture was added 2-fluoro-5-bromobenzyl bromide (1.319 g, 4.92 mmol) as a solution in N,N-dimethylformamide (3 ml). The resulting mixture was stirred at ambient temperature for two hours. The progress of the reaction was monitored by thin layer chromatography. The reaction mixture was partitioned between 1 M potassium carbonate and diethyl ether. The aqueous fraction was back extracted with diethyl ether. The organic fractions were combined, washed with brine (7x) and dried over sodium sulfate. The solvents were removed in vacuo. The title intermediate was used without further purification.

Yield: 1.023 g (75%)

Preparation of N,N-dimethyl-2-fluoro-5-bromobenzylamine

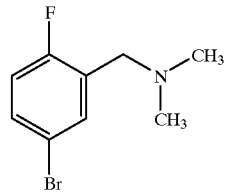

In a 50 ml flask, under a nitrogen atmosphere, 2-fluoro-5-bromobenzyl bromide (1.264 g, 4.72 mmol) was dissolved in methanol (10 ml). Dimethylamine (8 M in $H_2O$, 1.77 ml, 14.2 mmol) was added as a solution in methanol (5 ml), and the resulting mixture was stirred at ambient temperature for about two hours. The progress of the reaction was monitored by thin layer chromatography. The methanol was removed by evaporation. The residue was partitioned between 1 M potassium carbonate and diethyl ether. The aqueous fraction was back extracted with diethyl ether. The organic fractions were combined, washed with brine (7x) and dried over sodium sulfate. The solvents were removed in vacuo. The title intermediate was used without further purification.

Yield: 0.987 g

Preparation of 2-(2-fluoro-5-bromobenzyloxy)-(N-methyl)ethylamine

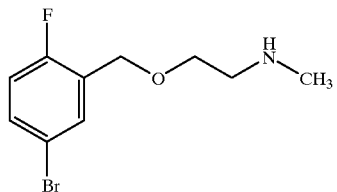

In a 50 ml flask, under a nitrogen atmosphere, 2-(2-fluoro-5-bromobenzyloxy)-(N,N-dimethyl)ethylamine (317 mg, 1.15 mmol) was dissolved in dichloroethane (3.5 ml). This solution was cooled to 0° C. and ACE•Cl (0.50 ml, 4.59 mmol) was added. The resulting mixture was warmed to ambient temperature, then heated to reflux and maintained at this temperature for about three hours. The progress of the reaction was monitored by thin layer chromatography. Methanol was added to the reaction mixture and the resulting mixture was stirred at ambient temperature for about three days. The mixture was then heated to reflux for thirty minutes. The solvents were removed in vacuo. The residue was taken up in methanol, heated to reflux for thirty minutes, and the solvents were then removed in vacuo. The title intermediate was used without further purification.

Yield: 210 mg

Preparation of N-methyl-2-fluoro-5-bromobenzyl amine

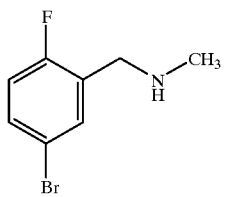

In a 25 ml flask, under a nitrogen atmosphere, 2-fluoro-5-bromobenzylbromide (755 mg, 2.82 mmol) was dissolved in methanol (10 ml). Methylamine (0.99 ml, 14.1 mmol) was added and the mixture was stirred at ambient temperature for about three hours. The progress of the reaction was monitored by thin layer chromatography. The solvents were removed by evaporation. The residue was partitioned between 1 M potassium carbonate and methylene chloride. The aqueous fraction was back extracted with methylene chloride. The organic fractions were combined and dried over sodium sulfate. The solvents were removed in vacuo. The title intermediate was further purified by liquid chromatography.

Yield: 0.435 g

NMR was consistent with the proposed title structure.

Preparation of N-methyl-3-[2-fluoro-5-bromobenzyloxy]propylamine

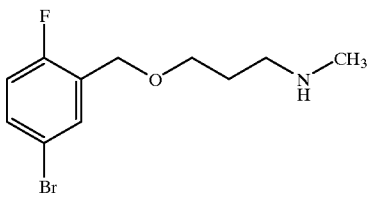

In a 15 m flask, under a nitrogen atmosphere, N,N-dimethyl-3-[2-fluoro-5-bromobenzyloxy]propylamine (351 mg, 1.21 mmol) was dissolved in dichloroethane (3.5 ml). To this solution ACE•Cl (0.78 ml, 7.26 mmol) was added and the resulting mixture was heated to reflux and maintained at this temperature for 18 hours. The reaction mixture was cooled to ambient temperature, and the solvents were removed in vacuo. The residue was taken up in methanol and refluxed for 1.5 hours. The methanol solution was then partitioned between 1 M potassium carbonate and methylene chloride. The aqueous fraction was back extracted with methylene chloride. The organic fractions were combined and dried over sodium sulfate. The solvents were removed in vacuo. The title intermediate was further purified by liquid chromatography.

NMR was consistent with the proposed title structure.

Preparation

Preparation of N,N-dimethyl-4-[2-fluoro-5-bromobenzyloxy]butylamine

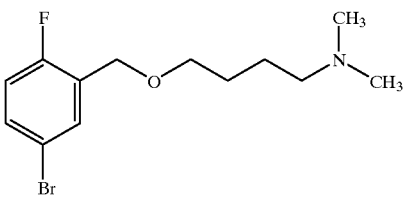

In a 50 ml flask, under a nitrogen atmosphere, 2-fluoro-5-bromobenzyl bromide (967 mg, 3.61 mmol) was dissolved in N,N-dimethylformamide (3.5 ml). To this solution sodium hydride (60%, 245 mg, 6.14 mmol) was added and the resulting mixture was stirred for ten minutes. To the reaction mixture 4-(N,N-dimethylamino)butanol (633 mg, 5.41 mmol) was added and the rsulting mixture was stirred for six hours. The progress of the reaction was monitored by thin layer chromatography. The reaction mixture was partitioned between 1 M potassium carbonate and methylene chloride. The aqueous fraction was back extracted with methylene chloride. The organic fractions were combined and dried over sodium sulfate. The solvents were removed in vacuo. The title intermediate was further purified by liquid chromatography.

Yield 260 mg (24%)

NMR was consistent with the proposed title structure.

Preparation

Preparation of N-methyl-4-[$^2$-fluoro-5-bromobenzyloxy]butylamine

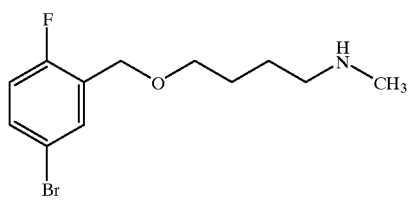

In a 10 ml flask, under a nitrogen atmosphere, N,N-dimethyl-4-[2-fluoro-5-bromobenzyloxy]butylamine (215 mg, 0.707 mmol) was dissolved in dichloroethane (2.0 ml). To this solution ACE•Cl (0.305 ml, 2.83 mmol) was added and the resulting mixture was heated to reflux. The reaction mixture was refluxed for four hours. The prgress of the reaciton was monitored by thin layer chromatography. The mixture was refluxed for an additional 16 hours. The solvents were removed in vacuo and the residue was taken up in methanol. The methanol solution was refluxed for 1.5 hours and the solvents were removed by evaporation. The residue was partitioned between 1 M potassium carbonate and methylene chloride. The aqueous fraction was back extracted with methylene chloride. The organic fractions were combined and dried over sodium sulfate. The solvents were removed in vacuo. The title intermediate was further purified by liquid chromatography.

Yield 108 mg.

NMR was consistent with the proposed title structure.

Preparation

Preparation of 5-[2-fluoro-5-bromobenzyloxy]pentyl chloride

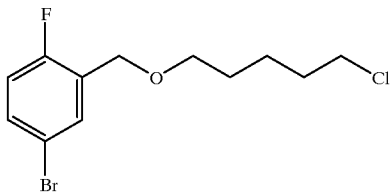

In a 50 ml flask, under a nitrogen atmosphere, 2-fluoro-5-bromobenzyl alcohol (2.139 g, 10.4 mmol) was dissolved in N,N-dimethylformamide (25 ml). To this solution sodium hydride (60%, 625 mg, 15.6 mmol) was added and the resulting mixture was stirred for twenty minutes. To the reaction mixture 5-chloropentyl bromide was added and the resulting mixture was stirred for two hours at ambient temperature. The progress of the reaction was monitored by thin layer chromatography. Sodium iodide (3.127 g, 20.9 mmol) was added and the resulting mixture was stirred at ambient temperature for three hours. The reaction mixture was diluted with diethyl ether and washed seven times with brine. The solvents were removed in vacuo. The title intermediate was further purified by silica gel.

Yield 1.82 g (56%)

NMR was consistent with the proposed title structure.

Preparation

Preparation of N,N-dimethyl-5-[2-fluoro-5-bromobenzyloxy]pentylamine

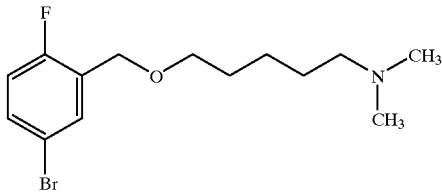

In a sealable tube, under a nitrogen atmosphere, 5-[2-fluoro-5-bromobenzyloxy]pentyl chloride (0.380 g, 1.23 mmol) was dissolved in N,N-dimethylformamide (5 ml). To this solution sodium iodide (55 mg, 0.368 mmol) was added and the resulting mixture was cooled to −78° C. To the reaction mixture dimethylamine (precondensed in anhydrous conditions) was added and the tube was sealed. The mixture was warmed to 85° C. and stirred for eight hours. The mixture was cooled to ambient temperature and stirred for another twelve hours. The mixture was bubbled with nitrogen gas for fifteen minutes to remove excess dimethylamine. The reaction mixture was partitioned between 1 M potassium carbonate and methylene chloride. The aqueous fraction was back-extracted with methylene chloride. The organic fractions were combined, dried over sodium sulfate, and the solvents were removed in vacuo. The title intermediate was further purified by silica gel.

Preparation

Preparation of N-methyl-5-[2-fluoro-5-bromobenzyloxy]pentylamine

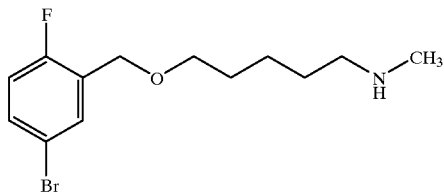

In a 25 ml flask, under a nitrogen atmosphere, N,N-dimethyl-5-[2-fluoro-5-bromobenzyloxy]pentylamine (696 mg, 1.87 mmol) was dissolved in dichloroethane (6.0 ml). To this solution ACE•Cl (0.305 ml, 2.83 mmol) was added and the resulting mixture was heated to reflux. The reaction mixture was refluxed for twenty hours. The progress of the reaction was monitored by thin layer chromatography. The mixture was refluxed for an additional 16 hours. The solvents were removed in vacuo and the residue was partitioned between 1 M potassium carbonate and methylene chloride. The aqueous fraction was back extracted with methylene chloride. The organic fractions were combined and dried over sodium sulfate. The solvents were removed in vacuo. The title intermediate was further purified by liquid chromatography.

Yield 248 mg.

NMR was consistent with the proposed title structure.

Analysis for $C_{13}H_{19}BrFNO$: Theory: C, 51.33; H, 6.30; N, 4.60. Found: C, 51.06; H, 6.12; N, 4.49.

Preparation

Preparation of 1-[2-fluoro-5-bromobenzyloxy]hexane

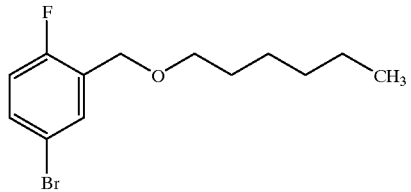

In a 100 ml flask, under a nitrogen atmosphere, n-hexanol (1.44 ml, 11.5 mmol) was dissolved in N,N-dimethylformamide (35 ml). To this solution sodium hydride (60%, 521 mg, 13.0 mmol) was added and the resulting mixture was stirred for ten minutes. To the reaction mixture 2-fluoro-5-bromobenzyl bromide (2.054, 7.67 mmol) was added and the resulting mixture was stirred at ambient temperature for six hours. The progress of the reaction was monitored by thin layer chromatography. The reaction mixture was partitioned between 1 M potassium carbonate/brine (1/1) and diethyl ether. The organic fraction was washed with brine six times. The organic fraction was dried over sodium sulfate. The solvents were removed in vacuo. The title intermediate was further purified by liquid chromatography.

Yield 1.32 g.

NMR was consistent with the proposed title structure.

Preparation

Preparation of 1-(t-butoxycarbonyl)-3-[2-(2-fluoro-5-bromobenzyloxy)ethyl]piperidine

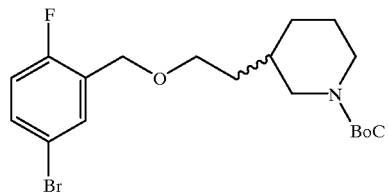

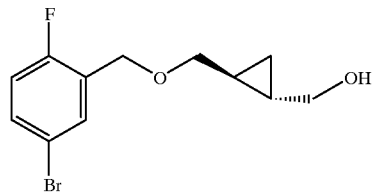

In a 25 ml round bottom flask, 2-[1-(t-butoxycarbonyl)piperidin-3-yl]ethyl bromide (1.011 g, 3.46 mmol) was dissolved in N,N-dimethylformamide (9 ml). Sodium iodide (1.037 g, 6.92 mmol) was added and the resulting mixture was stirred at ambient temperature for ten minutes. The 2-fluoro-5-bromobenzyl alcohol (0.852 g, 4.15 mmol) and sodium hydride (60%, 208 mg, 5.19 mmol) were then added and the resulting mixture began to froth and exotherm. After thirty minutes, the solution cooled and solidified. Three milliliters of N,N-dimethylformamide was added and the mass was slurried and stirred for three more hours. The progress of the reaction was monitored by thin layer chromatography. The reaction mixture was partitioned between brine and diethyl ether. The organic fraction was washed six times with brine, and then dried over sodium sulfate. The desired title product was further purified by liquid chromatography.

Yield: 0.540 grams.

NMR was consistent with proposed title structure.

Preparation

Preparation of 3-[2-(2-fluoro-5-bromobenzyloxy)ethyl]piperidine

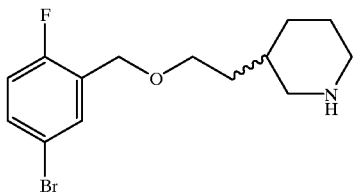

In a 1-ml round bottom flask 1-(t-butoxycarbonyl)-3-[2-(2-fluoro-5-bromobenzyloxy)ethyl]piperidine (0.495 g) was dissolved in methylene chloride (4 ml) under a nitrogen atmosphere. The solution was cooled to 0° C. and trifluoroacetic acid (1 ml) was slowly added dropwise. The resulting mixture was stirred for thirty minutes at ambient temperature. The progress of the reaction was monitored by thin layer chromatography. The reaction mixture was partitioned between 1 M potassium carbonate and methylene chloride. The aqueous fraction was back extracted with methylene chloride. The organic fractions were combined, and dried over sodium sulfate. The solvents were removed in vacuo. The resulting residue was used as is.

Yield: 240 mg.

NMR was consistent with the proposed title structure.

Preparation

Preparation of 1-hydroxymethyl-2-[2-(2-fluoro-5-bromobenyloxy)methyl]cyclopropane In a 100 ml round bottom flask, 1,2-di(hydroxymethyl)cyclopropane (398 mg, 3.90 mmol) was dissolved in N,N-dimethylformamide (15 ml). Sodium hydride (60%, 171 mg, 4.29 mmol) was added and the resulting mixture was stirred at 0° C. for fifteen minutes and then at ambient temperature for fifteen minutes. The reaction solution was cooled to 0° C. and 2-fluoro-5-bromobenzyl bromide (348 mg, 1.30 mmol) was then added as a solution in N,N-dimethylformamide. The resulting reaction was stirred at 0° C. for 1.5 hours and at ambient temperature for thirty minutes. The progress of the reaction was monitored by thin layer chromatography. The reaction mixture was partitioned between brine and diethyl ether. The organic fraction was washed seven times with brine, and then dried over sodium sulfate. The desired title product was further purified by liquid chromatography.

Yield: 0.240 grams (21%).

NMR was consistent with proposed title structure.

Preparation

Preparation of 1-bromomethyl-2-[2-(2-fluoro-5-bromobenzyloxy)methyl]cyclopropane

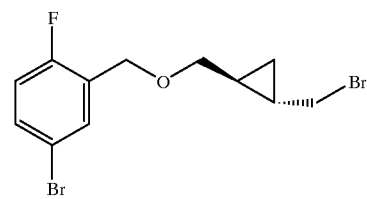

In a 50 ml flask 1-hydroxymethyl-2-[2-(2-fluoro-5-bromobenzyloxy)methyl]cyclopropane (420 mg, 1.45 mmol) was dissolved in diethyl ether (10 ml) under a nitrogen atmosphere. The reaction mixture was treated with triphenylphosphine (495 mg, 1.89 mmol) and carbon tetrabromide (626 mg, 1.89 mmol) stirred at ambient temperature for 17 hours. The progress of the reaction was monitored by thin layer chromatography. The reaction mixture was treated wtih another 0.19 grams of triphenylphosphine and 0.241 grams of carbon tetrabromide. After four additional hours of stirring at ambient temperature, the solvents were removed in vacuo. The title intermediate was further purified from the residue by liquid chromatography.

Yield: 0.389 grams (76%) as a clear oil.

Preparation

Preparation of 1-[(N-methylamino)methyl]-2-[2-(2-fluoro-5-bromobenzyloxy)methyl]cyclopropane

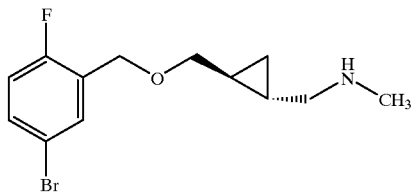

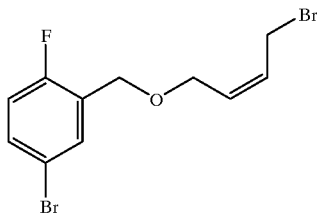

In a 100 ml flask 1-bromomethyl-2-[2-(2-fluoro-5-bromobenzyloxy)methyl]cyclopropane (344 mg, 0.977 mmol) was dissolved in dry tetrahydrofuran (5 ml) under a nitrogen atmosphere. The reaction mixture was treated with methylamine (2M in tetrahydrofuran, 1.9 ml, 3.91 mmol). The resulting mixture was stirred at ambient temperature for one hour and then additional methylamine (2 ml) was added. The resulting mixture was heated to reflux and maintained at this temperature for four hours. The progress of the reaction was monitored by thin layer chromatography. The reaction mixture partitioned between 1 M potassium carbonate and methylene chloride. The aqueous fraction was back extracted with methylene chloride. The organic fractions were combined and then dried over sodium sulfate. The solvents were removed in vacuo. The title intermediate was further purified by liquid chromatography.

Yield: 0.131 grams (44%) as a light yellow oil.

NMR was consistent with the proposed title structure.

Preparation

Preparation of cis 4-(2-fluoro-5-bromobenzyloxy)but-2-en-1-ol

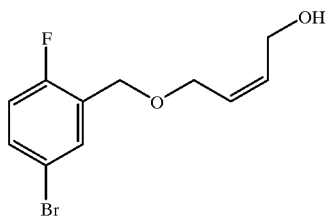

In a 500 ml flask, 1,4dihydroxybut-2-ene (6.13 ml, 74.5 mmol) was dissolved in N,N-dimethylformamide (150 ml) under a nitrogen atmosphere. Sodium hydride (60%, 2.98 g, 74.5 mmol) was added and the resulting mixture was stirred at ambient temperature for thirty minutes. The reaction mixture was cooled to 0° C. and 2-fluoro-5-bromobenzyl bromide (3.99 g, 14.9 mmol) was added dropwise. The resulting mixture was warmed to ambient temperature and stirred for four hours. The progress of the reaction was monitored by thin layer chromatography. The reaction mixture was partitioned between 1 M potassium carbonate and methylene chloride. The aqueous fraction was back-extracted with methylene chloride. The organic fractions were combined and dried over sodium sulfate. The desired title intermediate was further purified by liquid chromatography.

Yield: 2.145 grams (61%) as a clear oil.

NMR and MS were consistent with the proposed title structure.

Preparation

Preparation of cis 4-(2-fluoro-5-bromobenzyloxy)but-2-enyl bromide

In a 100 ml round bottom flask 4-(2-fluoro-5-bromobenzyloxy)but-2-en-1-ol (2.145 g, 7.80 mmol) was dissolved in diethyl ether under a nitrogen atmosphere. Triphenylphosphine (2.66 g, 10.1 mmol) and then carbon tetrabromide (3.36 g, 10.1 mmol) were added to the reaction mixture. The resulting mixture was stirred for six hours at ambient temperature. A white precipitate formed during the stirring. The progress of the reaction was monitored by thin layer chromatography. The solution was filtered and the filtrate was evaporated to give a thick oil. The desired title intermediate was further purified by liquid chromatography.

Yield: 2.16 g (83%).

NMR and MS were consistent with the proposed title structure.

Preparation

Preparation of cis N-methyl-4-(2-fluoro-5-bromobenzyloxy)but-2-enylamine

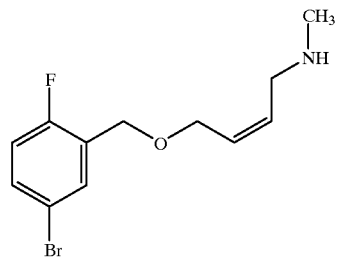

In a 250 ml flask 4-(2-fluoro-5-bromobenzyloxy)but-2-enyl bromide (1.968 g, 5.89 mmol) was dissolved in dry tetrahydrofuran (40 5 ml). To this solution methylamine (29.5 ml, 58.9 mmol) was added in one portion and the resulting mixture was stirred at ambient temperature for five hours. The progress of the reaciton was monitored by thin layer chromatography. The solvents were removed in vacuo and the residue was taken up in 1 M potassium carbonate and extracted thrice with methylene chloride. The organic fractions were combined, and dried over sodium sulfate. The solvents were removed in vacuo. The desired title intermediate was further purified by liquid chromatography.

Yield: 1.199 grams (70%).

NMR and MS were consistent with the proposed title structure.

Preparation

Preparation of N-(t-butoxycarbonyl )-4-(2-fluoro-5-bromobenzyloxy)butylamine

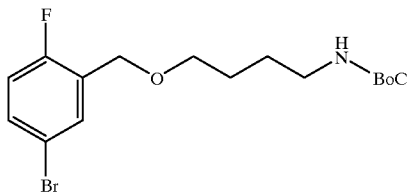

In a 25 ml flask 4-(t-butoxycarbonylamino)butanol was dissolved in tetrahydrofuran (15 ml) under a nitrogen atmosphere. The solution was cooled to −40° C. and potassium tert-butoxide (1M in tetrahydrofuran, 2.14 ml, 2.14 mmol) was added slowly. The resulting mixture was stirred at −40° C. for thirty minutes. To this reaction mixture was added 2-fluoro-5-bromobenzyl bromide (521 mg, 1.94 mmol), added dropwise as a solution in tetrahydrofuran (3.5 ml). The resulting mixture was slowly warmed to 0° C. and stirred at this temperature for two hours. The progress of the reaction was monitored by thin layer chromatography. The reaction mixture was partitioned between 1 M potassium carbonate and methylene chloride. The aqueous fraction was back-extracted with methylene chloride. The organic fractions were combined and dried over sodium sulfate. The solvents were removed in vacuo. The desired intermediate was further purified by liquid chromatography.

Yield: 335 mg (46%) as a yellow oil.

Analysis for $C_{16}H_{23}BrFNO_3$: Theory: C, 51.07; H, 6.16; N, 3.72. Found: C, 51.18; H, 6.18; N, 3.80.

Preparation

Preparation of 4-(2-fluoro-5-bromobenylozy)butylamine

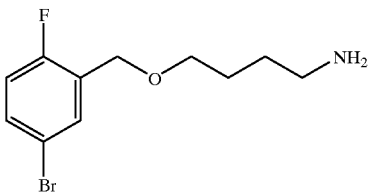

In a 250 ml flask, N-(t-butoxycarbonyl)-4-(2-fluoro-5-bromobenzyloxy)butylamine (3.5 grams) was dissolved in methylene chloride (60 ml) under a nitrogen atmosphere. Trifluoroacetic acid (15 ml) was added to the solution at 0° C. The resulting mixture was stirred at 0° C. for thirty minutes and then at ambient temperature for 15 minutes. The progress of the reaction was monitored by thin layer chromatography. The reaction mixture was partitioned between 1 M potassium carbonate and methylene chloride. The aqueous fraction was back-extracted with methylene chloride. The organic fractions were combined and dried over sodium sulfate. The solvents were removed in vacuo. The desired intermediate was further purified by liquid chromatography.

Yield: 1.82 g.

NMR was consistent with the proposed title structure.

Preparation

Preparation of 4-methyl-1H-indole-2-carboxylic acid

Under an argon atmosphere 4-methylindole (0.91 g, 6.96 mmol) was dissolved in 12 ml of tetrahydrofuran. The resulting solution was cooled in a dry ice/acetone bath. To this solution n-butyllithium (1.6 M in hexanes, 4.48 ml, 7.17 mmol) was carefully added and the resulting mixture was stirred for fifty minutes. Carbon dioxide was bubbled through 26 ml of tetrahydrofuran on a dry ice/acetone bath for twenty minutes. The cold carbon dioxide/tetrahydrofuran solution was cannulated into the organolithium solution. Carbon dioxide was bubbled through the reaction mixture, and the resulting mixture was stirred for thirty minutes over the dry ice/acetone bath. The reaction mixture was then stirred at room temperature for ten minutes with continued carbon dioxide bubbling. The carbon dioxide was shut off and the reaction mixture was stirred at room temperature for ninety minutes.

The solvents were removed in vacuo, argon was added to the reaction vessel, which was then rinsed with 5 ml of tetrahydrofuran. The solvents were removed in vacuo. The brown solid was stored overnight at 4° C. under an argon atmosphere.

The residue was then dissolved in 12 ml warm tetrahydrofuran and the resulting solution was cooled in a dry ice/acetone bath. To this solution t-butyllithium (1.7 M in pentane, 4.22 ml, 7.17 mmol) was carefully added over fifteen minutes. The resulting mixture was allowed to stir over the dry ice/acetone bath for about seventy minutes. In a separate vessel carbon dioxide was bubbled through 26 ml of tetrahydrofuran cooled over a dry ice/acetone bath. The carbon dioxide/tetrahydrofuran solution was added to the organolithium solution via cannula. The carbon dioxide was bubbled directly into the reaction mixture for an additional five minutes. The reaction mixture was stirred over dry ice/acetone for one hour and then carbon dioxide was bubbled through the reaction mixture for one half hour. One milliliter of water was added to the reaction mixture and the reaction mixture was allowed to stir at room temperature for several hours.

The reaction mixture was poured into a saturated ammonium chloride solution and extracted twice with diethyl ether. The organic fractions were combined and the solvents were removed in vacuo and recrystallized from water to obtain 0.17 grams of the desired intermediate. The aqueous fraction was acidified by adding 5% sulfuric acid and stirred for one hour at room temperature. The solids were removed by filtration to yield an additional 0.48 grams of the desired title intermediate.

NMR was consistent with the proposed title structure.

Preparation

Preparation of methyl 4-methyl-1H-indole-2-carboxylate

Under an argon atmosphere 4-methyl-1H-indole-2-carboxylic acid (0.64 g, 3.65 mmol) was dissolved in 20 ml of methanol. Concentrated sulfuric acid (0.5 ml) was added and the resulting mixture was heated to reflux and maintained at this temperature overnight. The progress of the reaction was monitored by thin layer chromatography. Some solvent was removed in vacuo and the resulting crystals were removed by filtration. The solids were taken up in diethyl ether, washed twice with saturated sodium bicarbonate, and then once with brine. The organic fraction was dried over magnesium sulfate and the solvents were removed in vacuo.

Yield: 0.38 grams (55.1%)

Preparation

Preparation of 2-[4-chlorophenoxymethyl]-3-(2-bromoacetyl)-1H-indole

Under a nitrogen atmosphere bromoacetylbromide (1.31 ml, 0.015 mol) was added to a slurry of 2-[4-chlorophenoxymethyl]-1H-indole (0.81 g, 0.003 mol), and lithium carbonate (2.22 g, 0.03 mol) in diethyl ether (37.5 ml). The resulting mixture was heated to 55° C. The progress of the reaction was monitored by thin layer chromatography. The reaction mixture was partitioned between diethyl ether and a sodium bicarbonate solution. The organic fraction was washed with water and then brine, and then dried over sodium sulfate. The solvents were removed in vacuo. Yield: 1.34 g. NMR was consistent with the proposed title structure.

Preparation
Preparation of 2-[4-chlorophenoxymethyl]-3-[2-[4-(piperidin-1-yl)piperidin-1-yl]acetyl)-1H-indole To a slurry of 2-[4-chlorophenoxymethyl]-3-(2-bromoacetyl)-1H-indole (3 mmol) and lithium carbonate (0.47 g, 6 mmol) in tetrahydrofuran (10 ml) 4-(piperidin-1-yl)piperidine (1.01 g, 6 mmol) was added. The resulting mixture was stirred at room temperature for about 2.5 hours. The progress of the reaction was monitored by thin layer chromatography. The reaction mixture was extracted thrice with 1 N hydrochloric acid. The combined acidic extracts were extracted with ethyl acetate, then basified with sodium carbonate, and then extracted twice with ethyl acetate, and then twice with methylene chloride. The organic fractions were combined and the solvents were removed in vacuo. After triturating with diethyl ether 0.46 grams of the desired product as crystalline material were obtained.

NMR, IR, and UV were consistent with the proposed title structure.

Exact Mass FAB for $C_{28}H_{35}ClN_3O_2$: Theory: 480.2418 Found: 480.2411

FDMS 479 (M+)

mp 144–145° C.

The following Examples were prepared essentially as described in the Schemes and Methods, supra. In the following Examples, unless otherwise noted, NMR was consistent with the proposed title struture.

EXAMPLE 1
Preparation of 2-[(4-chlorophenoxy)methyl]-1-methyl-3-(amino)methyl-1H-indole

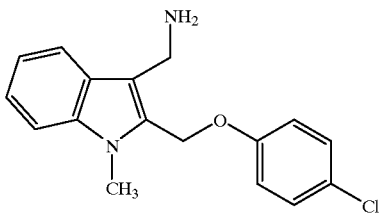

NMR (CDCl$_3$) was consistent with the proposed title structure.

FDMS 300 (M+).

Analysis for $C_{17}H_{17}ClN_2O$: Theory: C, 67.88; H, 5.70; N, 9.31. Found: C, 67.64; H, 5.86; N, 9.24.

EXAMPLE 2
Preparation of 2-[(4-chlorophenoxy)methyl]-1-methyl-3-[(N,N-dimethylamino)methyl]-1H-indole

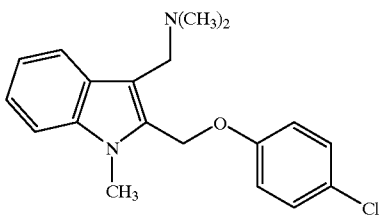

NMR (CDCl$_3$) was consistent with the proposed title structure.

FDMS 328 (M+)

Analysis for $C_{19}H_{21}ClN_2O$: Theory: C, 69.40; H, 6.44; N, 8.52. Found: C, 69.18; H, 6.73; N, 8.54.

EXAMPLE 3
Preparation of 2-[(4-chlorophenoxy)methyl]-1-methyl-3-[(N,N-diethylamino)methyl]-1H-indole hydrochloride

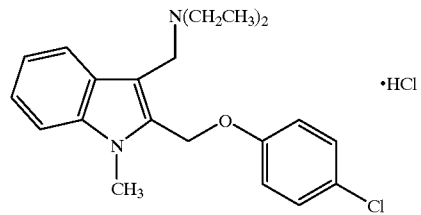

NMR (DMSO) was consistent with the proposed title structure.

FDMS 356 (M+).

Analysis for $C_{21}H_{25}ClN_2O_2 \cdot HCl$: Theory: C, 64.12; H, 6.66; N, 7.12. Found: C, 64.30; H, 6.69; N, 7.18.

EXAMPLE 4
Preparation of 2-[(4-chlorophenoxy)methyl]-1-methyl-3-[(N,N,N-trimethylammonium)methyl]-1H-indole iodide

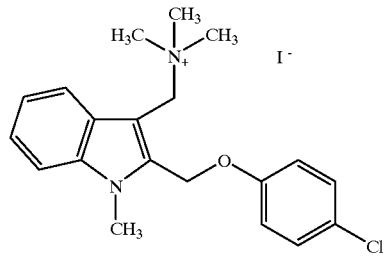

NMR (DMSO) was consistent with the proposed title structure.

FDMS 343 (M+)

Analysis for $C_{20}H_{24}ClN_2O \cdot I$: Theory: C, 51.03; H, 5.14; N, 5.95. Found: C, 50.80; H, 4.93; N, 6.00.

EXAMPLE 5
Preparation of 2-[(4-chlorophenoxy)methyl]-1-methyl-3-[(benzylamino)methyl]-1H-indole hydrochloride

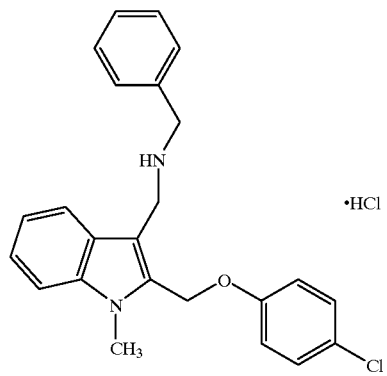

NMR (DMSO) was consistent with the proposed title structure.

FDMS 390 (M+).

Analysis for $C_{24}H_{23}ClN_2O \cdot HCl$: Theory: C, 67.45; H, 5.66; N, 6.56. Found: C, 67.63; H, 5.70; N, 6.60.

EXAMPLE 6
Preparation of 2-[(4-chlorophenoxy)methyl]-1-methyl-3-[(2-phenylethylamino)methyl]-1H-indole hydrochloride

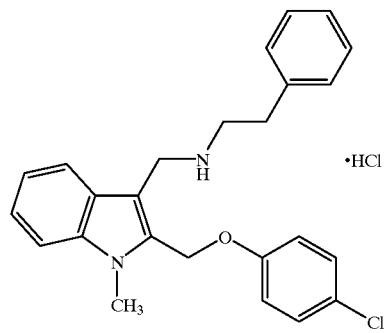

NMR (DMSO) was consistent with the proposed title structure.
FDMS 404 (M+).
Analysis for $C_{25}H_{25}ClN_2O \cdot HCl$: Theory: C, 68.03; H, 5.94; N, 6.35. Found: C, 68.27; H, 5.99; N, 6.60.

EXAMPLE 7
Preparation of 2-[(4-chlorophenoxy)methyl]-1-methyl-3-[(N-methyl-N-butylamino)methyl]-1H-indole

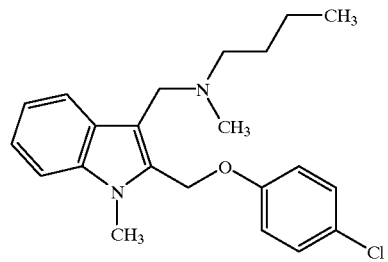

NMR (CDCl$_3$) was consistent with the proposed title structure.
IR was consistent with the desired title structure.
FDMS 370 (M+).
Analysis for $C_{22}H_{27}ClN_2O$: Theory: C, 71.24; H, 7.34; N, 7.55. Found: C, 71.19; H, 7.48; N, 7.39.

EXAMPLE 8
Preparation of 2-[(4-chlorophenoxy)methyl]-1-methyl-3-[(N-methyl-N-benzylamino)methyl]-1H-indole hydrochloride

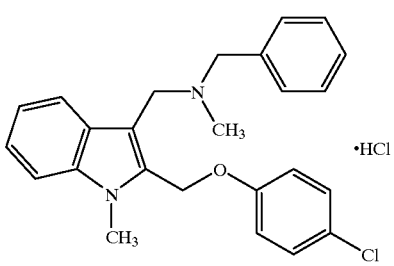

NMR, IR and UV were consistent with the desired title structure.
FDMS 404 (M+).
Analysis for $C_{25}H_{25}ClN_2O \cdot HCl$: Theory: C, 68.03; H, 5.94; N, 6.35. Found: C, 68.30; H, 5.92; N, 6.45.

EXAMPLE 9
Preparation of 2-[(4-chlorophenoxy)methyl)-1-methyl-3-[[N-methyl-N-(3-N',N'-dimethylaminopropyl)amino]methyl] 1H-indole

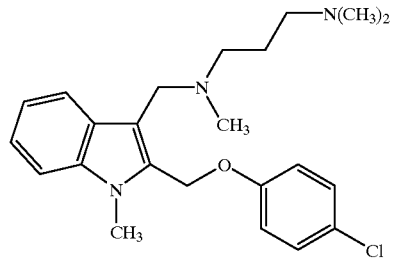

NMR (CDCl$_3$) was consistent with the proposed title structure.
FDMS 400 (M+1).
Analysis for $C_{23}H_{30}ClN_3O$: Theory: C, 69.07; H, 7.56; N, 10.51. Found: C, 69.33; H, 7.34; N, 10.41.

EXAMPLE 10
Preparation of 2-[(4-chlorophenoxy)methyl]-1-methyl-3-[[N-methyl-N-[3-(N',N'-dimethylamino)-2,2-dimethylpropyl]amino]methyl]-H-indole

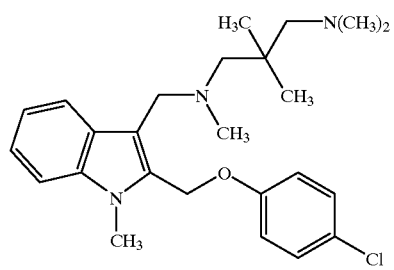

NMR (CDCl$_3$) was consistent with the proposed title structure.
FDMS 414 (M+1)
Analysis for $C_{24}H_{32}ClN_3O$: Theory: C, 69.93; H, 7.79; N, 10.15. Found: C, 69.67; H, 7.78; N, 10.17.

EXAMPLE 11
Preparation of 2-[(4-chlorophenoxy)methyl]-1-methyl-3-[(pyrrolidin-1-yl)methyl]-1H-indole hydrochloride

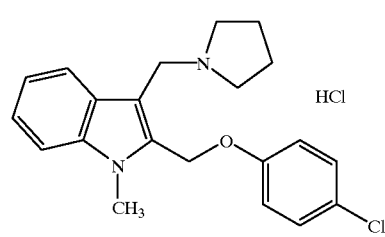

NMR (CDCl$_3$) was consistent with the proposed title structure.
FDMS 354 (M+).
Analysis for $C_{21}H_{23}ClN_2O \cdot HCl$: Theory: C, 64.45; H, 6.18; N, 7.16. Found: C, 64.66; H, 6.33; N, 7.03.

EXAMPLE 12
Preparation of 2-[(4-chlorophenoxy)methyl]-1-methyl-3-[(piperidin-1-yl)methyl]-1H-indole hydrochloride

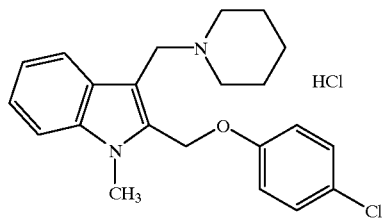

NMR, IR and IN were consistent with the desired title structure.

FDMS 368 (M+).

Analysis for $C_{22}H_{25}ClN_2O \cdot HCl$: Theory: C, 65.19; H, 6.46; N, 6.91. Found: C, 65.46; H, 6.52; N, 7.16.

EXAMPLE 13

Preparation of 2-[(4-chlorophenoxy)methyl]-1-methyl-3-[(3-methylpiperidin-1-yl)methyl]-1H-indole

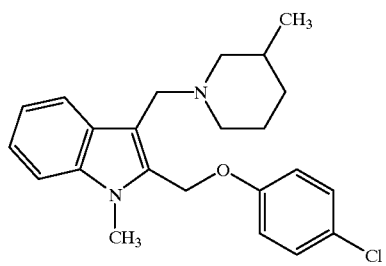

NMR (DMSO) was consistent with the proposed title structure.

FDMS 382 (M+).

Analysis for $C_{23}H_{27}ClN_2O$: Theory: C, 72.14; H, 7.11; N, 7.32. Found: C, 72.38; H, 7.22; N, 7.36.

EXAMPLE 14

Preparation of 2-[(4-chlorophenoxy)methyl]-1-methyl-3-[(4-methylpiperidin-1-yl)methyl]-1H-indole

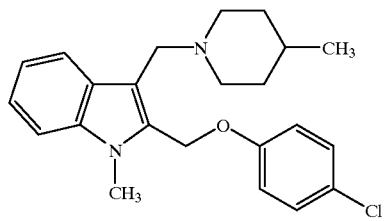

NMR (DMSO) was consistent with the proposed title structure.

FDMS 382 (M+).

Analysis for $C_{23}H_{27}ClN_2O$: Theory: C, 72.14; H, 7.11; N, 7.32. Found: C, 72.33; H, 7.22; N, 7.47.

EXAMPLE 15

Preparation of 2-[(4-chlorophenoxy)methyl]-1-methyl-3-[[4-(N,N-dimethylamino)piperidin-1-yl]methyl]-1H-indole

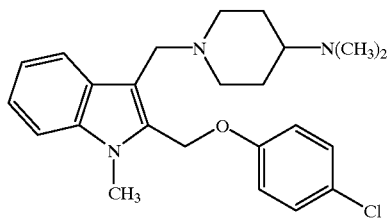

NMR (DMSO) was consistent with the proposed title structure.

FDMS 411 (M+).

Analysis for $C_{24}H_{30}ClN_3O$: Theory: C, 69.97; H, 7.34; N, 10.20. Found: C, 69.74; H, 7.38; N, 10.13.

EXAMPLE 16

Preparation of 2-[(4-chlorophenoxy)methyl]-1-methyl-3-[[4-(piperidin-1-yl)piperidin-1-yl]methyl]-1H-indole

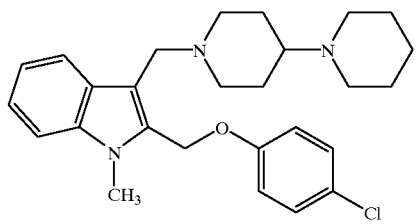

FDMS 451 (M+).

Analysis for $C_{27}H_{34}ClN_3O$: Theory: C, 71.74; H, 7.58; N, 9.30. Found: C, 71.55; H, 7.44; N, 9.14.

EXAMPLE 17

Preparation of 2-[(4-chlorophenoxy)methyl]-1-methyl-3-[(4-acetamido-4-phenylpiperidin-1-yl)methyl]-1H-indole

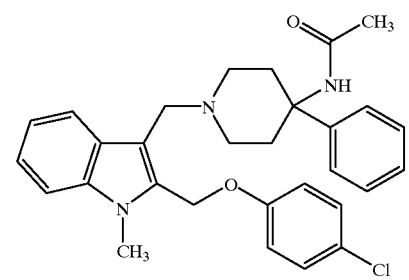

FDMS 501 (M+).

Analysis for $C_{30}H_{32}ClN_3O_2$: Theory: C, 71.77; H, 6.43; N, 8.37. Found: C, 71.79; H, 6.61; N, 8.52.

EXAMPLE 18

Preparation of 2-[(4-chlorophenoxy)methyl]-1-methyl-3-[(4-methylpiperazin-1-yl)methyl]-1H-indole

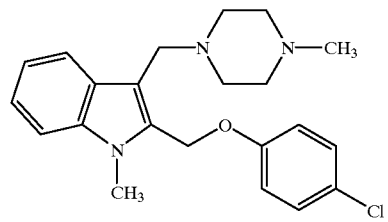

NMR (CDCl$_3$) was consistent with the proposed title structure.

FDMS 383 (M+).

Analysis for C$_{22}$H$_{26}$ClN$_3$O: Theory: C, 68.83; H, 6.83; N, 10.95. Found: C, 68.80; H, 6.71; N, 10.95.

EXAMPLE 19

Preparation of 2-[(4-chlorophenoxy)methyl]-1-methyl-3-[(4-isopropylpiperazin-1-yl)methyl]-1H-indole

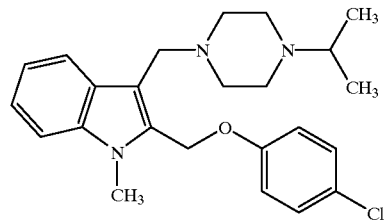

NMR (CDCl$_3$) was consistent with the proposed title structure.

FDMS 411 (M+).

Analysis for C$_{24}$H$_{30}$ClN$_3$O: Theory: C, 69.97; H, 7.34; N, 10.20. Found: C, 69.97; H, 7.36; N, 10.02.

EXAMPLE 20

Preparation of 2-[(4-chlorophenoxy)methyl]-1-methyl-3-[(4-phenylpiperazin-1-yl)methyl]-1H-indole

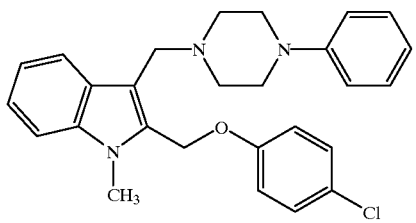

NMR was consistent with the desired title structure.

FDMS 445 (M+).

Analysis for C$_{27}$H$_{28}$ClN$_3$O: Theory: C, 72.71; H, 6.33; N, 9.42. Found: C, 73.00; H, 6.41; N, 9.51.

EXAMPLE 21

Preparation of 2-[(4-chlorophenoxy)methyl]-1-methyl-3-[(4-benzylpiperazin-1-yl)methyl]-1H-indole hydrochloride

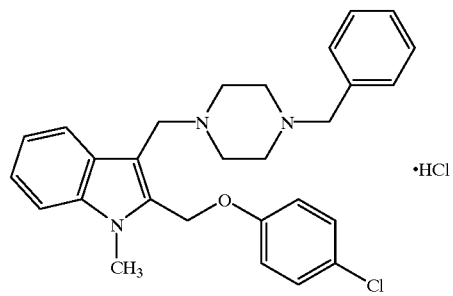

NMR (DMSO) was consistent with the proposed title structure.

FDMS 459 (M+).

Exact Mass (FAB+) for C$_{28}$H$_{31}$ClN$_3$O: Theory: 460.2155. Found: 460.2145.

EXAMPLE 22

Preparation of 2-[(4-chlorophenoxy)methyl]-1-methyl-3-[(4-cyclohexylpiperazin-1-yl)methyl]-1H-indole

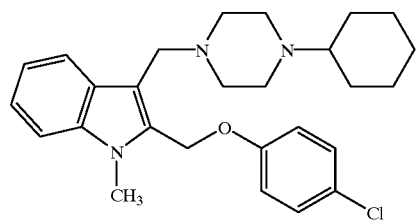

NMR (DMSO) was consistent with the proposed title structure.

FDMS 451 (M+).

Analysis for C$_{27}$H$_{34}$ClN$_3$O: Theory: C, 71.74; H, 7.58; N, 9.30. Found: C, 71.48; H, 7.53; N, 9.26.

EXAMPLE 23

Preparation of 2-[(4-chlorophenoxy)methyl]-1-methyl-3-[[4-(pyrimid-2-yl)piperazin-1-yl)methyl]-1H-indole

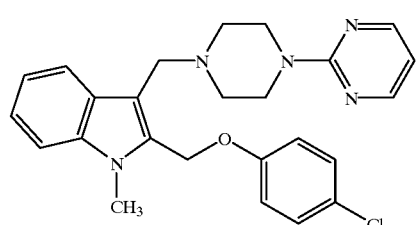

NMR (CDCl$_3$) was consistent with the proposed title structure.

FDMS 447 (M+).

Analysis for C$_{25}$H$_{26}$ClN$_5$O: Theory: C, 67.03; H, 5.85; N, 15.63. Found: C, 67.05; H, 5.93; N, 15.64.

EXAMPLE 24

Preparation of 2-[(4-chlorophenoxy)methyl]-1-methyl-3-(morpholin-4-yl)methyl]-1H-indole

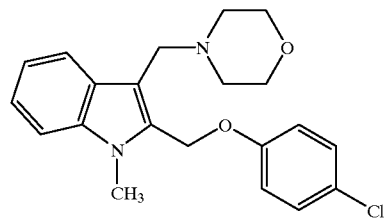

NMR was consistent with the desired title structure.

FDMS 370 (M+).

Analysis for $C_{21}H_{23}ClN_2O_2$: Theory: C, 68.01; H, 6.25; N, 7.55. Found: C, 67.84; H, 6.65; N, 7.25.

EXAMPLE 25

Preparation of 2-[(4-chlorophenoxy)methyl]-1-methyl-3-(tryptolin-2-yl)methyl]-1H-indole

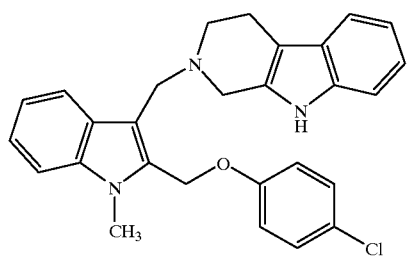

NMR (CDCl$_3$) was consistent with the proposed title structure.

FDMS 455 (M+).

Analysis for $C_{28}H_{26}ClN_3O$: Theory: C, 73.75; H, 5.75; N, 9.21. Found: C, 73.99; H, 6.00; N, 9.03.

EXAMPLE 26

Preparation of 2-[(2,4-dichlorophenoxy)methyl]-1-methyl-3-[N-(1-methylpiperidin-4-yl)-N-methylamino]methyl]-1H-indole dihydrochloride monohydrate

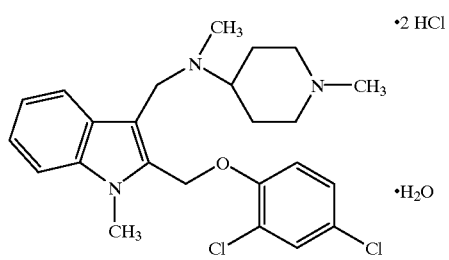

NMR was consistent with the desired title structure.

mp 196–197° C.

FDMS 446 (M+).

Analysis for $C_{24}H_{29}Cl_2N_3O \cdot 2HCl \cdot H_2O$: Theory: C, 53.64; H, 6.19; N, 7.82. Found: C, 53.66; H, 5.92; N, 8.10.

EXAMPLE 27

Preparation of 2-[(2,4-dichlorophenoxy)methyl]-1-methyl-3-[[4-(N,N-dimethylamino)piperidin-1-yl]methyl]-1H-indole

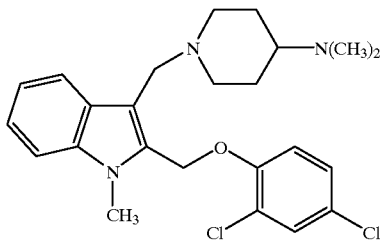

NMR, IR, and UV were consistent with the desired title structure.

mp 105–106° C.

FDMS 445 (M+).

Analysis for $C_{24}H_{29}Cl_2N_3O$: Theory: C, 64.57; H, 6.55; N, 9.41. Found: C, 64.27; H, 6.48; N, 9.49.

EXAMPLE 28

Preparation of 2-[(2,4-dichlorophenoxy)methyl]-1-methyl-3-[[4-(piperidin-1-yl)piperidin-1-yl]methyl]-1H-indole

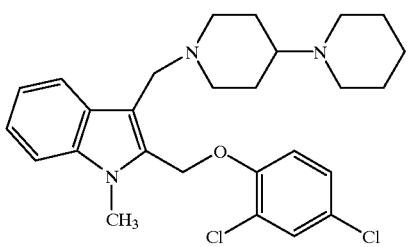

NMR, IR, and IN were consistent with the desired title structure.

FDMS 485(M+).

mp 106–107° C.

Analysis for $C_{27}H_{33}Cl_2N_3O$: Theory: C, 66.66; H, 6.84; N, 8.64. Found: C, 66.92; H, 7.04; N, 8.74.

EXAMPLE 29

Preparation of 2-[(4-chlorophenoxy)methyl]-1-methyl-3-(2-aminoethyl)-1H-indole

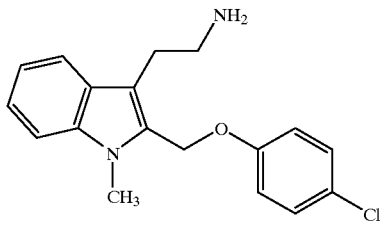

NMR (CDCl$_3$) was consistent with the proposed title structure.

FDMS 314 (M+).

Exact Mass (FAB) for $C_{18}H_{20}ClN_2O$: Theory: 315.1264. Found: 315.1246.

EXAMPLE 30

Preparation of 2-[(4-chlorophenoxy)methyl]-1-methyl-3-[2-[(3-dimethylaminopropyl)amino]ethyl]-1H-indole

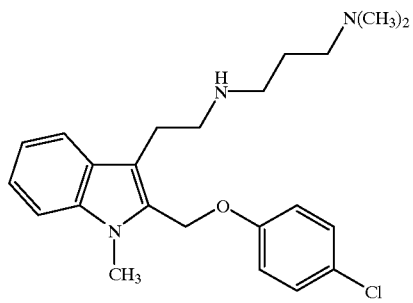

NMR (CDCl$_3$) was consistent with the proposed title structure.
FDMS 399 (M+).
Analysis for C$_{23}$H$_{30}$ClN$_3$O: Theory: C, 69.07; H, 7.56; N, 10.51. Found: C, 69.23; H, 7.79; N, 10.52.

EXAMPLE 31

Preparation of 2-[(4-chlorophenoxy)methyl]-1-methyl-3-[2-[N-methyl-N-(3-dimethylaminopropyl)amino]ethyl]-1H-indole dihydrochloride

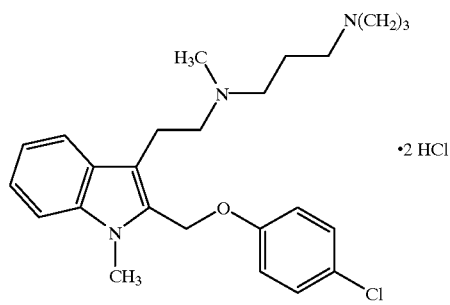

NMR (DMSO) was consistent with the proposed title structure.
FDMS 413 (M+).
Exact Mass (FAB) for C24H33ClN3O: Theory: 414.2312. Found: 414.2312.

EXAMPLE 32

Preparation of 2-[(4-chlorophenoxy)methyl]-1-methyl-3-[2-(piperidin-1-yl)ethyl]-1H-indole

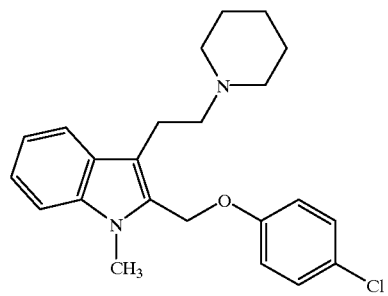

NMR (CDCl$_3$) was consistent with the proposed title structure.
FDMS 382 (M+).
Analysis for C$_{23}$H$_{27}$ClN$_2$O: Theory: C, 72.14; H, 7.11; N, 7.32. Found: C, 72.40; H, 7.26; N, 7.37.

EXAMPLE 33

Preparation of 2-[(4-chlorophenoxy)methyl]-1-methyl-3-[2-(4-methylpiperidin-1-yl)ethyl]-1H-indole

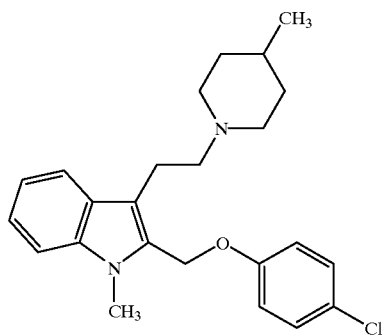

NMR (CDCl$_3$) was consistent with the proposed title structure.
FDMS 396 (M+).
Analysis for C$_{24}$H$_{29}$ClN$_2$O: Theory: C, 72.62; H, 7.36; N, 7.06. Found: C, 72.40; H, 7.35; N, 7.25.

EXAMPLE 34

Preparation of 2-[(4-chlorophenoxy)methyl]-1-methyl-3-[2-(4-benzylpiperidin-1-yl)ethyl]-1H-indole

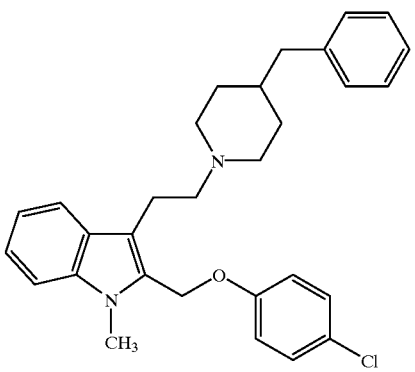

NMR (CDCl$_3$) was consistent with the proposed title structure.
FDMS 472 (M+).
Analysis for C$_{30}$H$_{33}$ClN$_2$O: Theory: C, 76.17; H, 7.03; N, 5.92. Found: C, 76.37; H, 7.15; N, 5.85.

EXAMPLE 35

Preparation of 2-[(4-chlorophenoxy)methyl]-1-methyl-3-[2-[4-(N,N-dimethylamino)piperidin-1-yl]ethyl]-1H-indole

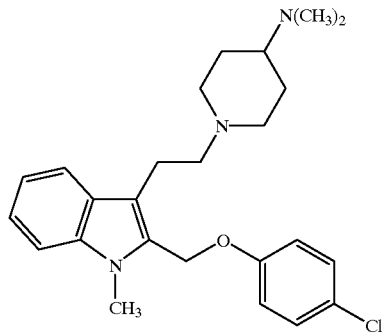

NMR (CDCl$_3$) was consistent with the proposed title structure.
Exact Mass (FAB) for C$_{25}$H$_{33}$ClN$_3$O: Theory: 426.2312. Found: 426.2297.

EXAMPLE 36

Preparation of 2-[(4-chlorophenoxy)methyl]-1-methyl-3-[2-[4-(piperidin-1-yl)piperidin-1-yl]ethyl]-1H-indole

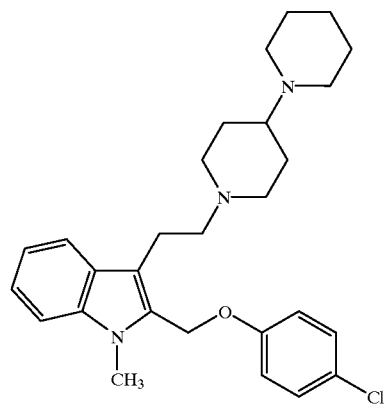

FDMS 465 (M+)

Analysis for $C_{28}H_{36}ClN_3O$: Theory: C, 72.16; H, 7.79; N, 9.02. Found: C, 72.09; H, 7.69; N, 9.09.

EXAMPLE 37

Preparation of 2-[(4-chlorophenoxy)methyl]-1-methyl-3-[2-(4-cyclohexylpiperazin-1-yl)ethyl]-1H-indole

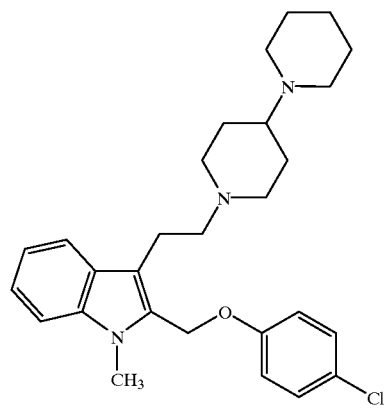

NMR (CDCl$_3$) was consistent with the proposed title structure.

FDMS 465 (M+).

Analysis for $C_{28}H_{36}ClN_3O$: Theory: C, 72.16; H, 7.79; N, 9.02. Found: C, 72.00; H, 7.88; N, 9.05.

EXAMPLE 38

Preparation of 2-[(2,4-dichlorophenoxy)methyl]-1-methyl-3-[2-[N-methyl-N-(1-methylpiperidin-4-yl)]ethyl]-1H-indole

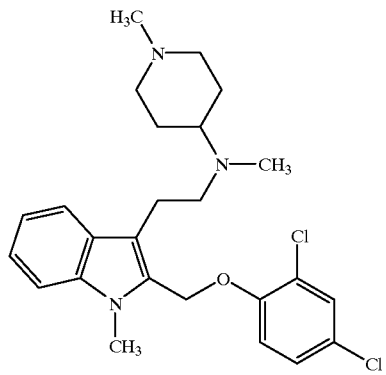

NMR (CDCl$_3$) was consistent with the proposed title structure.

FDMS 459 (M+).

Analysis for $C_{25}H_{31}Cl_2N_3O$: Theory: C, 65.21; H, 6.79; N, 9.13. Found: C, 65.07; H, 6.85; N, 9.06.

EXAMPLE 39

Preparation of 2-[(2,4-dichlorophenoxy)methyl]-1-methyl-3-[2-[4-(N,N-dimethylamino)piperidin-1-yl]ethyl]-1H-indole

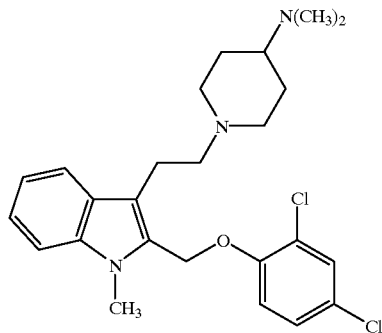

NMR (CDCl$_3$) was consistent with the proposed title structure.

Exact Mass for $C_{25}H_{32}Cl_2N_3O$: Theory: 460.1922. Found: 460.1890.

EXAMPLE 40

Preparation of 2-[(2,4-dichlorophenoxy)methyl]-1-methyl-3-[2-[4-(piperidin-1-yl)piperidin-1-yl]ethyl]-1H-indole

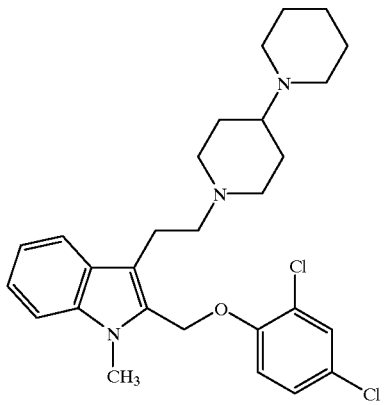

NMR (CDCl₃) was consistent with the proposed title structure.
Exact Mass for $C_{28}H_{36}Cl_2N_3O$: Theory: 500.2235. Found: 500.2215.

EXAMPLE 41
Preparation of 2-[(4-chlorophenoxy)methyl]-1-methyl-3-[3-[4-(N,N-dimethylamino)piperidin-1-yl]propyl]-1H-indole

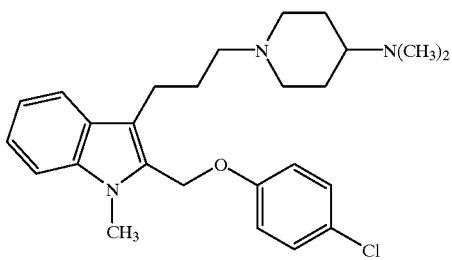

NMR (CDCl₃) was consistent with the proposed title structure.
IR was consistent with the desired title structure.
FABMS 440 (M+1)
Analysis for $C_{26}H_{34}ClN_3O$: Theory: C, 70.97; H, 7.79; N, 9.55. Found: C, 70.73; H, 7.65; N, 9.44.

EXAMPLE 42
Preparation of (RS) 2-[(4-chlorophenoxy)methyl]-1-methyl-3-[3-(piperidin-3-yl)propyl]-1H-indole

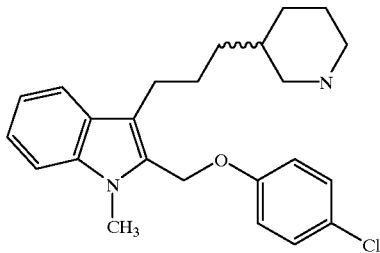

NMR (CDCl₃) was consistent with the proposed title structure.
Exact Mass for $C_{24}H_{30}ClN_2O$: Theory: 397.2047. Found: 397.2055.

EXAMPLE 43
Preparation of 2-[(4-chlorophenoxy)methyl]-1-methyl-3-[2-[[4-(dimethylamino)piperidin-1-yl]carbonyl]ethyl]-1H-indole

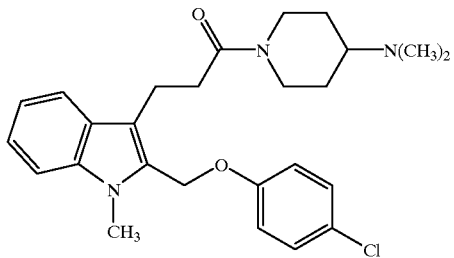

NMR (CDCl₃) was consistent with the proposed title structure.
IR was consistent with the desired title structure.
FDMS 453 (M+)
Analysis for $C_{26}H_{32}ClN_3O_2$: Theory: C, 68.78; H, 7.10; N, 9.26. Found: C, 68.74; H, 7.04; N, 9.38.

EXAMPLE 44
Preparation of 2-[(4-chlorophenoxy)methyl]-1-methyl-3-[2-[[4-(dimethylamino)piperidin-1-yl]carbonyl]ethenyl]-1H-indole

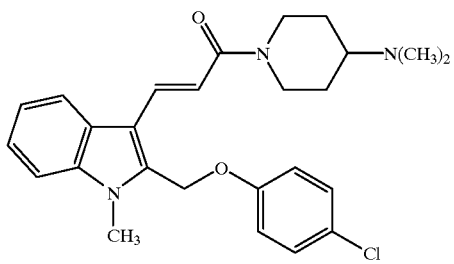

NMR (CDCl₃) was consistent with the proposed title structure.
Exact Mass (FAB) for $C_{26}H_{31}ClN_3O_2$: Theory: 452.2105. Found: 452.2099.

EXAMPLE 46
Preparation of 2-[(4-chlorophenoxy)methyl]-1-methyl-3-[1-hydroxy-2-[(3-acetamido)pyrrolidin-1-yl]ethyl]-1H-indole

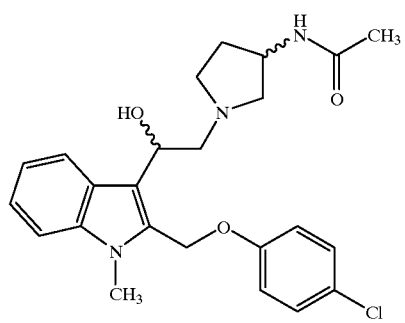

NMR (CDCl₃) was consistent with the proposed title structure.
FDMS 442 (M+).
Exact Mass FAB (M+1) for $C_{24}H_{29}ClN_3O_3$: Theory: 442.1897. Found: 442.1878.

EXAMPLE 47
Preparation of 2-[(4-chlorophenoxy)methyl]-1-methyl-3-[1-hydroxy-2-(piperidin-1-yl)ethyl]-1H-indole

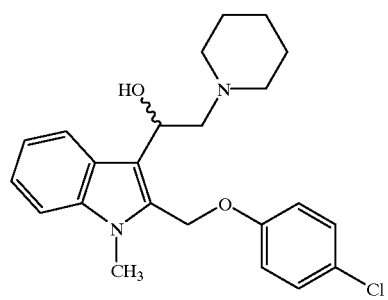

NMR (CDCl$_3$) was consistent with the proposed title structure.
FDMS 398 (M+).
Analysis for C$_{23}$H$_{27}$ClN$_2$O$_2$: Theory: C, 69.25; H, 6.82; N, 7.02. Found: C, 69.51; H, 6.86; N, 6.81.

EXAMPLE 48

Preparation of 2-[(4-chlorophenoxy)methyl]-1-methyl-3-[1-hydroxy-2-(4-methylpiperidin-1-yl)ethyl]-1H-indole

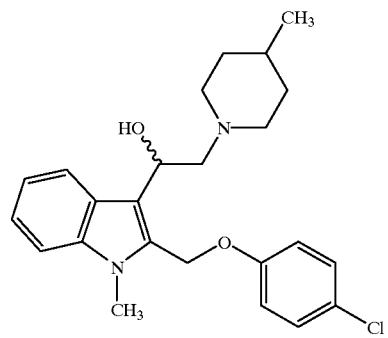

NMR (CDCl$_3$) was consistent with the proposed title structure.
FDMS 412, (M+).
Analysis for C$_{24}$H$_{29}$ClN$_2$O$_2$: Theory: C, 69.80; H, 7.08; N, 6.78. Found: C, 70.02; H, 7.13; N, 7.00.

EXAMPLE 49

Preparation of 2-[(4-chlorophenoxy)methyl)-1-methyl-3-[1-hydroxy-2-(4-benzylpiperidin-1-yl)ethyl]-1H-indole

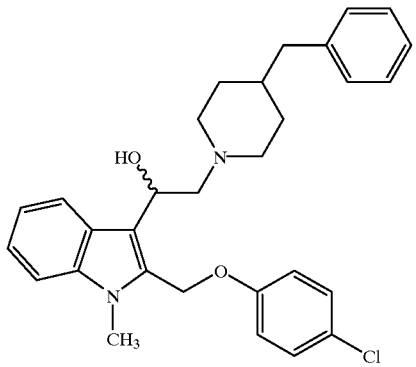

NMR (CDCl$_3$) was consistent with the proposed title structure.
FDMS 488 (M+).
Analysis for C$_{30}$H$_{33}$ClN$_2$O$_2$: Theory: C, 73.67; H, 6.80; N, 5.73. Found: C, 73.52; H, 6.87; N, 5.58.

EXAMPLE 50

Preparation of 2-[(4-chlorophenoxy)methyl]-1-methyl-3-[1-hydroxy-2-(4-dimethylaminopiperidin-1-yl)ethyl)-1H-indole

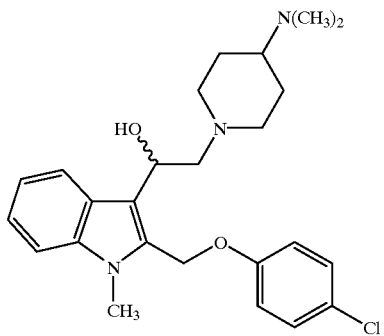

NMR (CDCl$_3$) was consistent with the proposed title structure.

IR was consistent with the desired title structure.

FDMS 442 (M+).

Analysis for C$_{25}$H$_{32}$ClN$_3$O$_2$: Theory: C, 67.94; H, 7.30; N, 9.51. Found: C, 67.73; H, 7.52; N, 9.75.

EXAMPLE 51

Preparation of 2-[(4-chlorophenoxy)methyl]-1-methyl-3-[1-hydroxy-2-[4-(piperidin-1-yl)piperidin-1-yl]ethyl]-1H-indole dihydrochloride

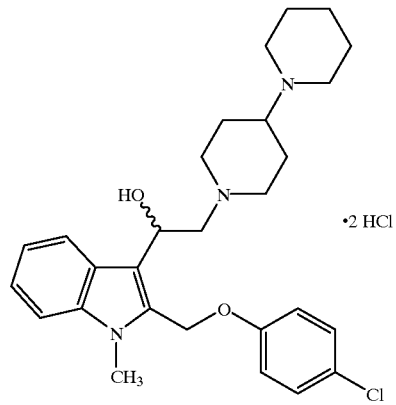

NMR (DMSO) was consistent with the proposed title structure.

FDMS 481 (M+1).

Analysis for C$_{28}$H$_{35}$ClN$_3$O$_2$.2HCl Theory: C, 60.71; H, 6.73; N, 7.59; Cl, 19.20. Found: C, 60.86; H, 6.90; N, 7.53; Cl, 19.19.

EXAMPLE 52

Preparation of 2-[(4-chlorophenoxy)methyl]-1-methyl-3-[1-hydroxy-2-(4-cyclohexylpiperazin-1-yl)ethyl)-1H-indole

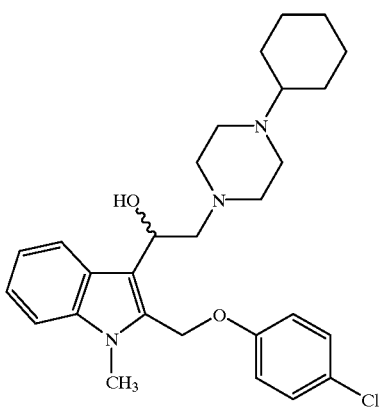

NMR (CDCl₃) was consistent with the proposed title structure.
FDMS 482 (M+1).
Analysis for $C_{28}H_{36}ClN_3O_2$: Theory: C, 69.76; H, 7.53; N, 8.72. Found: C, 70.06; H, 7.61; N, 8.46.

EXAMPLE 53
Preparation of 2-[(4-chlorophenoxy)methyl]-1-methyl-3-[1-hydroxy-3-(piperidin-4-yl)propyl]-1H-indole

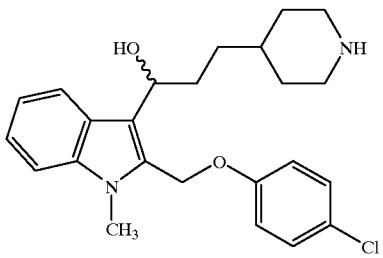

NMR (CDCl₃) was consistent with the proposed title structure.
FDMS 412 (M+).
Single compound of high purity as evidenced by chromatographic methods.
Analysis for $C_{24}H_{29}ClN_2O_2$: Theory: C, 69.80; H, 7.08; N, 6.78. Found: C, 68.18; H, 7.87; N, 6.58.

EXAMPLE 54
Preparation of 2-[(2,4-dichlorophenoxy)methyl-1-methyl-3-[1-hydroxy-2-[N-methyl-N-(1-methylpiperidin-4-yl)amino]ethyl]-1H-indole

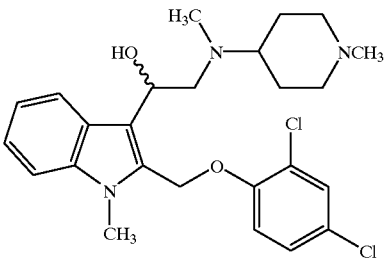

NMR (CDCl₃) was consistent with the proposed title structure.
FDMS 475 (M+).
Analysis for $C_{25}H_{31}Cl_2N_3O_2$: Theory: C, 63.02; H, 6.55; N, 8.82. Found: C, 63.43; H, 6.88; N, 8.92.

EXAMPLE 55
Preparation of 2-[(4-chlorophenoxy)methyl]-1-methyl-3-[1-hydroxy-2-(methoxycarbonyl)ethyl]-1H-indole

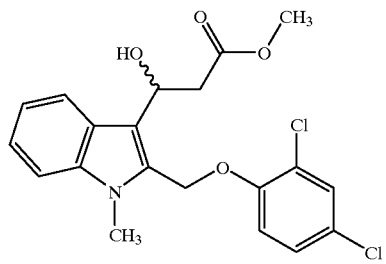

NMR (CDCl₃) was consistent with the proposed title structure.
IR was consistent with the desired title structure.
FDMS 373 (M+).
Analysis for $C_{20}H_{20}ClNO_4$: Theory: C, 64.26; H, 5.39; N, 3.75. Found: C, 64.55; H, 5.23; N, 3.79.

EXAMPLE 56
Preparation of 2-[(4-chlorophenoxy)methyl]-1-methyl-3-carboxy-1H-indole

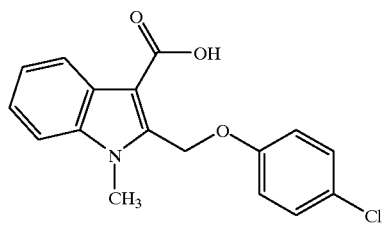

NMR (DMSO) was consistent with the desired title structure.
FDMS 315 (M+).
Analysis for $C_{17}H_{14}ClNO_3$: Theory: C, 64.67; H, 4.47; N, 4.44. Found: C, 64.84; H, 4.60; N, 4.54.

EXAMPLE 57
Preparation of 2-[(4-chlorophenoxy)methyl]-1-methyl-3-[[3-dimethylamino-2,3-dimethylpropylamino]carbonyl]-1H-indole

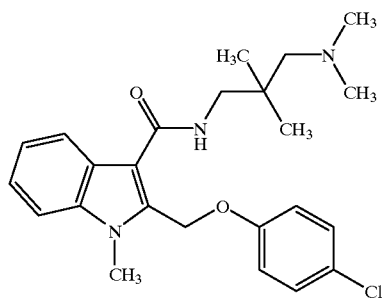

NMR (CDCl₃) was consistent with the proposed title structure.
FAB 426 (M−1).
Analysis for $C_{24}H_{30}ClN_3O_2$: Theory: C, 67.36; H, 7.07; N, 9.82. Found: C, 67.58; H, 6.79; N, 9.64.

EXAMPLE 58
Preparation of 2-[(4-chlorophenoxy)methyl]-1-methyl-3-[[N,N-bis(3-dimethylaminopropyl)amino]carbonyl] 1H-indole

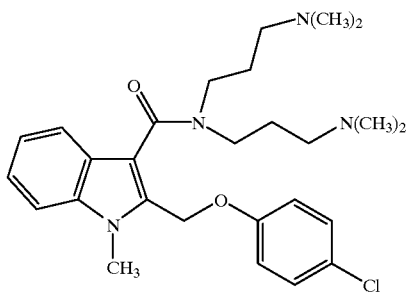

NMR (CDCl₃) was consistent with the proposed title structure.
FDMS 483 (M−1).
FABMS 485 (M+1)
Analysis for $C_{27}H_{37}ClN_4O_2$: Theory: C, 66.86; H, 7.69; N, 11.55. Found: C, 66.91; H, 7.54; N, 11.69.

EXAMPLE 59
Preparation of 2-[(4-chlorophenoxy)methyl]-1-methyl-3-[[N-methyl-N-(1-methylpiperidin-4-yl)amino]carbonyl]-1H-indole

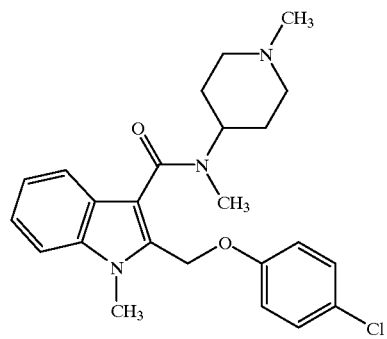

NMR (CDCl₃) was consistent with the proposed title structure.
FDMS 427 (M+2)
Analysis for $C_{24}H_{28}ClN_3O_2$: Theory: C, 67.67; H, 6.63; N, 9.86. Found: C, 67.38; H, 6.90; N, 9.94.

EXAMPLE 60
Preparation of 2-[(4-chlorophenoxy)methyl)-1-methyl-3-[[4-(piperidin-1-yl)piperidin-1-yl]carbonyl]-1H-indole

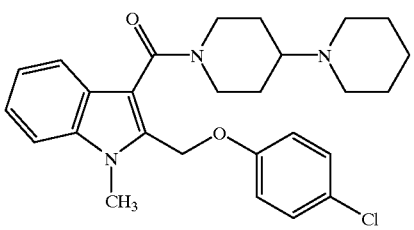

NMR (CDCl₃) was consistent with the proposed title structure.
FDMS 465 (M+).
Analysis for $C_{27}H_{32}ClN_3O_2$: Theory: C, 69.59; H, 6.92; N, 9.02. Found: C, 69.47; H, 7.00; N, 9.22.

EXAMPLE 61
Preparation of (RS) 2-[(4-chlorophenoxy)methyl]-1-methyl-3-[(piperidin-3-yl)acetyl]-1H-indole

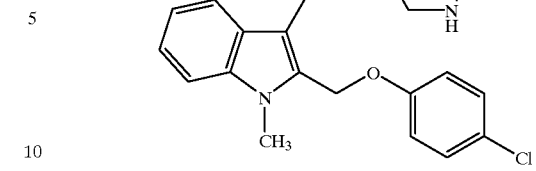

NMR (CDCl₃) was consistent with the proposed title structure.
FDMS 396 (M+)
Analysis for $C_{23}H_{25}ClN_2O_2$: Theory: C, 69.60; H, 6.35; N, 7.06. Found: C, 69.71; H, 6.28; N, 7.20.

EXAMPLE 62
Preparation of 2-[(4-chlorophenoxy)methyl]-1-methyl-3-[(1-tritylpiperidin-4-yl)acetyl]-1H-indole

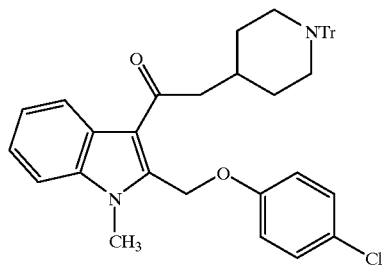

NMR (CDCl₃) was consistent with the proposed title structure.
FDMS 638 (M+)
Analysis for $C_{42}H_{39}ClN_2O_2$: Theory: C, 78.92; H, 6.15; N, 4.38. Found: C, 78.73; H, 6.15; N, 4.25.

EXAMPLE 63
Preparation of 2-[(4-chlorophenoxy)methyl]-1-methyl-3-[(piperidin-4-yl)acetyl]-1H-indole

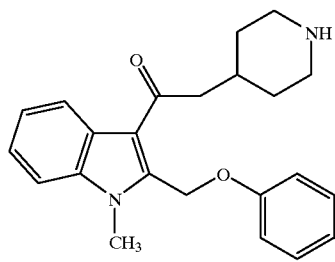

NMR (CDCl₃) was consistent with the proposed title structure.
FDMS 397 (M+1)
Analysis for $C_{23}H_{25}ClN_2O_2$: Theory: C, 69.60; H, 6.35; N, 7.06. Found: C, 69.34; H, 6.43; N, 6.86.

EXAMPLE 64
Preparation of 2-[(4-chlorophenoxy)methyl]-1-methyl-3-[[4-(piperidin-1-yl)piperidin-1-yl]acetyl]-1H-indole dihydrochloride

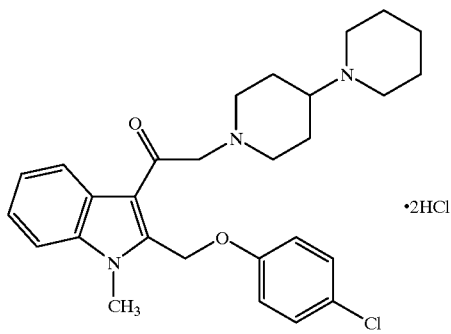

NMR (DMSO) was consistent with the proposed title structure.

FDMS 479 (M+)

Analysis for $C_{28}H_{34}ClN_3O_2 \cdot 2HCl$: Theory: C, 60.82; H, 6.56; N, 7.60. Found: C, 60.67; H, 6.70; N, 7.38.

EXAMPLE 65

Preparation of 2-[(4-chlorophenoxy)methyl]-1-methyl-3-[[2-(piperidin-3-yl)ethyl]carbonyl]-1H-indole

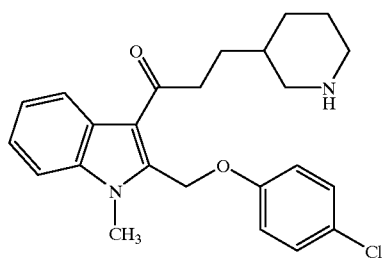

NMR (CDCl$_3$) was consistent with the proposed title structure.

FDMS 411 (M+1).

Analysis for $C_{24}H_{27}ClN_2O_2$: Theory: C, 70.15; H, 6.67; N, 6.82. Found: C, 70.38; H, 6.39; N, 7.02.

EXAMPLE 66

Preparation of 2-[(4-chlorophenoxy)methyl]-1-methyl-3-[[2-(1-tritylpiperidin-4-yl )ethyl]carbonyl]-1H-indole

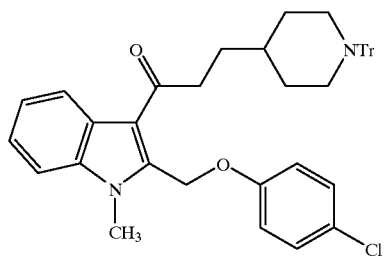

NMR (CDCl$_3$) was consistent with the proposed title structure.

$C_{43}H_{41}ClN_2O_2$ FDMS 652 (M+).

Single compound of high purity as evidenced by chromatographic means.

EXAMPLE 67

Preparation of 2-[(4-chlorophenoxy)methyl]-1-methyl-3-[[2-(piperidin-4-yl)ethyl]carbonyl]-1H-indole

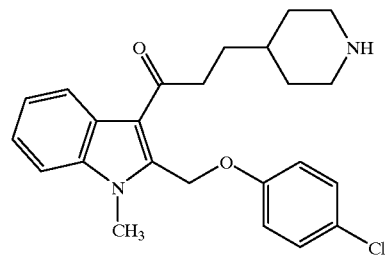

NMR (CDCl$_3$) was consistent with the proposed title structure.

FDMS 411 (M+1)

Analysis for $C_{24}H_{27}ClN_2O_2$: Theory: C, 70.15; H, 6.62; N, 6.82. Found: C, 69.87; H, 6.54; N, 6.79.

EXAMPLE 68

Preparation of 2-[(4-chlorophenoxy)methyl]-1-methyl-3-[[2-[1-[3-[(1-tritylpiperidin-4-yl)propyl]piperidin-4-yl]]ethyl]carbonyl]-1H-indole

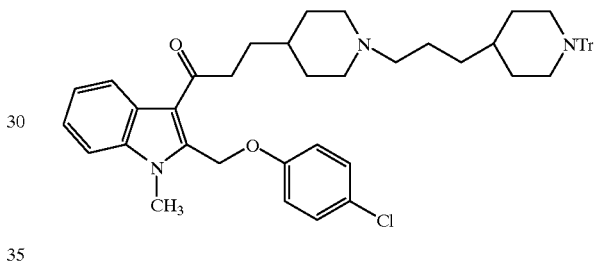

FDMS 779 (M+2)

Analysis for $C_{51}H_{56}ClN_3O$: Theory: C, 78.69; H, 7.25; N, 5.40. Found: C, 78.90; H, 7.34; N, 5.60.

EXAMPLE 69A

Preparation of 2-[(4-chlorophenoxy)methyl]-1-methyl-3-[[2-[1-[3-(piperidin-4-yl)propyl]piperidin-4-yl]]ethyl] carbonyl] 1H-indole

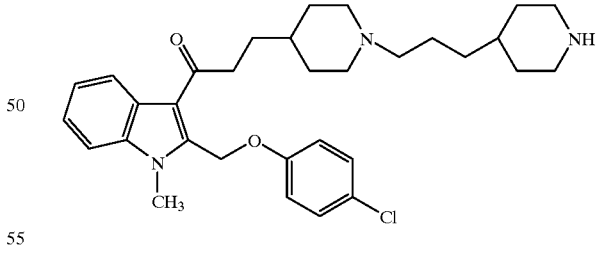

NMR (CDCl$_3$) was consistent with the proposed title structure.

FAB 536(M+).

Exact mass FAB (M+1) for $C_{32}H_{43}ClN_3O_2$: Theory: 536.3044. Found: 536.3044.

EXAMPLE 69B

Preparation of 2-[(4-chlorophenoxy)methyl]-1-methyl-3-[[2-[1-[3-(1-tritylpiperidin-3-yl)propyl]piperidin-4-yl]]ethyl]carbonyl]-1H-indole

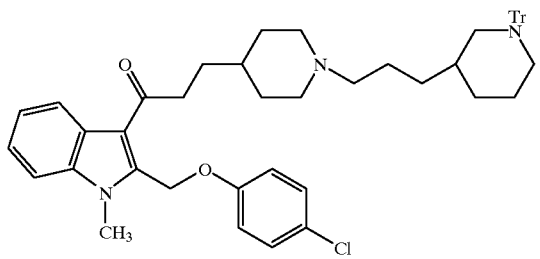

FDMS 779 (M+2).

Analysis for $C_{51}H_{56}ClN_3O_2$: Theory: C, 78.69; H, 7.25; N, 5.40. Found: C, 78.92; H, 7.41; N, 5.27.

EXAMPLE 69C

Preparation of 2-[(4-chlorophenoxy)methyl]-1-methyl-3-[[2-[1-[3-(piperidin-3-yl)propyl]piperidin-4-yl]]ethyl]carbonyl]-1H-indole

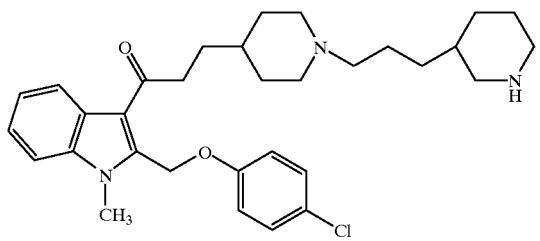

NMR (CDCl$_3$) was consistent with the proposed title structure.

FDMS 536 (M+1).

Analysis for $C_{32}H_{42}ClN_3O_2$: Theory: C, 71.69; H, 7.90; N, 7.84. Found: C, 71.45; H, 7.85; N, 7.61.

EXAMPLE 70

Preparation of (RS) 2-[(4-chlorophenoxy)methyl]-1-[3-(piperidin-3-yl)propyl]-3-[[4-(piperidin-1-yl)piperidin-1-yl]acetyl]-1H-indole

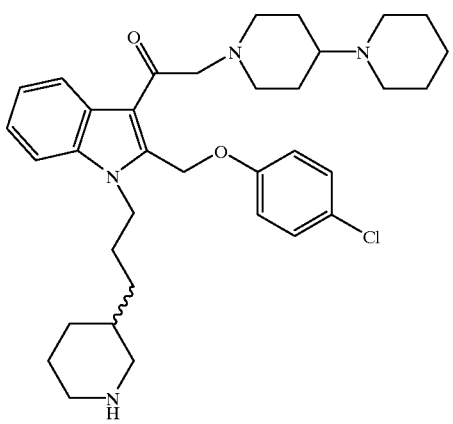

NMR (CDCl$_3$) was consistent with the proposed title structure.

Exact Mass FAB (M+) for $C_{35}H_{48}ClN_4O_2$: Theory: 591.3466. Found: 591.3476.

EXAMPLE 70A

Preparation of (S) 2-[(4-chlorophenoxy)methyl]-1-[3-(piperidin-3-yl)propyl]-3-[[4-(piperidin-1-yl)piperidin-1-yl]acetyl]-1H-indole

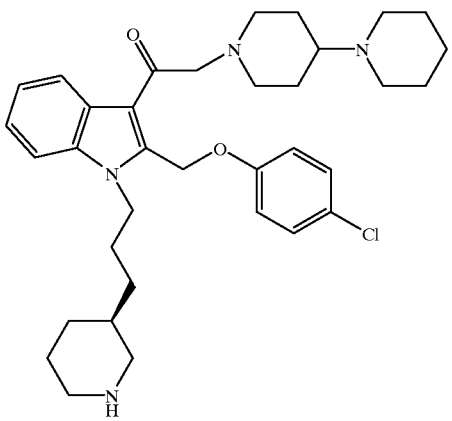

NMR (CDCl$_3$) was consistent with the proposed title structure.

FABMS 591.3476 (M+).

Analysis for $C_{35}H_{47}ClN_4O_2$: Theory: C, 71.10; H, 8.01; N, 9.48. Found: C, 70.82; H, 8.14; N, 9.23.

EXAMPLE 70B

Preparation of (R) 2-[(4-chlorophenoxy)methyl]-1-[3-(piperidin-3-yl)propyl]-3-[[4-(piperidin-1-yl)piperidin-1-yl]acetyl]-1H-indole

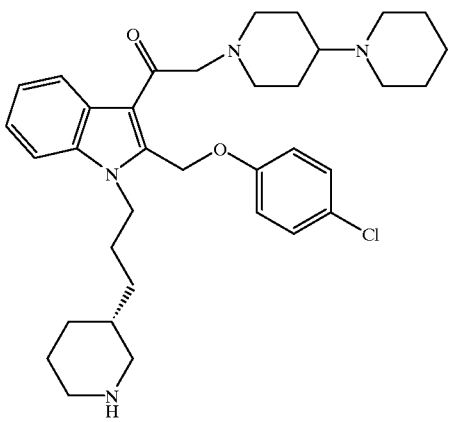

NMR (CDCl$_3$) was consistent with the proposed title structure.

Exact Mass for C35H48ClN4O2: Theory: 591.3466. Found: 591.3458.

EXAMPLE 71

Preparation of 2-[(4-chlorophenoxy)methyl]-1-[3-(piperidin-4-yl)propyl]-3-[[4-(piperidin-1-yl)piperidin-1-yl]acetyl]-1H-indole

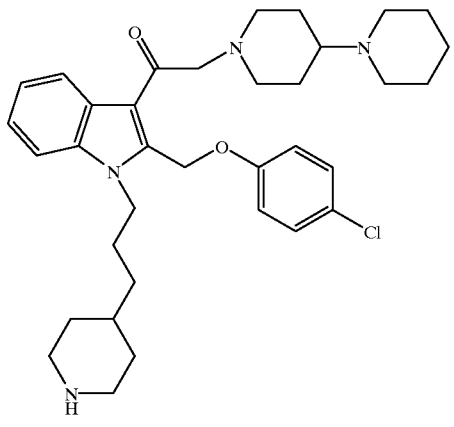

NMR (CDCl₃) was consistent with the proposed title structure.

Exact Mass for $C_{35}H_{48}ClN_4O_2$: Theory: 591.3466. Found: 591.3464.

EXAMPLE 72

Preparation of (RS) 2-[(4-chlorophenoxy)methyl]-1-[3-(piperidin-3-yl)propyl]-3-[3-(piperidin-3-yl)propanoyl]-1H-indole

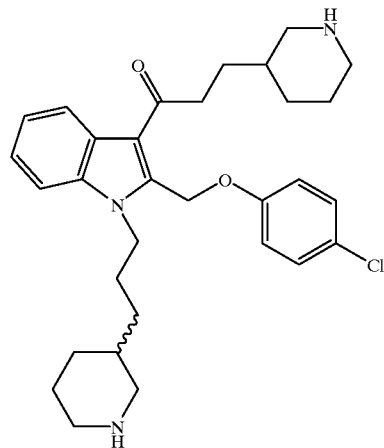

NMR (CDCl₃) was consistent with the proposed title structure.

Exact Mass for $C_{31}H_{41}ClN_3O_2$: Theory: 522.2887. Found: 522.2905.

EXAMPLE 73

Preparation of 2-[(4-chlorophenoxy)methyl]-1-[3-(piperidin-4-yl)propyl]-3-[3-(piperidin-3-yl)propanoyl]-1H-indole

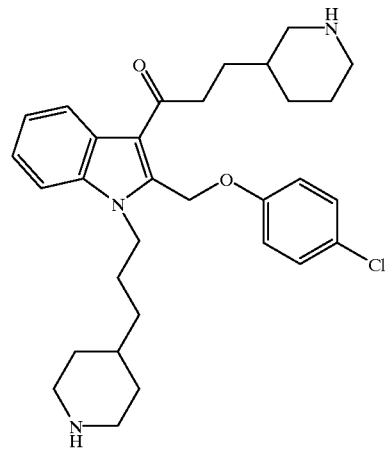

NMR (CDCl₃) was consistent with the proposed title structure.

Exact Mass for $C_{31}H_{41}ClN_3O_2$ (M+1): Theory: 522.2887. Found: 522.2910.

EXAMPLE 74

Preparation of 2-[(4-chlorophenoxy)methyl]-1-[3-(piperidin-3-yl)propyl]-3-[3-(piperidin-4-yl)propanoyl]-1H-indole

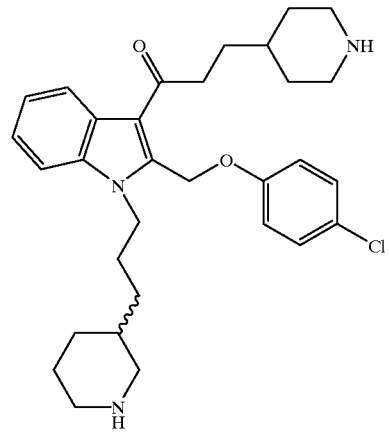

IR and NMR (CDCl₃) were consistent with the desired title structure.

FABMS 522 (M+1)

Analysis for $C_{31}H_{40}ClN_3O_2$: Theory: C, 71.31; H, 7.72; N, 8.05. Found: C, 71.04; H, 7.89; N, 7.78.

EXAMPLE 75

Preparation of 2-[(4-chlorophenoxy)methyl]-1-[3-(piperidin-4-yl)propyl]-3-[3-(piperidin-4-yl)propanoyl]-1H-indole

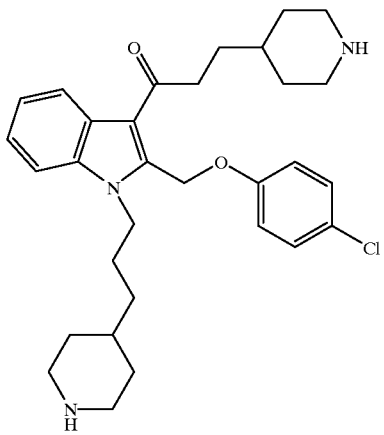

NMR (CDCl$_3$) was consistent with the proposed title structure.
FDMS 522 (M+1)
Analysis for C$_{31}$H$_{40}$ClN$_3$O$_2$: Theory: C, 71.31; H, 7.72; N, 8.05. Found: C, 71.10; H, 7.66; N, 7.97.

EXAMPLE 76
Preparation of 2-[(4-chlorophenoxy)methyl]-1-methyl-3-[[[3-(dimethylamino)propylamino]carbonyl]methyl]-1H-indole

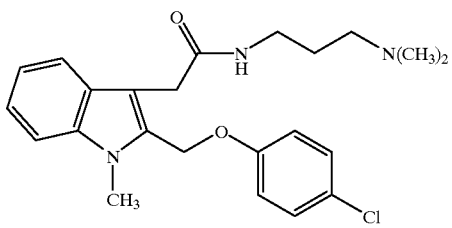

NMR (CDCl$_3$) was consistent with the proposed title structure.
FDMS 413 (M+).
Analysis for C$_{23}$H$_{28}$ClN$_3$O$_2$: Theory: C, 66.74; H, 6.82; N, 10.15. Found: C, 66.89; H, 6.96; N, 10.11.

EXAMPLE 77
Preparation of 2-[(4-chlorophenoxy)methyl]-1-methyl-3-[1-hydroxy-1-[[4-(piperidin-1-yl)piperidin-1-yl]carbonyl]methyl]-1H-indole

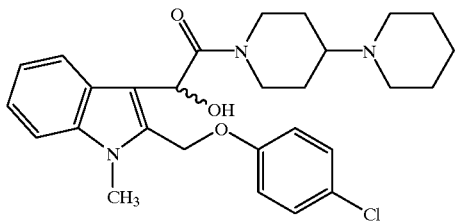

NMR (CDCl$_3$) was consistent with the proposed title structure.
FDMS 495 (M+).
Analysis for C$_{28}$H$_{34}$ClN$_3$O$_3$: Theory: C, 67.80; H, 6.91; N, 8.47. Found: C, 67.86; H, 6.90; N, 8.45.

EXAMPLE 78
Preparation of 2-[1-methyl-2-[(4-chlorophenoxy)methyl]indol-3-yl]glyoxylic acid

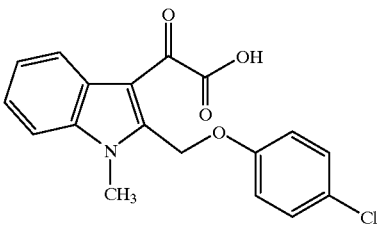

NMR (DMSO) was consistent with the proposed title structure.
FDMS 343 (M+)
Analysis for C$_{18}$H$_{14}$ClNO$_4$: Theory: C, 62.89; H, 4.11; N, 4.07. Found: C, 63.15; H, 4.37; N, 3.92.

EXAMPLE 79
Preparation of methyl 2-[1-methyl-2-[(4-chlorophenoxy)methyl]indol-3-yl]glyoxylate

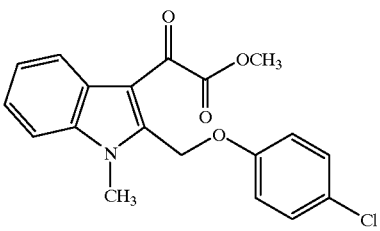

NMR (CDCl$_3$) and IR were consistent with the desired title structure.
Exact Mass FAB (M+1) for C$_{19}$H$_{17}$ClNO$_4$: Theory: 358.0846. Found: 358.0818.

EXAMPLE 80
Preparation of phenyl 2-[1-methyl-2-[(4-chlorophenoxy)methyl]indol-3-yl]glyoxylate

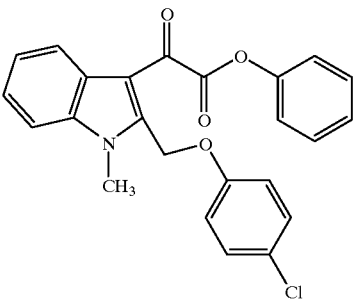

NMR (CDCl$_3$) was consistent with the proposed title structure.
FDMS 419 (M+)
Analysis for C$_{24}$H$_{18}$ClNO$_4$: Theory: C, 68.66; H, 4.32; N, 3.34. Found: C, 68.90; H, 4.49; N, 3.33.

EXAMPLE 81
Preparation of 2-[(4-chlorophenoxy)methyl]-1-methyl-3-[2-amino-1,2-ethanedionyl]-1H-indole

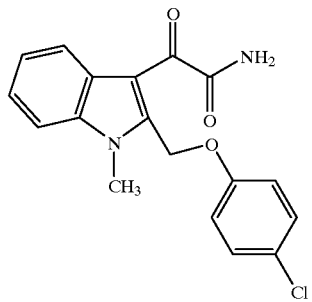

NMR (DMSO) was consistent with the proposed title structure.
FDMS 342 (M+).
Analysis for $C_{18}H_{15}ClN_2O_3$: Theory: C, 63.07; H, 4.41; N, 8.17. Found: C, 63.36; H, 4.50; N, 8.18.

EXAMPLE 82
Preparation of 2-[(4-chlorophenoxy)methyl]-1-methyl-3-[2-methylamino-1,2-ethanedionyl]-1H-indole

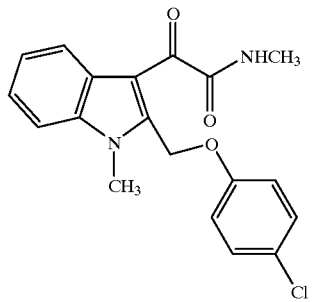

NMR (CDCl$_3$) was consistent with the proposed title structure.
FDMS 357 (M+1)
Analysis for $C_{19}H_{17}ClN_2O_3$: Theory: C, 63.96; H, 4.80; N, 7.85. Found: C, 63.97; H, 4.83; N, 7.82.

EXAMPLE 83
Preparation of 3-dimethylaminopropyl 2-[1-methyl-2-[(4-chlorophenoxy)methyl]indol-3-yl]glyoxylate

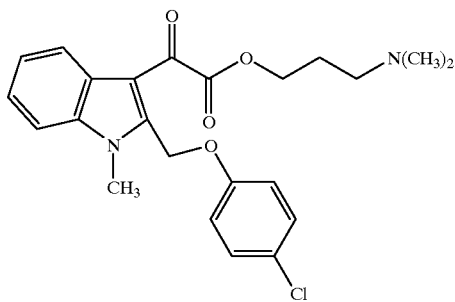

NMR (CDCl$_3$) was consistent with the proposed title structure.
$C_{23}H_{25}ClN_2O_4$: FAB 429 (M+).
Single compound of high purity as evidenced by chromatographic methods.

EXAMPLE 84
Preparation of 2-[(4-chlorophenoxy)methyl]-1-methyl-3-[2-[2-(dimethylamino)ethylamino]-1,2-ethanedionyl]-1H-indole hydrochloride

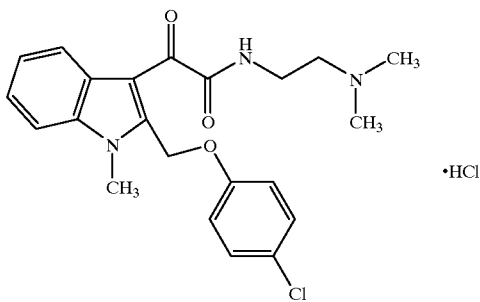

NMR (CDCl$_3$) was consistent with the proposed title structure.
IR was consistent with the desired title structure.
FDMS 413 (M+).
Analysis for $C_{22}H_{24}ClN_3O_3 \cdot HCl$: Theory: C, 58.67; H, 5.59; N, 9.33. Found: C, 58.38; H, 5.82; N, 9.48.

EXAMPLE 85
Preparation of 2-[(4-chlorophenoxy)methyl]-1-methyl-3-[2-[3-(dimethylamino)propylamino]-1,2-ethanedionyl]-1H-indole

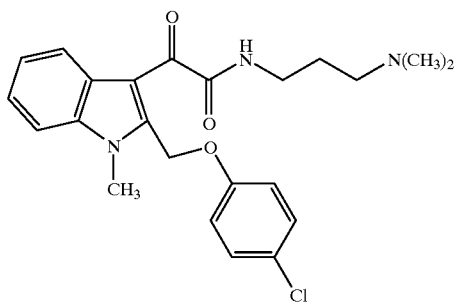

NMR (CDCl$_3$) was consistent with the proposed title structure.
Exact Mass FAB (M+1) for $C_{23}H_{27}ClN_3O_3$: Theory: 428.1741. Found: 428.1738.

EXAMPLE 86
Preparation of 2-[(4-chlorophenoxy)methyl]-1-methyl-3-[2-[3-aminopropylamino]-1,2-ethanedionyl]-1H-indole

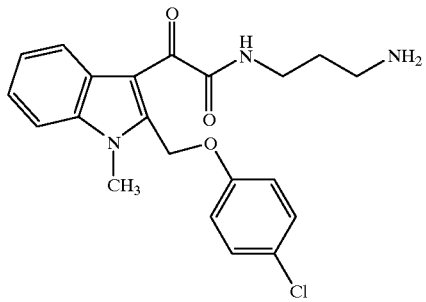

IR, NMR, and UV were consistent with the desired title structure.
FDMS 399 (M+).
Analysis for $C_{21}H_{22}ClN_3O_3$: Theory: C, 63.08; H, 5.55; N, 10.51. Found: C, 69.53; H, 6.18; N, 11.70.
Single compound of high purity as evidenced by chromatographic methods.

EXAMPLE 87

Preparation of 2-[(4-chlorophenoxy)methyl]-1-methyl-3-[2-[3-(t-butoxycarbonylamino)propylamino]-1,2-ethanedionyl]-1H-indole

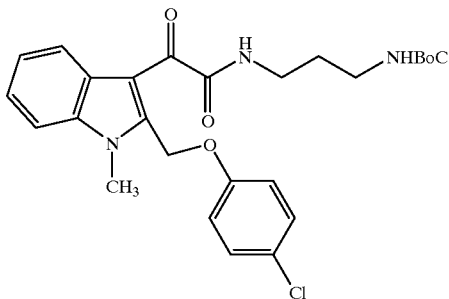

IR, NMR, and UV were consistent with the desired title structure.

FDMS 499 (M+).
mp 175–176° C.
Analysis for $C_{26}H_{30}ClN_3O_5$: Theory: C, 62.46; H, 6.05; N, 8.40. Found: C, 62.19; H, 6.08; N, 8.27.

EXAMPLE 88

Preparation of 2-[(4-chlorophenoxy)methyl]-1-methyl-3-[2-[2,2-dimethyl-3-(dimethylamino)propylamino]-1,2-ethanedionyl]-1H-indole

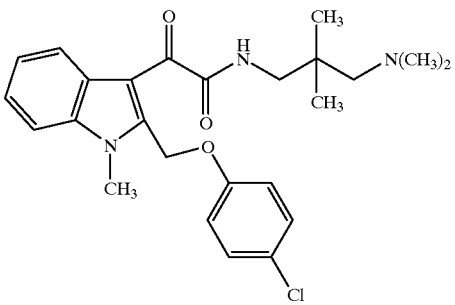

NMR (CDCl$_3$) was consistent with the proposed title structure.

FDMS 455 (M+).
Analysis for $C_{25}H_{30}ClN_3O_3$: Theory: C, 65.85; H, 6.63; N, 9.22. Found: C, 65.62; H, 6.76; N, 9.12.

EXAMPLE 89

Preparation of 2-[(4-chlorophenoxy)methyl]-1-methyl-3-[2-[6-(dimethylamino)hexylamino]-1,2-ethanedionyl]-1H-indole

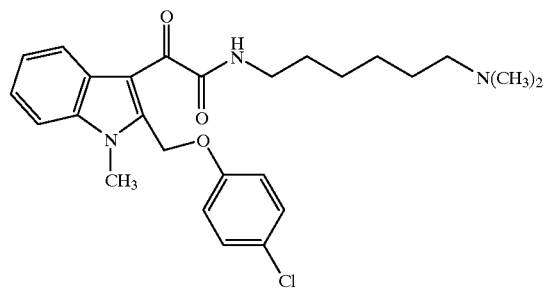

NMR (CDCl$_3$) was consistent with the proposed title structure.

IR was consistent with the desired title structure.

Exact Mass FAB (M+1) for $C_{27}H_{33}ClN_3O_3$: Theory: 470.2210. Found: 470.2196.

EXAMPLE 90

Preparation of 2-[(4-chlorophenoxy)methyl]-1-methyl-3-[2-[N-methyl-2-(dimethylamino)ethylamino]-1,2-ethanedionyl]-1H-indole

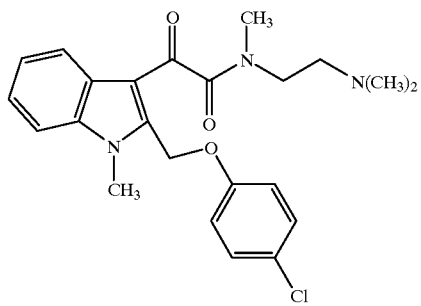

NMR, UV, and IR were consistent with the desired title structure.

FDMS 427 (M+).

mp 142–143° C.

Analysis for $C_{23}H_{26}ClN_3O_3$: Theory: C, 64.56; H, 6.12; N, 9.82. Found: C, 64.82; H, 6.32; N, 9.89.

EXAMPLE 91

Preparation of 2-[(4-chlorophenoxy)methyl]-1-methyl-3-[2-[N-methyl-3(dimethylamino)propylamino]-1,2-ethanedionyl]-1H-indole

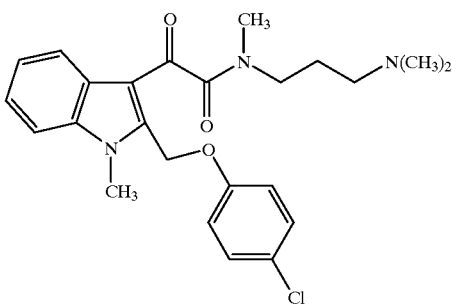

NMR (CDCl$_3$) was consistent with the proposed title structure.

IR was consistent with the desired title structure.

Exact Mass FAB (M+1) for $C_{24}H_{29}ClN_3O_3$: Theory: 442.1897. Found: 442.1904.

EXAMPLE 92

Preparation of 2-[(4-chlorophenoxy)methyl]-1-methyl-3-[2-[N-methyl-3-(dimethylamino)propylamino]-1,2-ethanedionyl]-1H-indole hydrochloride

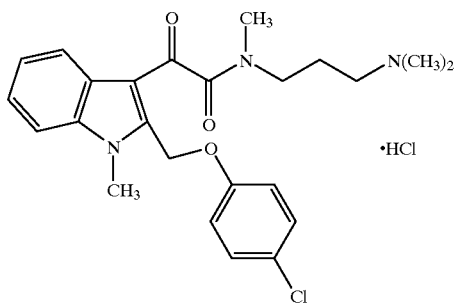

NMR (CDCl₃) was consistent with the proposed title structure.

IR was consistent with the desired title product.

FDMS 441 (M+).

Exact Mass FAB (M+1) for $C_{24}H_{29}ClN_3O_3$: Theory: 442.1897. Found: 442.1895.

EXAMPLE 93

Preparation of 2-[(4-chlorophenoxy)methyl]-1-methyl-3-[2-[bis[3-(dimethylamino)propyl]amino]-1,2-ethanedionyl]n-1H-indole

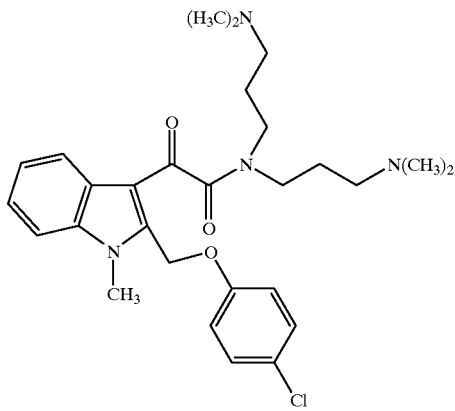

NMR (CDCl₃) was consistent with the proposed title structure.

FDMS 512 (M+)

Analysis for $C_{28}H_{37}ClN_4O_3$: Theory: C, 65.55; H, 7.27; N, 10.92. Found: C, 65.85; H, 7.46; N, 11.04.

EXAMPLE 94

Preparation of 2-[(4-chlorophenoxy)methyl]-1-methyl-3-[2-[N-benzyl-3-(dimethylamino)propylamino]-1,2-ethanedionyl]-1H-indole

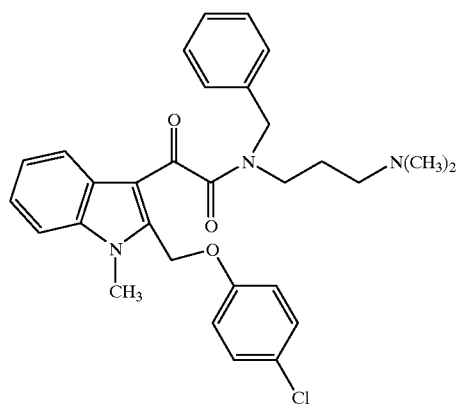

IR, NMR, and UV were consistent with the desired title structure.

FDMS 517 (M+).

Analysis for $C_{30}H_{32}ClN_3O_3$: Theory: C, 69.55; H, 6.23; N, 8.11. Found: C, 69.82; H, 6.31; N, 8.13.

EXAMPLE 95

Preparation of 2-[(4-chlorophenoxy)methyl]-1-methyl-3-[2-[N-methyl-3-[1-(t-butoxycarbonyl)piperidin-3-yl]propylamino]-1,2-ethanedionyl]-1H-indole

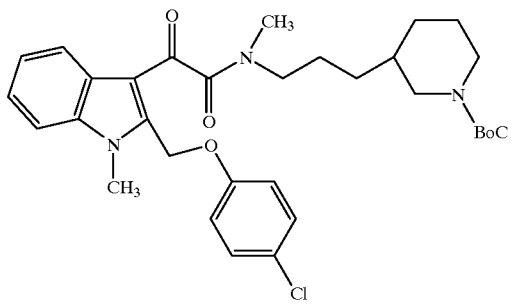

NMR (CDCl₃) was consistent with the proposed title structure.

FDMS 581 (M+).

Analysis for $C_{32}H_{40}ClN_3O_5$: Theory: C, 66.02; H, 6.93; N, 7.22. Found: C, 65.91; H, 7.14; N, 7.08.

EXAMPLE 96

Preparation of 2-[(4-chlorophenoxy)methyl)-1-methyl-3-[2-(1-methylpiperidin-3-yl)amino]-1,2-ethanedionyl]-1H-indole

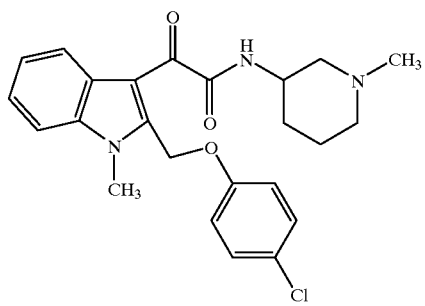

NMR (CDCl₃) was consistent with the proposed title structure.

IR was consistent with the desired title structure.

FDMS 439 (M+).

Analysis for $C_{24}H_{26}ClN_3O_3$: Theory: C, 65.52; H, 5.96; N, 9.55. Found: C, 65.80; H, 5.96; N, 9.56.

EXAMPLE 97

Preparation of 2-[(4-chlorophenoxy)methyl]-1-methyl-3-[2-[N-methyl-(1-methylpyrrolidin-3-yl)amino]-1,2-ethanedionyl]-1H-indole

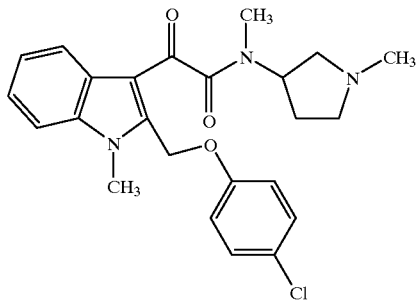

IR, NMR, and UV were consistent with the desired title structure.

FDMS 439 (M+).

Analysis for $C_2 4H_{26}ClN_3O_3$: Theory: C, 65.52; H, 5.96; N, 9.55. Found: C, 65.54; H, 6.03; N, 9.69.

EXAMPLE 98

Preparation of (RS) 2-[(4-chlorophenoxy)methyl]-1-methyl-3-[2-[N-methyl-(1-methylpiperidin-3-yl)amino]-1,2-ethanedionyl]-1H-indole

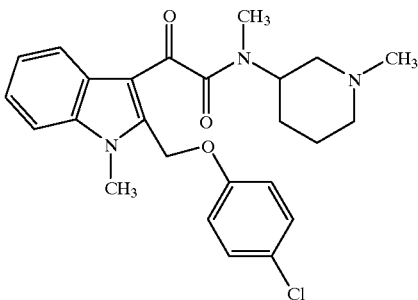

IR was consistent with the desired title structure. FDMS 453 (M+).

Analysis for $C_{25}H_{28}ClN_3O_3$: Theory: C, 66.14; H, 6.22; N, 9.26. Found: C, 65.86; H, 6.17; N, 9.29.

EXAMPLE 99

Preparation of 2-[(4-chlorophenoxy)methyl]-1-methyl-3-[2-[(quinuclidin-3-yl)amino]-1,2-ethanedionyl]-1H-indole

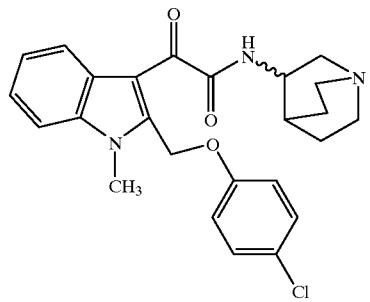

NMR, UV, and IR were consistent with the desired title structure.

FDMS 451 (M+).
mp 204–205° C.

Analysis for $C_{25}H_{26}ClN_3O_3$: Theory: C, 66.44; H, 5.80; N, 9.30. Found: C, 66.37; H, 5.88; N, 9.37.

EXAMPLE 100

Preparation of 2-[(4-chlorophenoxy)methyl]-1-methyl-3-[2-(piperidin-1-yl)-1,2-ethanedionyl]-1H-indole

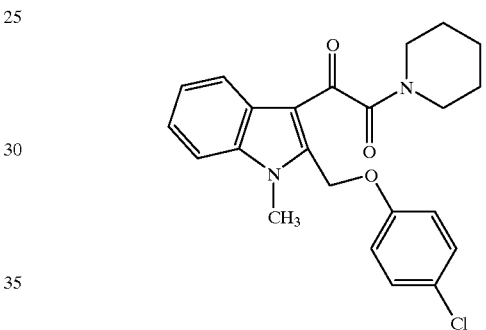

NMR (CDCl₃) was consistent with the proposed title structure.

FDMS 410 (M+).

Analysis for $C_{23}H_{23}ClN_2O_3$: Theory: C, 67.22; H, 5.64; N, 6.82. Found: C, 67.50; H, 5.81; N, 6.63.

EXAMPLE 101

Preparation of 2-[(4-chlorophenoxy)methyl]-1-methyl-3-[2-[2-(dimethylaminomethyl)cyclohexylamino]-1,2-ethanedionyl]-1H-indole hydrochloride

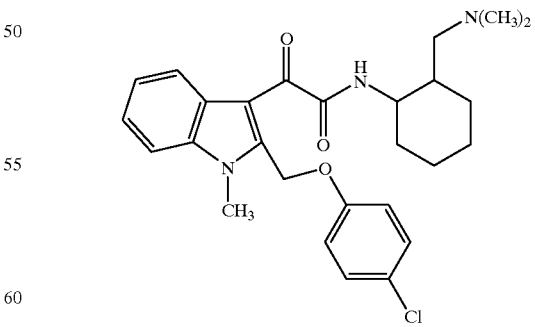

NMR (DMSO) was consistent with the proposed title structure.

FDMS 481 (M+).

Analysis for $C_{27}H_{32}ClN_3O_3 \cdot HCl$: Theory: C, 62.55; H, 6.42; N, 8.10. Found: C, 62.56; H, 6.44; N, 8.06.

EXAMPLE 102

Preparation of 2-[(4-chlorophenoxy)methyl]-1-methyl-3-[2-(4-methylpiperidin-1-yl)-1,2-ethanedionyl]-1H-indole

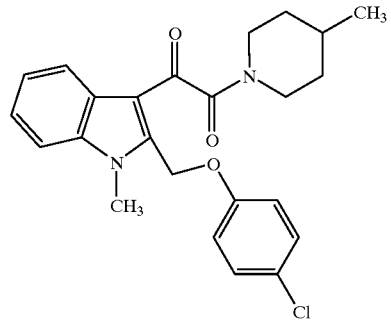

NMR (CDCl$_3$) was consistent with the proposed title structure.

IR was consistent with the desired title structure.

FDMS 424 (M+).

Analysis for C$_{24}$H$_{25}$ClN$_2$O$_3$: Theory: C, 67.84; H, 5.93; N, 6.59. Found: C, 68.04; H, 5.85; N, 6.74.

EXAMPLE 103

Preparation of 2-[(4-chlorophenoxy)methyl]-1-methyl-3-[2-(4-benzylpiperidin-1-yl)-1,2-ethanedionyl]-1H-indole

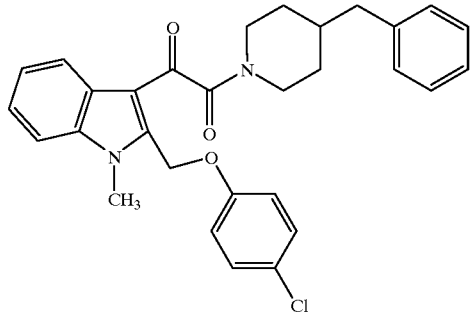

NMR (CDCl$_3$) was consistent with the proposed title structure.

IR was consistent with the desired title structure.

FDMS 500 (M+).

Analysis for C$_{30}$H$_{29}$ClN$_2$O$_3$: Theory: C, 71.92; H, 5.83; N, 5.59. Found: C, 71.69; H, 5.74; N, 5.38.

EXAMPLE 104

Preparation of 2-[(4-chlorophenoxy)methyl]-1-methyl-3-[2-(4-aminocarbonylpiperidin-1-yl)-1,2-ethanedionyl]-1H-indole

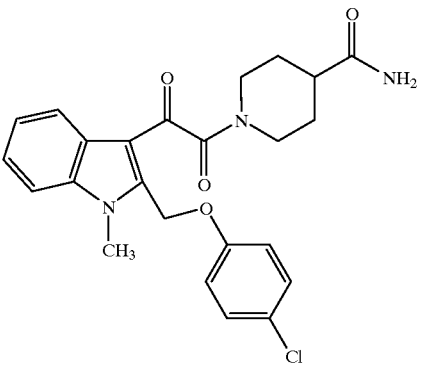

NMR, UV, and IR were consistent with the desired title structure.

FDMS 453 (M+).

mp 220–221° C.

Analysis for C$_{24}$H$_{24}$ClN$_3$O$_4$: Theory: C, 63.50; H, 5.33; N, 9.26. Found: C, 63.45; H, 5.50; N, 9.18.

EXAMPLE 105

Preparation of 2-[(4-chlorophenoxy)methyl]-1-methyl-3-[2-(4-dimethylaminopiperidin-1-yl)-1,2-ethanedionyl]-1H-indole

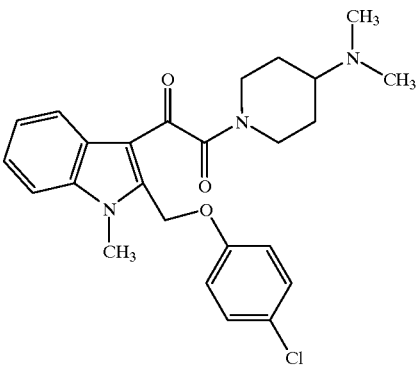

NMR (CDCl$_3$) was consistent with the proposed title structure.

Exact Mass FAB (M+1) for C$_{25}$H$_{29}$ClN$_3$O$_3$: Theory: 454.1897. Found: 454.1882.

EXAMPLE 106

Preparation of 2-[(4-chlorophenoxy)methyl]-1-methyl-3-[2-[4-(piperidin-1-yl)piperidin-1-yl]-1,2-ethanedionyl]-1H-indole

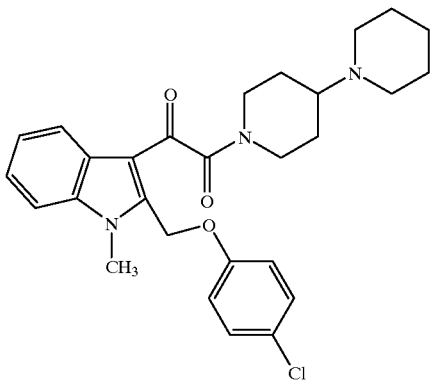

NMR (CDCl₃) and IR were consistent with the proposed title structure.

FDMS 493 (M+)

Analysis for $C_{28}H_{32}ClN_3O_3$: Theory: C, 68.07; H, 6.53; N, 8.51. Found: C, 67.97; H, 6.66; N, 8.27.

EXAMPLE 107

Preparation of 2-[(4-chlorophenoxy)methyl]-1-methyl-3-[2-(3-aminocarbonylpiperidin-1-yl)-1,2-ethanedionyl]-1H-indole

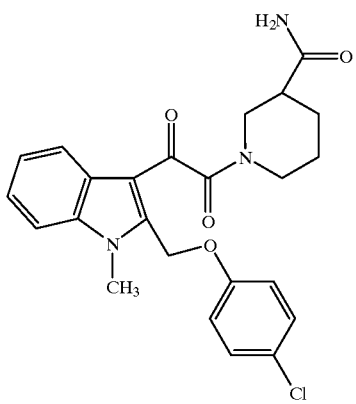

IR, NMR, and UV were consistent with the desired title structure.

FDMS 453.

mp 229–230° C.

Analysis for $C_{24}H_{24}ClN_3O_4$: Theory: C, 63.50; H, 5.33; N, 9.26. Found: C, 63.53; H, 5.44; N, 9.04.

EXAMPLE 108

Preparation of 2-[(4-chlorophenoxy)methyl]-1-methyl-3-[2-(piperazin-1-yl)-1,2-ethanedionyl]-1H-indole

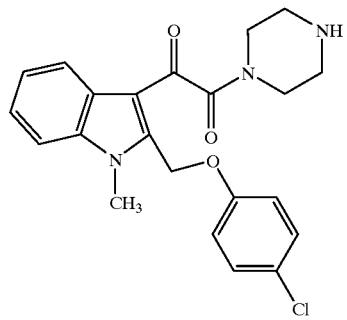

NMR (CDCl₃) was consistent with the proposed title structure.

FDMS 411 (M+)

mp 168–169° C.

Analysis for $C_{22}H_{22}ClN_3O_3$: Theory: C, 64.15; H, 5.38; N, 10.20. Found: C, 63.95; H, 5.36; N, 10.08.

EXAMPLE 109

Preparation of 2-[(4-chlorophenoxy)methyl]-1-methyl-3-[2-(4-isopropylpiperazin-1-yl)-1,2-ethanedionyl]-1H-indole

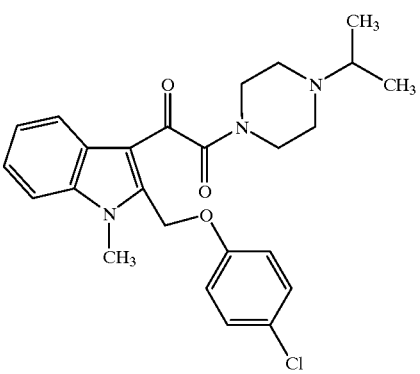

NMR (CDCl₃) was consistent with the proposed title structure.

FDMS 453 (M+).

Analysis for $C_{25}H_{28}ClN_3O_3$: Theory: C, 66.15; H, 6.22; N, 9.26. Found: C, 65.94; H, 6.48; N, 8.97.

EXAMPLE 110

Preparation of 2-[(4-chlorophenoxy)methyl]-1-methyl-3-[2-[4-(t-butoxycarbonyl)piperazin-1-yl]-1,2-ethanedionyl]-1H-indole

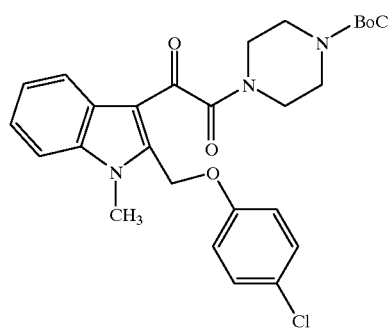

IR, NMR, and UV were consistent with the desired title structure.

FDMS 511 (M+).

mp 200–201° C.

Analysis for $C_{27}H_{30}ClN_3O_5$: Theory: C, 63.34; H, 5.91; N, 8.21. Found: C, 63.10; H, 5.80; N, 7.98.

EXAMPLE 111

Preparation of 2-[(4-chlorophenoxy)methyl]-1-methyl-3-[2-(4-cyclohexylpiperazin-1-yl)-1,2-ethanedionyl]-1H-indole

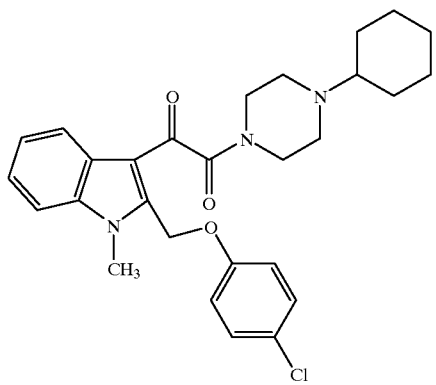

NMR (CDCl$_3$) was consistent with the proposed title structure.

IR was consistent with the desired title structure.

FDMS 493 (M+).

Analysis for $C_{28}H_{32}ClN_3O_3$: Theory: C, 68.07; H, 6.53; N, 8.50. Found: C, 67.81; H, 6.60; N, 8.24.

EXAMPLE 112

Preparation of 2-[(4-chlorophenoxy)methyl]-1-methyl-3-[2-[4-(2-dimethylaminoethyl)piperazin-1-yl)-1,2-ethanedionyl]-1H-indole dihydrochloride

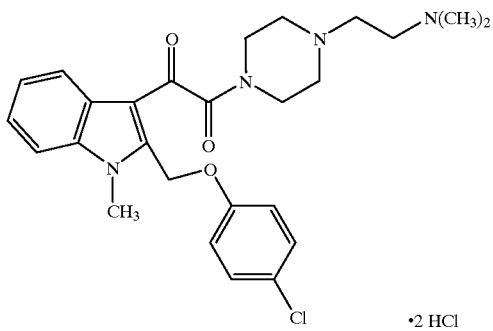

NMR (CDCl$_3$) was consistent with the proposed title structure.

IR was consistent with the desired title structure.

FDMS 482 (M+).

Analysis for $C_{26}H_{31}ClN_4O_3 \cdot 2HCl$: Theory: C, 56.17; H, 5.98; N, 10.07. Found: C, 56.47; H, 6.07; N, 10.05.

EXAMPLE 113

Preparation of 2-[(4-chlorophenoxy)methyl]-1-methyl-3-[2-[3-aminoacetylpyrrolidin-1-yl)-1,2-ethanedionyl]-1H-indole

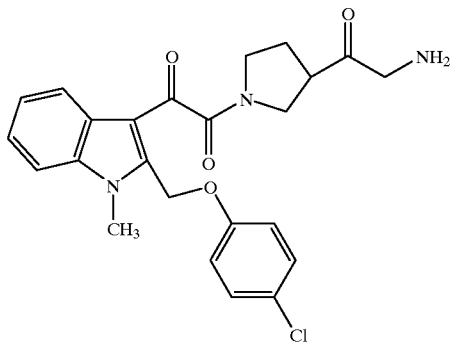

NMR (CDCl$_3$) was consistent with the proposed title structure.

IR was consistent with the desired title structure.

FDMS 453 (M+).

Analysis for $C_{24}H_{24}ClN_3O_4$: Theory: C, 63.50; H, 5.33; N, 9.26. Found: C, 63.75; H, 5.37; N, 9.21.

EXAMPLE 114

Preparation of 2-[(2,4-dichlorophenoxy)methyl]-1-methyl-3-[2-[N-methyl-3-(dimethylamino)propylamino]-1,2-ethanedionyl]-1H-indole

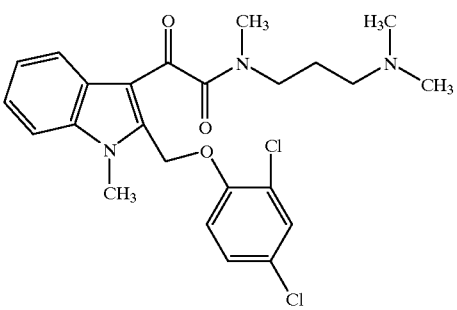

NMR (CDCl$_3$) was consistent with the proposed title structure.

UV was consistent with the desired title structure.

FDMS 475 (M+).

Analysis for $C_{24}H_{27}Cl_2N_3O_3$: Theory: C, 60.51; H, 5.71; N, 8.82. Found: C, 60.69; H, 5.80; N, 8.77.

EXAMPLE 115

Preparation of 2-[(2,4-dichlorophenoxy)methyl]-1-methyl-3-[2-[N-methyl-(1-methylpiperidin-4-yl)amino]-1,2-ethanedionyl]-1H-indole

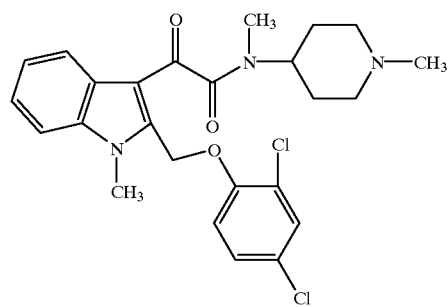

NMR (CDCl$_3$) was consistent with the proposed title structure.

$C_{25}H_{27}ClN_3O_3$: FDMS 487 (M+) Single compound of high purity as evidenced by chromatographic methods.

EXAMPLE 116

Preparation of 2-[(2,4-dichlorophenoxy)methyl]-1-methyl-3-[2-[4-(N,N-dimethylamino)piperidin-1-yl]-1,2-ethanedionyl]-1H-indole

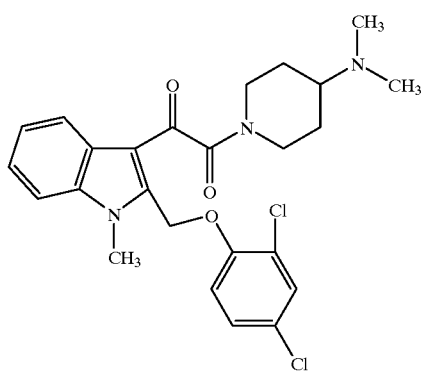

NMR (CDCl₃) was consistent with the proposed title structure.

UV was consistent with the desired title structure.

FDMS 487,489 (M+).

Analysis for $C_{25}H_{27}Cl_2N_3O_3$: Theory: C, 61.48; H, 5.57; N, 8.60. Found: C, 61.75; H, 5.63; N, 8.59.

EXAMPLE 117

Preparation of 2-[(2,4-dichlorophenoxy)methyl]-1-methyl-3-[2-[(4-(piperidin-1-yl)piperidin-1-yl]-1,2-ethanedionyl]-1H-indole

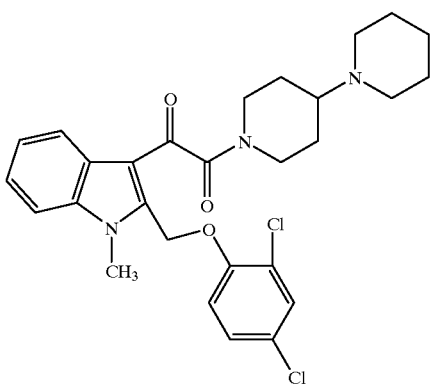

IR, NMR, and IN were consistent with the desired title structure.

FDMS 527,529 (M+).

Analysis for $C_{28}H_{31}Cl_2N_3O_3$: Theory: C, 63.64; H, 5.91; N, 7.95. Found: C, 63.82; H, 6.08; N, 7.85.

EXAMPLE 118

Preparation of 2-[(2-cyano-4-bromophenoxy)methyl]-1-methyl-3-[2-[N-methyl-(3-dimethylaminopropyl)amino]-1,2-ethanedionyl]-1H-indole

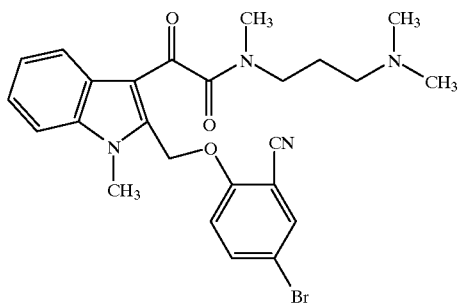

IR, NMR, and UV were consistent with the desired title structure.

FDMS 511,513 (M+).

Analysis for $C_{25}H_{27}BrN_4O_3 \cdot 0.5H_2O$: Theory: C, 57.70; H, 5.42; N, 10.75. Found: C, 57.56; H, 5.36; N, 10.60.

Exact Mass for $C_{25}H_{28}BrN_4O_3$: Theory: 511.1332. Found: 511.1345.

EXAMPLE 119

Preparation of 2-[(2-cyano-4-bromophenoxy)methyl]-1-methyl-3-[2-[N-methyl-(1-methylpiperidin-4-yl)amino]-1,2-ethanedionyl]-1H-indole

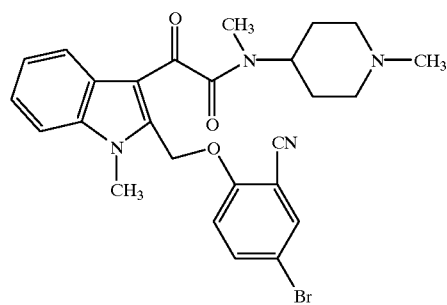

IR, NMR, and UV were consistent with the desired title structure.

FDMS 522,524 (M+).

Analysis for $C_{26}H_{27}BrN_4O_3$: Theory: C, 59.66; H, 5.20; N, 10.70. Found: C, 59.38; H, 5.24; N, 10.49.

EXAMPLE 120

Preparation of 2-[(2-cyano-4-bromophenoxy)methyl]-1-methyl-3-[2-(4-dimethylaminopiperidin-1-yl)]-1,2-ethanedionyl]-1H-indole

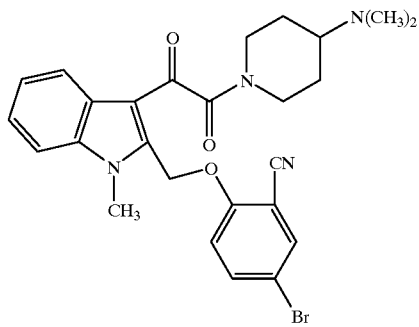

IR, NMR, and UV were consistent with the desired title structure.

FDMS 522,524 (M+).

Analysis for $C_{26}H_{27}BrN_4O_3 \cdot 0.5H_2O$: Theory: C, 58.65; H, 5.30; N, 10.52. Found: C, 58.61; H, 5.21; N, 10.42.

Exact Mass for $C_{26}H_{28}BrN_4O_3$: Theory: 523.1345. Found: 523.1365.

EXAMPLE 121

Preparation of 2-[(2-cyano-4-bromophenoxy)methyl]-1-methyl-3-[2-[4-(piperidin-1-yl)piperidin-1-yl]]-1,2-ethanedionyl]-1H-indole

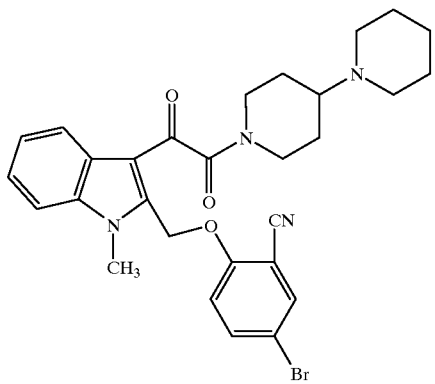

IR, NMR, and UV were consistent with the desired title structure.

FDMS 563,565 (M+).

Analysis for $C_{29}H_{31}BrN_4O_3$: Theory: C, 61.81; H, 5.54; N, 9.94. Found: C, 61.56; H, 5.62; N, 9.91.

EXAMPLE 122

Preparation of 2-[(4-chlorophenoxy)methyl]-1-ethyl-3-[2-(4-dimethylaminopiperidin-1-yl)]-1,2-ethanedionyl]-1H-indole

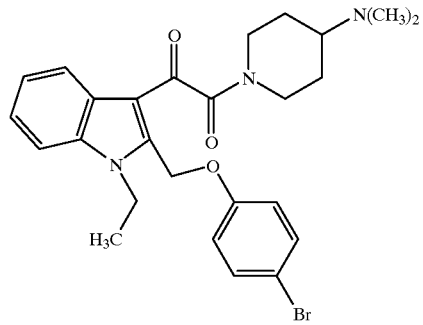

IR, NMR, and UV were consistent with the desired title structure.

FDMS 467.

Analysis for $C_{26}H_{30}ClN_3O_3$: Theory: C, 66.73; H, 6.46; N, 8.98. Found: C, 66.88; H, 6.57; N, 8.90.

EXAMPLE 123

Preparation of 2-[(4-chlorophenoxy)methyl]-1-ethyl-3-[2-[N-methyl-(1-methylpiperidin-4-yl)amino]-1,2-ethanedionyl]-1H-indole

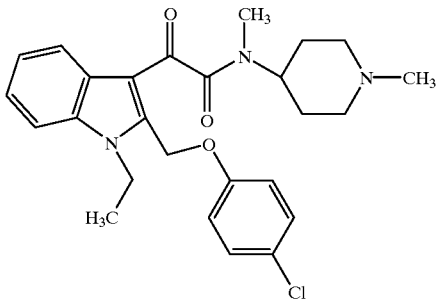

IR, NMR, and UV were consistent with the desired title structure.

FDMS 467.

Analysis for $C_{26}H_{30}ClN_3O_3$: Theory: C, 66.73; H, 6.46; N, 8.98. Found: C, 66.90; H, 6.70; N, 9.03.

EXAMPLE 124

Preparation of 2-[(4-chlorophenoxy)methyl]-1-benzyl-3-[2-(4-dimethylaminopiperidin-1-yl)]-1,2-ethanedionyl]-1H-indole

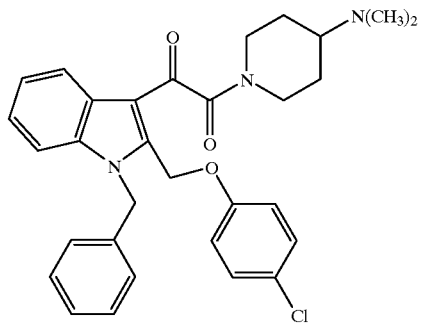

IR, NMR, and UN were consistent with the desired title structure.

FDMS 529.

Analysis for $C_{31}H_{32}ClN_3O_3$: Theory: C, 70.24; H, 6.08; N, 7.93. Found: C, 70.26; H, 6.18; N, 7.73.

EXAMPLE 125

Preparation of 2-[(4-chlorophenoxy)methyl]-1-(2-piperidin-1-ylethyl)-3-[2-[4-(piperidin-1-yl)piperidin-1-yl]-1,2-ethanedionyl]-1H-indole

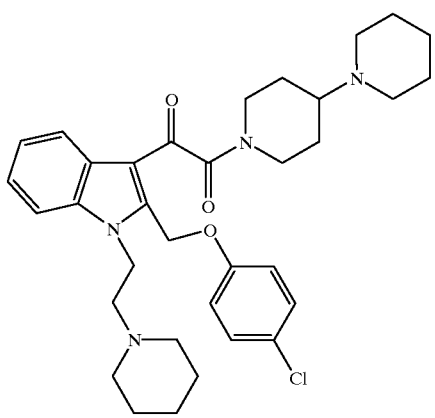

NMR (CDCl$_3$) was consistent with the proposed title structure.

Exact Mass FAB for $C_{34}H_{44}ClN_4O_5$: Theory: 591.3102. Found: 591.3100.

EXAMPLE 126

Preparation of 2-[(4-chlorophenoxy)methyl]-1-[3-(piperidin-3-yl)propyl)-3[piperidin-1-ylmethyl]-1H-indole

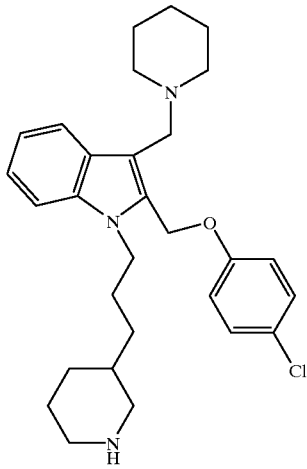

NMR (CDCl$_3$) was consistent with the proposed title structure.

Single compound of high purity as evidenced by chromatographic methods.

EXAMPLE 127

Preparation of 2-[(4-chlorophenoxy)methyl]-1-[3-(1-methylpiperidin-3-yl)propyl)-3-[piperidin-1-ylmethyl]-1H-indole

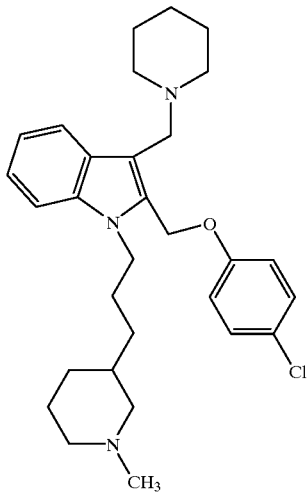

NMR (CDCl$_3$) was consistent with the proposed title structure.

Single compound of high purity as evidenced by chromatographic methods.

EXAMPLE 128

Preparation of 2-[(4-chlorophenoxy)methyl]-1-ethyl-3-[(4-dimethylaminopiperidin-1-yl)methyl]-1H-indole

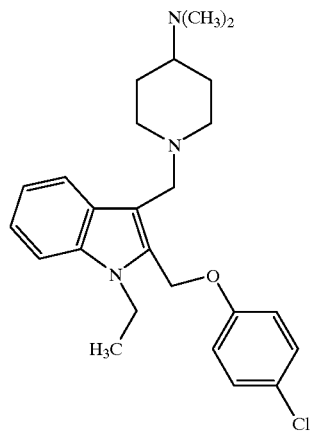

NMR and UV were consistent with the desired title structure. FDMS 425 (M+). mp 115–116° C.

Analysis for $C_{25}H_{32}ClN_3O$: Theory: C, 70.49; H, 7.57; N, 9.86. Found: C, 70.70; H, 7.67; N, 9.80.

EXAMPLE 129

Preparation of 2-[(4-chlorophenoxy)methyl]-1-benzyl-3-[(4-dimethylaminopiperidin-1-yl)methyl]-1H-indole

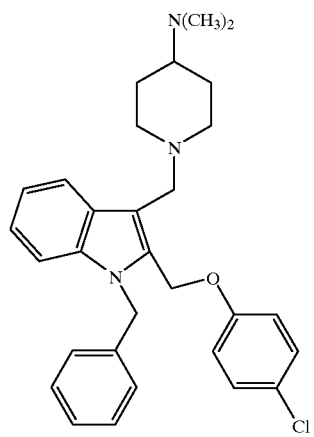

NMR and UV were consistent with the desired title structure. FDMS 488 (M+). mp 127–128° C.

Analysis for $C_{30}H_{34}ClN_3O$: Theory: C, 73.83; H, 7.02; N, 8.61. Found: C, 73.77; H, 7.21; N, 8.66.

EXAMPLE 130

Preparation of 2-[(4-chlorophenoxy)methyl]-1-[2-(piperidin-1-yl)ethyl]-3-[(4-dimethylaminopiperidin-1-yl)methyl]-1H-indole

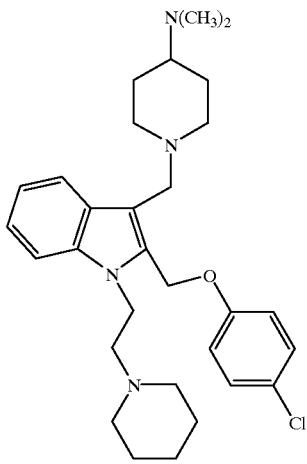

NMR (CDCl₃) was consistent with the proposed title structure.

Exact Mass FAB for $C_{30}H_{42}ClN_4O$: Theory: 509.3047. Found 509.3018.

EXAMPLE 131

Preparation of 2-[(4-chlorophenoxy)methyl]-1-[3-(piperidin-1-yl)propyl]-3-[(4-dimethylaminopiperidin-1-yl)methyl]-1H-indole trihydrochloride

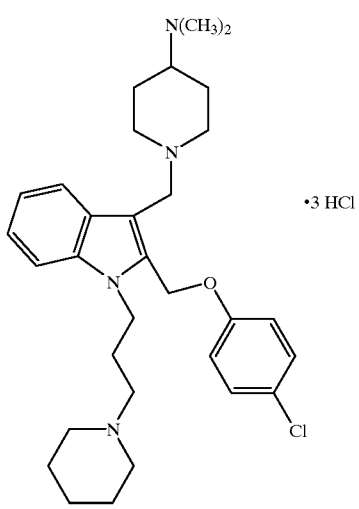

NMR and UV were consistent with the desired title structure.

FDMS 523 (M+1).

mp 240–242° C.

Analysis for $C_{31}H_{43}ClN_4O\cdot 3HCl$: Theory: C, 58.86; H, 7.33; N, 8.86. Found: C, 58.66; H, 7.09; N, 8.77.

EXAMPLE 132

Preparation of 2-[(4-chlorophenoxy)methyl]-1-[3-(piperidin-3-yl)propyl]-3-[(4-dimethylaminopiperidin-1-yl)methyl]-1H-indole

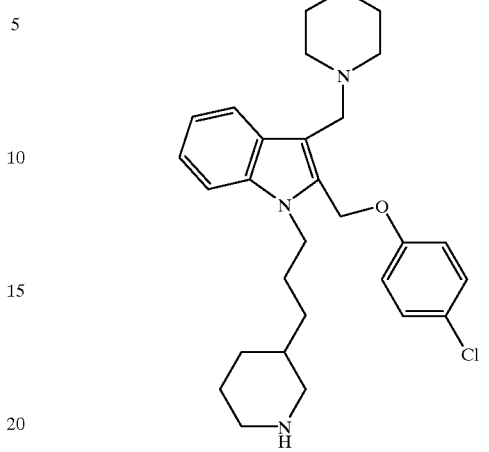

NMR (CDCl₃) was consistent with the proposed title structure.

$C_{31}H_{43}ClN_4O$: FDMS 522 (M+)

Single compound of high purity as evidenced by chromatographic methods.

EXAMPLE 133

Preparation of 2-[(4-chlorophenoxy)methyl]-1-ethyl-3-[[4-(piperidin-1-yl)piperidin-1-yl]methyl]-1H-indole

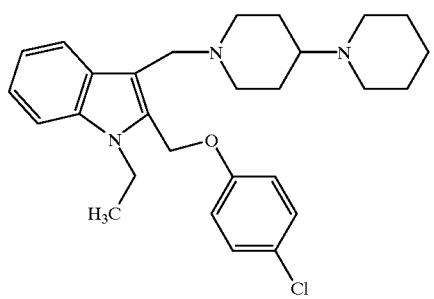

NMR and UV were consistent with the desired title structure. FDMS 465 (M+). mp 130–131° C.

Analysis for $C_{28}H_{36}ClN_3O$: Theory: C, 72.16; H, 7.79; N, 9.02. Found: C, 72.12; H, 7.78; N, 8.86.

EXAMPLE 134

Preparation of 2-[(4-chlorophenoxy)methyl]-1-benzyl-3-[[4-(piperidin-1-yl)piperidin-1-yl]methyl]-1H-indole

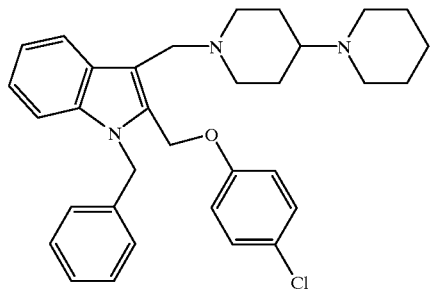

NMR and UV were consistent with the desired title structure.

FDMS 527 (M+).

mp 153–154° C.

Analysis for $C_{33}H_{38}ClN_3O$: Theory: C, 75.05; H, 7.25; N, 7.96. Found: C, 75.25; H, 7.40; N, 8.08.

EXAMPLE 135

Preparation of 2-[(4-chlorophenoxy)methyl]n-1-[2-(piperidin-1-yl)ethyl]-3-[[4-(piperidin-1-yl)piperidin-1-yl]methyl]-1H-indole

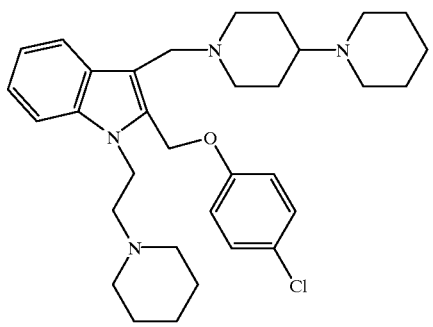

IR, NMR, and UN were consistent with the desired title structure.

FDMS 548 (M+)

mp 102–103° C.

Analysis for $C_{33}H_{45}ClN_4O$: Theory: C, 72.17; H, 8.26; N, 10.20. Found: C, 72.12; H, 8.31; N, 10.17.

EXAMPLE 136

Preparation of 2-[(4-chlorophenoxy)methyl]-1-[2-(piperidin-1-yl)ethyl]-1H-indole

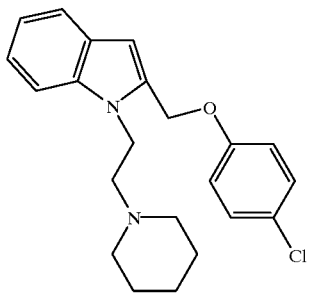

IR, NMR, and UV were consistent with the desired title structure.

FDMS 368 (M+).

FAB 369 (M+1).

Analysis for $C_{22}H_{25}ClN_2O$: Theory: C, 71.63; H, 6.83; N, 7.59. Found: C, 71.93; H, 7.28; N, 7.22.

Single compound of high purity as evidenced by chromatographic methods.

EXAMPLE 137

Preparation of 2-[(4-chlorophenoxy)methyl]-1-[2-(piperidin-4-yl)ethyl]-1H-indole

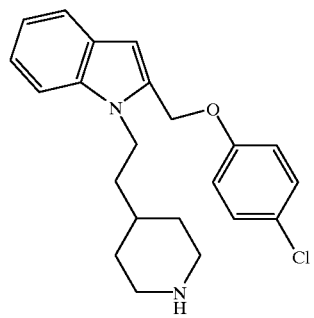

NMR (CDCl$_3$) was consistent with the proposed title structure.

FDMS 368 (M+).

Analysis for $C_{22}H_{25}ClN_2O$: Theory: C, 71.63; H, 6.83; N, 7.59. Found: C, 71.66; H, 6.86; N, 7.87

EXAMPLE 138

Preparation of 2-[(phenylthio)methyl]-1-[3-(piperidin-3-yl)propyl]-1H-indole

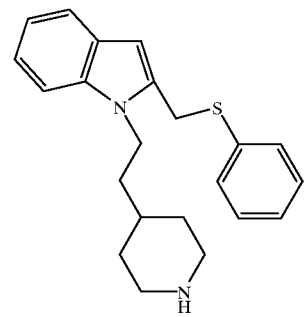

NMR (CDCl$_3$) was consistent with the proposed title structure.

FDMS 364 (M+).

Analysis for $C_{23}H_{28}N_2S$: Theory: C, 75.78; H, 7.75; N, 7.69. Found: C, 75.70; H, 7.73; N, 7.86.

EXAMPLE 139

Preparation of 2-[(4-chlorophenoxy)methyl]-1-[3-(piperidin-3-yl)propyl]-1H-indole

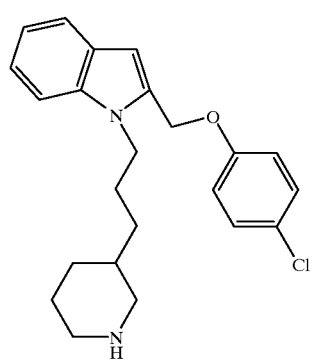

NMR (CDCl$_3$) was consistent with the proposed title structure.

Single compound of high purity as evidenced by chromatographic methods.

EXAMPLE 140

Preparation of 2-[(4-chlorophenoxy)methyl]-1-[3-(1-methylpiperidin-3-yl)propyl]-1H-indole

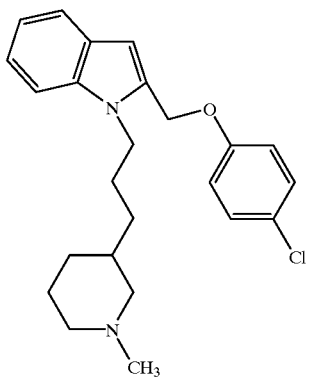

NMR and UV were consistent with the desired title structure.

mp 97–98° C.

Analysis for $C_{24}H_{29}ClN_2O$: Theory: C, 72.62; H, 7.36; N, 7.06. Found: C, 72.59; H, 7.48; N, 7.14.

EXAMPLE 141

Preparation of 2-[(4-chlorophenoxy)methyl]-1-[3-(piperidin-4-yl)propyl]-1H-indole

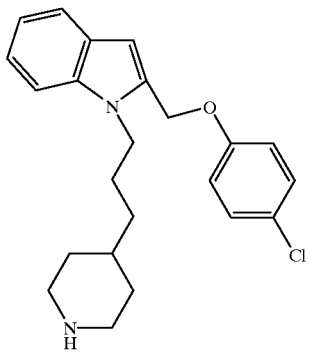

NMR (CDCl$_3$) was consistent with the proposed title structure.

$C_{23}H_{27}ClN_2O$: FDMS 382 (M+)

Single compound of high purity as evidenced by chromatographic methods.

EXAMPLE 142

Preparation of 2-[2-(4-chlorophenyl)ethyl]-1-methyl-3-[(piperidin-1-yl)methyl]-1H-indole hydrochloride

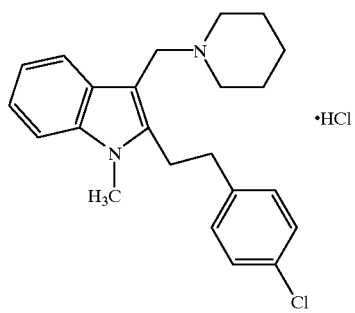

NMR (CDCl$_3$) was consistent with the proposed title structure.

FDMS 366 (M+).

Analysis for $C_{23}H_{27}ClN_2 \cdot HCl$: Theory: C, 68.48; H, 7.00; N, 6.94. Found: C, 68.26; H, 6.87; N, 6.75.

EXAMPLE 143

Preparation of 2-[(4-chlorophenylamino)methyl]-1-methyl-3-[(piperidin-1-yl)methyl]-1H-indole

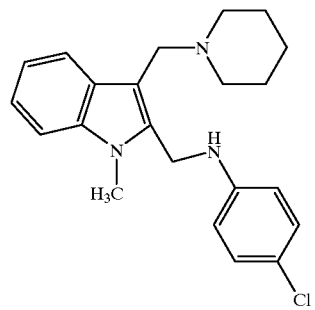

NMR, V, and IR were consistent with the desired title structure.

FDMS 367 (M+).

mp 169° C.

Analysis for $C_{22}H_{26}ClN_3$: Theory: C, 71.82; H, 7.12; N, 11.42. Found: C, 71.60; H, 7.05; N, 11.46.

EXAMPLE 146

Preparation of 2-[(2,4-dichlorophenylamino)methyl]-1-methyl-3-[(piperidin-1-yl)methyl]-1H-indole

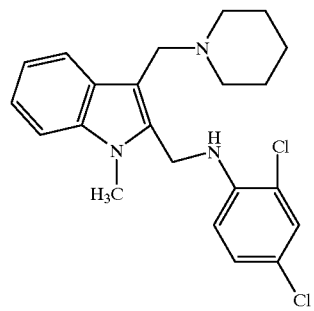

NMR, UV, and IR were consistent with the desired title structure.

FDMS 401,403 (M+).

mp 147–148° C.

Analysis for $C_{22}H_{25}Cl_2N_3$: Theory: C, 65.67; H, 6.26; N, 10.44. Found: C, 65.48; H, 6.30; N, 10.59.

EXAMPLE 147

Preparation of 2-[(4-chlorophenylamino)methyl]-3-[(piperidin-1-yl)methyl]-1H-indole

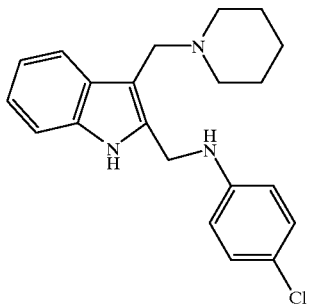

NMR, UV, and IR were consistent with the desired title structure.
FDMS 353, 354 (M+). mp 135° C.
Analysis for $C_{21}H_{24}ClN_3$: Theory: C, 71.27; H, 6.84; N, 11.87. Found: C, 71.90; H, 7.17; N, 12.02.

EXAMPLE 148

Preparation of 2-[(2,4-dichlorophenylamino)methyl]-1-methyl-3-[(piperidin-1-yl)methyl]-1H-indole

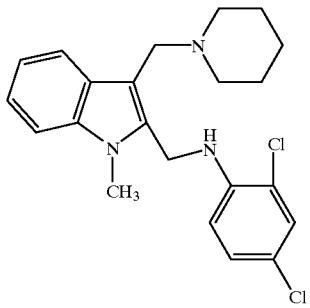

NMR (CDCl$_3$) was consistent with the proposed title structure.
FDMS 401 (M+)
mp 147–148° C.
Analysis for $C_{22}H_{25}Cl_2N_3$: Theory: C, 65.47; H, 6.26; N, 10.44. Found: C, 65.48; H, 6.30; N, 10.59.

EXAMPLE 149

Preparation of 2-[(cyclohexylamino)methyl]-1-methyl-3-[(piperidin-1-yl)methyl]-1H-indole

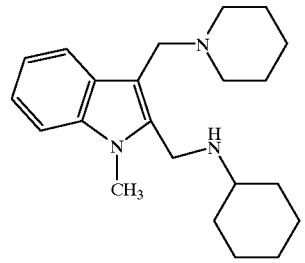

NMR, UV, and IR were consistent with the desired title structure.
FDMS 339 (M+).
mp 162–164° C.
Analysis for $C_{22}H_{33}N_3$: Theory: C, 77.83; H, 9.80; N, 12.38. Found: C, 75.98; H, 9.11; N, 12.67.
Exact Mass FAB for $C_{22}H_{34}N_3$: Theory: 340.2753. Found: 340.2770.

EXAMPLE 150

Preparation of 2-[(cyclohexylmethylamino)methyl]-1-methyl-3-[(piperidin-1-yl)methyl]-1H-indole dihydrochloride

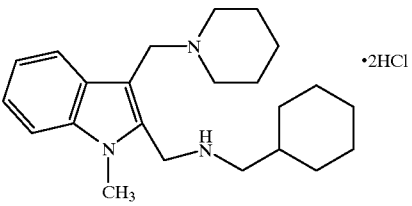

NMR, UV, and IR were consistent with the desired title structure.
FDMS 354, 390 (M+).
mp 159–161° C.
Analysis for $C_{23}H_{35}N_3 \cdot 2HCl$: Theory: C, 64.78; H, 8.75; N, 9.85. Found: C, 64.62; H, 8.82; N, 9.65.

EXAMPLE 151

Preparation of 2-[(naphth-2-ylamino)methyl]-1-methyl-3-[(piperidin-1-yl)methyl]-1H-indole

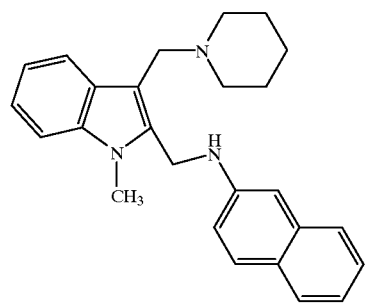

NMR (CDCl$_3$), IR, and UV were consistent with the proposed title structure.
FDMS 383 (M+).
mp 144° C.
Analysis for $C_{26}H_{29}N_3$: Theory: C, 81.42; H, 7.62; N, 10.96. Found: C, 81.26; H, 7.49; N, 10.89.

EXAMPLE 152

Preparation of 2-[[N-acetyl-N-(cyclohexylmethyl)amino]methyl]-1-methyl-3-[(piperidin-1-yl)methyl]-1H-indole hydrochloride

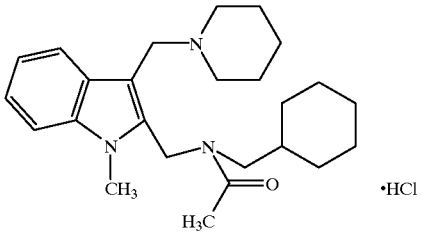

NMR, IV, and IR were consistent with the desired title structure.
FDMS 395 (M+).
Analysis for $C_{25}H_{37}N_3O \cdot HCl$: Theory: C, 69.50; H, 8.87; N, 9.73. Found: C, 68.87; H, 9.29; N, 9.30.
Exact Mass FAB for $C_{25}H_{38}N_3O$: Theory: 396.3015 Found: 396.3020

EXAMPLE 153

Preparation of 2-[[N-acetyl-N-(benzyl)amino]methyl]-1-methyl-3-[(piperidin-1-yl)methyl]-1H-indole hydrochloride

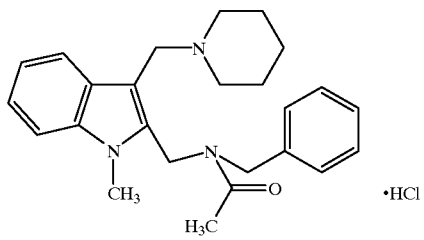

NMR, UV, and IR were consistent with the desired title structure.

FDMS 389 (M+).

mp 148–150° C.

Analysis for $C_{25}H_{31}N_3O \cdot HCl$: Theory: C, 70.49; H, 7.57; N, 9.86. Found: C, 70.21; H, 7.40; N, 9.73.

EXAMPLE 154

Preparation of 2-[[(3-chlorophenyl)amino]carbonyl]-1-methyl-3-[(piperidin-1-yl)methyl]-1H-indole

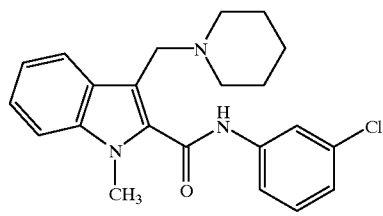

NMR, UV, and IR were consistent with the desired title structure.

FDMS 381, 383 (M+).

mp 137–138° C.

Analysis for $C_{22}H_{24}ClN_3O$: Theory: C, 69.19; H, 6.33; N, 11.00. Found: C, 69.39; H, 6.39; N, 11.20.

EXAMPLE 155

Preparation of 2-[[(2,4-dichlorophenyl)amino]carbonyl]-1-methyl-3-[(piperidin-1-yl)methyl]-1H-indole

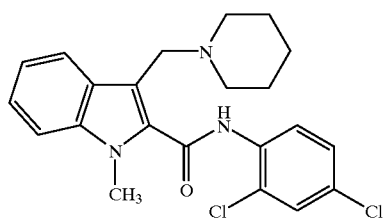

NMR, UV, and IR were consistent with the desired title structure.

FDMS 417 (M+).

mp 180–182° C.

Analysis for $C_{22}H_{23}Cl_2N_3O$: Theory: C, 63.47; H, 5.57; N, 10.09. Found: C, 63.27; H, 5.65; N, 10.18.

EXAMPLE 156

Preparation of 2-[[(cyclohexyl)amino]carbonyl]-1-methyl-3-[(piperidin-1-ylmethyl]-1H-indole

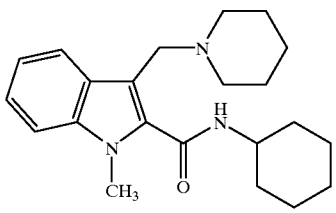

NMR, UV, and IR were consistent with the desired title structure.

FDMS 353 (M+).

mp 180° C.

Exact Mass FAB for $C_{22}H_{32}N_3O$: Theory: 354.2545. Found: 354.2543.

EXAMPLE 157

Preparation of 2-[[(cyclohexylmethyl)amino]carbonyl]-1-methyl-3-[(piperidin-1-yl)methyl]-1H-indole

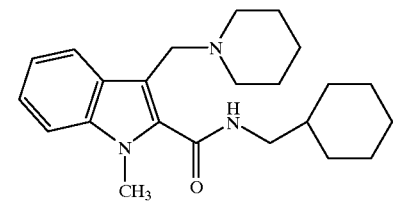

NMR (CDCl$_3$), IR, and UV were consistent with the proposed title structure.

mp 126° C.

Analysis for $C_{23}H_{33}N_3O$: Theory: C, 75.16; H, 9.05; N, 11.43. Found: C, 75.09; H, 9.03; N, 11.25.

EXAMPLE 158

Preparation of 2-[[(naphth-2-yl)amino]carbonyl]-1-methyl-3-[(piperidin-1-yl)methyl]-1H-indole

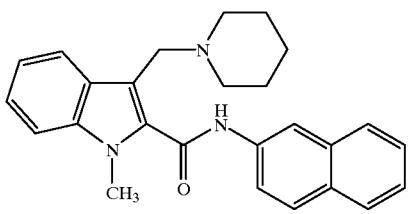

NMR, UV, and IR were consistent with the desired title structure.

FDMS 397 (M+).

mp 187° C.

Analysis for $C_{26}H_{27}N_3O$: Theory: C, 78.56; H, 6.85; N, 10.57. Found: C, 78.84; H, 7.02; N, 10.78.

EXAMPLE 159

Preparation of 2-[phenoxymethyl]-1-methyl-3-[(piperidin-1-yl)methyl]-1H-indole hydrochloride

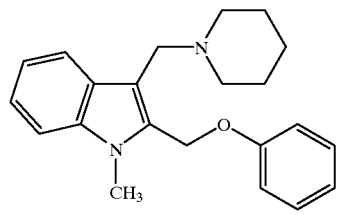

NMR, WV, and IR were consistent with the desired title structure.

FDMS 334 (M+).

mp 225° C.

Analysis for $C_{22}H_{26}N_2O \cdot HCl$: Theory: C, 71.32; H, 7.34; N, 7.55. Found: C, 71.45; H, 7.44; N, 7.79.

EXAMPLE 160

Preparation of 2-[(4-chlorophenoxy)methyl]-1-methyl-3-[(piperidin-1yl)methyl]-1H-indole hydrochloride salt

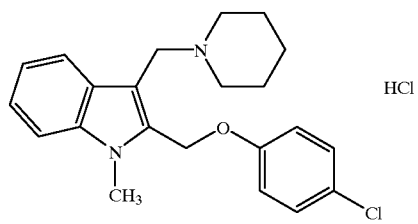

NMR, IR and UV were consistent with the desired title structure.

FDMS 368 (M+).

mp 214° C.

Analysis for $C_{22}H_{25}ClN_2O \cdot HCl$: Theory: C, 65.32; H, 6.46; N, 6.91. Found: C, 65.46; H, 6.52; N, 7.16.

EXAMPLE 161

Preparation of 2-[(4-chlorophenoxy)methyl]-1-methyl-3-[(piperidin-1-yl)methyl]-1H-indole

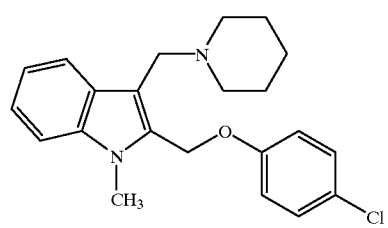

NMR was consistent with the desired title structure.

FDMS 368 (M+).

Analysis for $C_{22}H_{25}ClN_2O$: Theory: C, 71.63; H, 6.83; N, 7.59. Found: C, 68.39; H, 6.55; N, 6.16.

EXAMPLE 162

Preparation of 2-[(3-chlorophenoxy)methyl]-1-methyl-3-[(piperidin-1-yl)methyl]-1H-indole hydrochloride

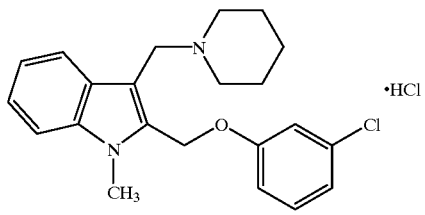

NMR, UV, and IR were consistent with the desired title structure.

FDMS 368 (M+).

mp 222° C.

Analysis for $C_{22}H_{25}ClN_2O \cdot HCl$: Theory: C, 65.19; H, 6.46; N, 6.91. Found: C, 65.15; H, 6.55; N, 6.95.

EXAMPLE 163

Preparation of 2-[(2-chlorophenoxy)methyl]-1-methyl-3-[(piperidin-1-yl)methyl]-1H-indole hydrochloride

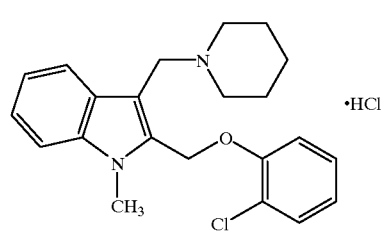

NMR, UV, and IR were consistent with the desired title structure.

FDMS 369 (M+).

Analysis for $C_{22}H_{25}ClN_2O \cdot HCl$: Theory: C, 65.19; H, 6.46; N, 6.91. Found: C, 65.48; H, 6.65; N, 6.98.

EXAMPLE 164

Preparation of 2-[(4-fluorophenoxy)methyl]-1-methyl-3-[(piperidin-1-yl)methyl]-1H-indole hydrochloride

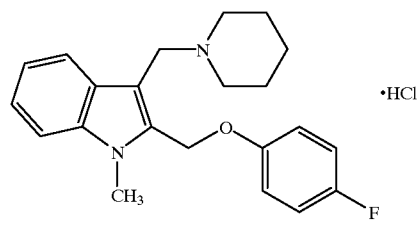

NMR ($CDCl_3$) was consistent with the proposed title structure.

FDMS 352 (M+).

Analysis for $C_{22}H_{25}FN_2O \cdot HCl$: Theory: C, 67.94; H, 6.74; N, 7.20. Found: C, 67.74; H, 6.77; N, 7.16.

EXAMPLE 165

Preparation of 2-[(3-fluorophenoxy)methyl]-1-methyl-3-[(piperidin-1-yl)methyl]-1H-indole hydrochloride

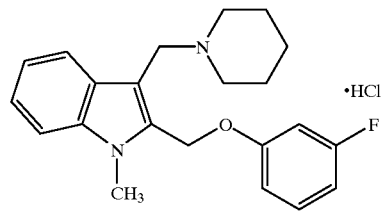

NMR (CDCl₃) was consistent with the proposed title structure.

FDMS 352 (M+).

Analysis for $C_{22}H_{25}FN_2O \cdot HCl$: Theory: C, 67.94; H, 6.74; N, 7.20. Found: C, 65.85; H, 6.51; N, 6.68.

SIngle compound of high purity as evidenced by chromatographic methods.

EXAMPLE 166

Preparation of 2-[(2-fluorophenoxy)methyl]-1-methyl-3-[(piperidin-1-yl)methyl]-1H-indole hydrochloride

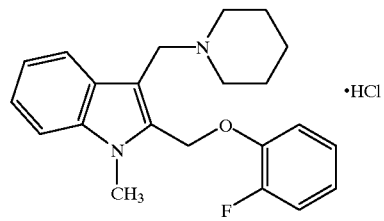

NMR (CDCl₃) was consistent with the proposed title structure.

FDMS 352 (M+).

Analysis for $C_{22}H_{25}FN_2O \cdot HCl$: Theory: C, 67.94; H, 6.74; N, 7.20. Found: C, 67.67; H, 6.63; N, 7.40.

EXAMPLE 167

Preparation of 2-[(4-trifluoromethylphenoxy)methyl]-1-methyl-3-[(piperidin-1-yl)methyl]-1H-indole hydrochloride

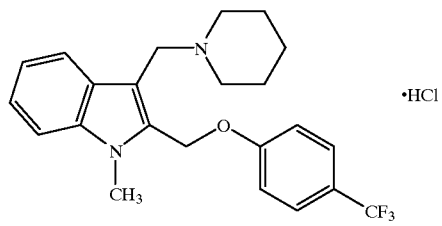

NMR, UV, and IR were consistent with the desired title structure.

FDMS 402 (M+).

Analysis for $C_{23}H_{25}F_3N_2O \cdot HCl$: Theory: C, 62.94; H, 5.97; N, 6.38. Found: C, 63.51; H, 6.05; N, 6.41.

Single compound of high purity as evidenced by chromatographic methods.

EXAMPLE 168

Preparation of 2-[(3-trifluoromethylphenoxy)methyl]-1-methyl-3-[(piperidin-1-yl)methyl]-1H-indole hydrochloride

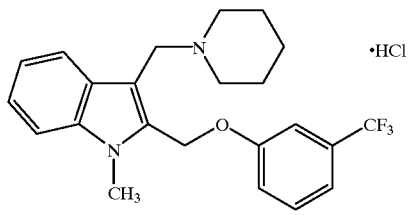

NMR, UV, and IR were consistent with the desired title structure.

FDMS 402 (M+).

Analysis for $C_{23}H_{25}F_3N_2O \cdot HCl$: Theory: C, 62.94; H, 5.97; N, 6.38. Found: C, 64.11; H, 6.07; N, 6.42.

Single compound of high purity as evidenced by chromatographic methods.

EXAMPLE 169

Preparation of 2-[(2-trifluoromethylphenoxy)methyl]-1-methyl-3-[(piperidin-1-yl)methyl]-1H-indole hydrochloride

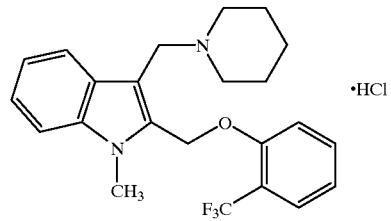

NMR, UV, and IR were consistent with the desired title structure.

FDMS 402 (M+).

Analysis for $C_{23}H_{25}F_3N_2O \cdot HCl$: Theory: C, 62.94; H, 5.97; N, 6.38. Found: C, 62.89; H, 6.02; N, 6.37.

EXAMPLE 170

Preparation of 2-[(4-acetylphenoxy)methyl]-1-methyl-3-[(piperidin-1-yl)methyl]-1H-indole hydrochloride

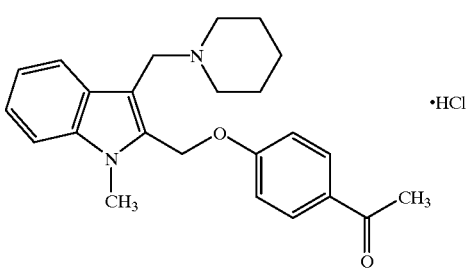

NMR, UV, and IR were consistent with the desired title structure.

FDMS 376 (M+)

Analysis for $C_{24}H_{28}N_2O \cdot HCl$: Theory: C, 69.80; H, 7.08; N, 6.78. Found: C, 69.69; H, 7.27; N, 6.72.

EXAMPLE 171

Preparation of 2-[(3-acetylphenoxy)methyl]-1-methyl-3-[(piperidin-1-yl)methyl]-1H-indole hydrochloride

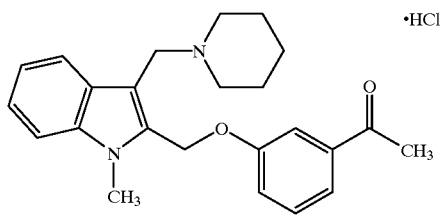

NMR, UV, and IR were consistent with the desired title structure.

FDMS 376 (M+).

Analysis for $C_{24}H_{28}N_2O_2 \cdot HCl$: Theory: C, 69.80; H, 7.08; N, 6.78. Found: C, 69.91; H, 7.18; N, 6.81.

EXAMPLE 172

Preparation of 2-[(2,4-dichlorophenoxy)methyl]-1-methyl-3-[(piperidin-1-yl)methyl]-1H-indole hydrochloride

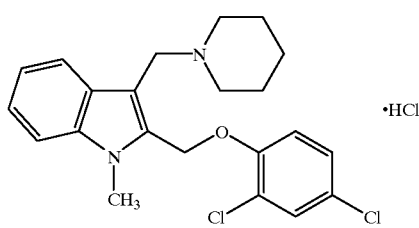

NMR and UV were consistent with the desired title structure.

FDMS 402 (M+).

Analysis for $C_{22}H_{24}Cl_2N_2O$: Theory: C, 60.26; H, 5.75; N, 6.39. Found: C, 61.61; H, 5.69; N, 6.34.

Single compound of high purity as evidenced by chromatographic methods.

EXAMPLE 173

Preparation of 2-[(2,4-dichlorophenoxy)methyl]-1-methyl-3-[(piperidin-1-yl)methyl]-1H-indole hydrochloride

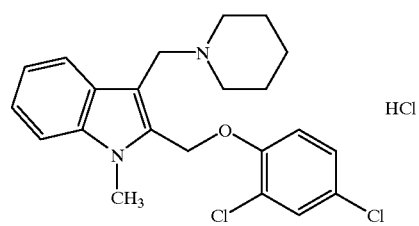

NMR, UV, and IR were consistent with the desired title structure. FDMS 402 (M+).

Analysis for $C_{22}H_{24}Cl_2N_2O \cdot HCl$: Theory: C, 60.08; H, 5.73; N, 6.37. Found: C, 60.31; H, 6.00; N, 6.62.

EXAMPLE 174

Preparation of 2-[(3,5-dichlorophenoxy)methyl]-1-methyl-3-[(piperidin-1-yl)methyl]-1H-indole hydrochloride

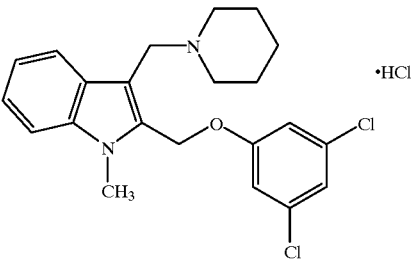

NMR, UV, and IR were consistent with the desired title structure.

FDMS 402 (M+).

Analysis for $C22H_{24}Cl_2N_2O \cdot HCl$: Theory: C, 60.08; H, 5.73; N, 6.37. Found: C, 58.13; H, 5.25; N, 5.99.

Single compound of high purity as evidenced by chromatographic methods.

EXAMPLE 175

Preparation of 2-[(2,5-dichlorophenoxy)methyl]-1-methyl-3-[(piperidin-1-yl)methyl]-1H-indole

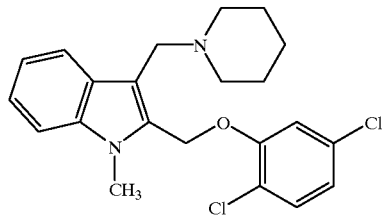

NMR, UV, and IR were consistent with the desired title structure.

FDMS 402 (M+).

Analysis for $C_{22}H_{24}Cl_2N_2O$: Theory: C, 65.51; H, 6.00; N, 6.95. Found: C, 65.71; H, 6.00; N, 6.93.

EXAMPLE 176

Preparation of 2-[(2,6-dichlorophenoxy)methyl]-1-methyl-3-[(piperidin-1-yl)methyl]-1H-indole hydrochloride

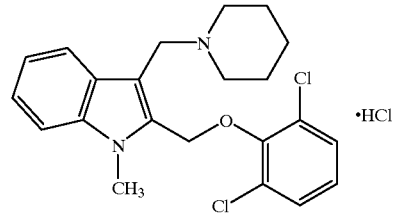

NMR, UV, and IR were consistent with the desired title structure.

FDMS 402 (M+).

Analysis for $C_{22}H_{24}Cl_2N_2O \cdot HCl$: Theory: C, 60.08; H, 5.73; N, 6.37. Found: C, 59.79; H, 5.43; N, 6.11.

EXAMPLE 177

Preparation of 2-[(3,4-dichlorophenoxy)methyl]-1-methyl-3-[(piperidin 1-yl)methyl]-1H-indole hydrochloride

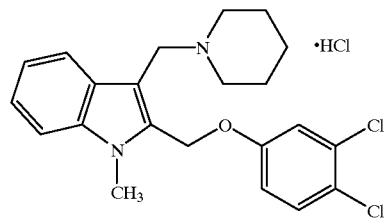

NMR, UV, and IR were consistent with the desired title structure.
FDMS 402 (M+).
Analysis for $C_{22}H_{24}Cl_2N_2O \cdot HCl$: Theory: C, 60.08; H, 5.73; N, 6.37. Found: C, 59.82; H, 5.72; N, 6.21.

EXAMPLE 178
Preparation of 2-[(2,3-dichlorophenoxy)methyl]-1-methyl-3-[(piperidin-1-yl)methyl]-1H-indole

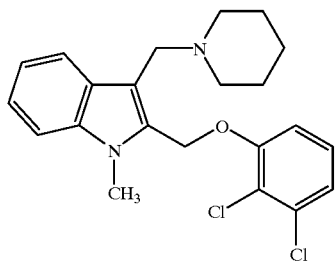

NMR, UV, and IR were consistent with the desired title structure.
FDMS 402 (M+).
Analysis for $C_{24}H_{24}Cl_2N_2O$: Theory: C, 65.51; H, 6.00; N, 6.95. Found: C, 65.23; H, 5.96; N, 6.82.

EXAMPLE 179
Preparation of 2-[(4-phenylphenoxy)methyl]-1-methyl-3-[(piperidin-1-yl)methyl]-1H-indole

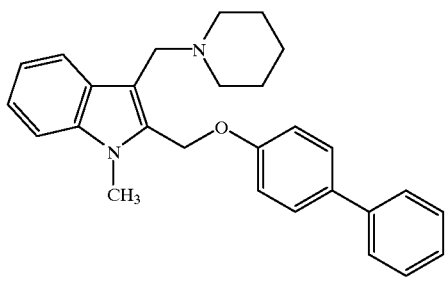

NMR, UV, and IR were consistent with the desired title structure.
FDMS 410 (M+).
Analysis for $C_{28}H_{30}N_2O$: Theory: C, 81.91; H, 7.36; N, 6.82. Found: C, 80.96; H, 7.34; N, 6.73.
Single compound of high purity as evidenced by chromatographic methods.

EXAMPLE 180
Preparation of 2-[(3-phenylphenoxy)methyl]-1-methyl-3-[(piperidin-1-yl)methyl]-1H-indole hydrochloride

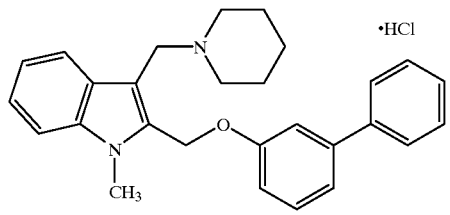

NMR, UV, and IR were consistent with the desired title structure.
FDMS 410 (M+).
Analysis for $C_{28}H_{30}N_2O \cdot HCl$: Theory: C, 75.23; H, 6.99; N, 6.27. Found: C, 74.74; H, 7.10; N, 6.23.
Single compound of high purity as evidenced by chromatographic methods.

EXAMPLE 181
Preparation of 2-[(2-phenylphenoxy)methyl]-1-methyl-3-[(piperidin-1-yl)methyl]-1H-indole hydrochloride

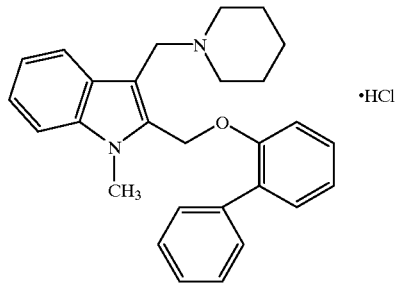

NMR, UV, and IR were consistent with the desired title structure.
FDMS 410 (M+).
Analysis for $C_{28}H_{30}N_2O \cdot HCl$: Theory: C, 75.23; H, 6.99; N, 6.27. Found: C, 74.03; H, 7.10; N, 6.35.
Single compound of high purity as evidenced by chromatographic methods.

EXAMPLE 182
Preparation of 2-[(4-methylphenoxy)methyl]-1-methyl-3-[(piperidin-1-yl)methyl]-1H-indole hydrochloride

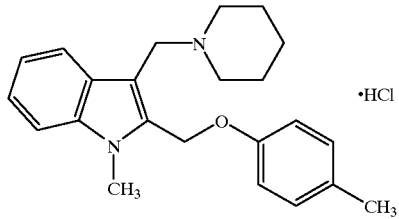

NMR, UV, and IR were consistent with the desired title structure.
FDMS 348 (M+).
Analysis for $C_{23}H_{28}N_2O \cdot HCl$: Theory: C, 71.76; H, 7.59; N, 7.28. Found: C, 70.88; H, 7.70; N, 7.32.
Single compound of high purity as evidenced by chromatographic methods.

EXAMPLE 183
Preparation of 2-[(3-methylphenoxy)methyl]-1-methyl-3-[(piperidin-1-yl)methyl]-1H-indole hydrochloride

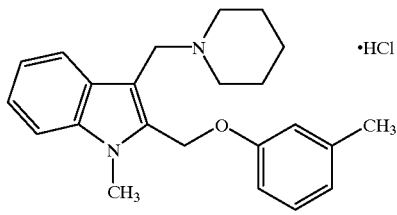

NMR, UV, and IR were consistent with the desired title structure.

FDMS 348 (M+).

Analysis for $C_{23}H_{28}N_2O \cdot HCl$: Theory: C, 71.76; H, 7.59; N, 7.28. Found: C, 72.41; H, 7.78; N, 7.29.

Single compound of high purity as evidenced by chromatographic methods.

EXAMPLE 184

Preparation of 2-[(2-methylphenoxy)methyl]-1-methyl-3-[(piperidin-1-yl)methyl]-1H-indole hydrochloride

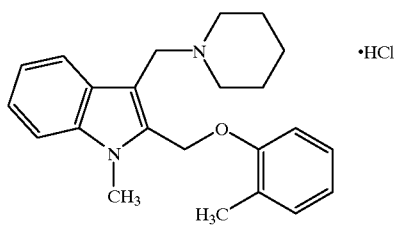

NMR, UV, and IR were consistent with the desired title structure.

FDMS 348 (M+).

Analysis for $C_{23}H_{28}N_2O \cdot HCl$: Theory: C, 71.76; H, 7.59; N, 7.28. Found: C, 71.71; H, 7.54; N, 7.21.

EXAMPLE 185

Preparation of 2-[(4-methoxyphenoxy)methyl]-1-methyl-3-[(piperidin-1-yl)methyl]-1H-indole hydrochloride

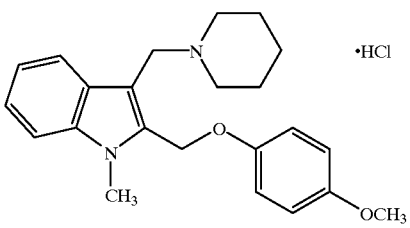

NMR, UV, and IR were consistent with the desired title structure.

FDMS 364 (M+).

Analysis for $C_{23}H_{28}N_2O_2 \cdot HCl$: Theory: C, 68.90; H, 7.29; N, 6.99. Found: C, 68.68; H, 7.30; N, 7.12.

EXAMPLE 186

Preparation of 2-[(3-methoxyphenoxy)methyl]-1-methyl-3-[(piperidin-1-yl)methyl]-1H-indole hydrochloride

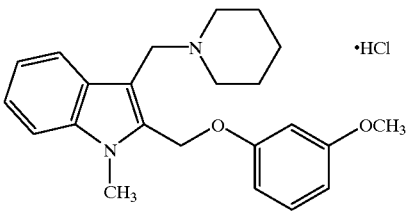

NMR, UV, and IR were consistent with the desired title structure.

FDMS 364 (M+).

Analysis for $C_{23}H_{28}N_2O_2 \cdot HCl$: Theory: C, 68.90; H, 7.29; N, 6.99. Found: C, 69.13; H, 7.38; N, 6.83.

EXAMPLE 187

Preparation of 2-[(2-methoxyphenoxy)methyl]-1-methyl-3-[(piperidin-1-yl)methyl]-1H-indole hydrochloride

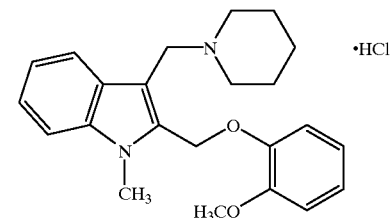

NMR, UV, and IR were consistent with the desired title structure.

FDMS 364 (M+).

Analysis for $C_{23}H_{28}N_2O_2 \cdot HCl$: Theory: C, 68.90; H, 7.29; N, 6.99. Found: C, 73.45; H, 7.94; N, 6.92.

Single compound of high purity as evidenced by chromatographic methods.

EXAMPLE 188

Preparation of 2-[2-hydroxyethyl]-1-methyl-3-[(piperidin-1-yl)methyl]-1H-indole

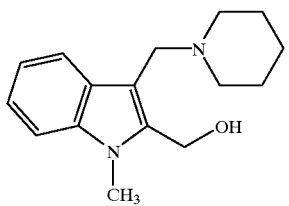

Analysis for $C_{16}H_{22}N_2O$: Theory: C, 74.38; H, 8.58; N, 10.84. Found: C, 74.35; H, 8.78; N, 10.96.

EXAMPLE 189

Preparation of 2-(2-methoxyethyl)-1-methyl-3-[(piperidin-1-yl)methyl]-1H-indole

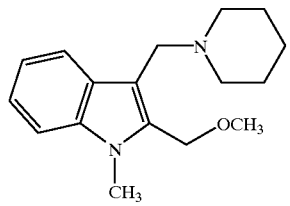

NMR was consistent with the desired title structure.

FDMS 272,273 (M+).

Analysis for $C_{17}H_{24}N_2O$: Theory: C, 74.96; H, 8.88; N, 10.28. Found: C, 73.31; H, 8.86; N, 9.97.

EXAMPLE 190

Preparation of 2-(2-allyloxyethyl)-1-methyl-3-[(piperidin-1-yl)methyl]-1H-indole hydrochloride salt

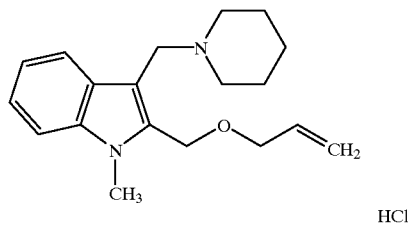

NMR, UV, and IR were consistent with the desired title structure.

FDMS 298 (M+).

Analysis for $C_{19}H_{26}N_2O\cdot HCl$: Theory: C, 68.14; H, 8.13; N, 8.37. Found: C, 68.30; H, 8.14; N, 8.39.

EXAMPLE 191

Preparation of 2-(benzyloxymethyl)-1-methyl-3-[(piperidin-1-yl)methyl]-1H-indole hydrochloride

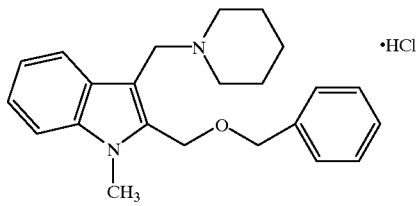

IR, UV, and NMR (CDCl$_3$) were consistent with the proposed title structure.

FDMS 384 (M+)

Analysis for $C_{23}H_{28}N_2O\cdot HCl$: Theory: C, 71.76; H, 7.59; N, 7.28. Found: C, 68.44; H, 7.04; N, 6.36.

Single compound of high purity as evidenced by chromatographic methods.

EXAMPLE 192

Preparation of 2-[(3-chlorobenzyloxy)methyl]-1-methyl-3-[(piperidin-1-yl)methyl]-1H-indole hydrochloride

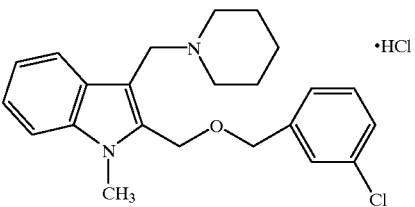

NMR was consistent with the desired title structure.

FDMS 382 (M+).

Analysis for $C_{23}H_{27}ClN_2O\cdot HCl$:

Theory: C, 72.14; H, 7.11; N, 7.32. Found: C, 71.92; H, 7.22; N, 7.43.

EXAMPLE 193

Preparation of 2-[(2-chlorobenzyloxy)methyl]-1-methyl-3-[(piperidin-1-yl)methyl]-1H-indole

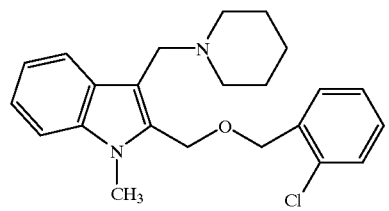

NMR was consistent with the desired title structure.

FDMS 382 (M+).

mp 82–83° C.

Analysis for $C_{23}H_{27}ClN_2O$: Theory: C, 72.14; H, 7.11; N, 7.32. Found: C, 71.87; H, 7.07; N, 7.36.

EXAMPLE 194

Preparation of 2-[(4-chlorobenzyloxy)methyl]-1-methyl-3-[(piperidin-1-yl)methyl]-1H-indole hydrochloride

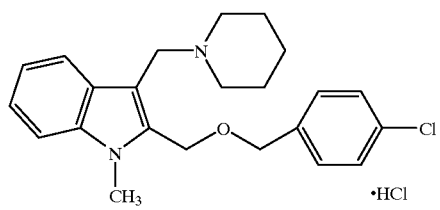

NMR (CDCl$_3$), IR, and UV were consistent with the proposed title structure.

FDMS 382 (M+)

Analysis for $C_{23}H_{27}ClN_2O\cdot HCl$: Theory: C, 65.87; H, 6.73; N, 6.68. Found: C, 65.54; H, 6.59; N, 6.39.

EXAMPLE 195

Preparation of 2-[(naphth-1-yloxy)methyl]-1-methyl-3-[(piperidin-1-yl)methyl]-1H-indole hydrochloride

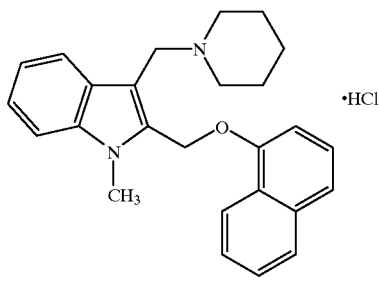

NMR, UV, and IR were consistent with the desired title structure.

FDMS 384 (M+).

Analysis for $C_{26}H_{28}N_2O \cdot HCl$: Theory: C, 74.18; H, 6.94; N, 6.65. Found: C, 74.47; H, 7.05; N, 6.64.

EXAMPLE 196

Preparation of 2-[(naphth-2-yloxy)methyl]-1-methyl-3-[(piperidin-1-yl)methyl]-1H-indole hydrochloride

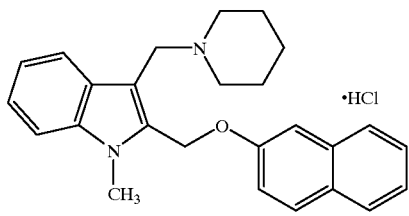

NMR, UV, and IR were consistent with the desired title structure.

FDMS 384 (M+).

Analysis for $C_{26}H_{28}N_2O \cdot HCl$: Theory: C, 74.18; H, 6.94; N, 6.65. Found: C, 71.44; H, 6.93; N, 6.67.

Single compound of high purity as evidenced by chromatographic methods.

EXAMPLE 197

Preparation of 2-[(thiazol-2-yl)methyl]-1-methyl-3-[(piperidin-1-yl)methyl]-1H-indole

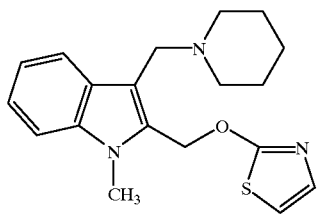

NMR was consistent with the desired title structure.

mp 175–176° C.

FDMS 341 (M+).

Analysis for $C_{19}H_{23}N_3OS$: Theory: C, 66.83; H, 6.79; N, 12.31. Found: C, 66.64; H, 6.82; N, 12.03.

EXAMPLE 198

Preparation of 2-[(pyrazin-2-yl)methyl]-1-methyl-3-[(piperidin-1-yl)methyl]-1H-indole

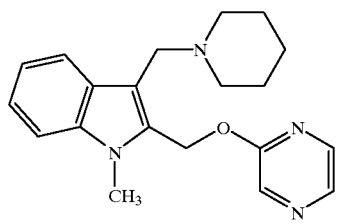

NMR, UV, and IR were consistent with the desired title structure.

FDMS 336 (M+).

mp 101° C.

Analysis for $C_{20}H_{24}N_4O$: Theory: C, 71.40; H, 7.19; N, 16.65. Found: C, 71.44; H, 7.33; N, 16.43.

EXAMPLE 199

Preparation of 2-[(6-chloropyrazin-2-yl)methyl]-1-methyl-3-[(piperidin-1-yl)methyl]-1H-indole

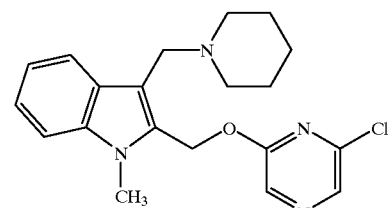

NMR, UV, and IR were consistent with the desired title structure.

FDMS 370 (M+).

mp 94–96° C.

Analysis for $C_{20}H_{23}ClN_4O$: Theory: C, 64.77; H, 6.25; N, 15.11. Found: C, 65.04; H, 6.45; N, 15.21.

EXAMPLE 200

Preparation of 2-[(pyrimidin-2-yl)methyl]-1-methyl-3-[(piperidin-1-yl)methyl]-1H-indole

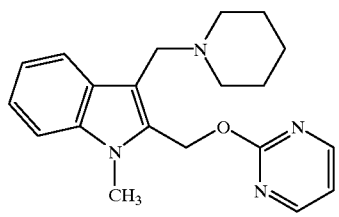

NMR, WV, and IR were consistent with the desired title structure.

FDMS 337 (M+1).

mp 123–125° C.

Analysis for $C_{20}H_{24}N_4O$: Theory: C, 71.40; H, 7.19; N, 16.65. Found: C, 71.60; H, 7.43; N, 16.59.

EXAMPLE 201

Preparation of 2-[(quinolin-2-yl)methyl]-1-methyl-3-[(piperidin-1-yl)methyl]-1H-indole

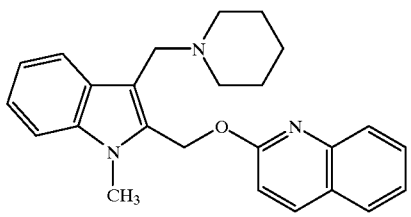

NMR, UV, and IR were consistent with the desired title structure.
FDMS 385 (M+1).
mp 113° C.
Analysis for $C_{25}H_{27}N_3O$: Theory: C, 77.89; H, 7.06; N, 10.90. Found: C, 77.64; H, 7.00; N, 11.05.

EXAMPLE 202

Preparation of 2-[(6-chloropyridazin-2-yl)methyl]-1-methyl-3-[(piperidin-1-yl)methyl]-1H-indole

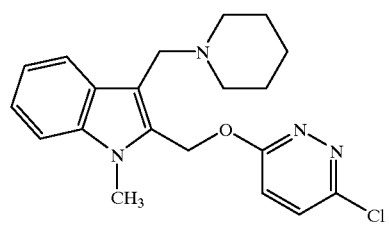

NMR, UV, and IR were consistent with the desired title structure.
FDMS 371 (M+1).
mp 138–139° C.
Analysis for $C_{20}H_{23}ClN_4O$: Theory: C, 64.77; H, 6.25; N, 15.11. Found: C, 64.84; H, 6.28; N, 15.00.

EXAMPLE 203

Preparation of 2-[(5,6,7,8-tetrahydronaphth-1-yl)methyl]-1-methyl-3-[(4-dimethylaminopiperidin-1-yl)methyl]-1H-indole

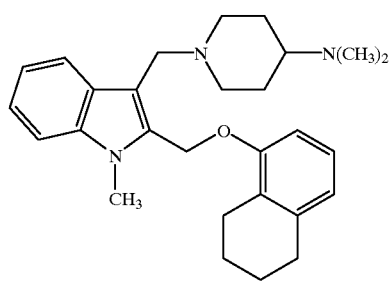

NMR was consistent with the desired title structure.
FDMS 431 (M+).
Analysis for $C_{28}H_{37}N_3O$: Theory: C, 77.92; H, 8.64; N, 9.74. Found: C, 75.79; H, 8.74; N, 8.74.

EXAMPLE 204

Preparation of 2-[(5,6,7,8-tetrahydronaphth-2-yl)methyl]-1-methyl-3-[(4-dimethylaminopiperidin-1-yl)methyl]-1H-indole dihydrochloride hydrate

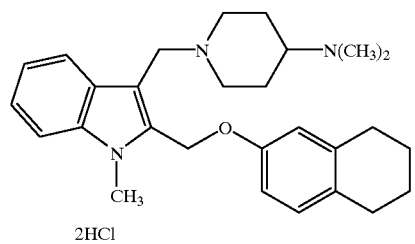

NMR and UV were consistent with the desired title structure.
FDMS 431,432 (M+).
mp 202° C.
Analysis for $C_{28}H_{37}N_3O.2HCl.H_2O$: Theory: C, 64.36; H, 7.91; N, 8.04. Found: C, 64.73; H, 7.50; N, 7.99.

EXAMPLE 205

Preparation of 2-[phenylthiomethyl]-1-methyl-3-[(piperidin-1-yl)methyl]-1H-indole hydrochloride

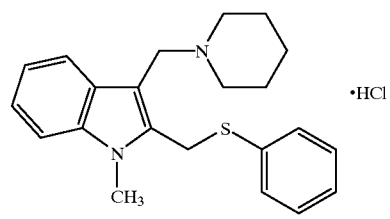

NMR, UV, and IR were consistent with the desired title structure.
FDMS 350 (M+1).
Analysis for $C_{22}H_{26}N_2S.HCl$: Theory: C, 68.28; H, 7.03; N, 7.24. Found: C, 68.03; H, 7.00; N, 7.10.

EXAMPLE 206

Preparation of 2-[(4-chlorophenylthio)methyl]-1-methyl-3-[(piperidin-1-yl)methyl]-1H-indole hydrochloride

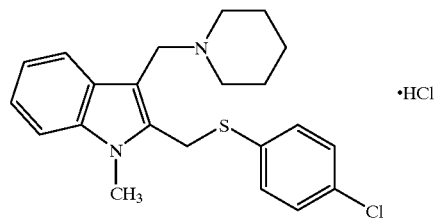

NMR, UV, and IR were consistent with the desired title structure.
FDMS 384 (M+).
Analysis for $C_{22}H_{25}ClN_2S.HCl$: Theory: C, 62.70; H, 6.22; N, 6.65. Found: C, 62.12; H, 6.42; N, 6.22.
Single compound of high purity as evidenced by chromatographic methods.

EXAMPLE 207

Preparation of 2-[(3-chlorophenylthio)methyl]-1-methyl-3-[(piperidin-1-yl)methyl]-1H-indole hydrochloride

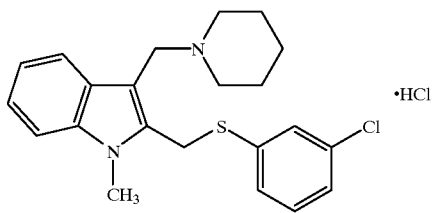

NMR, UV, and IR were consistent with the desired title structure.

FDMS 384 (M+).

Analysis for $C_{22}H_{25}ClN_2S \cdot HCl$: Theory: C, 62.70; H, 6.22; N, 6.65. Found: C, 62.94; H, 6.23; N, 6.93.

EXAMPLE 208

Preparation of 2-[(2-chlorophenylthio)methyl]-1-methyl-3-[(piperidin-1-yl)methyl]-1H-indole hydrochloride

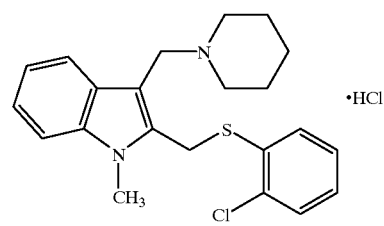

NMR, UV, and IR were consistent with the desired title structure.

FDMS 384 (M+).

Analysis for $C_{22}H_{25}ClN_2S \cdot HCl$: Theory: C, 62.70; H, 6.22; N, 6.65. Found: C, 62.76; H, 6.20; N, 6.67.

EXAMPLE 209

Preparation of 2-[(2,4-dichlorophenylthio)methyl]-1-methyl-3-[(piperidin-1-yl)methyl]-1H-indole hydrochloride

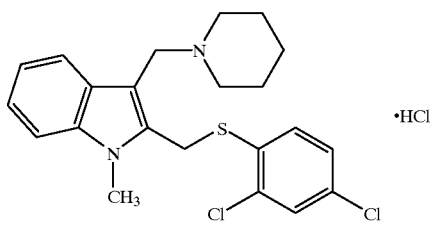

NMR, UV, and IR were consistent with the desired title structure.

FDMS 418 (M+).

Analysis for $C_{22}H_{24}Cl_2N_2S \cdot HCl$: Theory: C, 57.96; H, 5.53; N, 6.15. Found: C, 56.61; H, 5.70; N, 6.05.

Single compound of high purity as evidenced by chromatographic methods.

EXAMPLE 210

Preparation of 2-[(2,5-dichlorophenylthio)methyl]-1-methyl-3-[(piperidin-1-yl)methyl]-1H-indole hydrochloride

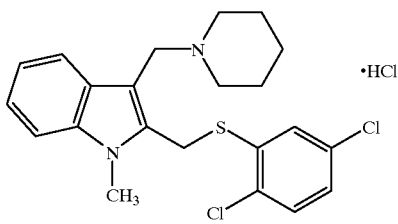

NMR, UV, and IR were consistent with the desired title structure.

FDMS 418,420 (M+1).

Analysis for $C_{22}H_{24}Cl_2N_2S \cdot HCl$: Theory: C, 57.96; H, 5.53; N, 6.15. Found: C, 57.87; H, 5.50; N, 5.99.

EXAMPLE 211

Preparation of 2-[(2,6-dichlorophenylthio)methyl]-1-methyl-3-[(piperidin-1-yl)methyl]-1H-indole hydrochloride

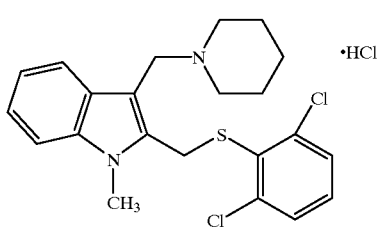

NMR, UV, and IR were consistent with the desired title structure.

FDMS 417 (M+).

Analysis for $C_{22}H_{24}Cl_2N_2S \cdot HCl$: Theory: C, 57.96; H, 5.53; N, 6.15. Found: C, 58.16; H, 5.68; N, 6.33.

EXAMPLE 212

Preparation of 2-[(3,4-dichlorophenylthio)methyl]-1-methyl-3-[(piperidin-1-yl)methyl]-1H-indole hydrochloride

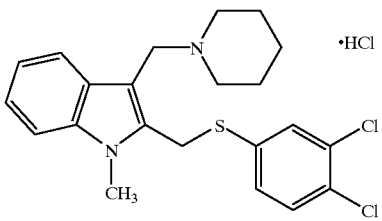

NMR, WV, and IR were consistent with the desired title structure.

FDMS 418,420 (M+1).

Analysis for $C_{22}H_{24}Cl_2N_2S \cdot HCl$: Theory: C, 57.96; H, 5.53; N, 6.15. Found: C, 57.98; H, 5.54; N, 6.16.

EXAMPLE 213

Preparation of 2-[(cyclohexylthio)methyl]-1-methyl-3-[(piperidin-1-yl)methyl]-1H-indole hydrochloride

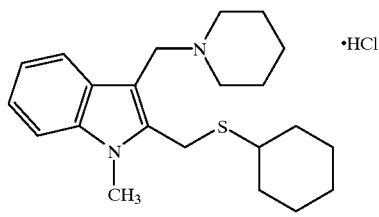

NMR (CDCl₃), UV, and IR were consistent with the proposed title structure.

FDMS 356 (M+).

Analysis for $C_{22}H_{32}N_2S \cdot HCl$: Theory: C, 67.23; H, 8.46; N, 7.13. Found: C, 66.28; H, 9.27; N, 7.71.

Single compound of high purity as evidenced by chromatographic methods.

EXAMPLE 214

Preparation of 2-[(n-propylthio)methyl]-1-methyl-3-[(piperidin-1-yl)methyl]-1H-indole hydrochloride

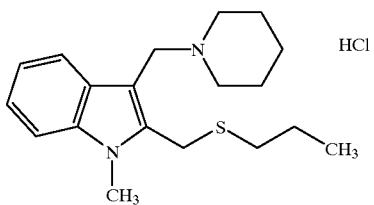

NMR (CDCl₃), UV, and IR were consistent with the proposed title structure.

FDMS 316 (M+)

Analysis for $C_{19}H_{28}N_2S \cdot HCl$: Theory: C, 64.65; H, 8.28; N, 7.94. Found: C, 64.72; H, 8.03; N, 8.12.

EXAMPLE 215

Preparation of 2-[(benzylthio)methyl]-1-methyl-3-[(piperidin-1-yl)methyl]-1H-indole hydrochloride

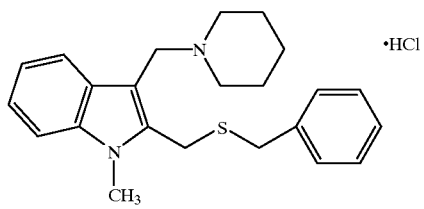

NMR, UV, and IR were consistent with the desired title structure.

FDMS 365 (M+).

Analysis for $C_{23}H_{28}N_2S \cdot HCl$: Theory: C, 68.89; H, 7.29; N, 6.99. Found: C, 68.63; H, 7.52; N, 7.11.

EXAMPLE 216

Preparation of 2-[(2-phenylethylthio)methyl]-1-methyl-3-[(piperidin-1-yl)methyl]-1H-indole

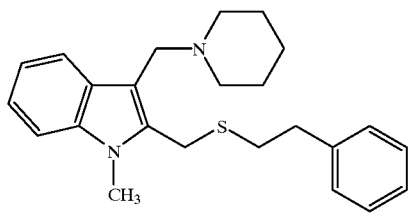

NMR (CDCl₃) was consistent with the proposed title structure.

$C_{24}H_{30}N_2S$: FDMS 379 (M+1).

Single compound of high purity as evidenced by chromatographic methods.

EXAMPLE 217

Preparation of 2-[(naphth-2-ylthio)methyl]-1-methyl-3-[(piperidin-1-yl)methyl]-1H-indole

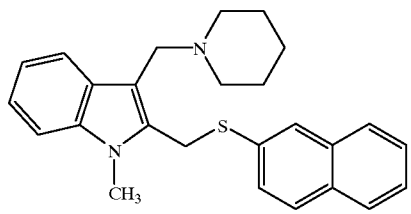

NMR (CDCl₃), UV, and IR were consistent with the proposed title structure.

FDMS 400 (M+)

Analysis for $C_{26}H_{28}N_2S \cdot HCl$: Theory: C, 71.45; H, 6.69; N, 6.41. Found: C, 69.59; H, 6.67; N, 6.21.

Single compound of high purity as evidenced by chromatographic methods.

EXAMPLE 220

Preparation of 2-phenyl-3-(piperidin-1-yl)methyl-1H-indole

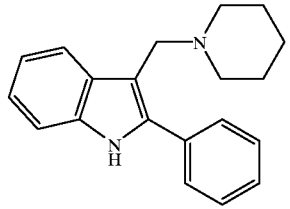

NMR, UV, and IR were consistent with the desired title structure.

FDMS 290 (M+).

Analysis for $C_{20}H_{22}N_2$: Theory: C, 82.72; H, 7.64; N, 9.65. Found: C, 82.97; H, 7.74; N, 9.81.

EXAMPLE 221

Preparation of 1-methyl-2-phenyl-3-(piperidin-1-yl)methyl-1H-indole

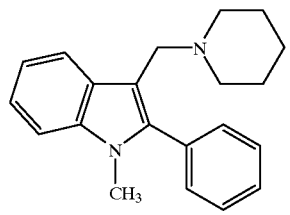

NMR, UV, and IR were consistent with the desired title structure.

FDMS 304,305 (M+1).

Analysis for $C_{21}H_{24}N_2$: Theory: C, 82.85; H, 7.95; N, 9.20. Found: C, 82.68; H, 7.92; N, 9.40.

EXAMPLE 222

Preparation of 2-phenyl-1-methyl-3-[2-(piperidin-1-yl)-1,2-ethanedionyl]-1H-indole

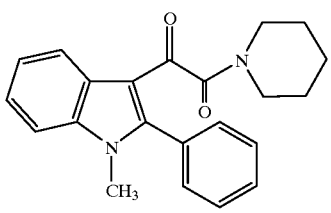

NMR (CDCl$_3$), IR, and UV were consistent with the proposed title structure.

FDMS 346 (M+)

Analysis for $C_{22}H_{22}N_2O_2$: Theory: C, 76.28; H, 6.40; N, 8.09. Found: C, 76.09; H, 6.35; N, 8.09.

EXAMPLE 223

Preparation of 2-phenyl-1-methyl-3-[2-[N-benzyl-N-3-(dimethylaminopropyl)amino]-1,2-ethanedionyl]-1H-indole

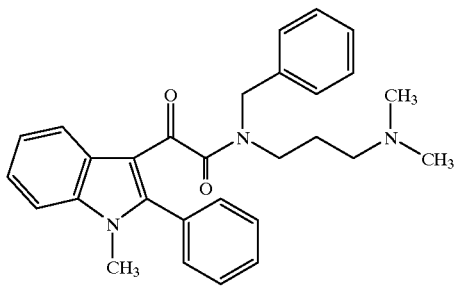

IR, NMR, and UV were consistent with the desired title structure.

FDMS 453 (M+).

Analysis for $C_{29}H_{31}N_3O_2$: Theory: C, 76.79; H, 6.89; N, 9.26. Found: C, 77.06; H, 7.02; N, 9.45.

EXAMPLE 224

Preparation of 2-phenyl-1-methyl-3-[2-(4-dimethylaminopiperidin-1-yl)-1,2-ethanedionyl]-1H-indole

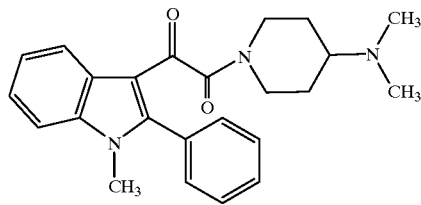

IR, NMR, and UV were consistent with the desired title structure.

FDMS 389 (M+).

Analysis for $C_{24}H_{27}N_3O_2$: Theory: C, 74.01; H, 6.99; N, 10.79. Found: C, 73.82; H, 6.98; N, 10.75.

EXAMPLE 225

Preparation of 1-methyl-3-[2-[N-benzyl-N-3-(dimethylaminopropyl)amino]-1,2-ethanedionyl]-1H-indole

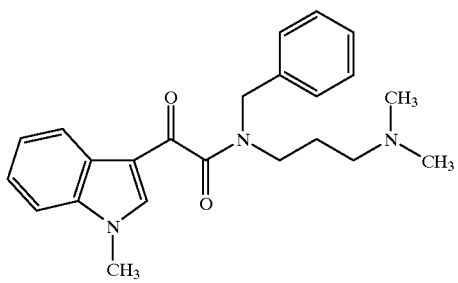

IR, NMR, and UV were consistent with the desired title structure.

FDMS 377 (M+).

FAB 378 (M+1).

Analysis for $C_{23}H_{27}N_3O_2$: Theory: C, 73.18; H, 7.21; N, 11.13. Found: C, 70.74; H, 7.14; N, 10.75.

Single compound of high purity as evidenced by chromatographic methods.

EXAMPLE 226

Preparation of 1-methyl-3-[2-(4-dimethylaminopiperidin-1-yl)-1,2-ethanedionyl]-1H-indole

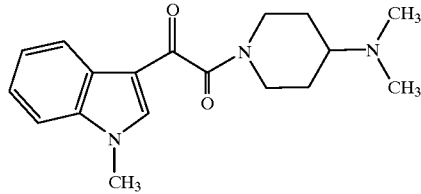

IR, NMR, and UV were consistent with the desired title structure.

FDMS 313 (M+1).

Analysis for $C_{18}H_{23}N_3O_2$: Theory: C, 68.98; H, 7.40; N, 13.41. Found: C, 68.97; H, 7.59; N, 13.43.

EXAMPLE 227

Preparation of 5-chloro-2-[(2,4-dichlorophenoxy)methyl]-1-methyl-3-[(piperidin-1-yl)methyl]-1H-indole hydrochloride

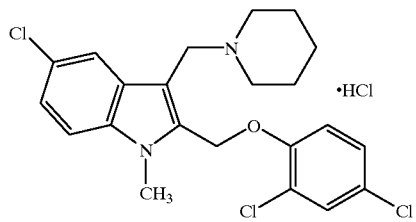

NMR (CDCl₃) was consistent with the proposed title structure.

mp 177–179° C.

Analysis for $C_{22}H_{23}Cl_3N_2O\cdot HCl$: Theory: C, 55.72; H, 5.10; N, 5.91. Found: C, 55.70; H, 5.21; N, 6.16.

EXAMPLE 228

Preparation of 5-methoxy-2-[(2,4-dichlorophenoxy)methyl]-1-methyl-3-[(piperidin-1-yl)methyl]-1H-indole

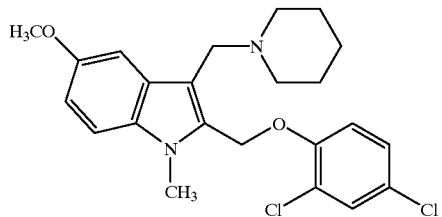

NMR (CDCl₃) was consistent with the proposed title structure.

FDMS 432 (M+).

mp 119–121° C.

Analysis for $C_{23}H_{26}Cl_2N_2O_2$: Theory: C, 63.74; H, 6.05; N, 6.46. Found: C, 63.70; H, 6.12; N, 6.46.

EXAMPLE 229

Preparation of 5-chloro-2-[(2,4-dichlorophenoxy)methyl]-1-methyl-3-[(4-dimethylaminopiperidin-1-yl)methyl]-1H-indole dihydrochloride

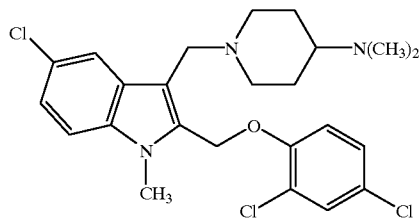

NMR (CDCl₃) was consistent with the proposed title structure.

Analysis for $C_{24}H_{28}Cl_3N_3O\cdot 2HCl$: Theory: C, 52.05; H, 5.46; N, 7.59. Found: C, 52.05; H, 5.41; N, 7.56.

EXAMPLE 230

Preparation of 5-chloro-2-[(2,4-dichlorophenoxy)methyl]-1-methyl-3-[[4-(piperidin-1-yl)piperidin-1-yl]methyl]-1H-indole dihydrochloride

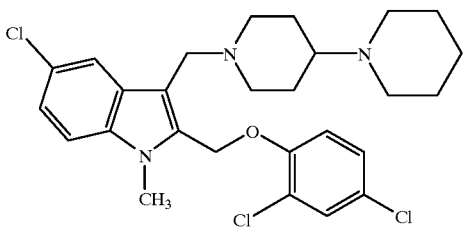

NMR (CDCl₃) was consistent with the proposed title structure.

Analysis for $C_{27}H_{32}Cl_3N_3O\cdot 2HCl$: Theory: C, 54.61; H, 5.77; N, 7.08. Found: C, 51.53; H, 6.53; N, 7.57.

EXAMPLE 231

Preparation of 5-bromo-2-[(2,4-dichlorophenoxy)methyl]-1-methyl-3-[2-(piperidin-1-yl)ethyl]-1H-indole

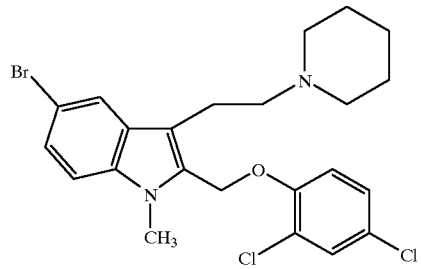

NMR and IR were consistent with the desired title structure.

mp 158–160° C.

Analysis for $C_{23}H_{25}BrCl_2N_2O$: Theory: C, 55.67; H, 5.08; N, 5.64. Found: C, 55.96; H, 5.28; N, 5.69.

EXAMPLE 232

Preparation of 2-[(4-chlorophenoxy)methyl]-1-methyl-1H-indole

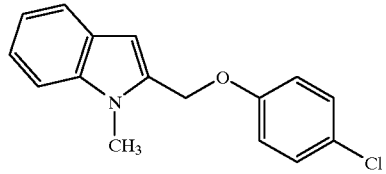

IR, NMR, and UV were consistent with the desired title structure.

FDMS 271 (M+).

Analysis for $C_{16}H_{14}ClNO$: Theory: C, 70.72; H, 5.19; N, 5.15. Found: C, 70.52; H, 5.26; N, 5.28.

EXAMPLE 233

Preparation of 2-[(2,4-dichlorophenoxy)methyl]-1-methyl-1H-indole

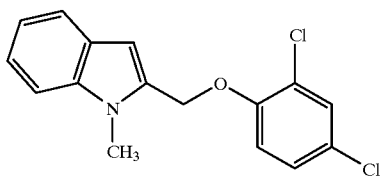

IR, NMR, and UV were consistent with the desired title structure.
FDMS 305.
Analysis for $C_{16}H_{13}Cl_2NO$: Theory: C, 62.76; H, 4.28; N, 4.57. Found: C, 63.37; H, 4.72; N, 4.37.

EXAMPLE 234
Preparation of 2-[(5,6,7,8-tetrahydronaphth-1-yloxy)methyl]-1-methyl-1H-indole

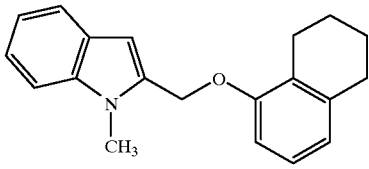

NMR was consistent with the desired title structure.
FDMS 292 (M+1).
Analysis for $C_{20}H_{21}NO$: Theory: C, 82.44; H, 7.26; N, 4.81. Found: C, 82.51; H, 7.28; N, 4.80.

EXAMPLE 235
Preparation of 2-[(5,6,7,8-tetrahydronaphth-2-yloxy)methyl]-1-methyl-1H-indole

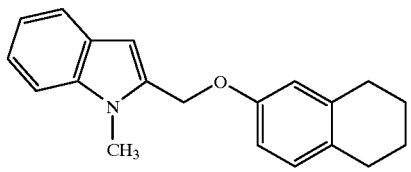

NMR (CDCl$_3$) was consistent with the proposed title structure.
FDMS 291 (M+).
Analysis for $C_{20}H_{21}NO$: Theory: C, 82.44; H, 7.26; N, 4.81. Found: C, 82.25; H, 6.98; N, 4.95.

EXAMPLE 236
Preparation of 2-[(4-chlorophenoxy)methyl]-3-formyl-1-methyl-1H-indole

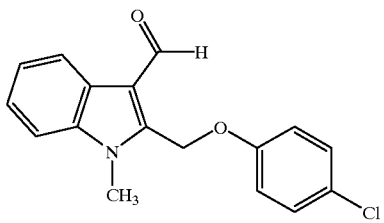

NMR (CDCl$_3$) was consistent with the proposed title structure.
FDMS 299 (M+).
Analysis for $C_{17}H_{14}ClNO_2$: Theory: C, 68.12; H, 4.71; N, 4.67. Found: C, 67.90; H, 4.93; N, 4.73.

EXAMPLE 237
Preparation of (RS) 1,2-dimethyl-3-[3-(piperidin-3-yl)propyl]-1H-indole

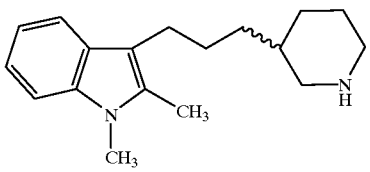

NMR (CDCl$_3$) was consistent with the proposed title structure.
Exact Mass for $C_{18}H_{27}N_2$: Theory: 271.2174. Found: 271.2176.

EXAMPLE 238
Preparation of 1-methyl-2-[[2-[(piperidin-1-yl)methyl]phenoxy]methyl]-1H-indole

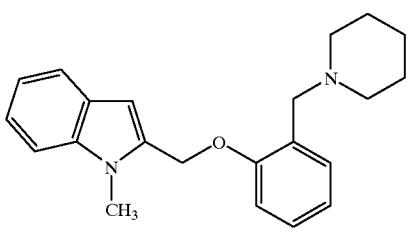

NMR (CDCl$_3$) was consistent with the proposed title structure.
FDMS 335 (M+).
Analysis for $C_{22}H_{26}N_2O$: Theory: C, 79.01; H, 7.84; N, 8.38. Found: C, 78.78; H, 7.58; N, 8.56.

EXAMPLE 239
Preparation of 1-methyl-3-[2-[(4-chlorophenoxy)methyl]piperidin-1-ylmethyl]-1H-indole

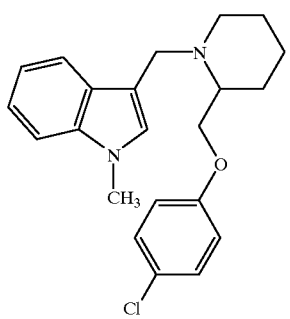

NMR (CDCl$_3$) was consistent with the proposed title structure.
FDMS 368 (M+).
Analysis for $C_{22}H_{25}ClN_2O \cdot HCl$: Theory: C, 65.19; H, 6.46; N, 6.91. Found: C, 64.93; H, 6.44; N, 6.78.

EXAMPLE 240
Preparation of 1-methyl-3-[3-[(4-chlorophenoxy)methyl]piperidin-1-ylmethyl]-1H-indole

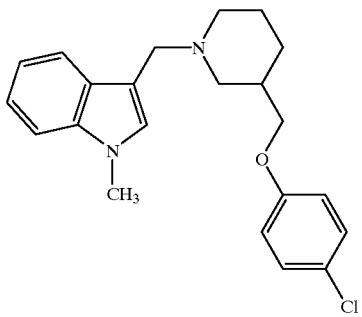

NMR (CDCl₃) was consistent with the proposed title structure.
FDMS 368 (M+).
Analysis for $C_{22}H_{25}ClN_2O$: Theory: C, 71.63; H, 6.83; N, 7.59. Found: C, 63.74; H, 6.54; N, 6.86.

EXAMPLE 241
Preparation of 1-methyl-3-[2-[2-(4-chlorophenoxy)ethyl]piperidin-1-ylmethyl]-1H-indole

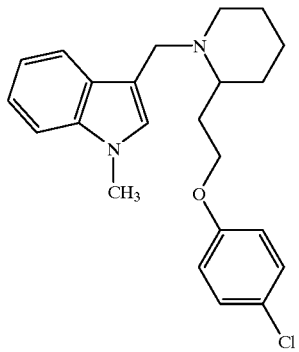

NMR (CDCl₃) was consistent with the proposed title structure.
FDMS 382 (M+).
Analysis for $C_{23}H_{27}ClN_2O$: Theory: C, 65.87; H, 6.73; N, 6.68. Found: C, 62.05; H, 6.36; N, 6.18.

EXAMPLE 243
Preparation of ethyl 3-[2-[(4-chlorophenoxy)methyl]-1-methyl-1H-indol-3-yl]propanoate

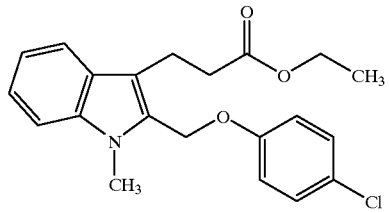

NMR (CDCl₃) was consistent with the proposed title structure.
FDMS 371 (M+)
Single compound of high purity as evidenced by chromatographic methods.

EXAMPLE 244
Preparation of (RS) ethyl 2-amino-3-[2-[(4-chlorophenoxy)methyl]-1-methyl-1H-indol-3-yl]propanoate

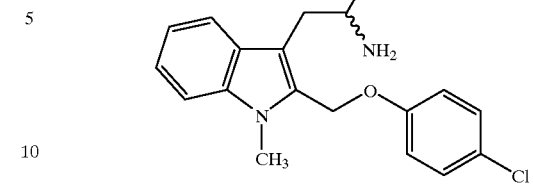

NMR was consistent with the desired title structure.
FDMS 386.
Analysis for $C_{21}H_{23}ClN_2O_3$: Theory: C, 65.20; H, 5.99; N, 7.24. Found: C, 64.95; H, 5.95; N, 7.27.

EXAMPLE 245
Preparation of ethyl 2-hydroxyimino-3-[2-[(4-chlorophenoxy)methyl]-1-methyl-1H-indol-3-yl]propanoate

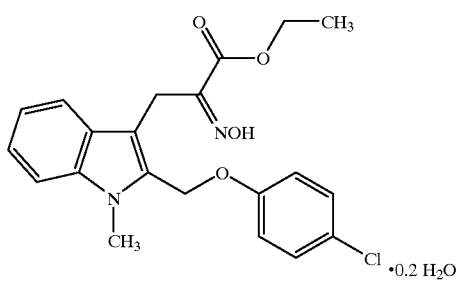

IR, NMR, and UV were consistent with the desired title structure.
FDMS 400 (M+).
mp 165–166° C.
Analysis for $C_{21}H_{21}ClN_2O_4 \cdot 0.2\ H_2O$: Theory: C, 62.36; H, 5.33; N, 6.93. Found: C, 62.38; H, 5.38; N, 6.87.

EXAMPLE 246
Preparation of (RS) methyl 2-methoxyimino-3-[2-[(4-chlorophenoxy)methyl]-1-methyl-1H-indol-3-yl]propanoate

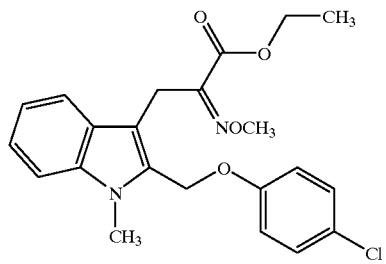

IR, NMR, and UV were consistent with the desired title structure.
FDMS 414 (M+).
mp 106–107° C.
Analysis for $C_{22}H_{23}ClN_2O_4$: Theory: C, 63.69; H, 5.59; N, 6.75. Found: C, 63.95; H, 5.57; N, 7.01.

EXAMPLE 247
Preparation of ethyl 2-benzoxyimino-3-[2-[(4-chlorophenoxy)methyl]-1-methyl-1H-indol-3-yl]propanoate

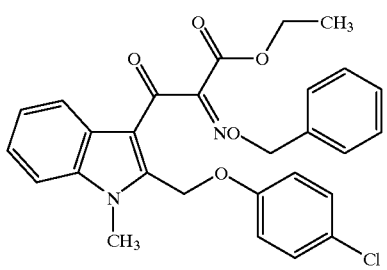

IR, NMR, and UV were consistent with the desired title structure.
FDMS 490 (M+).
mp 96° C.
Analysis for $C_{28}H_{27}ClN_2O_4$: Theory: C, 68.50; H, 5.54; N, 5.71. Found: C, 68.78; H, 5.67; N, 5.64.

EXAMPLE 248
Preparation of ethyl 2-ethanoyloxyimino-3-[2-[(4-chlorophenoxy)methyl]-1-methyl-1H-indol-3-yl]propanoate

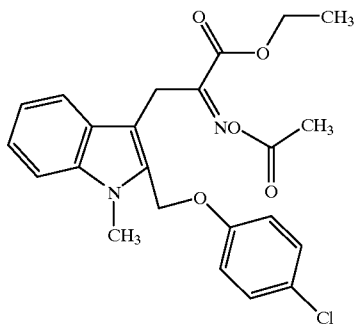

IR, NMR, and UV were consistent with the desired title structure.
FDMS 442 (M+).
mp 128–129° C.
Analysis for $C_{23}H_{23}ClN_2O_5$: Theory: C, 62.37; H, 5.23; N, 6.32. Found: C, 62.44; H, 5.40; N, 6.33.

EXAMPLE 249
Preparation of ethyl 2-benzoyloxyimino-3-[2-[(4-chlorophenoxy)methyl]-1-methyl-1H-indol-3-yl]propanoate

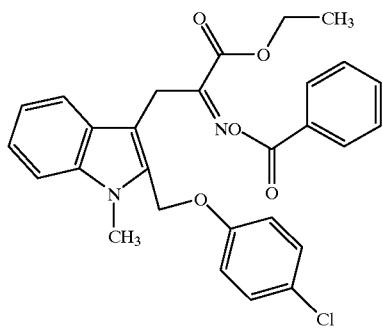

IR, NMR, and UV were consistent with the desired title structure.
FDMS 504 (M+).
mp 146–147° C.

Analysis for $C_{28}H_{25}ClN_2O_5$: Theory: C, 66.60; H, 4.99; N, 5.55. Found: C, 66.88; H, 5.22; N, 5.80.

EXAMPLE 250
Preparation of 2-[(4-chlorophenoxy)methyl]-3-(4-hydroxy-1-methylpiperidin-4-yl)-1-methyl-1H-indole

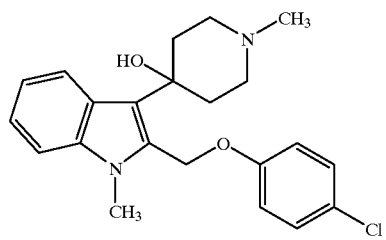

NMR, IR and UV were consistent with the desired title structure.
FDMS 384 (M+).
Analysis for $C_{22}H_{25}ClN_2O_2$: Theory: C, 68.65; H, 6.55; N, 7.28. Found: C, 69.46; H, 6.44; N, 7.28.
Single compound of high purity as evidenced by chromatographic methods.

EXAMPLE 251
Preparation of ethyl 2-hydroxyimino-3-[1-methyl-2-phenyl-1H-indol-3-yl]propanoate

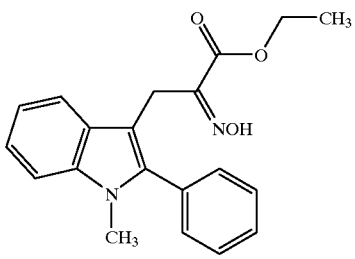

NMR ($CDCl_3$) was consistent with the proposed title structure.
UV and IR were consistent with the proposed title structure.
FDMS 322 (M+)
mp 141–142° C.
Analysis for $C_{19}H_{18}N_2O_3$: Theory: C, 70.79; H, 5.62; N, 8.69. Found: C, 70.64; H, 5.89; N, 8.58.

EXAMPLE 252
Preparation of ethyl 2-hydroxyimino-3-[1H-indol-3-yl]propanoate

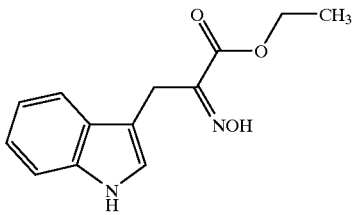

IR, NMR, and UV were consistent with the desired title structure.
FDMS 246 (M+).
mp 156° C.
Analysis for $C_{13}H_{14}N_2O_3 \cdot 0.3H_2O$: Theory: C, 62.04; H, 5.85; N, 11.13. Found: C, 61.77; H, 5.55; N, 11.07.

EXAMPLE 253
Preparation of 6-chloro-2-[(2,4-dichlorophenoxy)methyl]-1-methyl-3-[2-(piperidin-1-yl)ethyl]-1H-indole

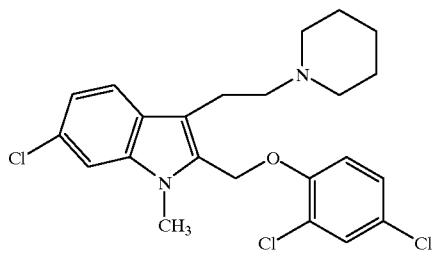

IR and NMR were consistent with the desired title structure. FDMS 450
(M+). mp 116.5–118.5° C.
Analysis for $C_{23}H_{25}Cl_3N_2O$: Theory: C, 61.14; H, 5.58; N, 6.20. Found: C, 61.43; H, 5.67; N, 6.26.

EXAMPLE 255
Preparation of 7-chloro-2-[(2,4-dichlorophenoxy)methyl]-1-methyl-3-[2-(piperidin-1-yl)ethyl]-1H-indole

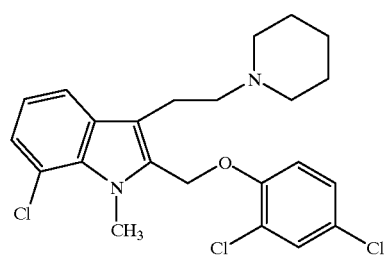

IR and NMR were consistent with the desired title structure. mp 134–136° C.
Analysis for $C_{23}H_{25}Cl_3N_2O$: Theory: C, 61.14; H, 5.58; N, 6.20. Found: C, 61.39; H, 5.71; N, 6.47.

EXAMPLE 256
Preparation of 4-methyl-2-[(2,4-dichlorophenoxy)methyl]-1-[3-(piperidin-3-yl)propyl]-1H-indole

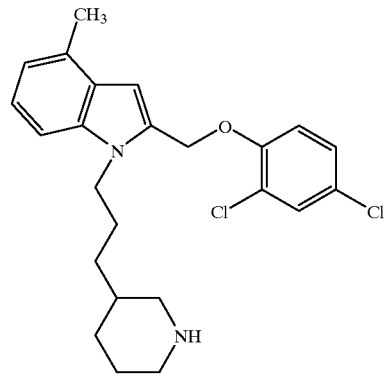

NMR (CDCl₃) was consistent with the proposed title structure.
Exact Mass FAB (M+1) for $C_{24}H_{30}ClN_2O$: Theory: 397.2047. Found: 397.2041.

EXAMPLE 257
Preparation of 5-chloro-2-[(2,4-dichlorophenoxy)methyl]-1-methyl-3-[(4-dimethylaminopiperidin-1-yl)methyl]-1H-indole dihydrochloride

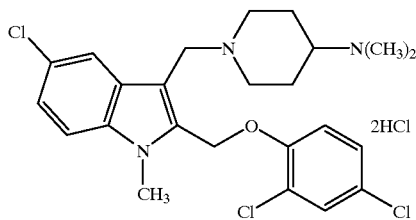

Analysis for $C_{24}H_{28}Cl_3N_3O$: Theory: C, 52.05; H, 5.46; N, 7.59. Found: C, 52.05; H, 5.41; N, 7.56.

EXAMPLE 258
Preparation of 7-methyl-2-[(2,4-dichlorophenoxy)methyl]-1-methyl-3-[3-(piperidin-1-yl)propyl]-1H-indole dihydrochloride

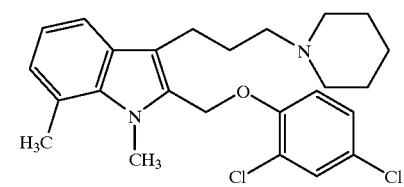

NMR (CDCl₃) was consistent with the proposed title structure.
mp 129–131° C.
Analysis for $C_{25}H_{30}Cl_2N_2O$: Theory: C, 67.41; H, 6.79; N, 6.29. Found: C, 67.34; H, 6.80; N, 6.05.

EXAMPLE 259
Preparation of 1,2-dimethyl-3-[[4-(piperidin-1-yl)piperidin-1-yl]acetyl]-1H-indole

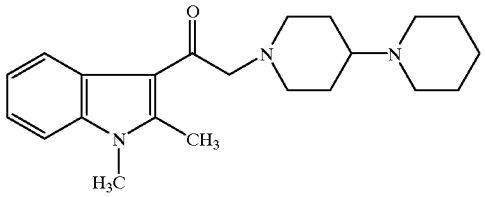

NMR, IR and UV were consistent with the desired title structure.
FDMS 353 (M+)
Analysis for $C_{22}H_{31}N_3O$: Theory: C, 74.75; H, 8.84; N, 11.89. Found: C, 74.76; H, 8.96; N, 11.76.

EXAMPLE 260
Preparation of 1,2-dimethyl-3-[[4-(N,N-dimethyamino)piperidin-1-yl]acetyl]-1H-indole

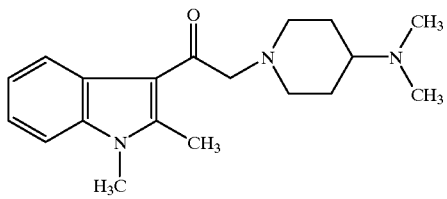

NMR was consistent with the desired title structure.
$C_{19}H_{27}N_3O$: FDMS 313 (M+).

EXAMPLE 261

Preparation of 2-[(4-chlorophenoxy)methyl]-3-[[(4-cyclohexyl)piperazin-1-yl]acetyl]-1-methyl-1H-indole

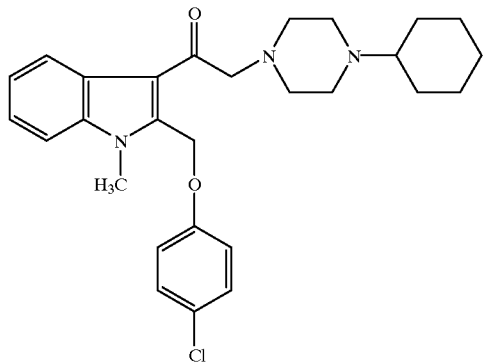

NMR was consistent with the desired title structure.
$C_{28}H_{34}ClN_3O_2$: FDMS 480 (M+)

EXAMPLE 262

Preparation of 2-[(4-chlorophenoxy)methyl]-3-[[(4-phenyl)piperazin-1-yl]acetyl]-1-methyl-1H-indole

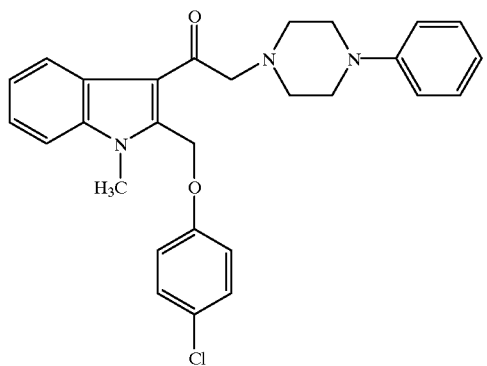

NMR was consistent for the desiredtitle structure.
$C_{28}H_{28}ClN3O_2$: FDMS 474 (M+)

EXAMPLE 263

Preparation of 2-[(4-chlorophenoxy)methyl]-3-[[4-(N,N-dimethylamino)piperidin-1-yl]acetyl]-1-methyl-1H-indole

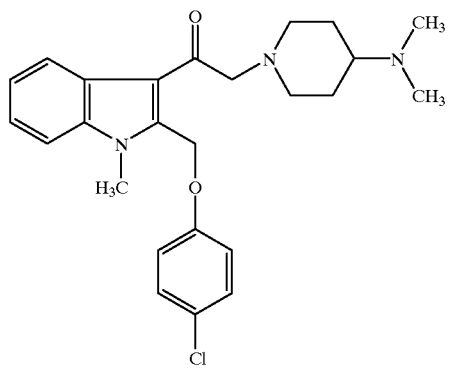

NMR, IR and UV were consistent with the desired title structure.
MSFD 439 (M+)
Analysis for $C_{25}H_{30}ClN_3O_2$: Theory: C, 68.25; H, 6.87; N, 9.55. Found: C, 67.98; H, 6.81; N, 9.40.

EXAMPLE 264

Preparation of 2-[(4-chlorophenoxy)methyl]-1-methyl-3-[[N-methyl-N-(3-N',N'-dimethylaminopropyl)amino]acetyl]-1H-indole

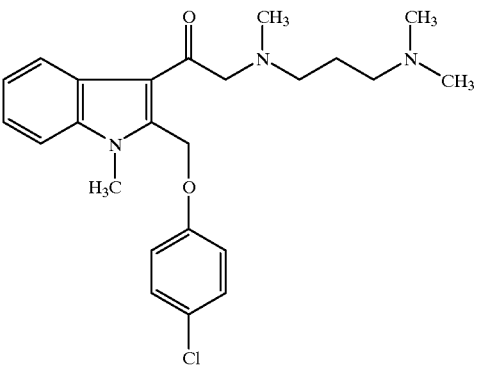

NMR and IR were consistent with the desired title structure.

FDMS 428 (M+1)

FAB exact mass Calculated for $C_{24}H_{31}ClN_3O_2$: 428.2105 Found: 428.2113

EXAMPLE 265

Preparation of 2[(4-chlorophenoxy)methyl]-1-methyl-3-[2-[(4-piperidin-1-yl)piperidin-1-yl]acetyl]-1H-indole

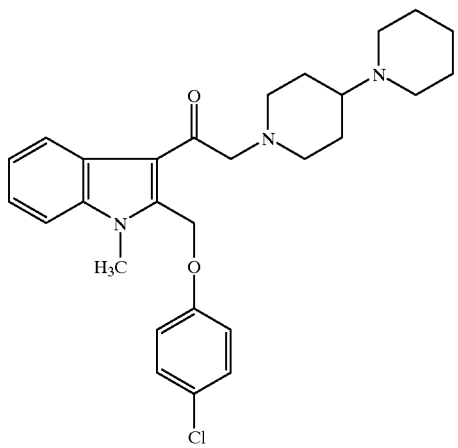

NMR, IR and UV were consistent with the desired title structure.

MSFD 479 ($M^{+1}$)

FAB exact mass Calculated for $C_{28}H_{35}ClN_3O_2$: 480.2418 Found 480.2411

EXAMPLE 266

Preparation of 2-[(4-chlorophenoxy)methyl]-3-[2-[(4-piperidin-1-yl)piperidin-1-yl]acetyl]-1-[2-(N,N-dimethylpiperidin-4-ylium)ethyl]-1H-indole iodide

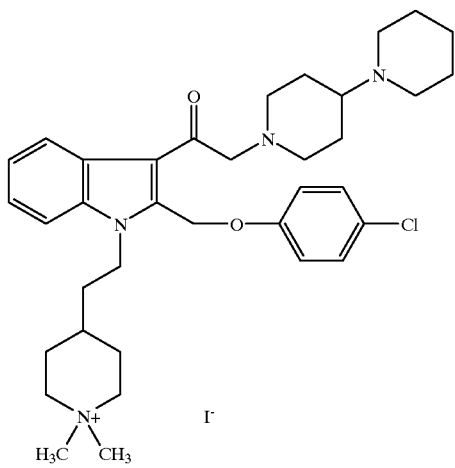

NMR was consistent with the desired title structure.

Analysis for $C_{36}H_{50}ClIN_4O_2 \cdot H_2O$: Theory: C, 57.56; H, 6.90; N, 7.46. Found: C, 57.85; H, 6.86; N, 7.04

EXAMPLE 267

2-[(4-chlorophenoxy)methyl]-1-[(2-piperidin-4-yl)ethyl]-3-[2-[4-(piperidin-1-yl)piperidin-1-yl]acet-1-yl]-1H-indole

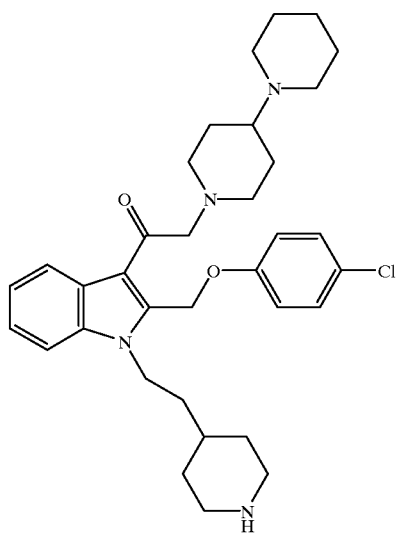

NMR was consistent with the desired title structure.

FABMS 577 (M+1)

Analysis for $C_{34}H_{45}ClN_4O_2$: Theory: C, 70.75; H, 7.86; N, 9.71 Found: C, 70.55; H, 7.87; N, 9.52

EXAMPLE 268

2-[(4-chlorophenoxy)methyl]-3-[2-(methylaminopropyldimethylamine)acet-1-yl]-1-[(2-piperidin-3-yl)ethyl]-indole

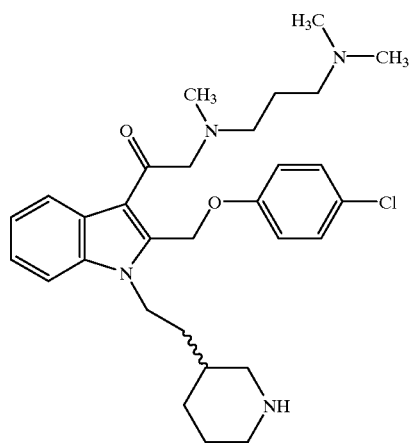

NMR was consistent with the desired title structure.

FABMS 525(M+1)

Exact Mass for $C_{30}H_{42}N_4O_2Cl$: Theory: 525.2996 Found: 525.3003

EXAMPLE 269

2-[(4-chlorophenoxy)methyl]-1-[(2-piperidin-3-yl)ethyl]-3-[2-(4-(piperidin-1-yl)piperidin-1-yl)acet-1-yl]-1H-indole

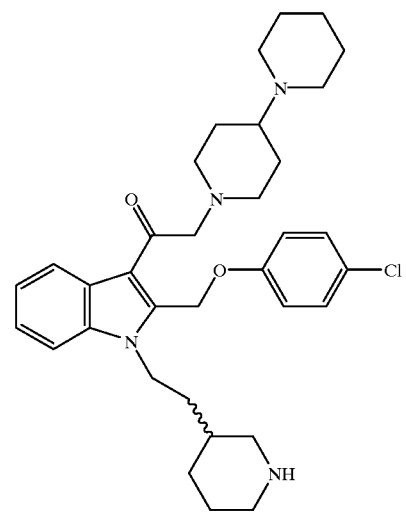

NMR was consistent with the desired title structure.

FDMS (M+1)

Analysis for: $C_{34}H_{45}N_4O_2Cl$: Theory: C, 70.75; H, 7.86; N, 9.71 Found: C, 70.72; H, 7.83; N, 9.63

EXAMPLE 270

2-[(4-chlorophenoxy)methyl]-3-[2-(methylaminopropyldimethylamine)acet-1-yl]-1-[(2-piperidin-4-yl)ethyl]-1H-indole

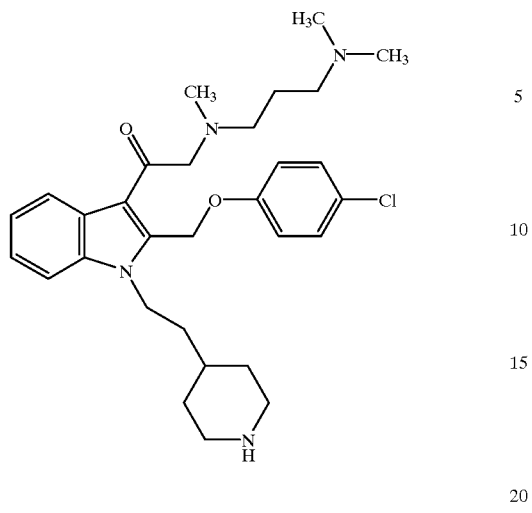

NMR was consistent with the desired title structure.

Exact Mass for $C_{30}H_{42}N_4O_4Cl$ (M+1): Theory: 525.2996 Found: 525.3013

EXAMPLE 271

S-2-[(4-chlorophenoxy)methyl]-3-[2-(4-(piperidin-1-yl)piperidin-1-yl)acet-1-yl]-1-[(3-piperidin-3-yl )propyl]-1H-indole

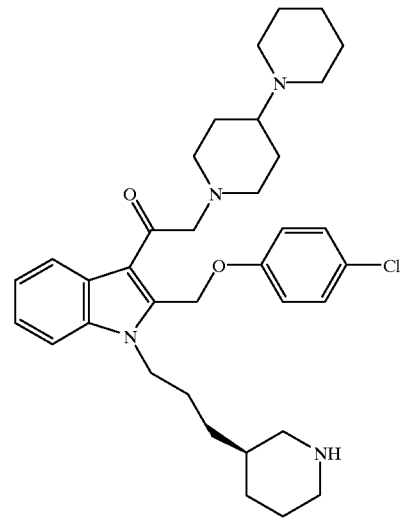

NMR was consistent with the desired title structure.

FABMS (M$^{+1}$)

Analysis for: $C_{35}H_{47}ClN_4O_2$ Theory: C, 71.10; H, 8.01; N, 9.48 Found: C, 70.82; H, 8.14; N, 9.23

EXAMPLE 272

R-2-[(4-chlorophenoxy)methyl]-3-[2-(4-(piperidin-1-yl)piperidin-1-yl)acet-1-yl] -1-[(3-piperidin-3-yl)propyl]-1H-indole

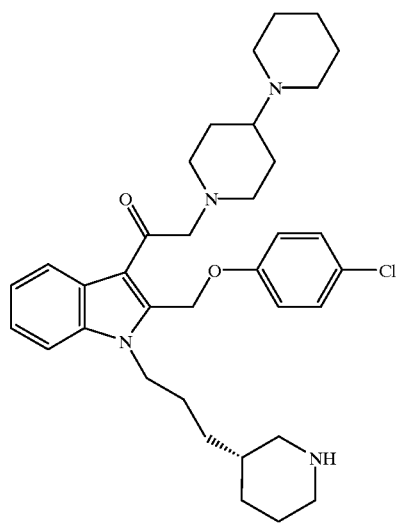

NMR was consistent with the desired title structure.

Exact Mass for $C_{35}H_{48}ClN_4O_2$: Theory: 591.3466 Found: 591.3458

EXAMPLE 273 cis/trans-2-[(4-chlorophenoxy)methyl]-1-methyl-3-[2-(4-(piperidin-1-yl)cyclohex-1-yl)acet-1-yl]-1H-indole

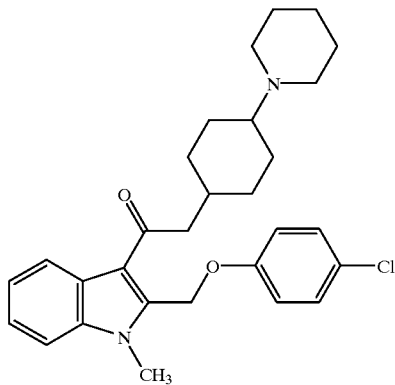

Mixture of cis/trans isomers 1 & 2

NMR was consistent with the desired title structure.

FDMS 478 (M+)

Analysis for: $C_{29}H_{35}ClN_2O_2$ Theory: C, 72.71; H, 7.36; N, 5.85 Found: C, 72.65; H, 7.61; N, 5.95

EXAMPLE 274

2-[(4-chlorophenoxy)methyl]-1-methyl-3-[2-(4-(piperidin-1-yl )cyclohex-1-yl)acet-1-yl]-1H-indole

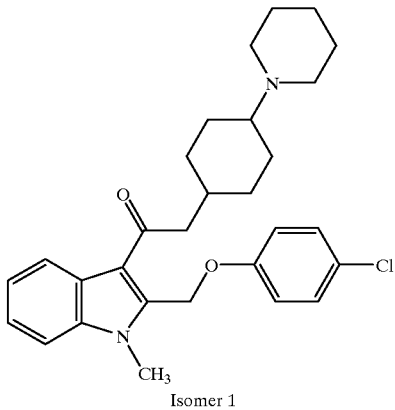

Isomer 1

NMR was consistent with the desired title structure.

FDMS 478 (M+)

Analysis for: $C_{29}H_{35}ClN_2O_2$ Theory: C, 72.71; H, 7.36; N, 5.85 Found: C, 72.55; H, 7.52; N, 5.67

EXAMPLE 275

2-[(4-chlorophenoxy)methyl] -3-[2-(4-(piperidin-1-yl)cyclohex-1-yl)acet-1-yl ]-1-[(2-piperidin-4-yl)ethyl]-1H-indole

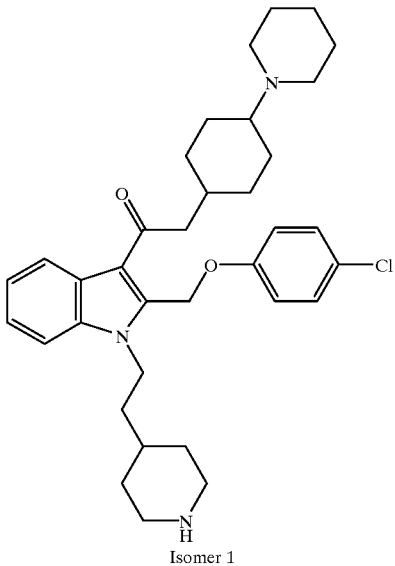

Isomer 1

NMR was consistent with the desired title structure.

FDMS 575 (M+)

Analysis for: $C_{35}H_{46}ClN_3O_2$ Theory: C, 72.95; H, 8.05; N, 7.29 Found: C, 72.88; H, 8.23; N, 7.53

EXAMPLE 276

2-[(4-chlorophenoxy)methyl]-1-methyl-3-[2-(4-(piperidin-1-yl)cyclohex-1-yl)acet-1-yl]-indole

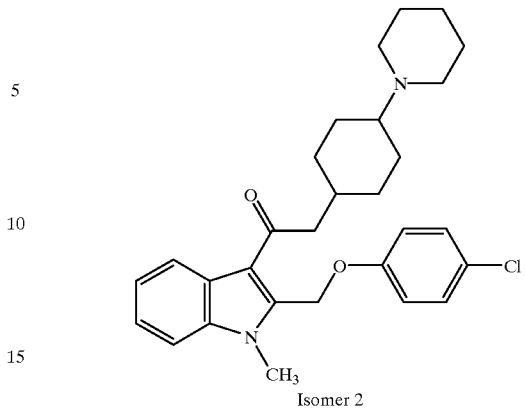

Isomer 2

NMR was consistent with the desired title structure.

FDMS 478 (M+)

Analysis for: $C_{29}H_{35}ClN_2O_2$ Theory: C, 72.71; H, 7.36; N, 5.85 Found: C, 72.43; H, 7.42; N, 5.86

EXAMPLE 277

2-[(4-chlorophenoxy)methyl]-5-fluoro-1-methyl-3-[2-(4-(piperidin-1-1)piperidin-1yl)acet-1-yl]-1H-indole

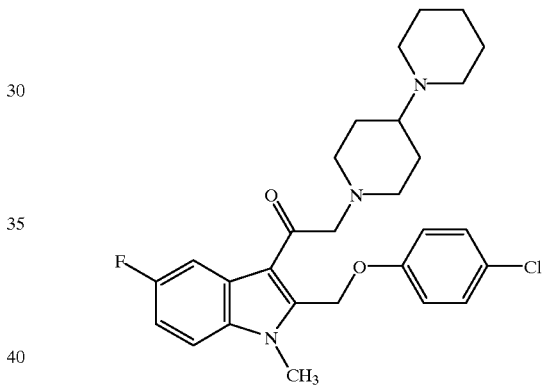

NMR was consistent with the desired title structure.

FABMS 498 (M+1)

Analysis for: $C_{28}H_{33}ClFN_3O_2$ Theory: C, 67.53; H, 6.68; N, 8.44 Found: C, 67.34; H, 6.59; N, 8.58

By substantially following the procedures described above one skilled in the art can prepare the other compounds of Formula I.

The compounds of the present invention bind to receptors specific for neuropeptide Y as well as the closely related neuropeptides. [For a review of neuropeptide Y receptors, see, D. Gehlert, *Life Sciences*, 55:551–562 (1994); P. A. Hipskind and D. R. Gehlert, *Annual Reports in Medicinal Chemistry*, 31:1 (1996)]. Receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13-36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. Several of the receptors have been successfully cloned to date. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity. C. Wahlestedt, et al., *Regulatory Peptides,* 13:307–318 (1986); C. Wahlestedt, etal., NEURONAL MESSENGERS IN VASCULAR FUNCTION, 231–241 (Nobin, et al., eds. 1987). Substitution of the amino acid at position 34 with a proline ($Pro^{34}$) results in a protein which is specific for the Y-1 receptor. E. K. Potter, et al., *European Journal of Pharmacology* 193:15–19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC cells. [For a review, see, B. J. McDermott, et al, *Cardiovascular Research,* 27:893–905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al, *Proceedings of the National Academy of Sciences (USA),* 89:57945798 (1992). The Y-1 receptor has been reported to couple to either second messenger system when studied using tissue preparations or cell lines naturally expressing the receptor. D. Gehlert, supra, at 553. The Y-1 receptor cannot, therefore, be distinguished solely on the basis of coupling to a single second messenger.

Modulation of a Y-1 receptor (either a typical or an atypical Y-1 receptor) is believed to influence multiple physiological conditions, including, but not limited to, obesity or appetite disorder, adult onset diabetes, bulimia nervosa, pheochromocytoma-induced hypertension, subarachnoid hemorrhage, neurogenic vascular hypertrophy, hypertension, anxiety, and anorexia nervosa. PCT Patent Publication WO 96/16542, published Jun. 6, 1996, at page 135, and the references cited therein.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13-36), though the 3-36 fragment of neuropeptide Y and peptide YY provides improved affinity and selectivity. Y. Dumont, et al., *Society for Neuroscience Abstracts,* 19:726 (1993). Like Y-1 receptor, this receptor is coupled to the inhibition of adenylate cyclase, though in some preparations it may not be sensitive to pertussis toxin. The Y-2 receptor was found to reduce the intracellular levels of calcium in the synapse by selective inhibition of N-type calcium channels. Like the Y-1 receptor, the Y-2 receptor may exhibit differential coupling to second messengers. The Y2 receptor is believed to be involved in modulating hypertension, epileptic seizure, and neurogenic vascular hypertrophy. PCT Patent Publication WO 96/16542, published Jun. 6, 1996, at page 135, and the references cited therein.

The Y-2 receptors are found in a variety of brain regions, including the hippocampus, substantia nigra-lateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters. The Y-2 receptor has been cloned using expression cloning techniques. P. M. Rose, et al., *Journal of Biological Chemistry.* 270:22661 (1995); C. Gerald, e., *Journal of Biological Chemistry,* 270:26758 (1995); D. R. Gehlert, et al., *Molecular Pharmacology* 49:224 (1996).

Y-3 Receptor

This receptor has high affinity for neuropeptide Y while having lower affinity for peptide YY. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology,* 182:207–208 (1990). This receptor is believed to modulate hypertension. PCT Patent Publication WO 96/16542, published Jun. 6, 1996, at page 135, and the references cited therein.

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences,* 50:PL7-PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al., *Endocrinology* 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to the crypt cells where intestinal chloride secretion is believed to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al., *Brain Research,* 604:304–317 (1993). While the pharmacology of this response resembled the Y-1 receptor, the 2-36 fragment of neuropeptide Y was significantly more potent than neuropeptide Y. In addition, intracerebroventricular neuropeptide Y(2-36) fully stimulates feeding, but does not reduce body temperature as does full length neuropeptide Y. F. B. Jolicoeur, et al., *Brain Research Bulletin,* 26:309–311 (1991). Two recent patent publications describe the cloning and expression of the Y5 receptor, believed to be the "feeding receptor". Patent Cooperation Treaty Publication WO 96/16542, published Jun. 6, 1996; and Australian Patent Publication AU 956467 AO, published Nov. 30, 1995.

The biological activity of the compounds of the present invention was evaluated employing an initial screening assay which rapidly and accurately measured the binding of the tested compound to known neuropeptide Y receptor sites. Assays useful for evaluating neuropeptide Y receptor antagonists are well known in the art. See. e.g., U.S. Pat. No. 5,284,839, issued Feb. 8, 1994, which is herein incorporated by reference. See also. M. W. Walker, etal., *Journal of Neurosciences*, 8:2438–2446 (1988).

Neuropeptide Y Binding Assay

The ability of the compounds of the instant invention were assessed as to their ability to bind to neuropeptide Y using a protocol essentially as described in M. W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at −70° C.

The pellets were resuspended using a glass homogenizer in mM HEPES (pH 7.4) buffer containing 2.5 mM calcium chloride, 1 mM magnesium chloride, and 2 g/L bacitracin. Incubations were performed in a final volume of 200 $\mu$l containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 $\mu$M neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

Many of the compounds prepared supra showed significant activity as neuropeptide Y receptor antagonists ($K_i$=10 $\mu$M to 0.1 nM). As the compounds of Formula I are effective neuropeptide Y receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, a compound of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range.

For examples, dosages per day normally fall within the range of about 0.5 to about 30 mg/kg of body weight. In the treatment of adult humans, the range of about 1 to about 15 mg,/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dipsersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compsoitions may be administered, preferably orally or nasally, from devices which deliver the formulation in an appropriate manner.

The following examples illustrate the pharmaceutical compositions of the present invention.

Formulation Preparation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |

| Ingredient | Quantity (mg/tablet) |
|---|---|
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
|---|---|
| Active Ingredient | 250.0 mg |
| Isotonic saline | 1000 ml |

Formulation Preparation 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g. U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of the formula

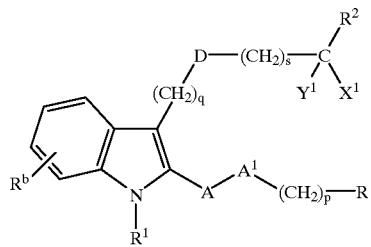

wherein:

$R^b$ is hydrogen, $C_1$–$C_6$ alkyl, $C_1$–$C_6$ alkoxy, $C_2$–$C_6$ alkanoyl, trifluoromethyl, hydroxy, or halo;

$R^1$ is hydrogen, $C_1$–$C_6$ alkyl, or —$(CH_2)_v$—$R^{1a}$;

where v is 1 to 12, and $R^{1a}$ is phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl, any one of which phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl groups may be substituted with one or more moieties selected from the groups consisting of $C_1$–$C_6$ alkyl, halo, trifluoromethyl, benzyl, phenyl, di($C_1$–$C_6$ alkyl)amino, $C_1$–$C_6$ alkylamino, $C_2$–$C_6$ alkanoyl, $C_2$–$C_6$ alkanoyloxy, and $C_3$–$C_8$ cycloalkyl, said said phenyl, benzyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy, or $R^{1a}$ may be substituted with —$(CH_2)_w$—$R^{1b}$, where w is 1 to 12 and $R^{1b}$ is piperidinyl, pyrimidyl, pyrrolidinyl, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, phenyl, $C_3$–$C_8$ cycloalkyl, pyrrolidinyl, and acetamido, said phenyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy;

A is a bond, —$(CH_2)_m$, or —$C(O)$—;

$A^1$ is —$NR^a$—, —O—, or —$S(O)_n$—;

q is 0 to 6;

p is 0 to 6;

n is 0, 1, or 2;

m is 0 to 6;

s is 0 to 6;

$R^a$ is hydrogen, $C_1$–$C_6$ alkyl, or $C_2$–$C_6$ alkanoyl;

D is a bond, $C_2$–$C_4$ alkenylenyl, or —$C(X)(Y)$—, where one of X and Y is hydroxy and the other is hydrogen, or both X and Y are hydrogen, or X and Y combine to form =O, or =$NOR^c$;

$R^c$ is hydrogen, benzyl, acetyl, benzoyl, or $C_1$–$C_6$ alkyl;

one of $X^1$ and $Y^1$ is hydroxy and the other is hydrogen, or both $X^1$ and $Y^1$ are hydrogen, or $X^1$ and $Y^1$ combine to form =O, or =$NOR^d$;

$R^d$ is hydrogen or $C_1$–$C_6$ alkyl;

$R^2$ is hydroxy, $C_1$–$C_6$ alkoxy, phenoxy, or a group of the formula

wherein $R^4$ and $R^5$ are independently hydrogen, $C_1$–$C_6$ alkyl, piperidinyl, phenyl, or phenyl($C_1$–$C_6$ alkylenyl)-, or $R^2$ is a heterocyclic ring selected from the group consisting of hexamethyleneiminyl, piperazinyl, heptamethyleneiminyl, imidazolinyl, piperidinyl, 2-tryptolinyl, pyrrolidinyl, quinuclidinyl, or morpholinyl;

any one of which $C_1$–$C_6$ alkoxy, —$NR^4R^5$, hexamethyleneiminyl, piperazinyl, heptamethyleneiminyl, imidazolinyl, piperidinyl, 2-tryptolinyl, pyrrolidinyl, quinuclidinyl, or morpholinyl groups may be substituted with one or more moieties selected from the group consisting of amino, aminocarbonyl, $C_1$–$C_6$ alkyl, halo, trifluoromethyl, benzyl, phenyl, di($C_1$–$C_6$ alkyl)amino, di($C_1$–$C_6$ alkyl)amino($C_1$–$C_6$ alkylenyl)-, $C_1$–$C_6$ alkylamino($C_1$–$C_6$ alkylenyl)-, $C_2$–$C_6$ alkanoyl, carboxamido, 2-aminoacetyl, $C_2$–$C_6$ alkanoyloxy, $C_1$–$C_6$ alkoxycarbonyl-, $C_1$–$C_6$ alkylamino, $C_3$–$C_8$ cycloalkyl, piperidinyl, pyrrolidinyl, pyrimidyl, phenyl($C_1$–$C_6$ alkylenyl)-, phenoxy($C_1$–$C_6$ alkylenyl)-, piperidinyl($C_1$–$C_6$ alkylenyl)-, pyrrolidinyl($C_1$–$C_6$ alkylenyl)-, pyrimidyl($C_1$–$C_6$ alkylenyl)-, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, and acetamido, any one of which benzyl, phenyl, piperidinyl, $C_3$–$C_8$ cycloalkyl, phenyl($C_1$–$C_6$ alkylenyl)-, phenoxy ($C_1$–$C_6$ alkylenyl)-, pyrrolidinyl, piperidinyl ($C_1$–$C_6$ alkylenyl)-, pyrrolidinyl($C_1$–$C_6$ alkylenyl)-, pyrimidyl($C_1$–$C_6$ alkylenyl)-, or pyrimidyl group may be substituted with one or more moieties selected from the group consisting of $C_1$–$C_6$ alkyl, halo, trifluoromethyl, acetamido, $C_2$–$C_6$ alkanoyl, $C_2$–$C_7$ alkanoyloxy, and $C_1$–$C_6$ alkoxy, or the nitrogen on said piperidinyl, pyrrolidinyl, piperidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl may be substituted with an amino-protecting group, or $R^2$ is a group of the formula

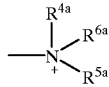

where $R^{4a}$, $R^{5a}$, and $R^{6a}$ are independently hydrogen, $C_1$–$C_6$ alkyl, trifluoromethyl, or $C_1$–$C_6$ alkoxy, or $R^{4a}$ is hydrogen, $C_1$–$C_6$ alkyl, trifluoromethyl, or $C_1$–$C_6$ alkoxy and $R^{5a}$ and $R^{6a}$ combine to form, together with the nitrogen to which they are attached, pyrrolidinyl, piperidinyl, hexamethyleneiminyl, or heptamethyleneiminyl, or $R^{4a}$ is oxygen, and $R^{5a}$ and $R^{6a}$ combine to form, together with the nitrogen to which they are attached, pyrrolidinyl, piperidinyl, hexamethyleneiminyl, or heptamethyleneiminyl;

R is phenyl, naphthyl, dihydronaphthyl, tetrahydronaphthyl, $C_3$–$C_8$ cycloalkyl, pyrazinyl, allyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl, any one of which phenyl, naphthyl, dihydronaphthyl, tetrahydronaphthyl, $C_3$–$C_8$ cycloalkyl, pyrazinyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl groups may be substituted with one or more moieties selected from the group consisting of $C_1$–$C_{12}$ alkyl, $C_2$–$C_{10}$ alkenyl, $C_2$–$C_{10}$ alkynyl, halo, trifluoromethyl, carboxamido, cyano, benzyl, phenyl, di($C_1$–$C_6$ alkyl)amino, $C_2$–$C_6$ alkanoyl, $C_2$–$C_6$ alkanoyloxy, $C_1$–$C_6$ alkylamino, oxazolyl, dihydrooxazolyl, piperidinyl($C_1$–$C_{12}$ alkoxy)-, piperidinyl($C_1$–$C_{12}$ alkoxy)($C_1$–$C_6$ alkylenyl)-, piperidinyl($C_1$–$C_{12}$ alkylenyl)-, phenyl ($C_1$–$C_{12}$ alkoxy)-, phenyl($C_2$–$C_{12}$ alkylenyl)-, $C_3$–$C_8$ cycloalkyl, piperidinyl, pyrimidyl, $C_1$–$C_6$ alkoxy, $C_1$–$C_6$ alkylthio, a group of the formula $R^xR^yN$—G—L-($C_0$–$C_6$ alkylenyl)-, and acetamido, where $R^x$ and $R^y$ are independently hydrogen, $C_1$–$C_6$ alkyl, phenyl, benzyl, piperidinyl, pyrrolidinyl, hexamethyleneiminyl, heptamethyleneiminyl, morpholinyl, piperazinyl, or $C_3$–$C_8$ cycloalkyl, or where $R^xR^yN$ is a ring selected from the group consisting of piperidinyl, pyrrolidinyl, hexamethyleneiminyl, heptamethyleneiminyl, azetidinyl, which may be attached to G at any appropriate place on the ring, G is $C_1$–$C_{12}$ alkylenyl, $C_2$–$C_{12}$ alkenylenyl, or $C_2$–$C_{12}$ alkynylenyl, and L is a bond, —O—, —S—, —S(O)—, —S(O)$_2$—, or —NH—;

with the proviso that when A is a bond, n cannot be 0, and when A=—C(O)—, $A^1$ cannot be —O—, and when —A—$A^1$— is —$CH_2$—$NR^a$—, —$CH_2$—S(O)$_n$, or —C(O)—$NR^a$—, $R^1$ cannot be hydrogen;

or a pharmaceutically acceptable salt or solvate thereof.

2. A compound as claimed in claim 1 wherein $R^1$ is hydrogen, or methyl or $R^{1a}$ is piperidinyl, pyrrolidinyl, piperazinyl, or quinuclidinyl, or a pharmaceutically acceptable salt or solvate thereof.

3. A compound as claimed in claim 2 wherein $R^{1a}$ is piperidin-3-yl, piperidin-2-yl, pyrrolidin-3-yl, or pyrrolidin-2-yl, piperidin-1-yl, piperidin-4-yl, pyrrolidin-1-yl, or pyrrolidin-4-yl, phenyl, or a pharmaceutically acceptable salt or solvate thereof.

4. A compound as claimed in claim 3 wherein $A^1$ is —O—, or a pharmaceutically acceptable salt or solvate thereof.

5. A compound as claimed in claim 4 wherein —($CH_2$)$_q$—D—($CH_2$)$_s$— is a bond, methylene, ethylene, or —C(O)—, or a pharmaceutically acceptable salt or solvate thereof.

6. A compound as claimed in claim 5 wherein both $X^1$ and $Y^1$ are hydrogen, or a pharmaceutically acceptable salt or solvate thereof.

7. A compound as claimed in claim 6 wherein $R^2$ is a piperidinyl group substituted with amino, di($C_1$–$C_6$ alkyl) amino, $C_1$–$C_6$ alkylamino, or piperidinyl, or $R^2$ is a pyrrolidinyl group substituted with amino, di($C_1$–$C_6$ alkyl)amino, $C_1$–$C_6$ alkylamino, or pyrrolidinyl, or $R^2$ is a piperazinyl group substituted with phenyl or cyclohexyl, or a pharmaceutically acceptable salt or solvate thereof.

8. A compound as claimed in claim 7 wherein —A—$A^1$— ($CH_2$)$_p$— is —$CH_2$—O—, —$CH_2$—NH—, or —$CH_2$—S—, or a pharmaceutically acceptable salt or solvate thereof.

9. A compound as claimed in claim 8 wherein R is naphthyl, phenyl, piperidinyl, pyrrolidinyl, or cyclohexyl, or a pharmaceutically acceptable salt or solvate thereof.

10. A compound as claimed in claim 9 wherein R is phenyl optionally independently substituted at the 4-position and at the 2-position with halo, or a pharmaceutically acceptable salt or solvate thereof.

11. A compound selected from the group consisting of 2-[(4-chlorophenoxy)methyl]-1-methyl-3-[(1-tritylpiperidin-4-yl)acetyl]-1H-indole, 2-[(4-chlorophenoxy)methyl]-1-methyl-3-[[2-(1-tritylpiperidin-4- yl)ethyl]carbonyl]-1H-indole, 2-[(4-chlorophenoxy) methyl]-1-methyl-3-[2-[3-(t-butoxycarbonylamino) propylamino]-1,2-ethanedionyl]-1H-indole, 2-[(4-chlorophenoxy)methyl]-1-methyl-3-[2-[N-methyl-(1-methylpyrrolidin-3-yl)amino]-1,2-ethanedionyl]-1H-indole, 2-[(4-chlorophenoxy)methyl]-1-methyl-3-[2-[(quinuclidin-3-yl)amino]-1,2-ethanedionyl]-1H-indole, 2-[(4-chlorophenoxy)methyl]-1-methyl-3-[2-[2-(dimethylaminomethyl)cyclohexylamino]-1,2-ethanedionyl]-1H-indole hydrochloride, 2-[2-hydroxyethyl]-1-methyl-3-[(piperidin-1-yl)methyl]-1H-indole, 2-(2-methoxyethyl)-1-methyl-3-[(piperidin-1-yl) methyl]-1H-indole, 2-[(n-propylthio)methyl]-1-methyl-3-[(piperidin-1-yl)methyl]-1H-indole hydrochloride, 2-[(4-chlorophenoxy)methyl]-3-formyl-1-methyl-1H-indole, (RS) ethyl 2-amino-3-[2-[(4-chlorophenoxy)methyl]-1-methyl-1H-indol-3-yl]propanoate, 2-[(4-chlorophenoxy)methyl]-3-(4-hydroxy-1-methylpiperidin-4-yl)-1-methyl-1H-indole, cis/trans-2-[(4-chlorophenoxy)methyl]-1-methyl-3-[2-(4-(piperidin-1-yl)cyclohex-1-yl)acet-1-yl]-1H-indole, 2-[(4-chlorophenoxy)methyl]-1-methyl-3-[2-(4-(piperidin-1-yl) cyclohex-1-yl)acet-1-yl]-1H-indole, 2-[(4-chlorophenoxy) methyl]-3-[2-(4-(piperidin-1-yl)cyclohex-1-yl)acet-1-yl]-1-[(2-piperidin-4-yl)ethyl]-1H-indole, or 2-[(4-chlorophenoxy)methyl]-1-methyl-3-[2-(4-(piperidin-1-yl) cyclohex-1-yl)acet-1-yl]-indole.

12. A compound selected from the group consisting of 2-[(4-chlorophenoxy)methyl]-1-[2-(piperidin-1-yl)ethyl]-1H-indole, 2-[(4-chlorophenoxy)methyl]-1-[2-(piperidin-4-yl)ethyl]-1H-indole, 2-[(phenylthio)methyl]-1-[3-(piperidin-3-yl)propyl]-1H-indole, 2-[(4-chlorophenoxy) methyl]-1-[3-(piperidin-3-yl)propyl]-1H-indole, 2-[(4-chlorophenoxy)methyl]-1-[3-(1-methylpiperidin-3-yl) propyl]-1H-indole, 2-[(4-chlorophenoxy)methyl]-1-[3-(piperidin-4-yl)propyl]-1H-indole, 1-methyl-3-[2-[N-benzyl-N-3-(dimethylaminopropyl)amino]-1,2-ethanedionyl]-1H-indole, 1-methyl-3-[2-(4-dimethylaminopiperidin-1-yl)-1,2-ethanedionyl]-1H-indole, 2-[(4-chlorophenoxy)methyl]-1-methyl-1H-indole, 2-[(2,4-dichlorophenoxy)methyl]-1-methyl-1H-indole, 2-[(5,6,7,8-tetrahydronaphth-1-yloxy)methyl]-1-methyl-1H-indole, 2-[(5,6,7,8-tetrahydronaphth-2-yloxy)methyl]-1-methyl-1H-indole, (RS) 1,2-dimethyl-3-[3-(piperidin-3-yl)propyl]-1H-indole, 1-methyl-2-[[2-[(piperidin-1-yl)methyl] phenoxy]methyl]-1H-indole, 1-methyl-3-[2-[(4-chlorophenoxy)methyl]piperidin-1-ylmethyl]-1H-indole, 1-methyl-3-[3-[(4-chlorophenoxy)methyl]piperidin-1-ylmethyl]-1H-indole, 1-methyl-3-[2-[2-(4-chlorophenoxy) ethyl]piperidin-1-ylmethyl]-1H-indole, ethyl 2-hydroxyimino-3-[1H-indol-3-yl]propanoate, 4-methyl-2-[(2,4-dichlorophenoxy)methyl]-1-[3-(piperidin-3-yl) propyl]-1H-indole, 1,2-dimethyl-3-[[4-(piperidin-1-yl) piperidin-1-yl]acetyl]-1H-indole, or 1,2-dimethyl-3-[[4-(N, N-dimethyamino)piperidin-1-yl]acetyl]-1H-indole.

13. A compound selected from the group consisting of 2-[2-(4-chlorophenyl)ethyl]-1-methyl-3-[(piperidin-1-yl) methyl]-1H-indole hydrochloride, 2-phenyl-3-(piperidin-1-yl)methyl-1H-indole, 1-methyl-2-phenyl-3-(piperidin-1-yl) methyl-1H-indole, 2-phenyl-1-methyl-3-[2-(piperidin-1-yl)-1,2-ethanedionyl]-1H-indole, 2-phenyl-1-methyl-3-[2-[N-benzyl-N-3-(dimethylaminopropyl)amino]-1,2-ethanedionyl]-1H-indole, 2-phenyl-1-methyl-3-[2-(4-dimethylaminopiperidin-1-yl)-1,2-ethanedionyl]-1H-indole, or ethyl 2-hydroxyimino-3-[1-methyl-2-phenyl-1H-indol-3-yl]propanoate.

14. A pharmaceutical formulation comprising a compound of the formula

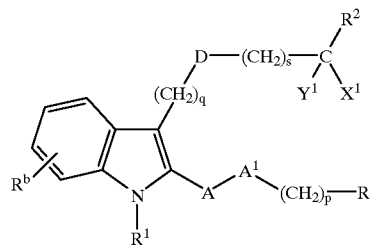

wherein:

$R^b$ is hydrogen, $C_1$–$C_6$ alkyl, $C_1$–$C_6$ alkoxy, $C_2$–$C_6$ alkanoyl, trifluoromethyl, hydroxy, or halo;

$R^1$ is hydrogen, $C_1$–$C_6$ alkyl, or —$(CH_2)_v$—$R^{1a}$;

where v is 1 to 12, and $R^{1a}$ is phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl, any one of which phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl groups may be substituted with one or more moieties selected from the groups consisting of $C_1$–$C_6$ alkyl, halo, trifluoromethyl, benzyl, phenyl, di($C_1$–$C_6$ alkyl)amino, $C_1$–$C_6$ alkylamino, $C_2$–$C_6$ alkanoyl, $C_2$–$C_6$ alkanoyloxy, and $C_3$–$C_8$ cycloalkyl, said said phenyl, benzyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy, or $R^{1a}$ may be substituted with —$(CH_2)_w$—$R^{1b}$, where w is 1 to 12 and $R^{1b}$ is piperidinyl, pyrimidyl, pyrrolidinyl, $C_1$–$C_6$ alkoxy, $C_1$–$C_6$ alkylthio, di[di ($C_1$–$C_6$ alkyl)amino($C_1$–$C_6$ alkylenyl)]amino, di($C_1$–$C_6$ alkyl)amino($C_1$–$C_6$ alkylenyl)amino, phenyl, $C_3$–$C_8$ cycloalkyl, pyrrolidinyl, and acetamido, said phenyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy;

A is a bond, —$(CH_2)_m$, or —$C(O)$—;

$A^1$ is —$NR^a$—, —O—, or —$S(O)_n$—;

q is 0 to 6;

p is 0 to 6;

n is 0, 1, or 2;

m is 0 to 6;

s is 0 to 6;

$R^a$ is hydrogen, $C_1$–$C_6$ alkyl, or $C_2$–$C_6$ alkanoyl;

D is a bond, $C_2$–$C_4$ alkenylenyl, or —$C(X)(Y)$—, where one of X and Y is hydroxy and the other is hydrogen, or both X and Y are hydrogen, or X and Y combine to form =O, or =$NOR^c$;

$R^c$ is hydrogen, benzyl, acetyl, benzoyl, or $C_1$–$C_6$ alkyl;

one of $X^1$ and $Y^1$ is hydroxy and the other is hydrogen, or both $X^1$ and $Y^1$ are hydrogen, or $X^1$ and $Y^1$ combine to form =O, or =$NOR^d$;

$R^d$ is hydrogen or $C_1$–$C_6$ alkyl;

$R^2$ is hydroxy, $C_1$–$C_6$ alkoxy, phenoxy, or a group of the formula

wherein $R^4$ and $R^5$ are independently hydrogen, $C_1$–$C_6$ alkyl, piperidinyl, phenyl, or phenyl($C_1$–$C_6$ alkylenyl)—, or $R^2$ is a heterocyclic ring selected from the group consisting of hexamethyleneiminyl, piperazinyl, heptamethyleneiminyl, imidazolinyl, piperidinyl, 2-tryptolinyl, pyrrolidinyl, quinuclidinyl, or morpholinyl;

any one of which $C_1$–$C_6$ alkoxy, —$NR^4R^5$, hexamethyleneiminyl, piperazinyl, heptamethyleneiminyl, imidazolinyl, piperidinyl, 2-tryptolinyl, pyrrolidinyl, quinuclidinyl, or morpholinyl groups may be substituted with one or more moieties selected from the group consisting of amino, aminocarbonyl, $C_1$–$C_6$ alkyl, halo, trifluoromethyl, benzyl, phenyl, di($C_1$–$C_6$ alkyl)amino, di($C_1$–$C_6$ alkyl)amino($C_1$–$C_6$ alkylenyl)-, $C_1$–$C_6$ alkylamino($C_1$–$C_6$ alkylenyl)-, $C_2$–$C_6$ alkanoyl, carboxamido, 2-aminoacetyl, $C_2$–$C_6$ alkanoyloxy, $C_1$–$C_6$ alkoxycarbonyl-, $C_1$–$C_6$ alkylamino, $C_3$–$C_8$ cycloalkyl, piperidinyl, pyrrolidinyl, pyrimidyl, phenyl($C_1$–$C_6$ alkylenyl)-, phenoxy($C_1$–$C_6$ alkylenyl)-, piperidinyl($C_1$–$C_6$ alkylenyl)-, pyrrolidinyl($C_1$–$C_6$ alkylenyl)-, pyrimidyl($C_1$–$C_6$ alkylenyl)-, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, and acetamido, any one of which benzyl, phenyl, piperidinyl, $C_3$–$C_8$ cycloalkyl, phenyl($C_1$–$C_6$ alkylenyl)-, phenoxy($C_1$–$C_6$ alkylenyl)-, pyrrolidinyl, piperidinyl ($C_1$–$C_6$ alkylenyl)-, pyrrolidinyl($C_1$–$C_6$ alkylenyl)-, pyrimidyl($C_1$–$C_6$ alkylenyl)-, or pyrimidyl group may be substituted with one or more moieties selected from the group consisting of $C_1$–$C_6$ alkyl, halo, trifluoromethyl, acetamido, $C_2$–$C_6$ alkanoyl, $C_2$–$C_7$ alkanoyloxy, and $C_1$–$C_6$ alkoxy, or the nitrogen on said piperidinyl, pyrrolidinyl, piperidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl may be substituted with an amino-protecting group, or $R^2$ is a group of the formula

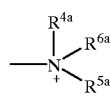

where $R^{4a}$, $R^{5a}$, and $R^{6a}$ are independently hydrogen, $C_1$–$C_6$ alkyl, trifluoromethyl, or $C_1$–$C_6$ alkoxy, or $R^4a$ is hydrogen, $C_1$–$C_6$ alkyl, trifluoromethyl, or $C_1$∫$C_6$ alkoxy and $R^{5a}$ and $R^{6a}$ combine to form, together with the nitrogen to which they are attached, pyrrolidinyl, piperidinyl, hexamethyleneiminyl, or heptamethyleneiminyl, or $R^{4a}$ is oxygen, and $R^{5a}$ and $R^{6a}$ combine to form, together with the nitrogen to which they are attached, pyrrolidinyl, piperidinyl, hexamethyleneiminyl, or heptamethyleneiminyl;

R is phenyl, naphthyl, dihydronaphthyl, tetrahydronaphthyl, $C_3$–$C_8$ cycloalkyl, pyrazinyl, allyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl, any one of which phenyl, naphthyl, dihydronaphthyl, tetrahydronaphthyl, $C_3$–$C_8$ cycloalkyl, pyrazinyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl groups may be substituted with one or more moieties selected from the group consisting of $C_1$–$C_{12}$ alkyl, $C_2$–$C_{10}$ alkenyl, $C_2$–$C_{10}$ alkynyl, halo, trifluoromethyl, carboxamido, cyano, benzyl, phenyl, di($C_1$–$C_6$ alkyl)amino, $C_2$–$C_6$ alkanoyl, $C_2$–$C_6$ alkanoyloxy, $C_1$–$C_6$ alkylamino, oxazolyl, dihydrooxazolyl, piperidinyl($C_1$–$C_{12}$ alkoxy)-, piperidinyl($C_1$–$C_{12}$ alkoxy)($C_1$–$C_6$ alkylenyl)-, piperidinyl($C_1$–$C_{12}$ alkylenyl)-, phenyl ($C_1$–$C_{12}$ alkoxy)-, phenyl($C_2$–$C_{12}$ alkylenyl)-, $C_3$–$C_8$ cycloalkyl, piperidinyl, pyrimidyl, $C_1$–$C_6$ alkoxy, $C_1$–$C_6$ alkylthio, a group of the formula $R_xR^yN$—G—L—($C_0$–$C_6$ alkylenyl)-, and acetamido, where $R^x$ and $R^y$ are independently hydrogen, $C_1$–$C_6$ alkyl, phenyl, benzyl, piperidinyl, pyrrolidinyl, hexamethyleneiminyl, heptamethyleneiminyl, morpholinyl, piperazinyl, or $C_3$–$C_8$ cycloalkyl, or where $R^xR^yN$ is a ring selected from the group consisting of piperidinyl, pyrrolidinyl, hexamethyleneiminyl, heptamethyleneiminyl, azetidinyl, which may be attached to G at any appropriate place on the ring, G is $C_1$–$C_{12}$ alkylenyl, $C_2$–$C_{12}$ alkenylenyl, or $C_2$–$C_{12}$ alkynylenyl, and L is a bond, —O—, —S—, —S(O)—, —S(O)2—, or —NH—;

with the proviso that when A is a bond, n cannot be 0, and when A=—C(O)—, $A^1$ cannot be —O—, and when —A—$A^1$— is —$CH_2$—$NR^a$—, —$CH^2$—$S(O)_n$, or —C(O)—$NR^a$—, $R^1$ cannot be hydrogen;

or a pharmaceutically acceptable salt or solvate thereof, in combination with one or more carriers, diluents, or excipients therefor.

15. A formulation as claimed in claim 14 employing a compound wherein $R^1$ is hydrogen, or methyl or $R^{1a}$ is piperidinyl, pyrrolidinyl, piperazinyl, or quinuclidinyl, or a pharmaceutically acceptable salt or solvate thereof.

16. A formulation as claimed in claim 15 employing a compound wherein $R^{1a}$ is piperidin-3-yl, piperidin-2-yl, pyrrolidin-3-yl, or pyrrolidin-2-yl, piperidin-1-yl, piperidin-4-yl, pyrrolidin-1-yl, or pyrrolidin-4-yl, phenyl, or a pharmaceutically acceptable salt or solvate thereof.

17. A formulation as claimed in claim 16 employing a compound wherein $A^1$ is —O—, or a pharmaceutically acceptable salt or solvate thereof.

18. A formulation as claimed in claim 17 employing a compound wherein —$(CH_2)_q$—D—$(CH_2)_s$— is a bond, methylene, ethylene, or —C(O)—, or a pharmaceutically acceptable salt or solvate thereof.

19. A formulation as claimed in claim 18 employing a compound wherein both $X^1$ and $Y^1$ are hydrogen, or a pharmaceutically acceptable salt or solvate thereof.

20. A formulation as claimed in claim 19 employing a compound wherein $R^2$ is a piperidinyl group substituted with amino, di($C_1$–$C_6$ alkyl)amino, $C_1$–$C_6$ alkylamino, or piperidinyl, or $R^2$ is a pyrrolidinyl group substituted with amino, di($C_1$–$C_6$ alkyl)amino, $C_1$–$C_6$ alkylamino, or pyrrolidinyl, or $R^2$ is a piperazinyl group substituted with phenyl or cyclohexyl, or a pharmaceutically acceptable salt or solvate thereof.

21. A formulation as claimed in claim 20 employing a compound wherein —A—$A^1$—$(CH_2)_p$— is —$CH_2$—O—, —$CH_2$—NH—, or —$CH_2$—S—, or a pharmaceutically acceptable salt or solvate thereof.

22. A formulation as claimed in claim 21 employing a compound wherein R is naphthyl, phenyl, piperidinyl, pyrrolidinyl, or cyclohexyl, or a pharmaceutically acceptable salt or solvate thereof.

23. A formulation as claimed in claim 22 employing a compound wherein R is phenyl optionally independently substituted at the 4-position and at the 2-position with with halo, or a pharmaceutically acceptable salt or solvate thereof.

24. A method of treating or preventing a physiological disorder associated with an excess of neuropeptide Y, which method comprises administering to a mammal in need of said treatment an effective amount of a compound of the formula

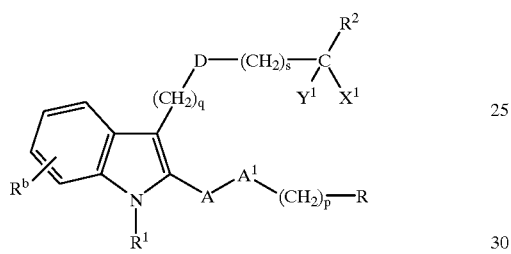

wherein:
$R^b$ is hydrogen, $C_1$–$C_6$ alkyl, $C_1$–$C_6$ alkoxy, $C_2$–$C_6$ alkanoyl, trifluoromethyl, hydroxy, or halo;

$R^1$ is hydrogen, $C_1$–$C_6$ alkyl, or —$(CH_2)_v$—$R^{1a}$;
where v is 1 to 12, and $R^{1a}$ is phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl, any one of which phenyl, naphthyl, hexamethyleneiminyl, piperazinyl, heptamethyleneiminyl, imidazolinyl, piperidinyl, tryptolinyl, pyrrolidinyl, quinuclidinyl, or morpholinyl groups may be substituted with one or more moieties selected from the groups consisting of $C_1$–$C_6$ alkyl, halo, trifluoromethyl, benzyl, phenyl, di($C_1$–$C_6$ alkyl)amino, $C_1$–$C_6$ alkylamino, $C_2$–$C_6$ alkanoyl, $C_2$–$C_6$ alkanoyloxy, and $C_3$–$C_8$ cycloalkyl, said phenyl, benzyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy,
or $R^{1a}$ may be substituted with —$(CH_2)_w$—$R^{1b}$, where w is 1 to 12 and $R^{1b}$ is piperidinyl, pyrimidyl, pyrrolidinyl, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, phenyl, $C_3$–$C_8$ cycloalkyl, pyrrolidinyl, and acetamido,
said phenyl, or $C_3$–$C_8$ cycloalkyl, being optionally substituted with one, two, or three moieties independently selected from the group consisting of $C_1$–$C_6$ alkyl, halo, or $C_1$–$C_6$ alkoxy;

A is a bond, —$(CH_2)_m$, or —C(O)—;
$A^1$ is —$NR^a$—, —O—, or $S(O)_n$—;
q is 0 to 6;

p is 0 to 6;
n is 0, 1, or 2;
m is 0 to 6;
s is 0 to 6;
$R^a$ is hydrogen, $C_1$–$C_6$ alkyl, or $C_2$–$C_6$ alkanoyl;
D is a bond, $C_2$–$C_4$ alkenylenyl, or —C(X)(Y)—,
wherein one of X and Y is hydroxy and the other is hydrogen, or both X and Y are hydrogen, or X and Y combine to form =O, or =$NOR^c$;
$R^c$ is hydrogen, benzyl, acetyl, benzoyl, or $C_1$–$C_6$ alkyl;
one of $X^1$ and $Y^1$ is hydroxy and the other is hydrogen, or both $X^1$ and $Y^1$ are hydrogen, or $X^1$ and $Y^1$ combine to form =O, or =$NOR^d$;
$R^d$ is hydrogen or $C_1$–$C_6$ alkyl;
$R^2$ is hydroxy, $C_1$–$C_6$ alkyl, $C_1$–$C_6$ alkoxy, phenoxy, or a group of the formula

wherein $R^4$ and $R^5$ are independently hydrogen, $C_1$–$C_6$ alkyl, piperidinyl, phenyl, or phenyl($C_1$–$C_6$ alkylenyl)-, or $R^2$ is a heterocyclic ring selected from the group consisting of hexamethyleneiminyl, piperazinyl, heptamethyleneiminyl, imidazolinyl, piperidinyl, 2-tryptolinyl, pyrrolidinyl, quinuclidinyl, or morpholinyl;

any one of which $C_1$–$C_6$ alkoxy, —$NR^4R^5$, hexamethyleneiminyl, piperazinyl, heptamethyleneiminyl, imidazolinyl, piperidinyl, 2-tryptolinyl, pyrrolidinyl, quinuclidinyl, or morpholinyl groups may be substituted with one or more moieties selected from the group consisting of amino, aminocarbonyl, $C_1$–$C_6$ alkyl, halo, trifluoromethyl, benzyl, phenyl, di($C_1$–$C_6$ alkyl)amino, di($C_1$–$C_6$ alkyl)amino($C_1$–$C_6$ alkylenyl)-, $C_1$–$C_6$ alkylamino($C_1$–$C_6$ alkylenyl)-, $C_2$–$C_6$ alkanoyl, carboxamido, 2-aminoacetyl, $C_2$–$C_6$ alkanoyloxy, $C_1$–$C_6$ alkoxycarbonyl-, $C_1$–$C_6$ alkylamino, $C_3$–$C_8$ cycloalkyl, piperidinyl, pyrrolidinyl, pyrimidyl, phenyl($C_1$–$C_6$ alkylenyl)-, phenoxy($C_1$–$C_6$ alkylenyl)-, piperidinyl($C_1$–$C_6$ alkylenyl)-, pyrrolidinyl($C_1$–$C_6$ alkylenyl)-, pyrimidyl($C_1$–$C_6$ alkylenyl)-, $C_1$–$C_6$ alkoxy, $C_1$–$C_6$ alkylthio, di[di($C_1$–$C_6$ alkyl)amino($C_1$–$C_6$ alkylenyl)]amino, di($C_1$–$C_6$ alkyl)amino($C_1$–$C_6$ alkylenyl)amino, and acetamido, any one of which benzyl, phenyl, piperidinyl, $C_3$–$C_8$ cycloalkyl, phenyl($C_1$–$C_6$ alkylenyl)-, phenoxy ($C_1$–$C_6$ alkylenyl)-, pyrrolidinyl, piperidinyl ($C_1$–$C_6$ alkylenyl)-, pyrrolidinyl($C_1$–$C_6$ alkylenyl)-, pyrimidyl($C_1$–$C_6$ alkylenyl)-, or pyrimidyl group may be substituted with one or more moieties selected from the group consisting of $C_1$–$C_6$ alkyl, halo, trifluoromethyl, acetamido, $C_2$–$C_6$ alkanoyl, $C_2$–$C_7$ alkanoyloxy, and $C_1$–$C_6$ alkoxy, or the nitrogen on said piperidinyl, pyrrolidinyl, piperidinyl($C_1$–$C_6$ alkylenyl)-, pyrrolidinyl($C_1$–$C_6$ alkylenyl)-, pyrimidyl($C_1$–$C_6$ alkylenyl)-, or pyrimidyl may be substituted with an amino-protecting group, or R² is a group of the formula

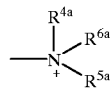

where $R^{4a}$, $R^{5a}$, and $R^{6a}$ are independently hydrogen, $C_1$–$C_6$ alkyl, trifluoromethyl, or $C_1$–$C_6$ alkoxy, or $R^{4a}$ is hydrogen, $C_1$–$C_6$ alkyl, trifluoromethyl, or $C_1$–$C_6$ alkoxy and $R^{5a}$ and $R^{6a}$ combine to form, together with the nitrogen to which they are attached, pyrrolidinyl, piperidinyl, hexamethyleneiminyl, or heptamethyleneiminyl, or $R^{4a}$ is oxygen, and $R^{5a}$ and $R^{6a}$ combine to form, together with the nitrogen to which they are attached, pyrrolidinyl, piperidinyl, hexamethyleneiminyl, or heptamethyleneiminyl;

R is phenyl, naphthyl, dihydronaphthyl, tetrahydronaphthyl, $C_3$–$C_8$ cycloalkyl, pyrazinyl, allyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl, any one of which phenyl, naphthyl, dihydronaphthyl, tetrahydronaphthyl, $C_3$–$C_8$ cycloalkyl, pyrazinyl, thiazolyl, furyl, pyrimidyl, pyridinyl, quinolinyl, isoquinolinyl, oxazolyl, pyridazinyl, imidazolyl, triazolyl, tetrazolyl, hexamethyleneiminyl, heptamethyleneiminyl, piperidinyl, pyrrolidinyl, quinuclidinyl, or morpholinyl groups may be substituted with one or more moieties selected from the group consisting of $C_1$–$C_{12}$ alkyl, $C_2$–$C_{10}$ alkenyl, $C_2$–$C_{10}$ alkynyl, halo, trifluoromethyl, carboxamido, cyano, benzyl, phenyl, di($C_1$–$C_6$ alkyl)amino, $C_2$–$C_6$ alkanoyl, $C_2$–$C_6$ alkanoyloxy, $C_1$–$C_6$ alkylamino, oxazolyl, dihydrooxazolyl, piperidinyl($C_1$–$C_{12}$ alkoxy)-, piperidinyl($C_1$–$C_{12}$ alkoxy)($C_1$–$C_6$ alkylenyl)-, piperidinyl($C_1$–$C_{12}$ alkylenyl)-, phenyl ($C_1$–$C_{12}$ alkoxy)-, phenyl($C_2$–$C_{12}$ alkylenyl)-, $C_3$–$C_8$ cycloalkyl, piperidinyl, pyrimidyl, $C_1$–$C_6$ alkoxy, $C_1$–$C_6$ alkylthio, a group of the formula $R_xR_yN$—G—L—($C_0$–$C_6$ alkylenyl)-, and acetamido, where $R_x$ and $R_y$ are independently hydrogen, $C_1$–$C_6$ alkyl, phenyl, benzyl, piperidinyl, pyrrolidinyl, hexamethyleneiminyl, heptamethyleneiminyl, morpholinyl, piperazinyl, or $C_3$–$C_8$ cycloalkyl, or where $R^xR^yN$ is a ring selected from the group consisting of piperidinyl, pyrrolidinyl, hexamethyleneiminyl, heptamethyleneiminyl, azetidinyl, which may be attached to G at any appropriate place on the ring, G is $C_1$–$C_{12}$ alkylenyl, $C_2$–$C_{12}$ alkenylenyl, or $C_2$–$C_{12}$ alkynylenyl, and L is a bond, —O—, —S—, —S(O)—, —S(O)2—, or —NH—;

or a pharmaceutically acceptable salt or solvate thereof.

25. A method as claimed in claim 24 employing a compound wherein $R^1$ is hydrogen, or methyl or $R^{1a}$ is piperidinyl, pyrrolidinyl, piperazinyl, or quinuclidinyl, or a pharmaceutically acceptable salt or solvate thereof.

26. A method as claimed in claim 25 employing a compound wherein $R^{1a}$ is piperidin-3-yl, piperidin-2-yl, pyrroldin-3-yl, or pyrrolidin-2-yl, piperidin-1-yl, piperidin-4-yl, pyrrolidin-1-yl, or pyrrolidin-4-yl, phenyl, or a pharmaceutically acceptable salt or solvate thereof.

27. A method as claimed in claim 26 employing a compound wherein $A^1$ is —O—, or a pharmaceutically acceptable salt or solvate thereof.

28. A method as claimed in claim 27 employing a compound wherein —($CH_2$)$_q$—D—($CH_2$)$_s$— is a bond, methylene, ethylene, or —C(O)—, or a pharmaceutically acceptable salt or solvate thereof.

29. A method as claimed in claim 28 employing a compound wherein both $X^1$ and $Y^1$ are hydrogen, or a pharmaceutically acceptable salt or solvate thereof.

30. A method as claimed in claim 29 employing a compound wherein $R^2$ is a piperidinyl group substituted with amino, di($C_1$–$C_6$ alkyl)amino, $C_1$–$C_6$ alkylamino, or piperidinyl, or $R^2$ is a pyrrolidinyl group substituted with amino, di($C_1$–$C_6$ alkyl)amino, $C_1$–$C_6$ alkylamino, or pyrrolidinyl, or $R^2$ is a piperazinyl group substituted with phenyl or cyclohexyl, or a pharmaceutically acceptable salt or solvate thereof.

31. A method as claimed in claim 30 employing a compound wherein —A—$A^1$—($CH_2$)$_p$— is —$CH_2$—O—, —$CH_2$—NH—, or —$CH_2$—S—, or a pharmaceutically acceptable salt or solvate thereof.

32. A method as claimed in claim 31 employing a compound wherein R is naphthyl, phenyl, piperidinyl, pyrrolidinyl, or cyclohexyl, or a pharmaceutically acceptable salt or solvate thereof.

33. A method as claimed in claim 32 employing a compound wherein R is phenyl optionally independently substituted at the 4-position and the 2-position with halo.

* * * * *